(12) United States Patent
Bakshi et al.

(10) Patent No.: US 7,160,886 B2
(45) Date of Patent: Jan. 9, 2007

(54) ACYLATED PIPERAZINE DERIVATIVES AS MELANOCORTIN-4 RECEPTOR AGONISTS

(75) Inventors: Raman K. Bakshi, Edison, NJ (US); Liangqin Guo, Edison, NJ (US); Qingmei Hong, Scotch Plains, NJ (US); Ravi P. Nargund, East Brunswick, NJ (US); Patrick G. Pollard, Oakhurst, NJ (US); Iyassu K. Sebhat, New York, NY (US); Feroze Ujjainwalla, Scotch Plains, NJ (US); Zhixiong Ye, Princeton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 62 days.

(21) Appl. No.: 10/788,859

(22) Filed: Feb. 27, 2004

(65) Prior Publication Data

US 2004/0204398 A1   Oct. 14, 2004

Related U.S. Application Data

(60) Provisional application No. 60/515,943, filed on Oct. 30, 2003, provisional application No. 60/451,502, filed on Mar. 3, 2003.

(51) Int. Cl.
*A61K 31/497* (2006.01)
*C07D 401/12* (2006.01)
*C07D 403/12* (2006.01)
*C07D 413/12* (2006.01)
*C07D 417/12* (2006.01)

(52) U.S. Cl. .......................... 514/252.02; 514/252.11; 514/252.13; 514/252.14; 514/253.05; 514/253.06; 514/253.09; 514/254.01; 514/254.02; 514/254.03; 514/254.05; 514/254.1; 514/254.13; 544/182; 544/238; 544/297; 544/322; 544/360; 544/363; 544/365; 544/366; 544/367; 544/369; 544/370; 544/371; 544/372; 544/379

(58) Field of Classification Search ..................... None
See application file for complete search history.

(56) References Cited

U.S. PATENT DOCUMENTS

| | | | |
|---|---|---|---|
| 5,576,290 A | 11/1996 | Hadley | |
| 6,051,555 A | 4/2000 | Hadley | |
| 6,329,403 B1 * | 12/2001 | Odaka et al. | 514/342 |
| 2003/0153556 A1 * | 8/2003 | Levy et al. | 514/218 |

FOREIGN PATENT DOCUMENTS

| | | |
|---|---|---|
| WO | WO 99/64002 | 12/1999 |
| WO | WO 00/74679 | 12/2000 |
| WO | WO 01/58891 | 8/2001 |
| WO | WO 01/70337 | 9/2001 |
| WO | WO 01/70708 | 9/2001 |
| WO | WO 01/91752 | 12/2001 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/068387 | 9/2002 |
| WO | WO 02/068388 | 9/2002 |
| WO | WO 02/070511 | 9/2002 |
| WO | WO 03/007949 | 1/2003 |
| WO | WO 03/009847 | 2/2003 |
| WO | WO 03/066597 | 8/2003 |
| WO | WO 03/093234 | 11/2003 |
| WO | WO 03/094918 | 11/2003 |
| WO | WO 2005/040109 | 5/2005 |

OTHER PUBLICATIONS

Huszar et al., Cell, vol. 88 (1997), pp. 131-141, "Targeted disruption of the melanocortin-4 receptor results in obesity in mice".
Dinsmore et al., Brit. Med. J., vol. 318 (1999), pp. 387-390, "ABC of sexual health—erectile dysfunction".
Kask et al., Biochem. & Biophys. Res. Comm., vol. 245 (1998), pp. 90-93, "Selective antagonist for the melanocortin 4 receptor (HSO014) increases food intake in free-feeding rats".
Chen et al., Cell, vol. 91 (1997), pp. 789-798, "Exocrine gland dysfunction in MC5-R-deficient mice . . . ".
Gingell et al., Exp. Opin. Ther. Patents, vol. 9 (1999), pp. 1689-1696, "Emerging pharmacological therapies for erectile dysfunction".
Moreland et al., Life Sciences, vol. 62, No. 20 (1998), pp. PL-309-318, "Sildenafil, A novel inhibitor of phosphodiesterase Type 5 in human corpus cavernosum smooth muscle cells".
Giraudo et al., Brain Res. vol. 809 (1998), pp. 302-306, "Feeding effects of hypothalamic injection of melanocortin 4 receptor ligands".
Graul, Drugs News & Perspectives, vol. 9 (1996), pp. 572-575, "Latest findings on the diagnosis and treatment of erectile dysfunction".
Kopelman, Nature, vol. 404 (2000), pp. 635-643, "Obesity as a medical problem".
Hill et al., Science, vol. 280 (1998), pp. 1371-1374, "Environmental contributions to the obesity epidemic".
Davidson et al., JAMA, vol. 281 (1999), pp. 235-242, "Weight control and risk factor reduction in obese subjects treated for 2 years with orlistat".
Guy Grand et al., Lancet, vol. 2 (1989), pp. 1142-1145, "Therapeutics: International trial of long-term dexfenfluramine in obesity".
Bray et al., Obesity Research, vol. 7 (1999), pp. 189-198, "Sibutramine produces dose-related weight loss".

(Continued)

Primary Examiner—Golam M. M. Shameem
Assistant Examiner—Andrew B. Freistein
(74) Attorney, Agent, or Firm—Baerbel R. Brown; Melvin Winokur

(57) ABSTRACT

Certain novel N-acylated piperazine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

31 Claims, No Drawings

OTHER PUBLICATIONS

Yoram et al., Current Opinion in Urology, vol. 7 (1997), pp. 349-353, "Oral pharmacotherapy in erectile dysfunction".

Heaton et al., Int'l J. of Impotence Res., vol. 9 (1997), pp. 115-121, "A therapeutic taxonomy of treatments for erectile dysfunction: an evolutionary imperative".

Dorr et al., Life Sciences, vol. 58, No. 20 (1996), pp. 1777-1784, "Evaluation of melanotan-II, a superpotent cyclic melanotropic peptide in a pilot phase-I clinical study".

Wessells et al., Urology, vol. 56 (2000), pp. 641-646, "Effect of an alpha-melanocyte stimulating hormone analog on penile erection and sexual desire in men with organic erectile dysfunction".

Douglas et al., Int. J. Obes. vol. 7 (1983), pp. 591-595, "Plasma phentermine levels, weight loss and side-effects".

Ford et al., JAMA, vol. 287(3) (2002), pp. 356-359, "Prevalence of the metabolic syndrome among US adults".

Peptides: Frontiers of Peptide Science, Proceedings of the 15th American Peptide Symposium, Jun. 14-19, 1997, Nashville, TN.

* cited by examiner

ACYLATED PIPERAZINE DERIVATIVES AS MELANOCORTIN-4 RECEPTOR AGONISTS

CROSS-REFERENCE TO RELATED APPLICATIONS

This application claims the benefit of U.S. Provisional Application No. 60/451502, filed on Mar. 3, 2003, now expired, and U.S. Provisional Application No. 60/5 15943, filed on Oct. 30, 2003, now expired.

FIELD OF THE INVENTION

The present invention relates to acylated piperazine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arterioscelerosis; heart disease; abnormal heart rhythms; and heart arrythmias (Kopelman, P. G., Nature 404, 635–643 (2000)). Obesity is further associated with premature death and with a significant increase in mortality and morbidity from stroke, myocardial infarction, congestive heart failure, coronary heart disease, and sudden death.

In the vast majority of obese individuals, the cause of the excess adiposity is not immediately apparent. A currently accepted working hypothesis is that obesity is the result of a maladaptation of the innate metabolic response to environmental challenges such as unlimited availability of low cost/energy dense foods and sedentariness (Hill et al., Science 1998; 280:1371). The study of energy intake in free living humans has met with only limited success and definitive experimental evidence that hyperphagia causes most forms of human obesity is lacking. Following the discovery of leptin, the interest in the neurohormonal regulation of food intake has regained momentum. However, while much knowledge has been gained on the regulation of food intake in rodents and other animal species, the understanding of the neurophysiology of feeding behavior in humans remains extremely limited.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., Cell, 88: 131–141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789–798 (1997)).

Weight loss drugs that are currently used to treat obesity have limited efficacy and significant side effects. Studies of the weight loss medications orlistat (Davidson, M. H. et al. (1999) JAMA 281:235–42), dexfenfluramine (Guy Grand, B. et al. (1989) Lancet 2:1142–5), sibutramine (Bray, G. A. et al. (1999) Obes. Res. &:189–98) and phentermine (Douglas, A. et al. (1983) Int. J. Obes. 7:591–5) have demonstrated a limited weight loss of about 5%–10% of body weight for drug compared to placebo. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Melanocortin receptor involvement in male and female sexual dysfunction has also been reported.

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," *Brit. Med. J.* 318: 387–390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction," *Exp. Opin. Ther. Patents* 9: 1689–1696 (1999)). Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," *Life Sci.*, 62: 309–318 (1998)]. Prior to the introduction of Viagra® on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. Tadalafil or IC-351 (ICOS Corp.) is claimed to have greater selectivity for PDE-V over PDE-VI than sildenafil. Other PDE-V inhibitors include vardenafil from Bayer, M-54033 and M-54018 from Mochida Pharmaceutical Co., and E-4010 from Eisai Co., Ltd.

Other pharmacological approaches to the treatment of erectile dysfunction have been described [see, e.g., "Latest Findings on the Diagnosis and Treatment of Erectile Dysfunction," *Drug News & Perspectives,* 9: 572–575 (1996); "Oral Pharmacotherapy in Erectile Dysfunction," *Current Opinion in Urology,* 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative," *Int. J. Impotence Res.,* 9: 115–121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.,* 160: 389–393 (1998); *Fifteenth American Peptide Symposium*, Jun. 14–19, 1997 (Nashville Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-$NH_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology*, 56: 641–646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine, piperidine and piperazine derivatives have been disclosed in WO 99/64002 (16 Dec. 1999); WO 00/74679 (14 Dec. 2000); WO 01/58891 (16 Aug. 2001); WO 01/70708 (27 Sep. 2001); WO 01/70337 (27 Sep. 2001); WO 01/91752 (6 Dec. 2001); WO 02/059095 (1 Aug. 2002); WO 02/059107 (1 Aug. 2002); WO 02/059108 (1 Aug. 2002); WO 02/059117 (1 Aug. 2002); WO 02/068387 (6 Sep. 2002); WO 02/068388 (6 Sep. 2002); WO 02/070511 (12 Sep. 2002); WO 03/007949 (30 Jan. 2003); WO 03/009847 (6 Feb. 2003); WO 03/093234 (13 Nov. 2003); and WO 03/094918 (20 Nov. 2003) as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated piperazine derivatives which are melanocortin receptor agonists and thereby useful to treat obesity, diabetes, male sexual dysfunction, and female sexual dysfunction.

It is another object of the present invention to provide acylated piperazine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel 4-substituted N-acylated piperazines of structural formula I:

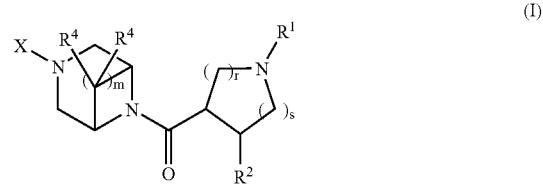

These acylated piperazine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin-4 receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to prevent or treat the condition.

The present invention also relates to methods for treating or preventing diabetes by administering the compounds of the present invention in combination with a therapeutically effective amount of another agent known to be useful to prevent or treat the condition.

DETAILED DESCRIPTION OF THE INVENTION

The present invention relates to 4-substituted N-acylated piperazine derivatives useful as melanocortin receptor agonists, in particular, as selective MC-4R agonists. Compounds of the present invention are described by structural formula I:

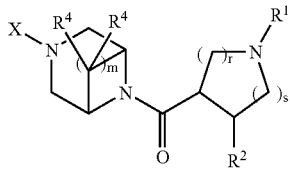

(I)

or a pharmaceutically acceptable salt thereof;
wherein
X is selected from the group consisting of
(1) $C_{1-8}$ alkyl,
(2) —$(CH_2)_n C_{3-8}$ cycloalkyl,
(3) —$(CH_2)_n$-phenyl,
(4) —$(CH_2)_n$-naphthyl,
(5) —$(CH_2)_n$-heteroaryl,
(6) —$(CH_2)_n$heterocycloalkyl,
(7) —$(CH_2)_n C(R^5)(R^6)(R^7)$,
(8) —$(CH_2)_n C \equiv N$,
(9) —$(CH_2)_n CON(R^8)_2$,
(10) —$(CH_2)_n CO_2 R^8$,
(11) —$(CH_2)_n COR^8$,
(12) —$(CH_2)_n NR^8 C(O)R^8$,
(13) —$(CH_2)_n NR^8 CO_2 R^8$,
(14) —$(CH_2)_n NR^8 C(O)N(R^8)_2$,
(15) —$(CH_2)_n NR^8 SO_2 R^8$,
(16) —$(CH_2)_n S(O)_p R^8$,
(17) —$(CH_2)_n SO_2 N(R^8)_2$,
(18) —$(CH_2)_n OR^8$,
(19) —$(CH_2)_n OC(O)R^8$,
(20) —$(CH_2)_n OC(O)OR^8$,
(21) —$(CH_2)_n OC(O)N(R^8)_2$,
(22) —$(CH_2)_n N(R^8)_2$, and
(23) —$(CH_2)_n NR^8 SO_2 N(R^8)_2$, wherein phenyl, naphthyl, and heteroaryl are unsubstituted or substituted with one to three groups independently selected from $R^3$, and alkyl, cycloalkyl, and heterocycloalkyl are unsubstituted or substituted with one to three groups independently selected from $R^3$ and oxo, and wherein any methylene ($CH_2$) in X is unsubstituted or substituted with one to two groups independently selected from halogen, hydroxy, and $C_{1-4}$ alkyl;

$R^1$ is selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl, wherein phenyl, naphthyl, and heteroaryl are unsubstituted or substituted with one to three groups independently selected from $R^3$, and alkyl and cycloalkyl are unsubstituted or substituted with one to three groups independently selected from $R^3$ and oxo;

$R^2$ is selected from the group consisting of
(1) phenyl,
(2) naphthyl, and
(3) heteroaryl, wherein phenyl, naphthyl, and heteroaryl are unsubstituted or substituted with one to three groups independently selected from $R^3$;

each $R^3$ is independently selected from the group consisting of
(1) $C_{1-8}$ alkyl,
(2) $C_{2-8}$ alkenyl,
(3) —$(CH_2)_n$-phenyl,
(4) —$(CH_2)_n$-naphthyl,
(5) —$(CH_2)_n$-heteroaryl,
(6) —$(CH_2)_n C_{2-7}$ heterocycloalkyl,
(7) —$(CH_2)_n C_{3-7}$ cycloalkyl,
(8) halogen,
(9) $OR^9$,
(10) —$(CH_2)_n C(O)R^9$,
(11) —$(CH_2)_n OC(O)R^9$,
(12) —$(CH_2)_n C(O)OR^9$,
(13) —$(CH_2)_n C \equiv N$,
(14) $NO_2$,
(15) —$(CH_2)_n N(R^9)_2$,
(16) —$(CH_2)_n C(O)N(R^9)_2$,
(17) —$(CH_2)_n NR^9 C(O)R^9$,
(18) —$(CH_2)_n NR^9 C(O)OR^9$,
(19) —$(CH_2)_n NR^9 C(O)$-heteroaryl,
(20) —$(CH_2)_n NR^9 C(O)N(R^9)_2$,
(21) —$(CH_2)_n C(O)NR^9 N(R^9)_2$,
(22) —$(CH_2)_n C(O)NR^9 NR^9 C(O)R^9$,
(23) —$(CH_2)_n NR^9 S(O)_p R^9$,
(24) —$(CH_2)_n S(O)_p N(R^9)_2$,
(25) —$(CH_2)_n S(O)_p R^9$,
(26) $O(CH_2)_n C(O)N(R^9)_2$,
(27) $CF_3$,
(28) $CH_2 CF_3$,
(29) $OCF_3$, and
(30) $OCH_2 CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
(1) hydrogen,
(2) $C_{1-8}$ alkyl,
(3) —$(CH_2)_n C_{3-6}$ cycloalkyl,
(4) —$(CH_2)_n$-aryl,
(5) hydroxy,
(6) halogen, and
(7) amino;

$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_n C_{3-7}$ cycloalkyl,
(7) —$(CH_2)_n C_{2-7}$ heterocycloalkyl,
(8) —$(CH_2)_n$-phenyl,
(9) —$(CH_2)_n$-naphthyl,
(10) —$(CH_2)_n$-heteroaryl, and
(11) —$(CH_2)_n C_{3-7}$ bicycloalkyl, wherein phenyl, naphthyl, and heteroaryl are unsubstituted or substituted with one to three groups independently selected from $R^3$, and alkyl, alkenyl, alkynyl, alkoxy, cycloalkyl, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
  (1) hydrogen, and
  (2) $C_{1-8}$ alkyl;
$R^7$ is selected from the group consisting of
  (1) $-(CH_2)_nN(R^8)_2$,
  (2) $-(CH_2)_nNR^8C(O)R^8$,
  (3) $-(CH_2)_nNR^8C(O)OR^8$,
  (4) $-(CH_2)_nNR^8C(O)N(R^8)_2$,
  (5) $-(CH_2)_nNR^8S(O)R^8$,
  (6) $-(CH_2)_nNR^8S(O)_2R^8$, and
  (7) $-(CH_2)_nNR^8S(O)_2N(R^8)_2$, wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
  (1) hydrogen,
  (2) $C_{1-8}$ alkyl,
  (3) $C_{2-8}$ alkenyl,
  (4) $-(CH_2)_nC_{3-7}$ cycloalkyl,
  (5) $-(CH_2)_nC_{2-7}$ heterocycloalkyl,
  (6) $-(CH_2)_nC_{3-7}$ bicycloalkyl,
  (7) $-(CH_2)_n$-phenyl,
  (8) $-(CH_2)_n$-naphthyl, and
  (9) $-(CH_2)_n$-heteroaryl, wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and $-NC_{1-4}$ alkyl;

each $R^9$ is independently selected from the group consisting of
  (1) hydrogen,
  (2) $C_{1-8}$ alkyl,
  (3) phenyl,
  (4) heteroaryl,
  (5) $-(CH_2)_n$ heterocycloalkyl, and
  (6) $C_{3-6}$ cycloalkyl, wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and $-NC_{1-4}$ alkyl;

r is 1 or 2;
s is 0, 1, or 2;
m is 0, 1, 2, 3, or 4;
n is 0, 1, 2, 3, or 4; and
p is 0, 1, or 2.

In one embodiment of the compounds of structural formula I, $R^1$ is selected from the group consisting of hydrogen, $C_{1-6}$ alkyl, $-(CH_2)_{0-1}C_{3-6}$ cycloalkyl, and $-(CH_2)_{0-1}$-phenyl, wherein phenyl is unsubstituted or substituted with one to three groups independently selected from $R^3$, and alkyl and cycloalkyl are optionally substituted with one to three groups independently selected from $R^3$ and oxo. In a class of this embodiment, $R^1$ is hydrogen or $C_{1-6}$ alkyl.

In a second embodiment of the compounds of structural formula I, $R^2$ is phenyl or thienyl, optionally substituted with one to three groups independently selected from $R^3$. In a class of this embodiment, $R^2$ is phenyl optionally substituted with one to three groups independently selected from $R^3$. In another class of this embodiment, $R^2$ is thienyl unsubstituted or substituted with one to three groups independently selected from $R^3$. In another class of this embodiment, $R^2$ is thienyl substituted with one to three groups independently selected from $R^3$. In another class of this embodiment, $R^2$ is phenyl substituted with one to three groups independently selected from $R^3$.

In a third embodiment of the compounds of structural formula I, each $R^4$ is independently selected from the group consisting of hydrogen, halogen, or hydroxy. In a class of this embodiment, one $R^4$ is hydrogen. In another class of this embodiment, both $R^4$ groups are hydrogen.

In a fourth embodiment of compounds of formula I, X is selected from the group consisting of
  (1) $C_{1-8}$ alkyl,
  (2) $-(CH_2)_nC_{3-8}$ cycloalkyl,
  (3) $-(CH_2)_n$-phenyl,
  (4) $-(CH_2)_n$-heteroaryl,
  (5) $-(CH_2)_n$heterocycloalkyl, and
  (6) $-(CH_2)_nC(R^5)(R^6)(R^7)$, wherein phenyl and heteroaryl are unsubstituted or substituted with one to three groups independently selected from $R^3$, and alkyl, cycloalkyl, and heterocycloalkyl are unsubstituted or substituted with one to three groups independently selected from $R^3$ and oxo, and wherein any methylene ($CH_2$) in X is unsubstituted or substituted with one to two groups independently selected from halogen, hydroxy, and $C_{1-4}$ alkyl. In a class of this embodiment, X is phenyl or heteroaryl optionally substituted with one to three groups independently selected from $R^3$. In another class of this embodiment, X is $(CH_2)_nC(R^5)(R^6)(R^7)$. In a subclass of this class, n is 0, $R^6$ is hydrogen, and $R^5$ is selected from the group consisting of
  (1) $C_{1-8}$ alkyl,
  (2) $-(CH_2)_nC_{3-7}$ cycloalkyl,
  (3) $-(CH_2)_nC_{2-7}$ heterocycloalkyl,
  (4) $-(CH_2)_n$-phenyl, and
  (5) $-(CH_2)_n$-heteroaryl, wherein phenyl, and heteroaryl are unsubstituted or substituted with one to three groups independently selected from $R^3$, and alkyl, cycloalkyl and heterocycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl. In a subclass of this subclass, $R^5$ is selected from the group consisting of —$(CH_2)_{0-1}$-phenyl, —$(CH_2)_{0-1}$-heteroaryl, —$(CH_2)_{0-1}$—$C_{2-7}$ heterocycloalkyl, and —$(CH_2)_{0-1}$—$C_{3-8}$ cycloalkyl, wherein phenyl and heteroaryl are optionally substituted with one to three groups independently selected from $R^3$, and cycloalkyl and heterocycloalkyl are optionally substituted with one to three groups independently selected from $R^3$ and oxo, and wherein ($CH_2$) is unsubstituted or substituted with one to two groups independently selected from halogen, hydroxy, and $C_{1-4}$ alkyl. In another subclass of this subclass, $R^5$ is phenyl optionally substituted with one to three groups independently selected from $R^3$. In yet another subclass of this subclass, $R^5$ is $C_{5-6}$ cycloalkyl optionally substituted with one to three groups independently selected from $R^3$.

In a fifth embodiment of compounds of structural formula I, r is 1. In a class of this embodiment, r is 1 and s is 1.

In a sixth embodiment of compounds of structural formula I, r is 2. In a class of this embodiment, r is 2 and s is 1.

In a seventh embodiment of the compounds of structural formula I, each $R^3$ is independently selected from the group consisting of: (1) $C_{1-8}$ alkyl, (2) halogen, (3) —$(CH_2)_n$-phenyl, (4) —$(CH_2)_n$-naphthyl, (5) —$(CH_2)_n$-heteroaryl, (6) —$(CH_2)_n C_{2-7}$ heterocycloalkyl, (7) —$(CH_2)_n C_{3-7}$ cycloalkyl, (8) —$(CH_2)_{1-4}C(O)R^9$, (9) —$(CH_2)_n OC(O)R^9$, (10) —$(CH_2)_{1-4}C(O)OR^9$, (11) —$(CH_2)_n C\equiv N$, (12) —$(CH_2)_{1-4}N(R^9)_2$, (13) —$(CH_2)_{1-4}C(O)N(R^9)_2$, (14) —$(CH_2)_n NR^9 C(O)R^9$, (15) —$(CH_2)_n NR^9 C(O)OR^9$, (16) —$(CH_2)_n NR^9 C(O)$-heteroaryl, (17) —$(CH_2)_n NR^9 C(O)N(R^9)_2$, (18) —$(CH_2)_n C(O)NR^9 N(R^9)_2$, (19) —$(CH_2)_n C(O)NR^9 NR^9 C(O)R^9$, (20) —$(CH_2)_n NR^9 S(O)_p R^9$, (21) —$(CH_2)_{1-4}S(O)_p N(R^9)_2$, (22) —$(CH_2)_n S(O)_p R^9$, (23) $O(CH_2)_n C(O)N(R^9)_2$, (24) $CH_2 CF_3$, and (25) $OCH_2 CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group. In a class of this embodiment, each $R^3$ is independently selected from the group consisting of: (1) —$(CH_2)_n C_{2-7}$ heterocycloalkyl, (2) —$(CH_2)_{1-4}C(O)R^9$, (3) —$(CH_2)_{1-4}C(O)OR^9$, (4) —$(CH_2)_{1-4}N(R^9)_2$, (5) —$(CH_2)_{1-4}C(O)N(R^9)_2$, and (6) —$(CH_2)_{1-4}S(O)_p N(R^9)_2$, wherein any heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group.

In an eighth embodiment of the compounds of structural formula I, each $R^3$ is independently selected from the group consisting of: (1) $C_{1-8}$ alkyl, (2) halogen, (3) —$(CH_2)_n$-phenyl, (4) —$(CH_2)_n$-naphthyl, (5) —$(CH_2)_n$-heteroaryl, (6) —$(CH_2)_{1-4}C_{2-7}$ heterocycloalkyl, (7) —$(CH_2)_n C_{3-7}$ cycloalkyl, (8) —$(CH_2)_n C(O)C_{1-6}$alkyl, (9) —$(CH_2)_n OC(O)R^9$, (10) —$(CH_2)_n C(O)OC_{1-6}$alkyl, (11) —$(CH_2)_n C\equiv N$, (12) —$(CH_2)_{1-4}N(R^9)_2$, (13) —$(CH_2)_{1-4}C(O)N(R^9)_2$, (14) —$(CH_2)_n NR^9 C(O)R^9$, (15) —$(CH_2)_n NR^9 C(O)OR^9$, (16) —$(CH_2)_n NR^9 C(O)$-heteroaryl, (17) —$(CH_2)_n NR^9 C(O)N(R^9)_2$, (18) —$(CH_2)_n C(O)NR^9 N(R^9)_2$, (19) —$(CH_2)_n C(O)NR^9 NR^9 C(O)R^9$, (20) —$(CH_2)_n NR^9 S(O)_p R^9$, (21) —$(CH_2)_{1-4}S(O)_p N(R^9)_2$, (22) —$(CH_2)_n S(O)_p R^9$, (23) $O(CH_2)_n C(O)N(R^9)_2$, (24) $CH_2 CF_3$, and (25) $OCH_2 CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group. In a class of this embodiment, each $R^3$ is independently selected from the group consisting of: (1) —$(CH_2)_{1-4}C_{2-7}$ heterocycloalkyl, (2) —$(CH_2)_n C(O)C_{1-6}$alkyl, (3) —$(CH_2)_n C(O)OC_{1-6}$alkyl, (4) —$(CH_2)_{1-4}N(R^9)_2$, (5) —$(CH_2)_{1-4}C(O)N(R^9)_2$, and (6) —$(CH_2)_{1-4}S(O)_p N(R^9)_2$, wherein alkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group.

In a ninth embodiment of the compounds of structural formula I, each $R^9$ is independently selected from the group consisting of: (1) hydrogen, (2) $C_{1-8}$ alkyl, (3) phenyl, (4) heteroaryl, (5) —$(CH_2)_n$ heterocycloalkyl, and (6) $C_{3-6}$ cycloalkyl, wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 3 to 8-membered mono- or bicyclic ring system optionally containing an additional heteroatom selected from O, S, and —$NC_{1-4}$ alkyl.

In a further embodiment of the compounds of the present invention, there are provided compounds of structural formula IIa or IIb of the indicated relative stereochemical configurations having the trans orientation of the $R^2$ and piperazinecarbonyl substituents:

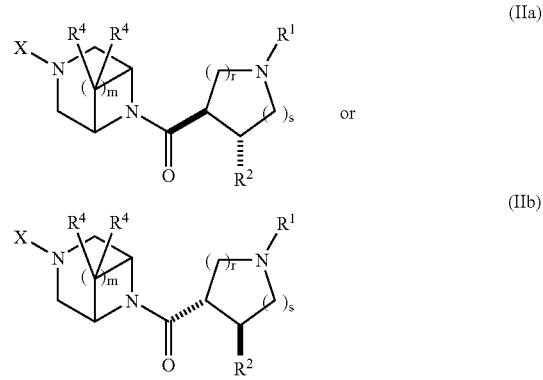

or a pharmaceutically acceptable salt thereof;

wherein

X is selected from the group consisting of
  (1) $C_{1-8}$ alkyl,
  (2) —$(CH_2)_n C_{3-8}$ cycloalkyl,
  (3) —$(CH_2)_n$-phenyl,
  (4) —$(CH_2)_n$-heteroaryl, (5) —(CH$_2$)$_n$heterocycloalkyl, and
(6) —(CH$_2$)$_n$C(R$^5$)(R$^6$)(R$^7$), wherein phenyl and heteroaryl are unsubstituted or substituted with one to three groups independently selected from R$^3$, and alkyl, cycloalkyl, and heterocycloalkyl are unsubstituted or substituted with one to three groups independently selected from R$^3$ and oxo, and wherein any methylene (CH$_2$) in X is unsubstituted or substituted with one to two groups independently selected from halogen, hydroxy, and C$_{1-4}$ alkyl;

R$^1$ is selected from the group consisting of hydrogen, amidino, C$_{1-4}$ alkyliminoyl, C$_{1-6}$ alkyl, C$_{5-6}$ cycloalkyl, —(CH$_2$)$_{0-1}$ phenyl, and —(CH$_2$)$_{0-1}$ heteroaryl, wherein phenyl and heteroaryl are unsubstituted or substituted with one to three groups independently selected from R$^3$, and alkyl and cycloalkyl are unsubstituted or substituted with one to three groups independently selected from R$^3$ and oxo;

R$^2$ is phenyl or thienyl, optionally substituted with one to three groups independently selected from R$^3$;

each R$^3$ is independently selected from the group consisting of
(1) C$_{1-8}$ alkyl,
(2) C$_{2-8}$ alkenyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$C$_{2-7}$ heterocycloalkyl,
(7) —(CH$_2$)$_n$C$_{3-7}$ cycloalkyl,
(8) halogen,
(9) OR$^9$,
(10) —(CH$_2$)$_n$C(O)R$^9$,
(11) —(CH$_2$)$_n$OC(O)R$^9$,
(12) —(CH$_2$)$_n$C(O)OR$^9$,
(13) —(CH$_2$)$_n$C≡N,
(14) NO$_2$,
(15) —(CH$_2$)$_n$N(R$^9$)$_2$,
(16) —(CH$_2$)$_n$C(O)N(R$^9$)$_2$,
(17) —(CH$_2$)$_n$NR$^9$C(O)R$^9$,
(18) —(CH$_2$)$_n$NR$^9$C(O)OR$^9$,
(19) —(CH$_2$)$_n$NR$^9$C(O)-heteroaryl,
(20) —(CH$_2$)$_n$NR$^9$C(O)N(R$^9$)$_2$,
(21) —(CH$_2$)$_n$C(O)NR$^9$N(R$^9$)$_2$,
(22) —(CH$_2$)$_n$C(O)NR$^9$NR$^9$C(O)R$^9$,
(23) —(CH$_2$)$_n$NR$^9$S(O)$_p$R$^9$,
(24) —(CH$_2$)$_n$S(O)$_p$N(R$^9$)$_2$,
(25) —(CH$_2$)$_n$S(O)$_p$R$^9$,
(26) O(CH$_2$)$_n$C(O)N(R$^9$)$_2$,
(27) CF$_3$,
(28) CH$_2$CF$_3$,
(29) OCF$_3$, and
(30) OCH$_2$CF$_3$, wherein alkenyl, phenyl, naphthyl, heteroaryl are unsubstituted or substituted with one to three substituents independently selected from halogen, hydroxy, C$_{1-4}$ alkyl, trifluoromethyl, and C$_{1-4}$ alkoxy, and wherein any alkyl, cycloalkyl, heterocycloalkyl, and methylene (CH$_2$) carbon atom in R$^3$ is unsubstituted or substituted with one to two groups independently selected from halogen, hydroxy, oxo, C$_{1-4}$ alkyl, trifluoromethyl, and C$_{1-14}$ alkoxy, or two R$^3$ substituents on the same carbon atom are taken together with the carbon atom to form a cyclopropyl group;

each R$^4$ is independently selected from the group consisting of
(1) hydrogen,
(2) C$_{1-8}$ alkyl,
(3) —(CH$_2$)$_{0-1}$C$_{3-6}$ cycloalkyl,
(4) —(CH$_2$)$_{0-1}$-aryl,
(5) hydroxy,
(6) halogen, and
(7) amino;

R$^5$ is independently selected from the group consisting of
(1) hydrogen,
(2) C$_{1-8}$ alkyl,
(3) C$_{2-8}$ alkenyl,
(4) C$_{2-8}$ alkynyl,
(5) C$_{1-8}$ alkoxy,
(6) —(CH$_2$)$_n$C$_{3-7}$ cycloalkyl,
(7) —(CH$_2$)$_n$C$_{2-7}$ heterocycloalkyl,
(8) —(CH$_2$)$_n$-phenyl,
(9) —(CH$_2$)$_n$-naphthyl,
(10) —(CH$_2$)$_n$-heteroaryl, and
(11) —(CH$_2$)$_n$C$_{3-7}$ bicycloalkyl, wherein phenyl, naphthyl, and heteroaryl are unsubstituted or substituted with one to three groups independently selected from R$^3$, and alkyl, alkenyl, alkynyl, alkoxy, cycloalkyl, heterocycloalkyl, and bicycloalkyl are unsubstituted or substituted with one to three groups independently selected from R$^3$ and oxo, and wherein any methylene (CH$_2$) in R$^5$ is unsubstituted or substituted with one to two groups independently selected from halogen, hydroxy, and C$_{1-4}$ alkyl;

R$^6$ is selected from the group consisting of
(1) hydrogen, and
(2) C$_{1-8}$ alkyl;

R$^7$ is selected from the group consisting of
(1) —(CH$_2$)$_n$N(R$^8$)$_2$,
(2) —(CH$_2$)$_n$NR$^8$C(O)R$^8$,
(3) —(CH$_2$)$_n$NR$^8$C(O)OR$^8$,
(4) —(CH$_2$)$_n$NR$^8$C(O)N(R$^8$)$_2$,
(5) —(CH$_2$)$_n$NR$^8$S(O)R$^8$,
(6) —(CH$_2$)$_n$NR$^8$S(O)$_2$R$^8$, and
(7) —(CH$_2$)$_n$NR$^8$S(O)$_2$N(R$^8$)$_2$, wherein any methylene (CH$_2$) in R$^7$ is unsubstituted or substituted with one to two groups independently selected from halogen, hydroxy, and C$_{1-4}$ alkyl, or two R$^8$ substituents together with the carbon, nitrogen or sulfur atom to which they are attached form a 5, 6, or 7-membered saturated or unsaturated nitrogen containing ring optionally substituted with one to three groups independently selected from C$_{1-8}$ alkyl and oxo;

each R$^8$ is independently selected from the group consisting of
(1) hydrogen,
(2) C$_{1-8}$ alkyl,
(3) C$_{2-8}$ alkenyl,
(4) —(CH$_2$)$_n$C$_{3-7}$ cycloalkyl,
(5) —(CH$_2$)$_n$C$_{2-7}$ heterocycloalkyl,
(6) —(CH$_2$)$_n$C$_{3-7}$ bicycloalkyl,
(7) —(CH$_2$)$_n$-phenyl,
(8) —(CH$_2$)$_n$-naphthyl, and
(9) —(CH$_2$)$_n$-heteroaryl, wherein alkyl, alkenyl, cycloalkyl, heterocycloalkyl, and bicycloalkyl are unsubstituted or substituted with one to three groups independently selected from R$^3$ and oxo, and wherein phenyl, naphthyl, and heteroaryl are unsubstituted or substituted with one to three groups independently selected from R$^3$, and wherein any methylene (CH$_2$) in R$^8$ is unsubstituted or substituted with one to two groups independently selected from halogen, hydroxy, and C$_{1-4}$ alkyl, or two R$^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_n$ heterocycloalkyl, and
(6) $C_{3-6}$ cycloalkyl, wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;

r is 1 or 2;
s is 0, 1 or 2;
m is 0, 1, 2, 3 or 4;
n is 0, 1, 2, 3 or 4; and
p is 0, 1, or 2.

In a class of this embodiment, $R^2$ is thienyl unsubstituted or substituted with one to three groups independently selected from $R^3$. In another class of this embodiment, $R^2$ is thienyl substituted with one to three groups independently selected from $R^3$. In another class of this embodiment, $R^2$ is phenyl unsubstituted or substituted with one to three groups independently selected from $R^3$. In another class of this embodiment, $R^2$ is phenyl substituted with one to three groups independently selected from $R^3$.

In yet a further embodiment of the compounds of the present invention, there are provided compounds of structural formula IIIa or IIIb of the indicated relative stereochemical configurations having the trans orientation of the phenyl and piperazinecarbonyl substituents:

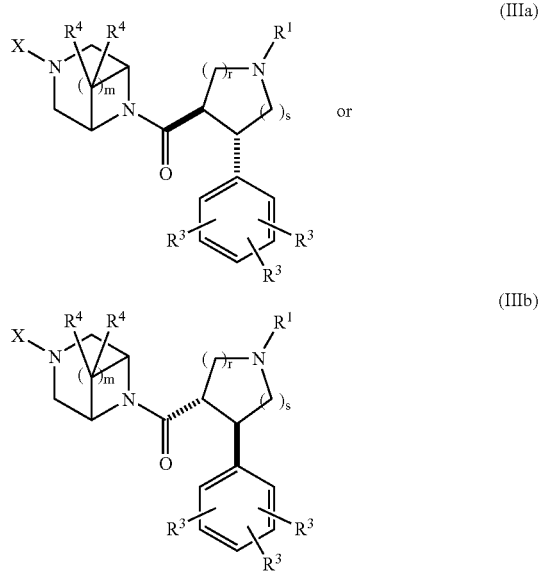

or a pharmaceutically acceptable salt thereof;

wherein
X is selected from the group consisting of
(1) —$(CH_2)_{0-1}$-phenyl,
(2) —$(CH_2)_{0-1}$-heteroaryl, and
(3) —$(CH_2)_{0-1}C(R^5)(R^6)(R^7)$, wherein phenyl and heteroaryl are unsubstituted or substituted with one to three groups independently selected from $R^3$, and wherein any methylene ($CH_2$) in X is unsubstituted or substituted with one to two groups independently selected from halogen, hydroxy, and $C_{1-4}$ alkyl;

$R^1$ is selected from the group consisting of hydrogen, $C_{1-4}$ alkyl, and —$(CH_2)_{0-1}$ phenyl;

each $R^3$ is independently selected from the group consisting of
(1) $C_{1-8}$ alkyl,
(2) $C_{2-8}$ alkenyl,
(3) —$(CH_2)_{0-1}$-phenyl,
(4) —$(CH_2)_{0-1}$-naphthyl,
(5) —$(CH_2)_{0-1}$-heteroaryl,
(6) —$(CH_2)_{0-1}$—$C_{2-7}$ heterocycloalkyl,
(7) —$(CH_2)_{0-1}$—$C_{3-7}$ cycloalkyl,
(8) halogen,
(9) $OR^9$,
(10) —$(CH_2)_{0-1}$—$C(O)R^9$,
(11) —$(CH_2)_{0-1}$—$OC(O)R^9$,
(12) —$(CH_2)_{0-1}$—$C(O)OR^9$,
(13) —$(CH_2)_{0-1}$—C≡N,
(14) $NO_2$,
(15) —$(CH_2)_{0-1}$—$N(R^9)_2$,
(16) —$(CH_2)_{0-1}$—$C(O)N(R^9)_2$,
(17) —$(CH_2)_{0-1}$—$NR^9C(O)R^9$,
(18) —$(CH_2)_{0-1}$—$NR^9C(O)OR^9$,
(19) —$(CH_2)_{0-1}NR^9C(O)$-heteroaryl,
(20) —$(CH_2)_{0-1}NR^9C(O)N(R^9)_2$,
(21) —$(CH_2)_{0-1}C(O)NR^9N(R^9)_2$,
(22) —$(CH_2)_{0-1}$—$C(O)NR^9NR^9C(O)R^9$,
(23) —$(CH_2)_{0-1}$—$NR^9S(O)_{1-2}R^9$,
(24) —$(CH_2)_{0-1}$—$S(O)_{1-2}N(R^9)_2$,
(25) —$(CH_2)_{0-1}$—$S(O)_{0-2}R^9$,
(26) $O(CH_2)_{0-1}$—$C(O)N(R^9)_2$,
(27) $CF_3$,
(28) $CH_2CF_3$,
(29) $OCF_3$, and
(30) $OCH_2CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
(1) hydrogen,
(2) $C_{1-8}$ alkyl,
(3) —$(CH_2)_{0-1}$—$C_{3-6}$ cycloalkyl,
(4) —$(CH_2)_{0-1}$-aryl,
(5) hydroxy,
(6) halogen, and
(7) amino;

$R^5$ is independently selected from the group consisting of
(1) hydrogen,
(2) $C_{1-8}$ alkyl,
(3) $C_{2-8}$ alkenyl, (4) $C_{2-8}$ alkynyl,
(5) $C_{1-8}$ alkoxy,
(6) —$(CH_2)_{0-1}$—$C_{3-7}$ cycloalkyl,
(7) —$(CH_2)_{0-1}$—$C_{2-7}$ heterocycloalkyl,
(8) —$(CH_2)_{0-1}$-phenyl,
(9) —$(CH_2)_{0-1}$-naphthyl,
(10) —$(CH_2)_{0-1}$-heteroaryl, and
(11) —$(CH_2)_{0-1}$—$C_{3-7}$ bicycloalkyl, wherein phenyl, naphthyl, and heteroaryl are unsubstituted or substituted with one to three groups independently selected from $R^3$, and alkyl, alkenyl, alkynyl, alkoxy, cycloalky, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
(1) hydrogen, and
(2) $C_{1-8}$ alkyl;

$R^7$ is selected from the group consisting of
(1) —$(CH_2)_{0-3}$—$N(R^8)_2$,
(2) —$(CH_2)_{0-3}$—$NR^8C(O)R^8$,
(3) —$(CH_2)_{0-3}$—$NR^8C(O)OR^8$,
(4) —$(CH_2)_{0-3}$—$NR^8C(O)N(R^8)_2$,
(5) —$(CH_2)_{0-3}$—$NR^8S(O)R^8$,
(6) —$(CH_2)_{0-3}$—$NR^8S(O)_2R^8$, and
(7) —$(CH_2)_{0-3}$—$NR^8S(O)_2N(R^8)_2$, wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
(1) hydrogen,
(2) $C_{1-8}$ alkyl,
(3) $C_{2-8}$ alkenyl,
(4) —$(CH_2)_{0-1}$—$C_{3-7}$ cycloalkyl,
(5) —$(CH_2)_{0-1}$—$C_{2-7}$ heterocycloalkyl,
(6) —$(CH_2)_{0-1}$—$C_{3-7}$ bicycloalkyl,
(7) —$(CH_2)_{0-1}$-phenyl,
(8) —$(CH_2)_{0-1}$-naphthyl, and
(9) —$(CH_2)_{0-1}$-heteroaryl, wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_{0-1}$ heterocycloalkyl, and
(6) $C_{3-6}$ cycloalkyl, wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;

r is 1 or 2;
s is 0, 1 or 2; and
m is 0, 1, 2, 3 or 4.

In yet a further embodiment of the compounds of the present invention, there are provided compounds of structural formula IV:

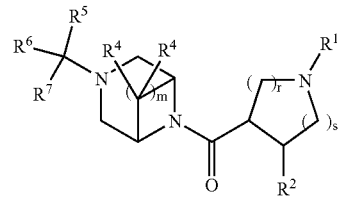

IV or a pharmaceutically acceptable salt thereof;

wherein
$R^1$ is selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
(8) —$(CH_2)_n$-heteroaryl, wherein phenyl, naphthyl, and heteroaryl are unsubstituted or substituted with one to three groups independently selected from $R^3$, and alkyl and cycloalkyl are unsubstituted or substituted with one to three groups independently selected from $R^3$ and oxo;

$R^2$ is selected from the group consisting of
(1) phenyl,
(2) naphthyl, and
(3) heteroaryl, wherein phenyl, naphthyl, and heteroaryl are unsubstituted or substituted with one to three groups independently selected from $R^3$;

each $R^3$ is independently selected from the group consisting of
(1) $C_{1-8}$ alkyl,
(2) $C_{2-8}$ alkenyl,
(3) —$(CH_2)_n$-phenyl,
(4) —$(CH_2)_n$-naphthyl,
(5) —$(CH_2)_n$-heteroaryl,
(6) —$(CH_2)_n C_{2-7}$ heterocycloalkyl,
(7) —$(CH_2)_n C_{3-7}$ cycloalkyl,
(8) halogen,
(9) $OR^9$,
(10) —$(CH_2)_n C(O)R^9$,
(11) —$(CH_2)_n OC(O)R^9$,

(12) —(CH$_2$)$_n$C(O)OR$^9$,
(13) —(CH$_2$)$_n$C≡N,
(14) NO$_2$,
(15) —(CH$_2$)$_n$N(R$^9$)$_2$,
(16) —(CH$_2$)$_n$C(O)N(R$^9$)$_2$,
(17) —(CH$_2$)$_n$NR$^9$C(O)R$^9$,
(18) —(CH$_2$)$_n$NR$^9$C(O)OR$^9$,
(19) —(CH$_2$)$_n$NR$^9$C(O)-heteroaryl,
(20) —(CH$_2$)$_n$NR$^9$C(O)N(R$^9$)$_2$,
(21) —(CH$_2$)$_n$C(O)NR$^9$N(R$^9$)$_2$,
(22) —(CH$_2$)$_n$C(O)NR$^9$NR$^9$C(O)R$^9$,
(23) —(CH$_2$)$_n$NR$^9$S(O)$_p$R$^9$,
(24) —(CH$_2$)$_n$S(O)$_p$N(R$^9$)$_2$,
(25) —(CH$_2$)$_n$S(O)$_p$R$^9$,
(26) O(CH$_2$)$_n$C(O)N(R$^9$)$_2$,
(27) CF$_3$,
(28) CH$_2$CF$_3$,
(29) OCF$_3$, and
(30) OCH$_2$CF$_3$, wherein alkenyl, phenyl, naphthyl, heteroaryl are unsubstituted or substituted with one to three substituents independently selected from halogen, hydroxy, C$_{1-4}$ alkyl, trifluoromethyl, and C$_{1-4}$ alkoxy, and wherein any alkyl, cycloalkyl, heterocycloalkyl, and methylene (CH$_2$) carbon atom in R$^3$ is unsubstituted or substituted with one to two groups independently selected from halogen, hydroxy, oxo, C$_{1-4}$ alkyl, trifluoromethyl, and C$_{1-4}$ alkoxy, or two R$^3$ substituents on the same carbon atom are taken together with the carbon atom to form a cyclopropyl group;

each R$^4$ is independently selected from the group consisting of
(1) hydrogen,
(2) C$_{1-8}$ alkyl,
(3) —(CH$_2$)$_n$C$_{3-6}$ cycloalkyl,
(4) —(CH$_2$)$_n$-aryl,
(5) hydroxy,
(6) halogen, and
(7) amino;

R$^5$ is independently selected from the group consisting of
(1) hydrogen,
(2) C$_{1-8}$ alkyl,
(3) C$_{2-8}$ alkenyl,
(4) C$_{2-8}$ alkynyl,
(5) C$_{1-8}$ alkoxy,
(6) —(CH$_2$)$_n$C$_{3-7}$ cycloalkyl,
(7) —(CH$_2$)$_n$C$_{2-7}$ heterocycloalkyl,
(8) —(CH$_2$)$_n$-phenyl,
(9) —(CH$_2$)$_n$-naphthyl,
(10) —(CH$_2$)$_n$-heteroaryl, and
(11) —(CH$_2$)$_n$C$_{3-7}$ bicycloalkyl, wherein phenyl, naphthyl, and heteroaryl are unsubstituted or substituted with one to three groups independently selected from R$^3$, and alkyl, alkenyl, alkynyl, alkoxy, cycloalkyl, heterocycloalkyl, and bicycloalkyl are unsubstituted or substituted with one to three groups independently selected from R$^3$ and oxo, and wherein any methylene (CH$_2$) in R$^5$ is unsubstituted or substituted with one to two groups independently selected from halogen, hydroxy, and C$_{1-4}$ alkyl;

R$^6$ is selected from the group consisting of
(1) hydrogen, and
(2) C$_{1-8}$ alkyl;

R$^7$ is selected from the group consisting of
(1) —(CH$_2$)$_n$N(R$^8$)$_2$,
(2) —(CH$_2$)$_n$NR$^8$C(O)R$^8$,
(3) —(CH$_2$)$_n$NR$^8$C(O)OR$^8$,
(4) —(CH$_2$)$_n$NR$^8$C(O)N(R$^8$)$_2$,
(5) —(CH$_2$)$_n$NR$^8$S(O)R$^8$,
(6) —(CH$_2$)$_n$NR$^8$S(O)$_2$R$^8$, and
(7) —(CH$_2$)$_n$NR$^8$S(O)$_2$N(R$^8$)$_2$, wherein any methylene (CH$_2$) in R$^7$ is unsubstituted or substituted with one to two groups independently selected from halogen, hydroxy, and C$_{1-4}$ alkyl, or two R$^8$ substituents together with the carbon, nitrogen or sulfur atom to which they are attached form a 5, 6, or 7-membered saturated or unsaturated nitrogen containing ring optionally substituted with one to three groups independently selected from C$_{1-8}$ alkyl and oxo;

each R$^8$ is independently selected from the group consisting of
(1) hydrogen,
(2) C$_{1-8}$ alkyl,
(3) C$_{2-8}$ alkenyl,
(4) —(CH$_2$)$_n$C$_{3-7}$ cycloalkyl,
(5) —(CH$_2$)$_n$C$_{2-7}$ heterocycloalkyl,
(6) —(CH$_2$)$_n$C$_{3-7}$ bicycloalkyl,
(7) —(CH$_2$)$_n$-phenyl,
(8) —(CH$_2$)$_n$-naphthyl, and
(9) —(CH$_2$)$_n$-heteroaryl, wherein alkyl, alkenyl, cycloalkyl, heterocycloalkyl, and bicycloalkyl are unsubstituted or substituted with one to three groups independently selected from R$^3$ and oxo, and wherein phenyl, naphthyl, and heteroaryl are unsubstituted or substituted with one to three groups independently selected from R$^3$, and wherein any methylene (CH$_2$) in R$^8$ is unsubstituted or substituted with one to two groups independently selected from halogen, hydroxy, and C$_{1-4}$ alkyl, or two R$^8$ groups together with the atom to which they are attached form a 5- to 8-memberd mono- or bicyclic ring system optionally containing an additional heteroatom selected from O, S, and —NC$_{1-4}$ alkyl;

each R$^9$ is independently selected from the group consisting of
(1) hydrogen,
(2) C$_{1-8}$ alkyl,
(3) phenyl,
(4) heteroaryl,
(5) —(CH$_2$)$_n$ heterocycloalkyl, and
(6) C$_{3-6}$ cycloalkyl, wherein alkyl, phenyl, heteroaryl, heterocycloalkyl, and cycloalkyl are unsubstituted or substituted with one to three groups independently selected from halogen, C$_{1-4}$ alkyl, hydroxy, and C$_{1-4}$ alkoxy, or two R$^9$ groups together with the atom to which they are attached form a 4- to 8-membered mono- or bicyclic ring system optionally containing an additional heteroatom selected from O, S, and —NC$_{1-4}$ alkyl;

r is 1 or 2;
s is 0, 1 or 2;
m is 0, 1, 2, 3, or 4;
n is 0, 1, 2, 3, or 4; and
p is 0, 1, or 2.

In a class of this embodiment, R$^2$ is phenyl unsubstituted or substituted with one to three groups independently selected from R$^3$. In another class of this embodiment, R$^2$ is phenyl substituted with one to three groups independently selected from R$^3$.

In yet a further embodiment of the compounds of the present invention, there are provided compounds of structural formula Va or Vb of the indicated relative stereochemical configurations having the trans orientation of the phenyl and piperazinecarbonyl substituents:

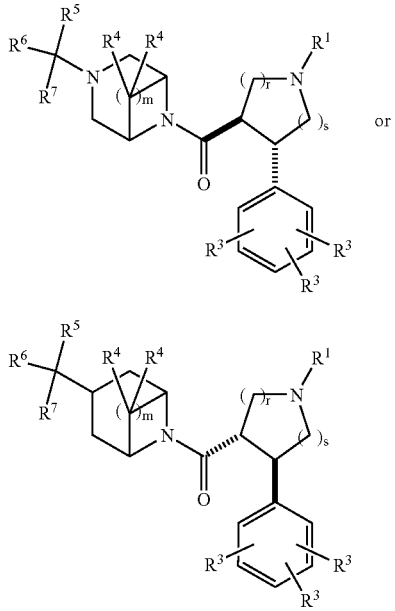

(Va)

(Vb)

or a pharmaceutically acceptable salt thereof;
wherein
$R^1$ is selected from the group consisting of hydrogen, $C_{1-4}$ alkyl, and —$(CH_2)_{0-1}$ phenyl;
each $R^3$ is independently selected from the group consisting of
(1) $C_{1-8}$ alkyl,
(2) $C_{2-8}$ alkenyl,
(3) —$(CH_2)_{0-1}$-phenyl,
(4) —$(CH_2)_{0-1}$-naphthyl,
(5) —$(CH_2)_{0-1}$-heteroaryl,
(6) —$(CH_2)_{0-1}$—$C_{2-7}$ heterocycloalkyl,
(7) —$(CH_2)_{0-1}$—$C_{3-7}$ cycloalkyl,
(8) halogen,
(9) $OR^9$,
(10) —$(CH_2)_{0-1}$—$C(O)R^9$,
(11) —$(CH_2)_{0-1}$—$OC(O)R^9$,
(12) —$(CH_2)_{0-1}$—$C(O)OR^9$,
(13) —$(CH_2)_{0-1}$—$C\equiv N$,
(14) $NO_2$,
(15) —$(CH_2)_{0-1}$—$N(R^9)_2$,
(16) —$(CH_2)_{0-1}$—$C(O)N(R^9)_2$,
(17) —$(CH_2)_{0-1}$—$NR^9C(O)R^9$,
(18) —$(CH_2)_{0-1}$—$NR^9C(O)OR^9$,
(19) —$(CH_2)_{0-1}NR^9C(O)$-heteroaryl,
(20) —$(CH_2)_{0-1}NR^9C(O)N(R^9)_2$,
(21) —$(CH_2)_{0-1}C(O)NR^9N(R^9)_2$,
(22) —$(CH_2)_{0-1}$—$C(O)NR^9NR^9C(O)R^9$,
(23) —$(CH_2)_{0-1}$—$NR^9S(O)_{1-2}R^9$,
(24) —$(CH_2)_{0-1}$—$S(O)_{1-2}N(R^9)_2$,
(25) —$(CH_2)_{0-1}$—$S(O)_{0-2}R^9$,
(26) $O(CH_2)_{0-1}$—$C(O)N(R^9)_2$,
(27) $CF_3$,
(28) $CH_2CF_3$,
(29) $OCF_3$, and
(30) $OCH_2CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;
each $R^4$ is independently selected from the group consisting of
(1) hydrogen,
(2) $C_{1-8}$ alkyl,
(3) —$(CH_2)_{0-1}$—$C_{3-6}$ cycloalkyl,
(4) —$(CH_2)_{0-1}$-aryl,
(5) hydroxy,
(6) halogen, and
(7) amino;
$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_{0-1}$—$C_{3-7}$ cycloalkyl,
(7) —$(CH_2)_{0-1}$—$C_{2-7}$ heterocycloalkyl,
(8) —$(CH_2)_{0-1}$-phenyl,
(9) —$(CH_2)_{0-1}$-naphthyl,
(10) —$(CH_2)_{0-1}$-heteroaryl, and
(11) —$(CH_2)_{0-1}$—$C_{3-7}$ bicycloalkyl, wherein phenyl, naphthyl, and heteroaryl are unsubstituted or substituted with one to three groups independently selected from $R^3$, and alkyl, alkenyl, alkynyl, alkoxy, cycloalky, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;
$R^6$ is selected from the group consisting of
(1) hydrogen, and
(2) $C_{1-8}$ alkyl;
$R^7$ is selected from the group consisting of
(1) —$(CH_2)_{0-3}$—$N(R^8)_2$,
(2) —$(CH_2)_{0-3}$—$NR^8C(O)R^8$,
(3) —$(CH_2)_{0-3}$—$NR^8C(O)OR^8$,
(4) —$(CH_2)_{0-3}$—$NR^8C(O)N(R^8)_2$,
(5) —$(CH_2)_{0-3}$—$NR^8S(O)R^8$,
(6) —$(CH_2)_{0-3}$—$NR^8S(O)_2R^8$, and
(7) —$(CH_2)_{0-3}$—$NR^8S(O)_2N(R^8)_2$, wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;
each $R^8$ is independently selected from the group consisting of
(1) hydrogen,
(2) $C_{1-8}$ alkyl,
(3) $C_{2-8}$ alkenyl,
(4) —$(CH_2)_{0-1}$—$C_{3-7}$ cycloalkyl,
(5) —$(CH_2)_{0-1}$—$C_{2-7}$ heterocycloalkyl, (6) —(CH$_2$)$_{0-1}$—C$_{3-7}$ bicycloalkyl,
(7) —(CH$_2$)$_{0-1}$-phenyl,
(8) —(CH$_2$)$_{0-1}$-naphthyl, and
(9) —(CH$_2$)$_{0-1}$-heteroaryl, wherein alkyl, alkenyl, cycloalkyl, heterocycloalkyl, and bicycloalkyl are unsubstituted or substituted with one to three groups independently selected from R$^3$ and oxo, and wherein phenyl, naphthyl, and heteroaryl are unsubstituted or substituted with one to three groups independently selected from R$^3$, and wherein any methylene (CH$_2$) in R$^8$ is unsubstituted or substituted with one to two groups independently selected from halogen, hydroxy, and C$_{1-4}$ alkyl, or two R$^8$ groups together with the atom to which they are attached form a 5- to 8-membered mono- or bicyclic ring system optionally containing an additional heteroatom selected from O, S, and —NC$_{1-4}$ alkyl;

each R$^9$ is independently selected from the group consisting of
(1) hydrogen,
(2) C$_{1-8}$ alkyl,
(3) phenyl,
(4) heteroaryl,
(5) —(CH$_2$)$_{0-1}$ heterocycloalkyl, and
(6) C$_{3-6}$ cycloalkyl, wherein alkyl, phenyl, heteroaryl, heterocycloalkyl, and cycloalkyl are unsubstituted or substituted with one to three groups independently selected from halogen, C$_{1-4}$ alkyl, hydroxy, and C$_{1-4}$ alkoxy, or two R$^9$ groups together with the atom to which they are attached form a 4- to 8-membered mono- or bicyclic ring system optionally containing an additional heteroatom selected from O, S, and —NC$_{1-4}$ alkyl;

r is 1 or 2;
s is 0, 1 or 2; and
m is 0, 1, 2, 3 or 4.

In yet a further embodiment of the compounds of the present invention, there are provided compounds of structural formula VI:

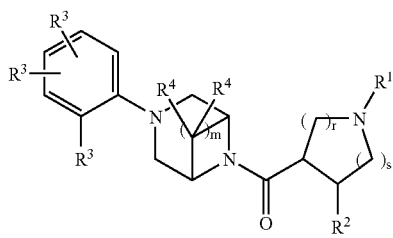

VI or a pharmaceutically acceptable salt thereof;
wherein
R$^1$ is selected from the group consisting of
(1) hydrogen,
(2) amidino,
(3) C$_{1-4}$ alkyliminoyl,
(4) C$_{1-10}$ alkyl,
(5) —(CH$_2$)$_n$—C$_{1-4}$ cycloalkyl,
(6) —(CH$_2$)$_n$-phenyl,
(7) —(CH$_2$)$_n$-naphthyl, and
(8) —(CH$_2$)$_n$-heteroaryl, wherein phenyl, naphthyl, and heteroaryl are unsubstituted or substituted with one to three groups independently selected from R$^3$, and alkyl and cycloalkyl are unsustituted or substituted with one to three groups independently selected from R$^3$ and oxo;

R$^2$ is selected from the group consisting of
(1) phenyl,
(2) naphthyl, and
(3) heteroaryl, wherein phenyl, naphthyl, and heteroaryl are unsubstituted or substituted with one to three groups independently selected from R$^3$;

each R$^3$ is independently selected from the group consisting of
(1) C$_{1-8}$ alkyl,
(2) C$_{2-8}$ alkenyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$—C$_{2-7}$ heterocycloalkyl,
(7) —(CH$_2$)$_n$—C$_{3-7}$ cycloalkyl,
(8) halogen,
(9) OR$^9$,
(10) —(CH$_2$)$_n$—C(O)R$^9$,
(11) —(CH$_2$)$_n$—OC(O)R$^9$,
(12) —(CH$_2$)$_n$—C(O)OR$^9$,
(13) —(CH$_2$)$_n$—C≡N,
(14) NO$_2$,
(15) —(CH$_2$)$_n$N(R$^9$)$_2$,
(16) —(CH$_2$)$_n$C(O)N(R$^9$)$_2$,
(17) —(CH$_2$)$_n$NR$^9$C(O)R$^9$,
(18) —(CH$_2$)$_n$NR$^9$C(O)OR$^9$,
(19) —(CH$_2$)$_n$NR$^9$C(O)-heteroaryl,
(20) —(CH$_2$)$_n$NR$^9$C(O)N(R$^9$)$_2$,
(21) —(CH$_2$)$_n$C(O)NR$^9$N(R$^9$)$_2$,
(22) —(CH$_2$)$_n$C(O)NR$^9$NR$^9$C(O)R$^9$,
(23) —(CH$_2$)$_n$NR$^9$S(O)$_p$R$^9$,
(24) —(CH$_2$)$_n$S(O)$_p$N(R$^9$)$_2$,
(25) —(CH$_2$)$_n$S(O)$_p$R$^9$,
(26) O(CH$_2$)$_n$C(O)N(R$^9$)$_2$,
(27) CF$_3$,
(28) CH$_2$CF$_3$,
(29) OCF$_3$, and
(30) OCH$_2$CF$_3$, wherein alkenyl, phenyl, naphthyl, heteroaryl are unsubstituted or substituted with one to three substituents independently selected from halogen, hydroxy, C$_{1-4}$ alkyl, trifluoromethyl, and C$_{1-4}$ alkoxy, and wherein any alkyl, cycloalkyl, heterocycloalkyl, and methylene (CH$_2$) carbon atom in R$^3$ is unsubstituted or substituted with one to two groups independently selected from halogen, hydroxy, oxo, C$_{1-4}$ alkyl, trifluoromethyl, and C$_{1-4}$ alkoxy, or two R$^3$ substituents on the same carbon atom are taken together with the carbon atom to form a cyclopropyl group;

each R$^4$ is independently selected from the group consisting of
(1) hydrogen,
(2) C$_{1-8}$ alkyl,
(3) —(CH$_2$)$_n$C$_{3-6}$ cycloalkyl,
(4) —(CH$_2$)$_n$-aryl,
(5) hydroxy,
(6) halogen, and
(7) amino;

each R$^9$ is independently selected from the group consisting of
(1) hydrogen,
(2) C$_{1-8}$ alkyl,
(3) phenyl, (4) heteroaryl,
(5) —(CH$_2$)$_n$ heterocycloalkyl, and
(6) C$_{3-6}$ cycloalkyl, wherein alkyl, phenyl, heteroaryl, heterocycloalkyl, and cycloalkyl are unsubstituted or substituted with one to three groups independently selected from halogen, C$_{1-4}$ alkyl, hydroxy, and C$_{1-4}$ alkoxy or two R$^9$ groups together with the atom to which they are attached form a 4- to 8-membered mono- or bicyclic ring system optionally containing an additional heteroatom selected from O, S, and —NC$_{1-4}$ alkyl;

r is 1 or 2;
s is 0, 1 or 2;
m is 0, 1, 2, 3 or 4;
n is 0, 1, 2, 3, or 4; and
p is 0, 1, or 2.

In a class of this embodiment, m is 0. In another class of this embodiment m is 1. In another class of this embodiment r is 1 and s is 1. In yet another class of this embodiment, r is 2 and s is 1.

In another class of this embodiment, R$^2$ is phenyl unsubstituted or substituted with one to three groups independently selected from R$^3$. In another class of this embodiment, R$^2$ is phenyl substituted with one to three groups independently selected from R$^3$.

In yet a further embodiment of the compounds of the present invention, there are provided compounds of structural formula VIIa or VIIb of the indicated relative stereochemical configurations having the trans orientation of the phenyl and piperazinecarbonyl substituents:

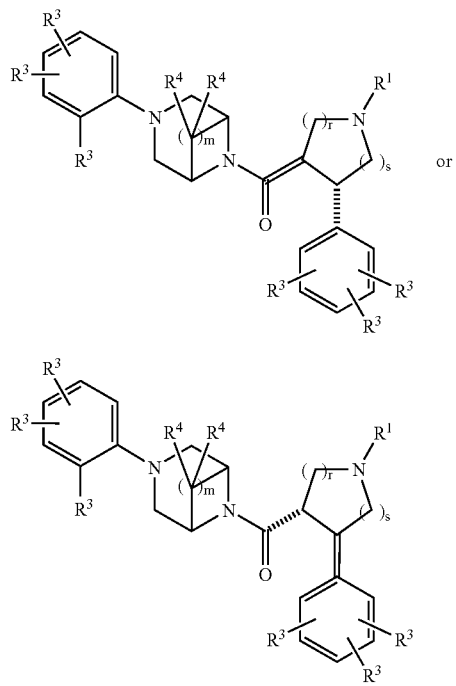

or a pharmaceutically acceptable salt thereof;
wherein
R$^1$ is selected from the group consisting of hydrogen, C$_{1-4}$ alkyl, and —(CH$_2$)$_{0-1}$ phenyl;

each R$^3$ is independently selected from the group consisting of
(1) C$_{1-8}$ alkyl,
(2) C$_{2-8}$ alkenyl,
(3) —(CH$_2$)$_{0-1}$-phenyl,
(4) —(CH$_2$)$_{0-1}$-naphthyl,
(5) —(CH$_2$)$_{0-1}$-heteroaryl,
(6) —(CH$_2$)$_{0-1}$—C$_{2-7}$ heterocycloalkyl,
(7) —(CH$_2$)$_{0-1}$—C$_{3-7}$ cycloalkyl,
(8) halogen,
(9) OR$^9$,
(10) —(CH$_2$)$_{0-1}$—C(O)R$^9$,
(11) —(CH$_2$)$_{0-1}$—OC(O)R$^9$,
(12) —(CH$_2$)$_{0-1}$—C(O)OR$^9$,
(13) —(CH$_2$)$_{0-1}$—C≡N,
(14) NO$_2$,
(15) —(CH$_2$)$_{0-1}$—N(R$^9$)$_2$,
(16) —(CH$_2$)$_{0-1}$—C(O)N(R$^9$)$_2$,
(17) —(CH$_2$)$_{0-1}$—NR$^9$C(O)R$^9$,
(18) —(CH$_2$)$_{0-1}$—NR$^9$C(O)OR$^9$,
(19) —(CH$_2$)$_{0-1}$NR$^9$C(O)-heteroaryl,
(20) —(CH$_2$)$_{0-1}$NR$^9$C(O)N(R$^9$)$_2$,
(21) —(CH$_2$)$_{0-1}$C(O)NR$^9$N(R$^9$)$_2$,
(22) —(CH$_2$)$_{0-1}$—C(O)NR$^9$NR$^9$C(O)R$^9$,
(23) —(CH$_2$)$_{0-1}$—NR$^9$S(O)$_{1-2}$R$^9$,
(24) —(CH$_2$)$_{0-1}$—S(O)$_{1-2}$N(R$^9$)$_2$,
(25) —(CH$_2$)$_{0-1}$—S(O)$_{0-2}$R$^9$,
(26) O(CH$_2$)$_{0-1}$—C(O)N(R$^9$)$_2$,
(27) CF$_3$,
(28) CH$_2$CF$_3$,
(29) OCF$_3$, and
(30) OCH$_2$CF$_3$, wherein alkenyl, phenyl, naphthyl, heteroaryl are unsubstituted or substituted with one to three substituents independently selected from halogen, hydroxy, C$_{1-4}$ alkyl, trifluoromethyl, and C$_{1-4}$ alkoxy, and wherein any alkyl, cycloalkyl, heterocycloalkyl, and methylene (CH$_2$) carbon atom in R$^3$ is unsubstituted or substituted with one to two groups independently selected from halogen, hydroxy, oxo, C$_{1-4}$ alkyl, trifluoromethyl, and C$_{1-4}$ alkoxy, or two R$^3$ substituents on the same carbon atom are taken together with the carbon atom to form a cyclopropyl group;

each R$^4$ is independently selected from the group consisting of
(1) hydrogen,
(2) C$_{1-8}$ alkyl,
(3) —(CH$_2$)$_{0-1}$—C$_{3-6}$ cycloalkyl,
(4) —(CH$_2$)$_{0-1}$-aryl,
(5) hydroxy,
(6) halogen, and
(7) amino;

each R$^9$ is independently selected from the group consisting of
(1) hydrogen,
(2) C$_{1-8}$ alkyl,
(3) phenyl,
(4) heteroaryl,
(5) —(CH$_2$)$_{0-1}$ heterocycloalkyl, and
(6) C$_{3-6}$ cycloalkyl, wherein alkyl, phenyl, heteroaryl, heterocycloalkyl, and cycloalkyl are unsubstituted or substituted with one to three groups independently selected from halogen, C$_{1-4}$ alkyl, hydroxy, and C$_{1-4}$ alkoxy, or two R$^9$ groups together with the atom to which they are attached form a 4- to 8-membered mono- or bicyclic ring system optionally containing an additional heteroatom selected from O, S, and —NC$_{1-4}$ alkyl;

r is 1 or 2;
s is 0, 1 or 2; and
m is 0, 1, 2, 3 or 4.

In a class of this embodiment, m is 0. In another class of this embodiment m is 1. In another class of this embodiment r is 1 and s is 1. In yet another class of this embodiment, r is 2 and s is 1.

Illustrative but nonlimiting examples of compounds of the present invention that are useful as melanocortin-4 receptor agonists are the following:

-continued

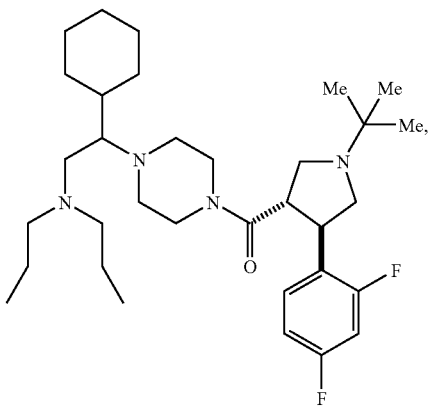

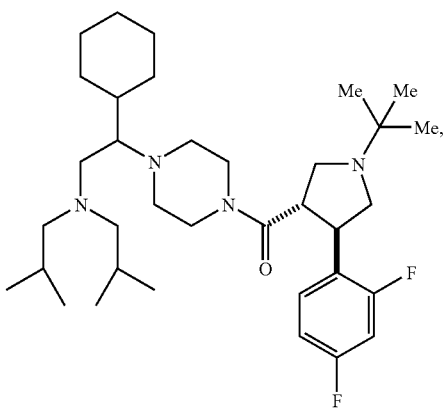

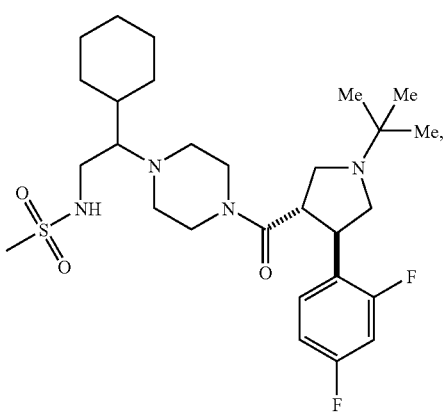

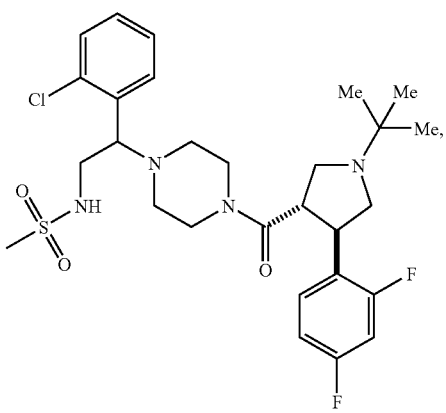

-continued
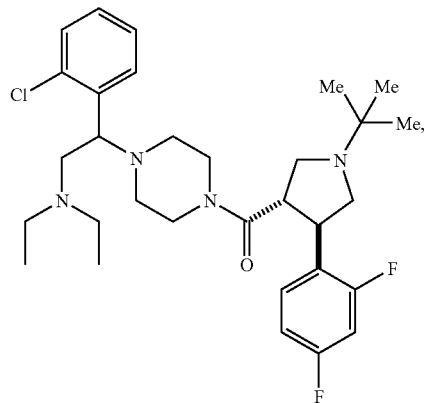
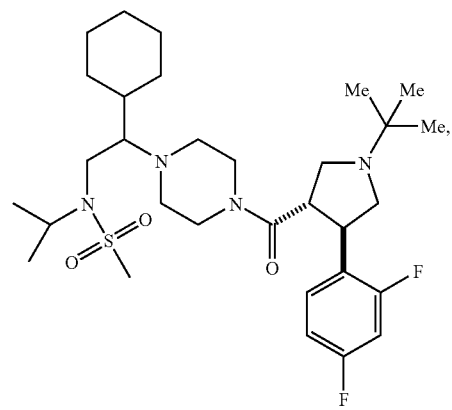
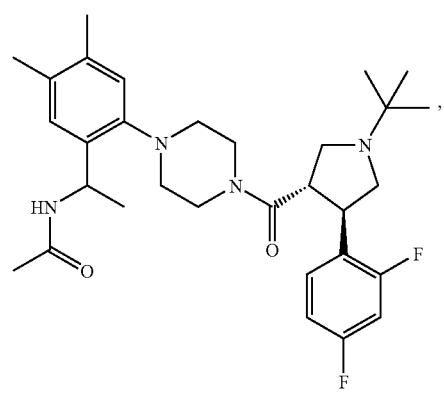
-continued
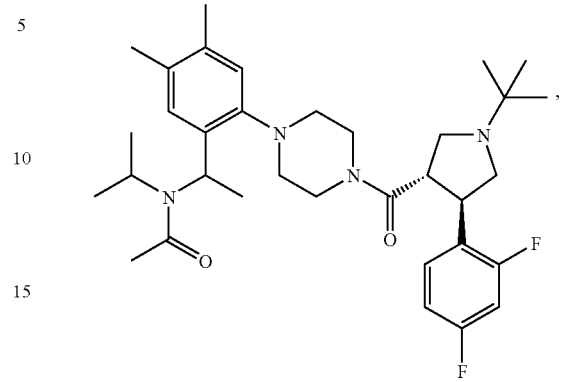
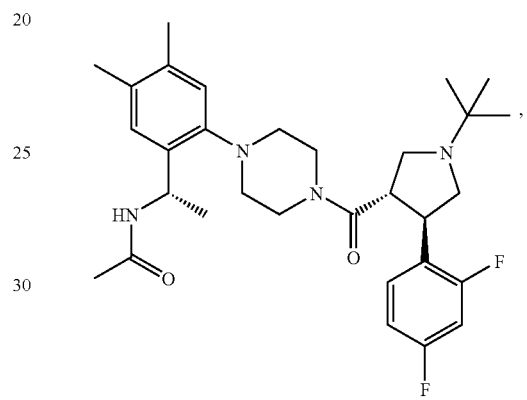
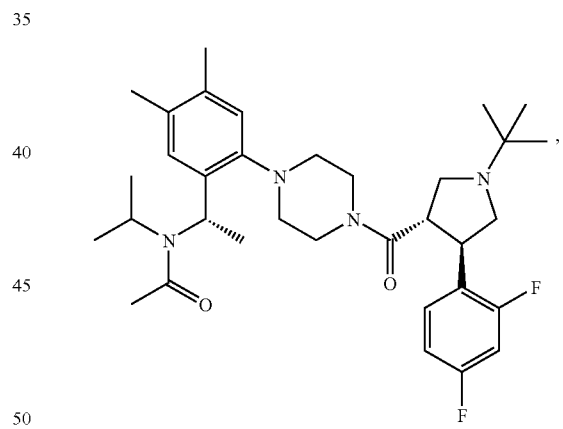
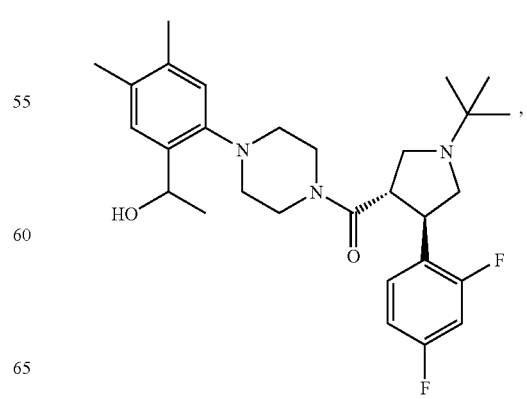

-continued
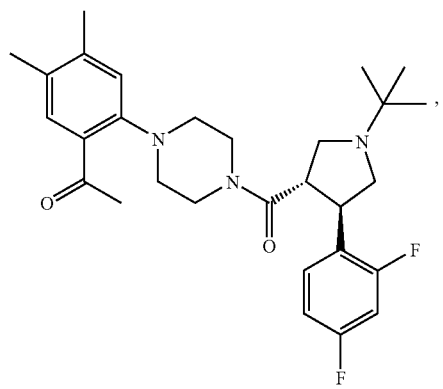
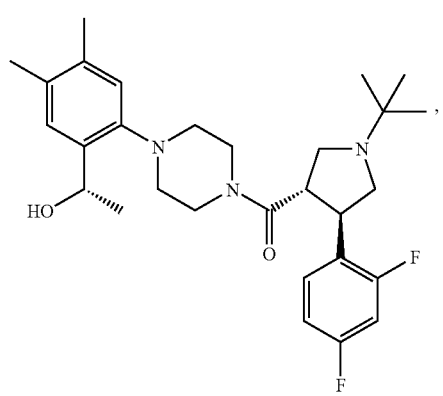
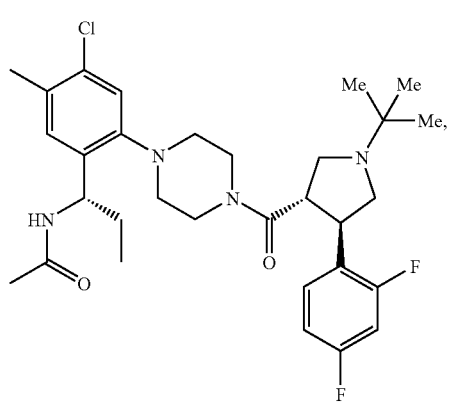
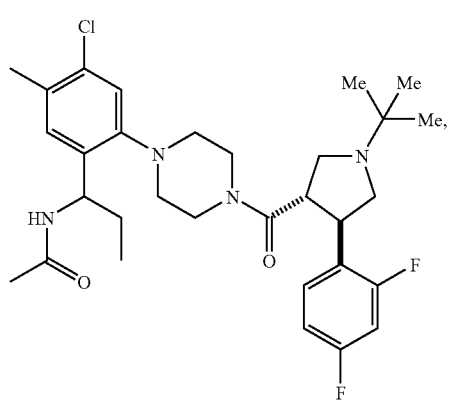
-continued
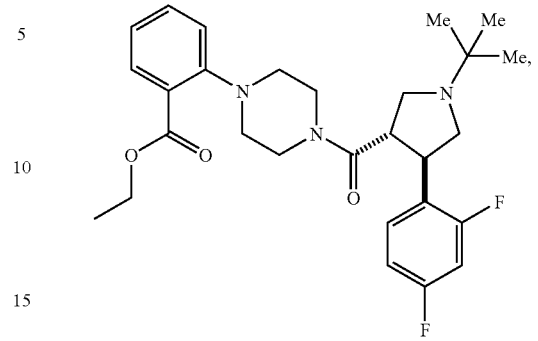
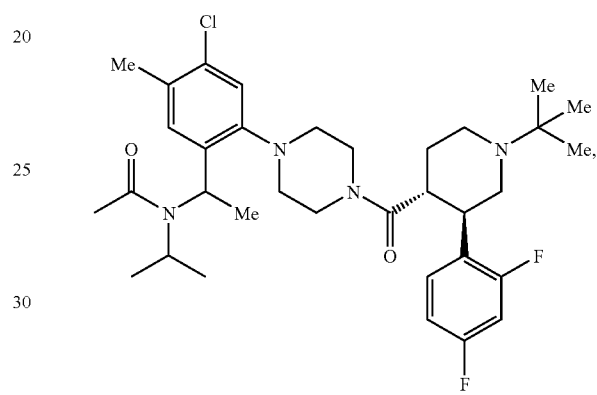
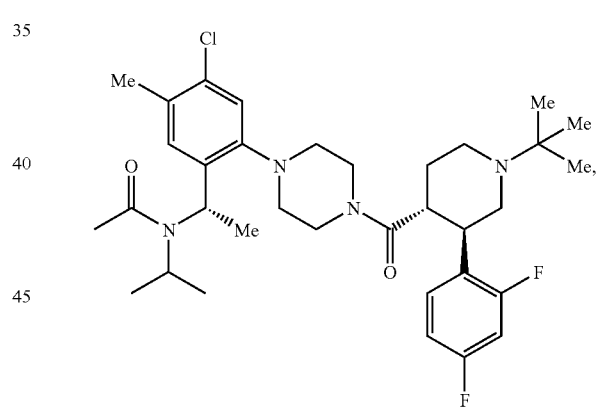
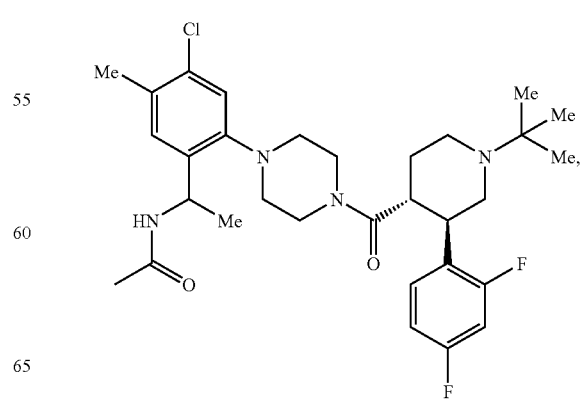

-continued
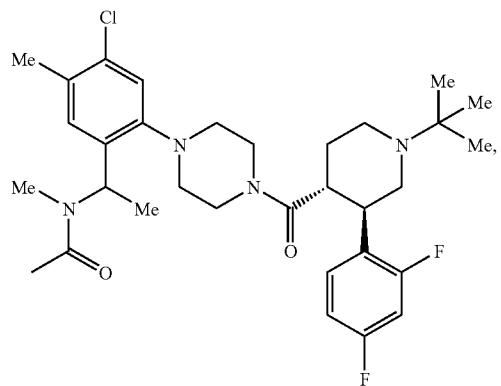
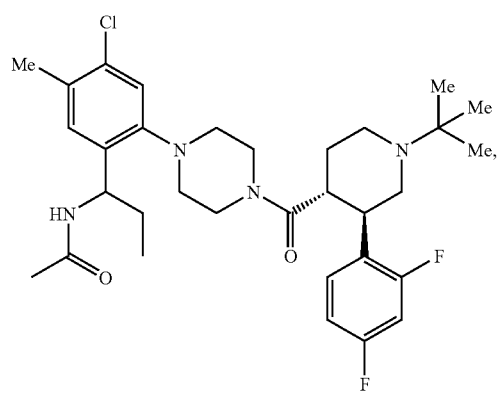
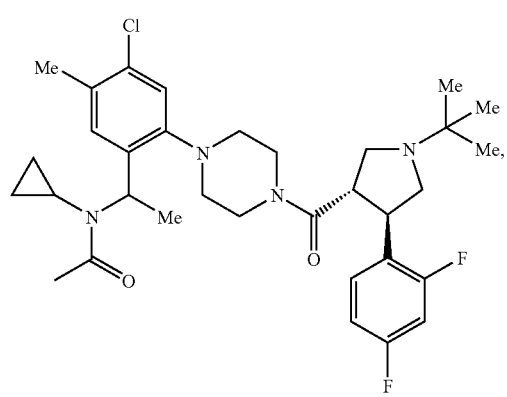
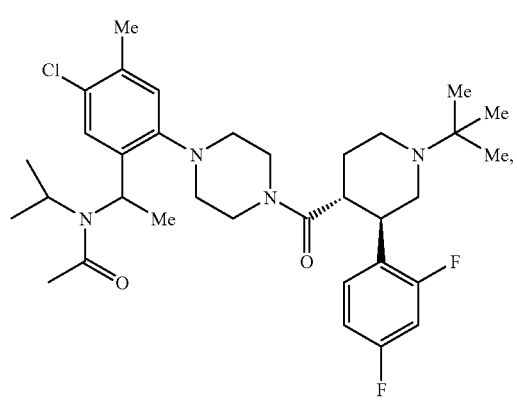
-continued
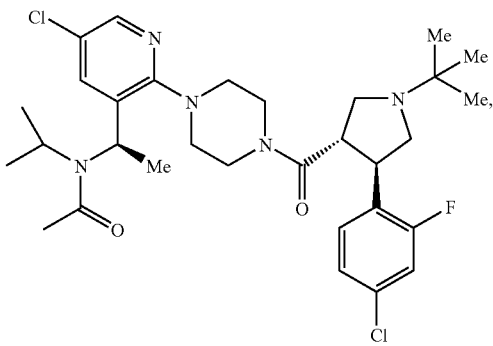
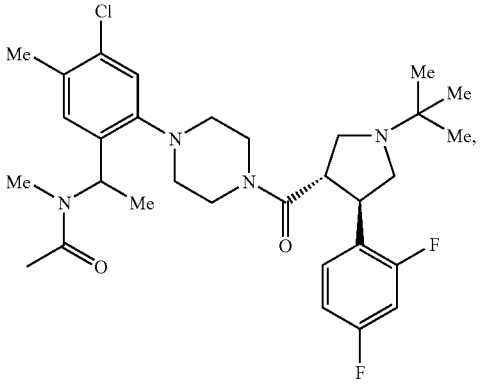
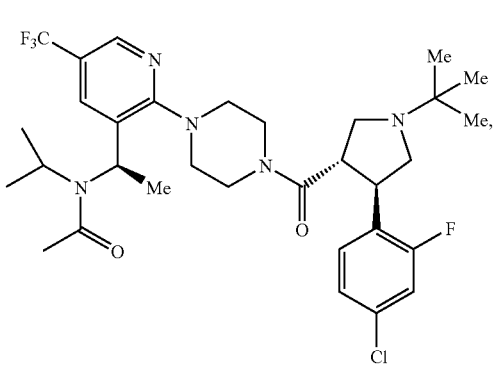
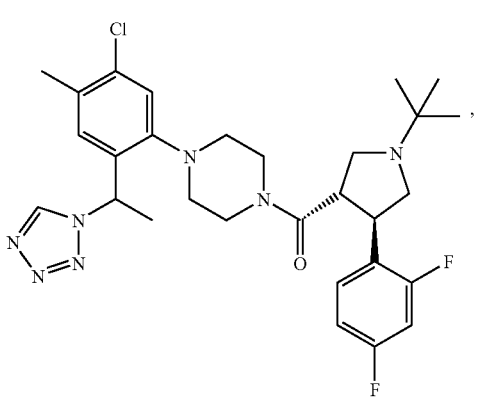

-continued
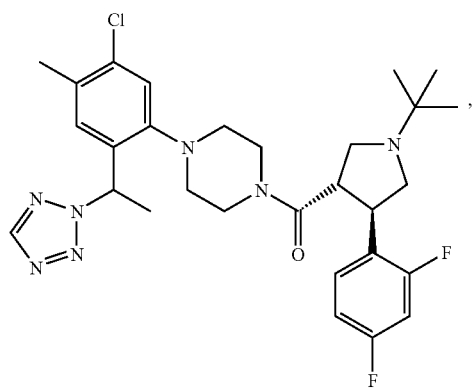
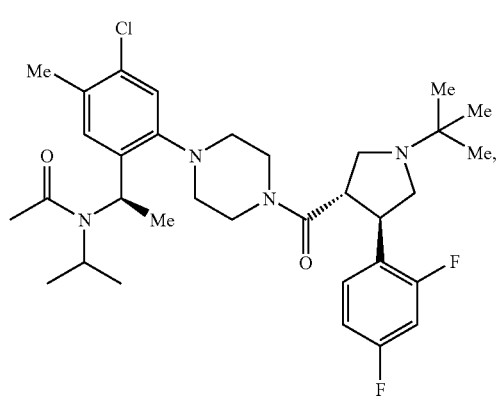
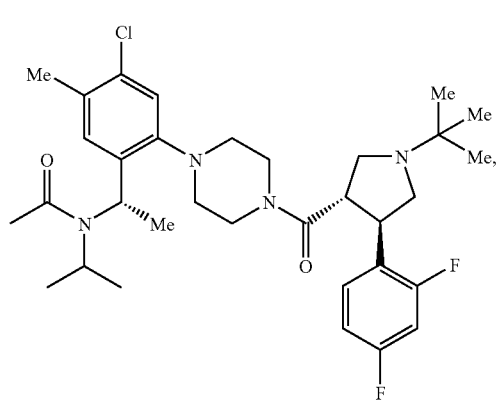
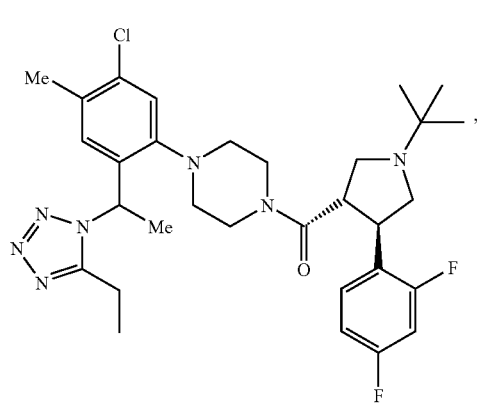
-continued
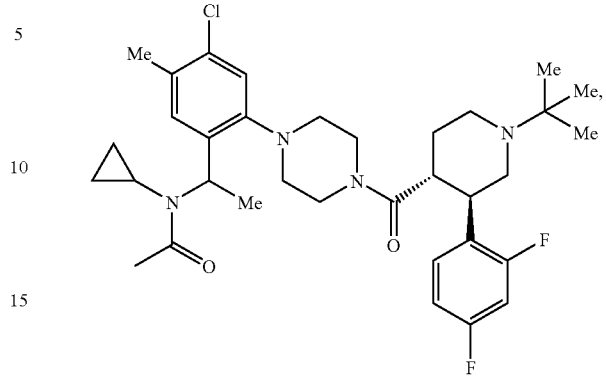
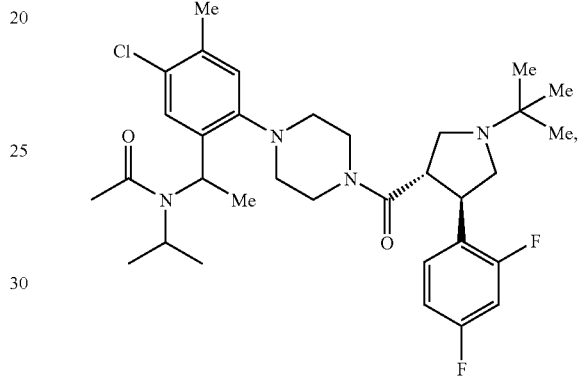
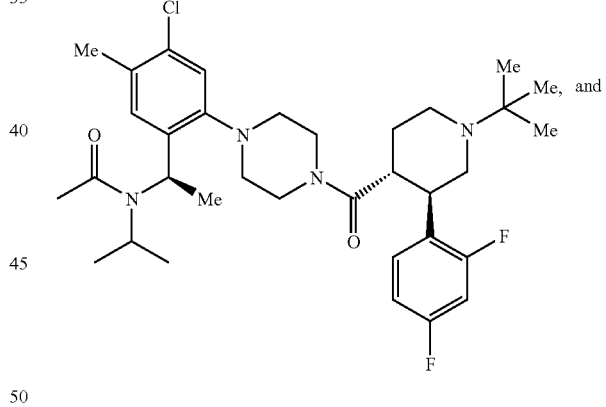
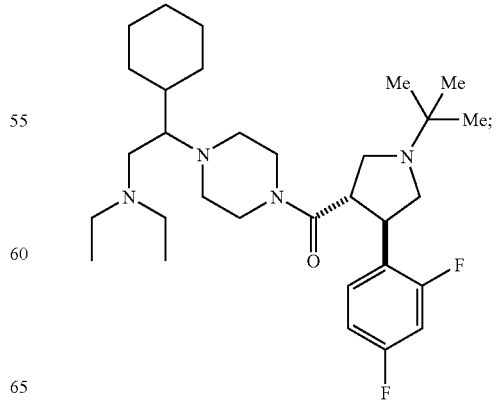

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal in need thereof which comprises administering to said mammal a therapeutically or prophylactically effective amount of a compound of structural formula I.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I in combination with a therapeutically effective amount of another agent known to be useful for the treatment of these conditions.

Yet another aspect of the present invention provides a method for the treatment or prevention of obesity which comprises administering to a mammal in need of such treatment or prevention a therapeutically or prophylactically effective amount of a compound of structural formula I in combination with a therapeutically effective amount of another agent known to be useful for the treatment of this condition.

Yet another aspect of the present invention relates to the use of a compound of formula I for the manufacture of a medicament useful for the treatment or prevention, or suppression of a disease mediated by the melanocortin-4 receptor in a mammal in need thereof.

Yet another aspect of the present invention relates to the use of a compound of formula I for the manufacture of a medicament useful for the treatment or prevention, or suppression of a disease mediated by the melanocortin-4 receptor, wherein the disease is selected from the group consisting of obesity, diabetes, male sexual dysfunction and female sexual dysfunction in a mammal in need thereof.

Yet another aspect of the present invention relates to the use of a compound of formula I for the manufacture of a medicament useful for the treatment or prevention, or suppression of male erectile dysfunction in a mammal in need thereof.

Yet another aspect of the present invention relates to the use of a therapeutically effective amount of a compound of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, and a ghrelin receptor antagonist, or a pharmaceutically acceptable salt thereof, for the manufacture of a medicament useful for the treatment, control, or prevention of diabetes or obesity in a mammal in need of such treatment.

Yet another aspect of the present invention relates to the use of a therapeutically effective amount of a compound of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, and a ghrelin receptor antagonist, and pharmaceutically acceptable salts and esters thereof, for the manufacture of a medicament for treatment or prevention of diabetes or obesity which comprises an effective amount of a compound of formula I and an effective amount of the agent, together or separately.

Yet another aspect of the present invention relates to the use of a therapeutically effective amount of a compound of formula I, or a pharmaceutically acceptable salt thereof, and a therapeutically effective amount of an agent selected from the group consisting of: a type V cyclic-GMP-selective phosphodiesterase inhibitor, an $\alpha_2$-adrenergic receptor antagonist, and a dopaminergic agent, or a pharmaceutically acceptable salt thereof, for the manufacture of a medicament useful for the treatment, control, or prevention of erectile dysfunction in a mammal in need of such treatment.

Yet another aspect of the present invention relates to the use of a therapeutically effective amount of a compound of formula I, and pharmaceutically acceptable salts and esters thereof; and a therapeutically effective amount of an agent selected from the group consisting of a type V cyclic-GMP-selective phosphodiesterase inhibitor, an $\alpha_2$-adrenergic receptor antagonist, and a dopaminergic agent, and pharmaceutically acceptable salts and esters thereof; for the manufacture of a medicament for treatment or prevention of erectile dysfunction which comprises an effective amount of a compound of formula I and an effective amount of the agent, together or separately.

Melanocortin receptor agonist compounds can be provided in kit. Such a kit typically contains an active compound in dosage forms for administration. A dosage form contains a sufficient amount of active compound such that a beneficial effect can be obtained when administered to a subject during regular intervals, such as 1 to 6 times a day, during the course of 1 or more days. Preferably, a kit contains instructions indicating the use of the dosage form for weight reduction (e.g., to treat obesity or overweight) or sexual dysfunction, and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "halogen" includes fluorine, chlorine, bromine and iodine.

The term "$C_{1-4}$ alkyliminoyl" means $C_{1-3}C(=NH)-$.

The term "aryl" includes mono- or bicyclic aromatic rings containing only carbon atoms. Examples of aryl include phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" is intended to include non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs.

The term "mammal in need thereof" refers to a mammal who is in need of treatment or prophylaxis as determined by a researcher, veterinarian, medical doctor or other clinician.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers-Diastereomers-Geometric Isomers-Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I. For example, compound VIII

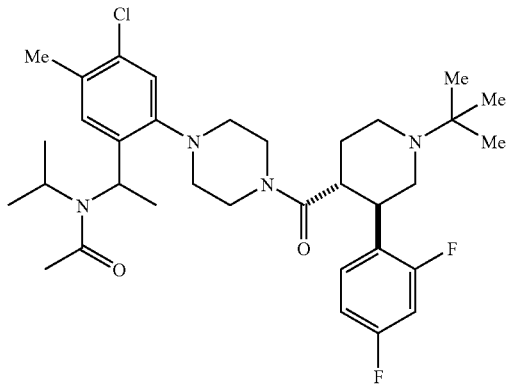

corresponds to the diastereomers VIIIa and VIIIb:

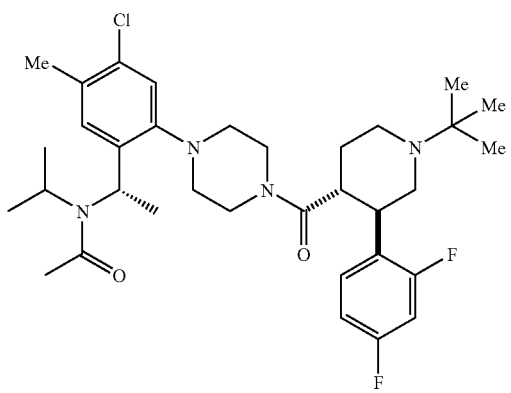

and

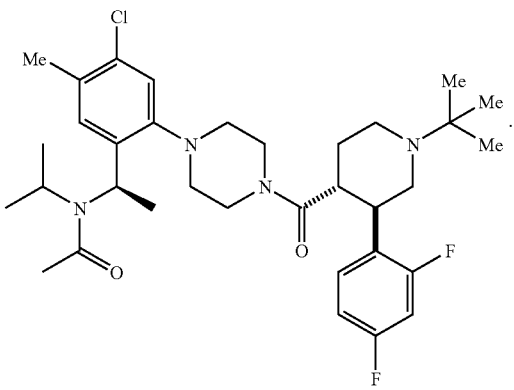

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formulae I, IIa, IIb, IIIa, IIIb, IV, Va, Vb, VI, VIIa, and VIIb may be obtained by stereospecific synthesis using optically pure starting materials or reagents of known absolute configuration.

Salts

It will be understood that the compounds of formula I include crystalline, hydrated crystalline, and amorphous forms of the compounds of formula I and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts, trifluoroacetic acid salts and phosphate salts. It will also be understood that references to pharmaceutically acceptable salts are meant to include multiple salt forms in addition to the mono salt form, such as the bis salt form, the tri salt form, the quaternary salt form, or any other pharmaceutically acceptable salt form and equilibrium mixtures of thereof. For example, the phosphoric acid salt, or the phosphate salt, of the compounds of formula I may be understood to mean the mono phosphate salt and the bis phosphate salt of the compounds of formula I.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity, diabetes mellitus, hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction, fever, inflammation, immunomodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor (MC-4R) relative to MC-1R, MC-2R, MC-3R, and MC-5R, which makes them especially useful in the prevention and treatment of obesity, as well as male and/or female sexual dysfunction, including erectile dysfunction.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356–359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholestrol, non-HDL cholesterol, triglyceride, HDL cholesterol or other lipid analyte profiles.

Prevention of diabetes mellitus refers to the administration of a compound or combination of the present invention to prevent the onset of diabetes in a mammal at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asia-Pacific, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male mammal in need thereof. One outcome of treatment may be a decrease in impotence. Another outcome of treatment may be an increase in libido. Yet another outcome of treatment may be a decrese in the magnitude or frequency of erectile dysfunction.

Treatment of male sexual dysfunction refers to the administration of a compound or combination of the present invention to treat one or more of the symptoms of male sexual dysfunction in a male mammal in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm.

Prevention of male sexual dysfunction and male erectile dysfunction refers to the administration of the compounds or combinations of the present invention to prevent the symptoms of sexual dysfunction and erectile dysfunction in a male mammal at risk thereof.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Male and Female Sexual Dysfunction

The terms "administration of" and or "administering" a compound should be understood to mean providing a compound of the invention or a prodrug of a compound of the invention to a subject in need of treatment.

The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art.

The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder.

The therapeutically or prophylactically effective amount, or dosage, of an individual compound is determined, in the final analysis, by the physician in charge of the case, but depends on factors such as the exact disease to be treated, the severity of the disease and other diseases or conditions from which the subject suffers, the chosen route of administration, other drugs and treatments which the subject may concomitantly require, and other factors in the physician's judgement.

Administration and Dose Ranges

Any suitable route of administration may be employed for providing a mammal, especially a human with an effective amount, or dosage, of a compound of the present invention. For example, oral, rectal, topical, parenteral, ocular, pulmonary, nasal routes of administration, and the like may be employed. Dosage forms include tablets, troches, dispersions, suspensions, solutions, capsules, creams, ointments, aerosols, and the like. Preferably compounds of Formula I are administered orally or topically.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response. It may be necessary to use dosages outside these limits in some cases.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response. It may be necessary to use dosages outside these limits in some cases.

For the treatment of sexual dysfunction compounds of the present invention are given in a dose range of 0.001 milligram to about 100 milligram per kilogram of body weight, preferably as a single dose orally or as a nasal spray.

In the case where an oral composition is employed, a suitable dosage range is, e.g. from about 0.01 mg to about 1500 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 350, 500, 750, 1000, 1250 or 1500 milligrams of the active ingredient for the symptomatic adjustment of the dosage to the subject to be treated.

For use where a composition for intranasal administration is employed, intranasal formulations for intranasal administration comprising 0.001–10% by weight solutions or suspensions of the compounds of Formula I in an acceptable intranasal formulation may be used.

For use where a composition for intravenous administration is employed, a suitable dosage range is from about 0.001 mg to about 100 mg (preferably from 0.01 mg to about 50 mg, more preferably 0.1 mg to 10 mg) of a compound of Formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001–1% by weight solutions or suspensions of the compounds of Formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual subject. Such dosage may be ascertained readily by a person skilled in the art.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like), and compounds disclosed in WO97/10813, 97/27857, 97/28115, 97/28137, and 97/27847; (ii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73–7) (insulintropin); and GLP-1 (7–36)-$NH_2$);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) antioxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO97/28149; and (h) anti-obesity agents, such as (1) growth hormone secretagogues, growth hormone secretagogue receptor agonists/antagonists, such as NN703, hexarelin, MK-0677, SM-130686, CP-424,391, L-692,429 and L-163,255, and such as those disclosed in U.S. Pat. Nos. 5,536,716, and 6,358,951, U.S. patent application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), and SR-147778 (Sanofi Synthelabo), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, and EPO Application No. EP-658546; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,140,354, 6,191,160, 6,313,298, 6,337,332, 6,329,395, 6,326,375, 6,335,345, and 6,340,683, European Patent Nos. EP-01010691, and EP-01044970, and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/06245, WO 02/04433, and WO 02/51809, and Japanese Patent Application No. JP 13226269; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II or those described in WO 99/64002 and WO 00/74679; (15) other Mc4r (melanocortin 4 receptor) agonists, such as CHIR86036 (Chiron), ME-10142, and ME-10145 (Melacure), and those disclosed in PCT Application Nos. WO 01/991752, WO 01/74844, WO 02/12166, WO 02/11715, and WO 02/12178; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR146131, and those discribed in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349–55 (2000)), piperidine-containing histamine H3-receptor antagonists (Lazewska, D. et al., Pharmazie, 56:927–32 (2001), benzophenone derivatives and related compounds (Sasse, A. et al., Arch. Pharm. (Weinheim) 334:45–52 (2001)), substituted N-phenylcarbamates (Reidemeister, S. et al., Pharmazie, 55:83–6 (2000)), and proxifan derivatives (Sasse, A. et al., J. Med. Chem. 43:3335–43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors;

(28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists; (33) CNTF (Ciliary neurotrophic factors), such as GI-181771 (GlaxoSmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as those disclosed in PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202–9 (2001); (44) fatty acid transporter inhibitors; (45) dicarboxylate transporter inhibitors; (46) glucose transporter inhibitors; (47) phosphate transporter inhibitors; (48) Metformin (Glucophage®); (49) Topiramate (Topimax®); (50) peptide YY, PYY 3–36, peptide YY analogs, and PYY agonists such as those disclosed in WO 03/026591, WO 03/057235, and WO 03/027637; and (51) cyclo-oxygenase-2 inhibitors such as rofecoxib, celecoxib, and arcoxia.

Examples of other anti-obesity agents that can be employed in combination with a compound of Formula I are disclosed in "Patent focus on new anti-obesity agents," *Exp. Opin. Ther. Patents*, 10: 819–831 (2000); "Novel anti-obesity drugs," *Exp. Opin. Invest. Drugs*, 9: 1317–1326 (2000); and "Recent advances in feeding suppressing agents: potential therapeutic strategy for the treatment of obesity, *Exp. Opin. Ther. Patents*, 11: 1677–1692 (2001). The role of neuropeptide Y in obesity is discussed in *Exp. Opin. Invest. Drugs*, 9: 1327–1346 (2000). Cannabinoid receptor ligands are discussed in *Exp. Opin. Invest. Drugs*, 9: 1553–1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the MC-4R agonist and the second active ingredient is realized by the subject at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day, is also encompassed herein. A single oral dosage formulation comprised of both a MC-4R agonist and a second active ingredient is preferred. A single dosage formulation will provide convenience for the subject, which is an important consideration especially for subjects with diabetes or obese subjects who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form.

The kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of structural formula I of the present invention can be prepared according to the procedures of the following Schemes and Examples, using appropriate materials and are further exemplified by the following specific examples. Moreover, by utilizing the procedures described in detail in PCT International Application Publications WO 02/068387 (6 Sep. 2002) and WO 002/068387 (6 Sep. 2002), which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention: aq is aqueous; BINAP is 2,2'-bis(diphenylphosphino)-1,1'-binaphthyl; BOC (boc) is t-butyloxycarbonyl; Bu is butyl; calc. or calcd. is calculated; CBZ (Cbz) is benzyloxycarbonyl; $CH_2Cl_2$ is methylene chloride; $CH_3OH$ is methanol; DMAP is dimethylaminopyridine; DIEA is diisopropylethylamine; DMF is N,N-dimethylformamide; DPPA is Diphenylphosphoryl azide; EDC is 1-(3-dimethylaminopropyl)3-ethylcarbodiimide HCl; $Et_3N$ is triethyl amine; ES-MS or ESI-MS is electron spray ion-mass spectroscopy; Et is ethyl; EtOAc is ethyl acetate; h or hr is hour or hours; HATU is O-(7-azabenzotriazol-1-yl)-1,1,3,3-tetramethyluronium hexafluorophosphate; HOAt or HOAT is 1-hydroxy-7-azabenzotriazole; HOBt is 1-hydroxybenzotriazole hydrate; HPLC is high pressure liquid chromatography IPA is isopropyl alcohol; L is liter; LC-MS is liquid chromatography mass spectrum; LiHMDS is lithium hexamethyl disilazide; MC-xR is melanocortin receptor (x being a number); M is molar; Me is methyl; min is minute(s); mL is milliliter; MPLC is medium pressure liquid chromatography; MS is mass spectrum; Ms is Methanesulfonyl; MTBE is methyl tert-butyl ether; N is normal; NaHMDS is sodium hexamethyl disilazide; NaOAc is sodium acetate; Otf or OTf is Trifluoromethanesulfonyl; $Pd(OAc)_2$ is palladium acetate; PG is protecting group; Ph is phenyl; Pr is propyl; PyBrop is bromo-tris-pyrrolidino-phosphonium hexafluorophosphate; r.t. or RT is room temperature; t-bu is tert-butyl; TEA is triethyl amine; TFA is trifluoroacetic acid; THF is tetrahydrofuran; and TLC is thin-layer chromatography.

Reaction Scheme A illustrates the general method employed in the synthesis of the compounds of structural formula I. As shown in reaction Scheme A, the compounds of structural formula (I), denoted by A-3, A-5, and A-7 are derived by coupling a 4-substituted piperazine intermediate of general formula A-1 with either a pyrrolidine acid A-2, piperidine acid A-4, or piperidine acid A-6. The preparation of piperazines of general formula A-1 is provided in general Schemes B, C and D and in the Examples. The preparation of pyrrolidine acid A-2, piperidine acid A-4, and piperidine acid A-6 is provided in Schemes E-1. All substituents in the Schemes are as defined above unless indicated otherwise.

As illustrated in Scheme A, the amide bond coupling reaction of A-1 to form compounds A-3, A-5, and A-7 is conducted in an appropriate inert solvent such as dimethylformamide (DMF), methylene chloride or the like and may be performed with a variety of reagents suitable for amide coupling reactions such as O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC) or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxy-7-azabenzotriazole (HOAt) or 1-hydroxybenzotriazole (HOBt). Alternatively, 4-substituted piperazines of formula A-1 may be treated with an active ester or acid chloride derived from carboxylic acid A-2, A-4, or A-6, which also affords compounds of structural formula A-3, A-5, or A-7. The amide bond coupling shown in reaction Scheme A is usually conducted at temperatures between 0° C. and room temperature, occasionally at elevated temperatures, and the coupling reaction is the synthesis and deprotected under acidic conditions, for instance using trifluoroacetic acid in a solvent like methylene chloride or hydrogen chloride in a solvent such as ethyl acetate at room temperature.

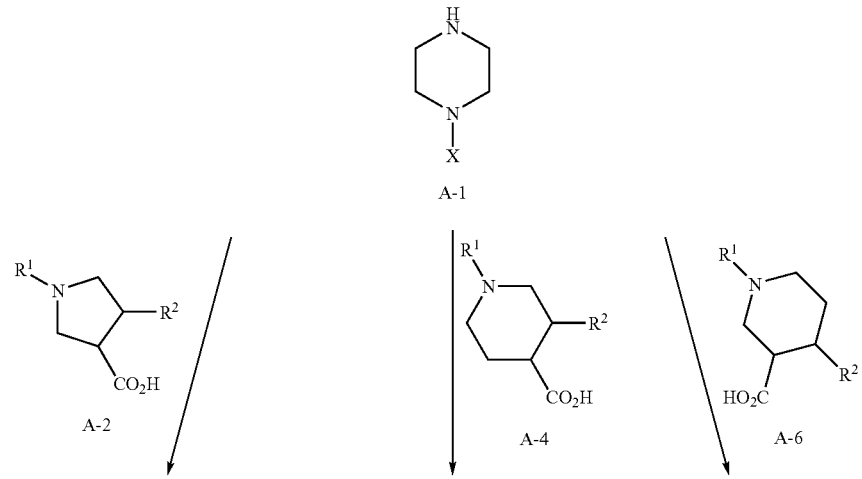

-continued

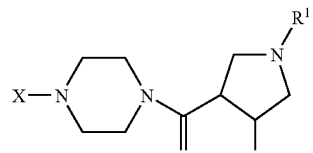
A-3

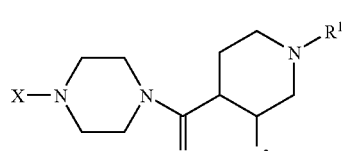
A-5

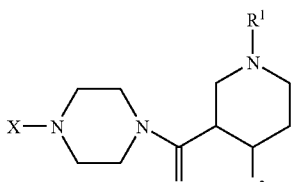
A-7

$X$, $R^1$, and $R^2$ are as defined supra.

The synthesis of compounds of general structural formula A-2, A-4 and A-6 is describe in WO 02/068387 (6 Sep. 2002); WO 02/068388 (6 Sep. 2002), which are incorporated by reference herein in their entirety.

Scheme B illustrates the preparation of piperazines A-1, wherein X is $(CH_2)_0C(R^5)(R^6)(R^7)$, $R^7$ is $(CH_2)_nN(R)^2$, n is 1, and R may be as defined in Scheme B. Aldehyde B-1 is converted to the hydroxy nitro compound B-2 by a nitro aldol reaction. Alkene B-3 is formed by subsequent dehydration of B-2. Compound B-5 is formed by the Michael addition of the Boc piperazine B-4 to compound B-3 in an organic solvent, such as methylene chloride at room temperature. The nitro compound B-5 is reduced to form an alkylated amine B-7, followed by removal of the protecting group PG to give piperazine B-8, which corresponds to a compound of general formula A-1.

Scheme B

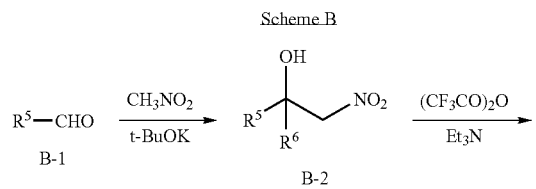

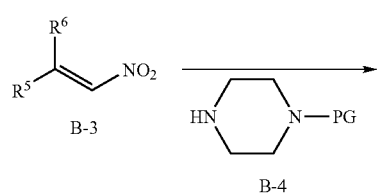

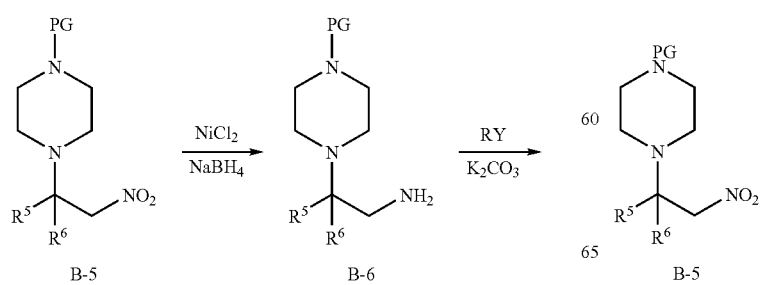

-continued

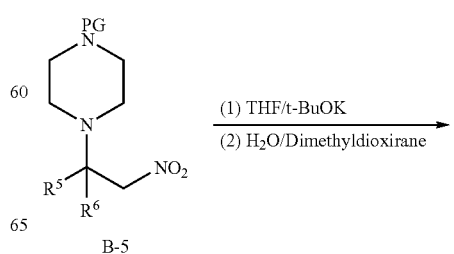

$R^1$, $R^2$, $R^5$, $R^6$, $R^8$ and n are as defined supra; Y is halogen. R may be selected from $R^8$, —C(O)$R^8$, —C(O)O$R^8$, —C(O)N($R^8$)$_2$, —S(O)$R^8$, S(O)$_2R^8$ and —S(O)$_2$N($R^8$)$_2$; and PG is an amine protecting group, such as Boc or CBZ.

Scheme C illustrates the preparation of piperazines of formula A-1, wherein X is $(CH_2)_0C(R^5)(R^6)(R^7)$, $R^7$ is $(CH_2)_nNH_2$, and n is 2. As shown in Scheme C, nitropiperazine B-5 may be converted to aldehyde C-2, which can undergo a Horner Emmons reaction to form alkene C-3. The double bond of the alkene may be reduced by hydrogenation in the presence of a hydrogenation catalyst, such as palladium/carbon, to give alkane C-4. The ester of alkane C-4 may be hydrolyzed to the corresponding acid C-5, which may be subsequently treated with DPPA to form the CBZ protected amine C-6. The CBZ group may be removed under standard conditions known to one skilled in the art to give free amine C-7. The protecting group PG of compound C-7 may be removed to give compound C-8, which corresponds to a compound of formula A-1. Alternatively, the amine of compound C-7 may be substituted, as shown in Scheme B, followed by protecting group removal, to give a compound of formula A-1 wherein X is $(CH_2)_0C(R^5)(R^6)(R^7)$, $R^7$ is $(CH_2)_nN(R)_2$, n is 2 and R may be as defined in Scheme B.

Scheme C

(1) THF/t-BuOK
(2) H$_2$O/Dimethyldioxirane

-continued

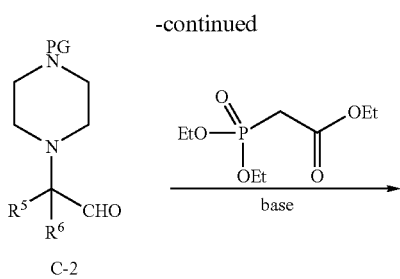
C-2

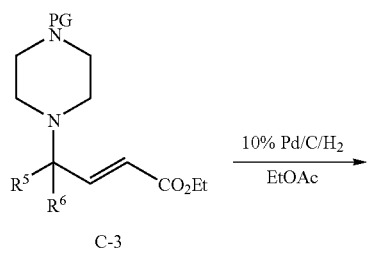
C-3

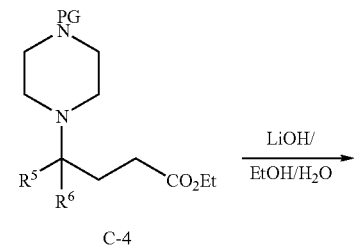
C-4

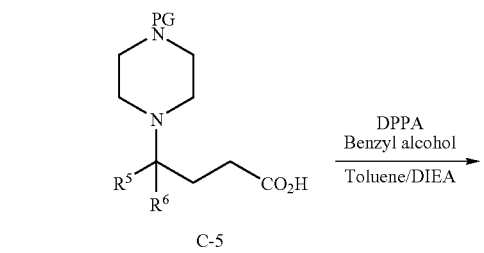
C-5

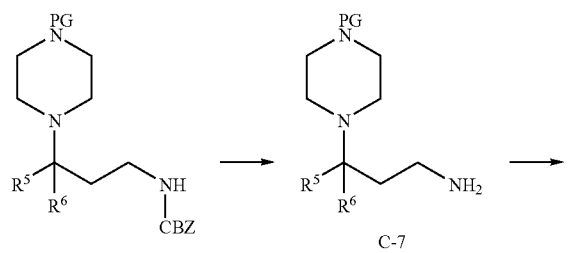
C-6    C-7

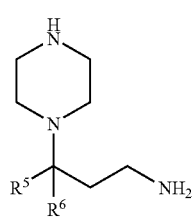
C-8

$R^5$ and $R^6$ are as defined supra; PG is a protecting group such as Boc or CBZ.

Scheme D illustrates the preparation of piperazines of formula A-1, wherein X is $(CH_2)_0C(R^5)(R^6)(R^7)$, $R^7$ is $(CH_2)_nN(R)^2$, and n is 3. As shown in Scheme D, ester D-2 may be formed by a Michael addition of nitropiperazine B-5 to methyl acrylate, followed by treatment with tributyl tin hydride and AIBN to remove the nitro group, to yield ester D-3. The ester D-3 may be hydrolyzed to the corresponding acid D-4, which may be subsequently treated with DPPA to form the CBZ protected amine D-5. The CBZ group may be removed under standard conditions known to one skilled in the art to give free amine D-6. The protecting group PG of compound D-6 may be removed to give compound D-7, which corresponds to a compound of formula A-1. Alternatively, compound D-6 may be substituted, as shown in Scheme B, followed by protecting group removal, to give a compound of formula A-1 wherein X is $(CH_2)_0C(R^5)(R^6)(R^7)$, $R^7$ is $(CH_2)_nN(R)_2$, n is 3 and R may be as defined in Scheme B.

Scheme D

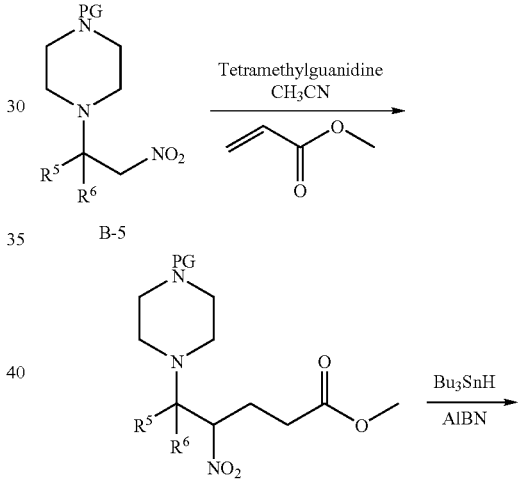
B-5

D-2

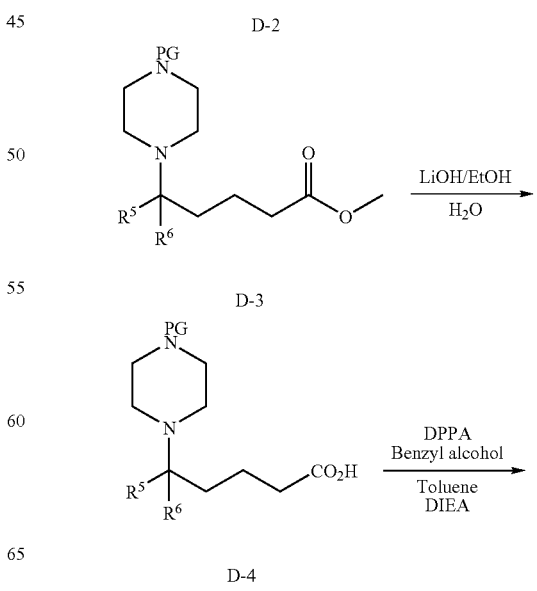
D-3

D-4

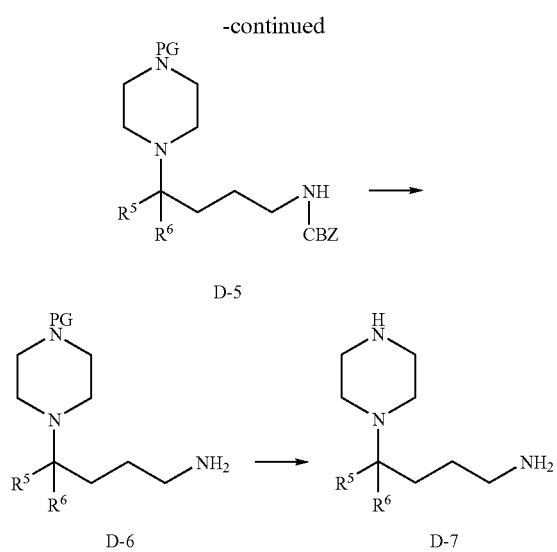

D-5

D-6 → D-7

$R^5$ and $R^6$ are as defined supra; PG is a protecting group such as Boc or CBZ.

Reaction Schemes E-1 illustrate methods for the synthesis of the pyrrolidine and piperidine carboxylic acids of general formula A-2, A-4 and A-6 that are utilized in the amide bond coupling reaction shown in reaction Scheme A.

Reaction Scheme E illustrates a preferred method for the synthesis of compounds of general formula A-4 such that the resulting heterocycle is a 3-aryl-4-piperidine carboxylic acid derivative E-8. The synthesis of E-8 begins with a commercially available β-keto ester such as E-1. Generally a protecting group interchange of an N-BOC group for the N-benzyl group is performed initially. Thus a O-keto ester of formula E-1 is subjected to debenzylation by hydrogenolysis using a palladium-on-carbon catalyst in a solvent system such as 1:1 ethanol-water under a hydrogen atmosphere. The resulting piperidone E-2 is then protected as its tert-butyl carbamate using BOC anhydride in the presence of a base and a suitable solvent. For example, this can be accomplished in a two phase mixture of chloroform and aqueous sodium bicarbonate as shown. Incorporation of the 3-aryl substituent is then performed in two steps. First, the β-keto ester group is converted to the corresponding vinyl triflate E-4 using trifluoromethanesulfonic anhydride and an organic base like N,N-diisopropylethylamine in an aprotic solvent such as methylene chloride. The resulting vinyl triflate E-4 is then subjected to a palladium-catalyzed cross-coupling reaction with an aryl boronic acid E-5 using a palladium (1) catalyst such as [1,1'-bis(diphenylphosphino)-ferrocene]dichloropalladium(II). Preferred conditions for this reaction are the use of a toluene-ethanol-aqueous sodium carbonate solvent system at an elevated temperature, for instance 50–100° C., for a period of 2–24 hours. The resulting aryl-substituted tetrahydropyridine derivative E-6 can be reduced to a piperidine such as E-7 using a variety of known techniques and the method chosen will determine the stereochemical outcome of the product. For instance, hydrogenation of E-6 with a palladium on carbon catalyst in a solvent such as ethanol affords cis-3,4-disubstituted piperidines of general formula E-7. Alternatively, a dissolving metal reduction using a metal, such as magnesium in methanol, reduces the double bond of E-6 and produces a mixture of both cis and trans 3,4-disubstituted piperidines of formula E-7. The resulting mixture of cis and trans diastereoisomers may be separated chromatographically or it may be subsequently epimerized to afford the pure trans isomer of E-7 by treating the mixture with a base like sodium methoxide in methanol. Finally, hydrolysis of either the cis or trans 3-aryl-4-piperidine carboxylic ester E-7 affords either a cis or trans 3-aryl-4-piperidine carboxylic acid of general formula E-8, corresponding to an acid of general formula A-4. The cis or trans carboxylic acids of general formula E-8 are produced as racemates and either may be resolved to afford enantiomerically pure compounds by methods known in organic synthesis. Preferred methods include resolution by crystallization of diastereoisomeric salts derived from acids E-8 and a chiral amine base or the use of chiral stationary phase liquid chromatography columns.

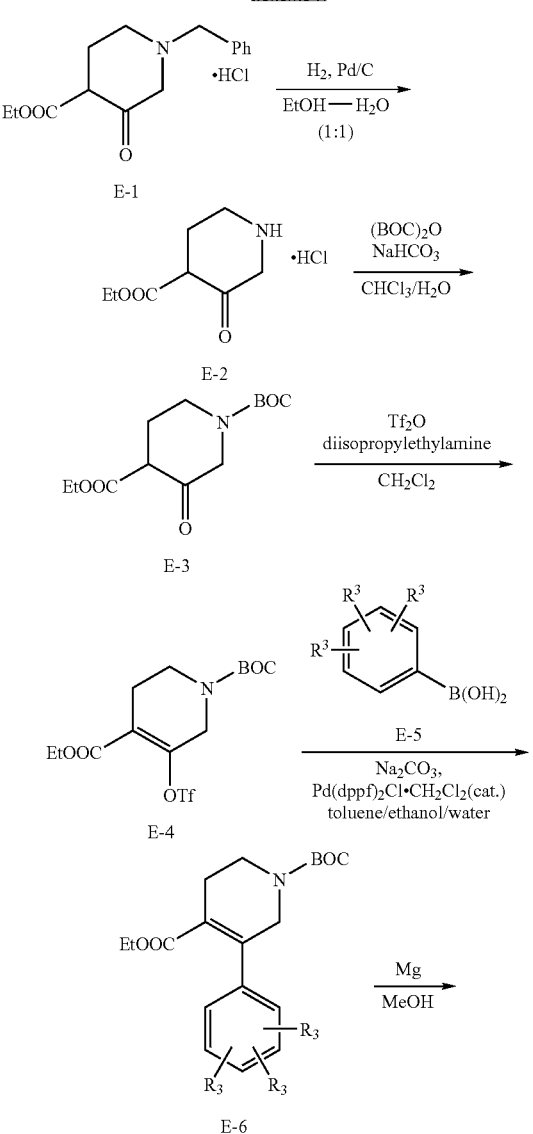

Scheme E

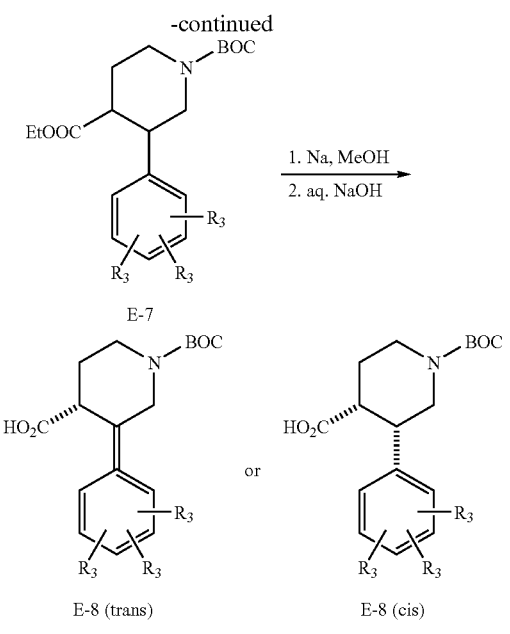

E-7

E-8 (trans)   or   E-8 (cis)

The N-Boc protected acids of formula A-6

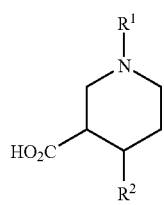

A-6 may also be prepared using the synthetic sequence of Scheme E and starting with the appropriate commercially available starting materials. Piperidine acids of formula A-6 may subsequently be coupled with a piperazine of general formula A-1 to give a compound of formula (I).

The synthesis of the N-BOC protected carboxylic acids of general formula E-8 illustrated in reaction Scheme E is useful for the preparation of title compounds of structural formula I bearing a variety of $R^1$ substituents as noted above. For the synthesis of certain title compounds of structural formula I, for instance when it is desired that $R^1$ be a tert-butyl group, it is preferable to incorporate that $R^1$ substituent at an earlier stage of the synthesis. The synthesis of a 1-substituted-3-ketopiperidine-4-carboxylic ester F-4 is shown in reaction Scheme F. A primary amine F-1 bearing a desired $R^1$ substituent like a tert-butyl group is reacted with ethyl 4-bromobutyrate at elevated temperature in the absence of a solvent to afford the N-substituted ethyl 4-aminobutyrate F-2. The amino ester F-2 is then alkylated a second time with ethyl bromoacetate in a high boiling inert solvent such as toluene and in the presence of a base such as powdered potassium carbonate. The resulting aminodiesters of general formula F-3 are then cyclized using an intramolecular Dieckmann reaction to afford piperidines such as F-4. The Dieckmann reaction is performed using a strong base such as potassium tert-butoxide or the like, in an aprotic solvent such as THF at temperatures between room temperature and the boiling point of the solvent. The resulting 1-substituted-3-ketopiperidine-4-carboxylic ester F-4 corresponds to a compound of general formula E-3 shown in reaction Scheme E, where the BOC group is replaced with the desired $R^1$ substituent. The compounds of general formula F-4 may then be converted to compounds of general formula A-4 where the $R^1$ substituent replaces the BOC group using the reaction sequence illustrated in reaction Scheme E.

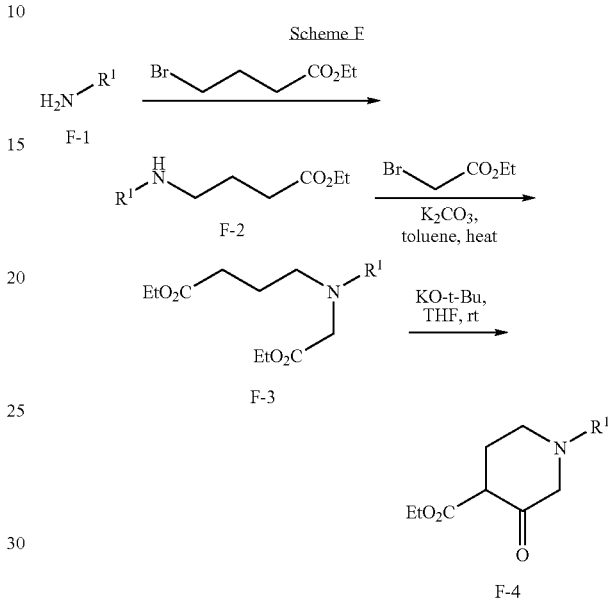

The $R^1$ protected esters of formula A-6

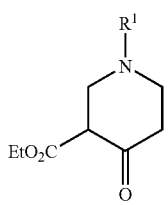

A-6 may also be prepared using the synthetic sequence of Scheme F and starting with the appropriate commercially available starting materials. Piperidine acids of formula A-6 may subsequently be coupled with a piperazine of general formula A-1 to give a compound of formula (I).

Reaction Scheme G illustrates a strategy for the synthesis of pyrrolidine acids of general formula A-2. The preferred method for the synthesis of compounds of general formula A-2 involves the azomethine ylid 3+2 cycloaddition reaction of an azomethine ylid precursor of general formula G-2 and a substituted cinnamic ester G-1. The azomethine cycloaddition reaction of G-1 and G-2 affords the 3,4-disubstituted pyrrolidine G-3, and the stereochemical relationship of the substituents on the newly formed pyrrolidine ring is determined by the stereochemistry of the double bond in the cinnamate ester G-1. Thus the trans ester G-1 affords a trans 3,4-disubstituted pyrrolidine of formula G-3 as shown. The corresponding cis cinnamate ester affords a cis 3,4-disubstituted pyrrolidine of general formula G-3. Cis or trans 3-arylpyrrolidine-4-carboxylic esters of general formula G-3 may be resolved to afford enantiomerically pure compounds using a method such as resolution by crystallization of the diastereoisomeric salts derived from G-3 and a chiral carboxylic acid, or directly by the use of chiral stationary phase liquid chromatography columns. Reaction Scheme G illustrates the case where a trans cinnamic ester G-1 is converted to a trans 3,4-disubstituted pyrrolidine G-3 and its subsequent resolution affords the enantiomerically pure trans pyrrolidine esters G-4 and G-5. Finally, the esters of general formula G-3 (or their pure enantiomers G-4 and G-5) are hydrolyzed to the corresponding amino acid hydrochlorides of general formula G-6 as shown at the bottom of reaction Scheme G.

Amino acids of general formula G-6 are zwitterionic. Therefore it is in some cases difficult to achieve efficient separation and purification of these compounds from aqueous reactions or workups. In these cases it is preferred to effect the hydrolysis using a reagent such potassium trimethylsilanolate in diethyl ether. Under these conditions the potassium salt of the carboxylic acid is produced which affords an easily isolated precipitate in ether. The resulting salt is then converted to the corresponding amino acid hydrochloride by treatment with excess hydrogen chloride in a suitable solvent such as ethyl acetate. Alternatively, esters such as G-3 may be converted directly to the amino acid hydrochlorides G-6 under acidic hydrolysis conditions. The hydrolysis of the ester G-3 is achieved by prolonged reaction with concentrated hydrochloric acid at an elevated temperature. For example, this reaction may be conducted in 8 M hydrochloric acid at reflux overnight. The reaction mixture is then cooled and evaporated in vacuo to afford the amino acid hydrochloride G-6. The amino acid hydrochlorides of general formula G-6 correspond to an amino acid hydrochloride of general formula A-2 and may be employed directly in the amide bond coupling step illustrated in reaction Scheme A to produce the compounds of structural formula I.

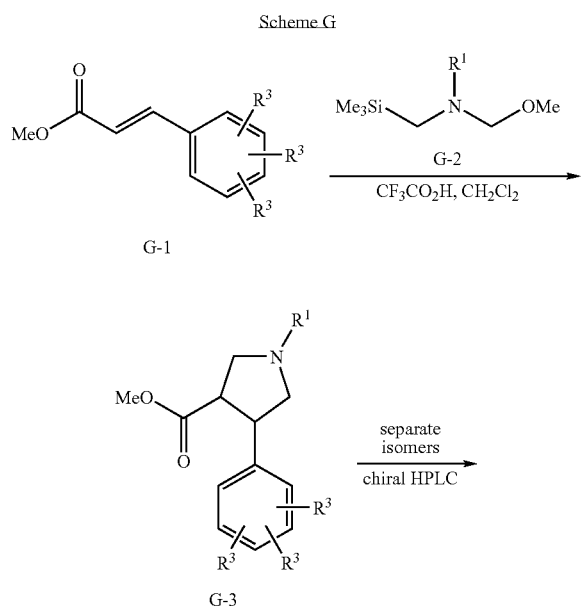

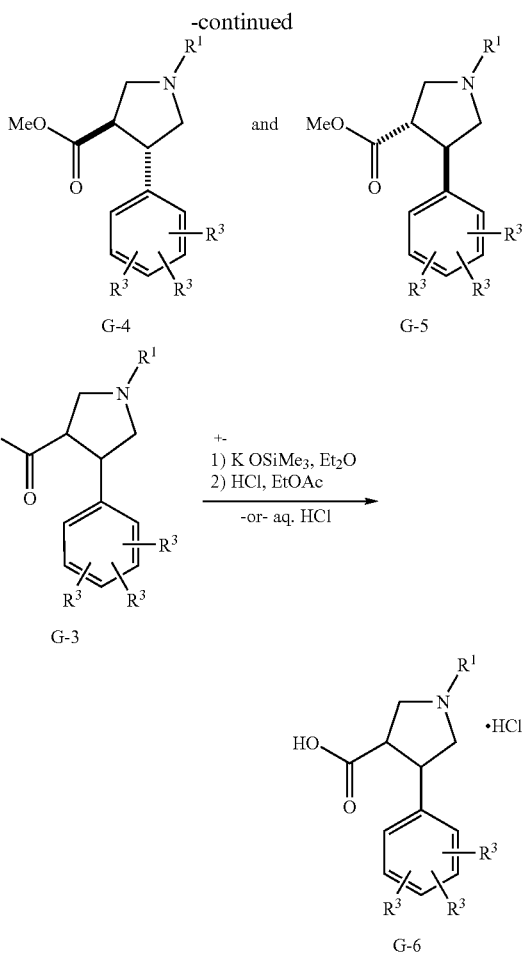

Another preferred method for the synthesis of enantiomerically pure 3-arylpyrrolidine-4-carboxylic acid derivatives is illustrated in reaction Scheme H. In this synthetic method, a substituted cinnamic acid of general formula H-1 is first derivatized with a chiral auxilliary such as (S)-(−)-4-benzyl-2-oxazolidinone H-2. The acylation of chiral auxiliary 30 with cinnamic acids of formula H-1 is performed by initial activation of the acid to afford a mixed anhydride. Typically acids of general formula H-1 are reacted with an acid chloride such as pivaloyl chloride in the presence of a base such as triethylamine and in a suitable aprotic solvent such as THF. The intermediate cinnamyl-pivaloyl anhydride is converted to the product H-3 by reaction with the oxazolidinone H-2 in the presence of lithium chloride, an amine base such as triethylamine and in a solvent such as THF, and the reaction is conducted at temperatures between −20° C. and room temperature for periods of 1–24 hours. Alternatively, the oxazolidinone H-2 may be deprotonated with a strong base such as n-butyllithium in THF at low temperatures such as −78° C. and then reacted with a mixed anhydride obtained from acid H-1 and an acid chloride like pivaloyl chloride as noted above. The cinnamyl oxazolidinone of general formula H-3, which is produced by either of these methods, is then reacted with the azomethine ylid precursor G-2 in a manner similar to that described in reaction Scheme F, and the products of the reaction are the substituted pyrrolidines of general formulas H-5 and H-6 as shown. The products H-5 and H-6 are diastereoisomers of each other and may therefore be separated by standard methods such as recrystallization or by liquid chromatography on a solid support such as silica gel. As discussed above, if the trans isomer of the cinnamic acid of general formula H-1 is employed in the first step of reaction Scheme G, then a trans isomer of the substituted cinnamyl oxazolidinone H-3 is produced. If such a trans cinnamyl oxazolidinone is then subjected to the azomethine ylid cycloaddition with an azomethine ylid precursor of formula G-2, the products are the diastereoisomeric trans-disubstituted pyrrolidines related to H-5 and H-6.

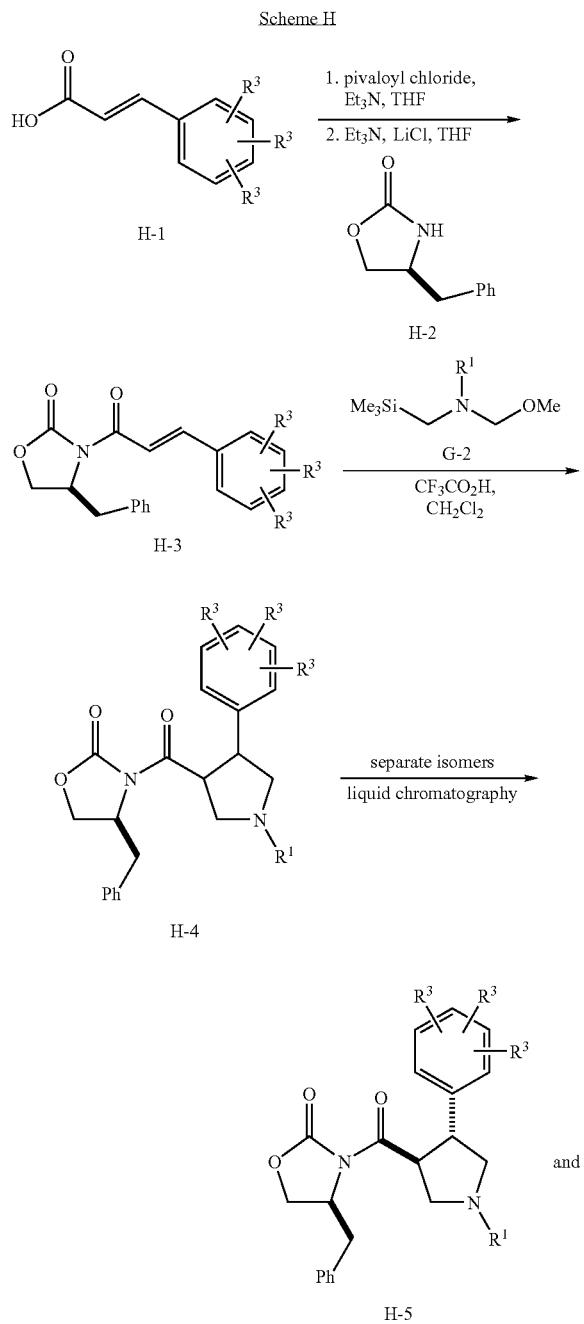

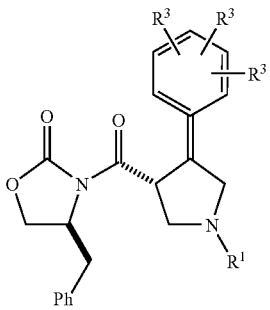

The azomethine ylid cycloaddition reactions shown in reaction Schemes G and H are generally conducted with the commercially available azomethine ylid precursor N-(methoxymethyl)-N-(trimethylsilylmethyl)-benzylamine (G-2, $R^1$=—$CH_2$Ph). When the $R^1$ substituent in the title compounds of structural formula I is chosen to be a group other than benzyl, it is generally preferable to remove the benzyl group from the substituted pyrrolidine compound at this point, and replace it with a more readily removed protecting group such as an N-BOC group. Reaction Scheme I illustrates this process with a generalized 3,4-disubstituted pyrrolidine of formula I-1. The preferred method for removal of the N-benzyl group from compounds of general formula I-1 will depend upon the identity of the $R^3$ substituents. If these substituents are unaffected by hydrogenation conditions, then the N-benzyl group may be removed by hydrogenolysis using a palladium on carbon catalyst in a solvent such as ethanol and in the presence of hydrogen gas or a hydrogen donor such as formic acid. Occasionally it may be preferred that one of the substituents $R^3$ be a halogen or another substituent defined above which would be reactive under hydrogenation conditions. In these cases, the compound of general formula I-1 is reacted with 1-chloroethyl chloroformate in an inert solvent such as toluene at temperatures between room temperature and 110° C. (Olafson, R. A. et al. *J. Org. Chem.* 1984, 49, 2081). The toluene is then removed, and the residue is heated in methanol for a period of 15–60 minutes, and the product is the debenzylated pyrrolidine of general formula I-2. The resulting pyrrolidine I-2 is then protected as its tert-butyl carbamate I-3 using BOC anhydride in the presence of a base and a suitable solvent. For example, this can be accomplished in a two phase mixture of chloroform and aqueous sodium bicarbonate as shown in reaction Scheme I.

The oxazolidinone chiral auxilliary is next hydrolyzed from the pyrrolidines of general formula I-3 as shown at the bottom of reaction Scheme I. The hydrolysis reaction is accomplished using lithium hydroperoxide generated in situ from lithium hydroxide and 30% aqueous hydrogen peroxide. The reaction is typically conducted in a solvent system such as aqueous THF, and the reaction is performed at temperatures between 0° C. and room temperature for a period of 1–6 hours. The resulting carboxylic acids of general formula I-4 correspond to carboxylic acids of general formula A-2. Using the methodology presented in reaction Scheme A, the compounds of general formula I-4 may then be converted to the compounds of the present invention of structural formula (I).

Scheme I

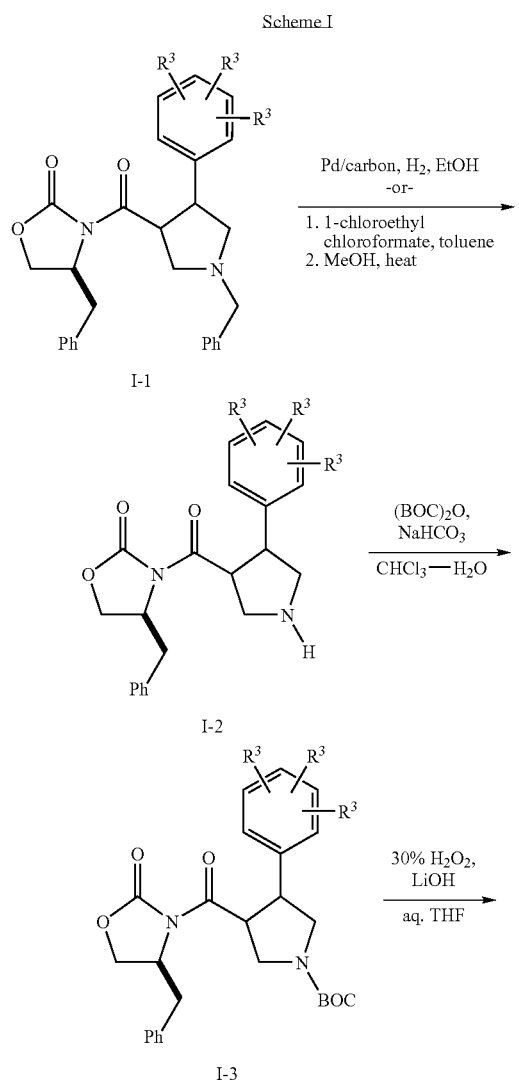

As noted previously in the discussion of reaction Scheme G, it may occasionally be preferable to incorporate the $R^1$ substituent into the substituted pyrrolidine of general formula I-4 at an earlier stage of the synthesis, for instance when it is desired that $R^1$ be a tert-butyl group. In such cases, it is possible to utilize an azomethine ylid precursor G-2 bearing the desired $R^1$ substituent in the cycloaddition reactions illustrated in reaction Schemes G and H. Reaction Scheme J illustrates the preparation of azomethine precursors of formula G-2 starting with amines of general formula J-1. Reaction of the amine of formula J-1 with chloromethyltrimethylsilane at high temperature and in the absence of solvent affords the N-trimethylsilylmethyl-substituted amine of general formula J-2. Subsequent reaction of J-2 with aqueous formaldehyde in the presence of methanol and a base such as potassium carbonate then affords the generalized ylid precursor G-2 which can be utilized in the cycloaddition reactions discussed above.

Scheme J

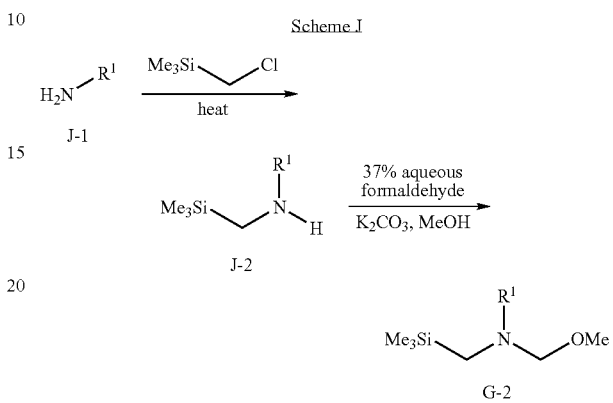

The following Intermediates and Examples are provided to illustrate the invention and are not to be construed as limiting the scope of the invention in any manner. Scheme 1 illustrates the preparation of the cyclohexyl BOC piperazine amine intermediate 1-6. Other piperazine intermediates may be prepared as shown in Scheme 1 by substituting the appropriate alkyl, cycloalkyl, heterocycloalkyl, aryl and heteroaryl group for the cyclohexyl group of cyclohexanecarboxaldehyde 1–1. Scheme 2 illustrates the conversion of the BOC piperazine intermediate 1-6 into the substituted, de-protected amino piperazine intermediate 2-2. Scheme 3 illustrates the preparation of the phenyl BOC piperazine intermediate 3-5.

Scheme 1

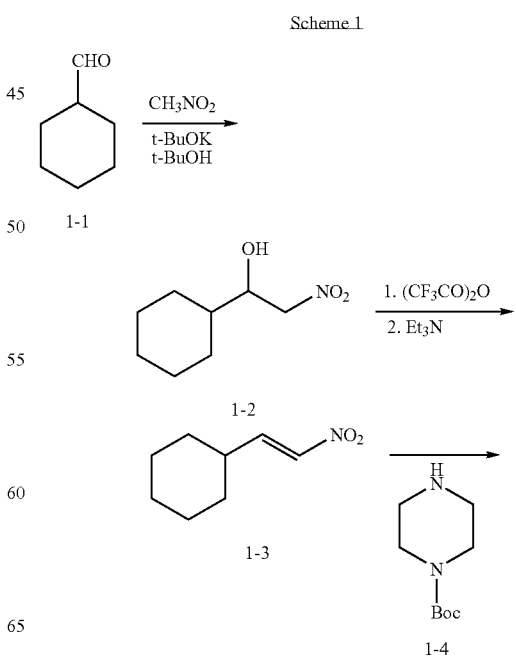

-continued

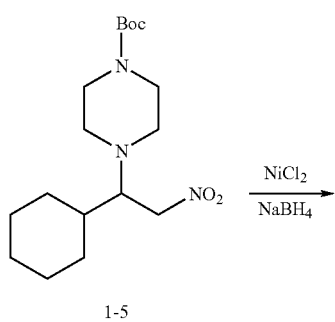

Preparation of Intermediate 1-6

Step A:

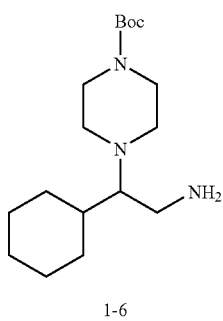

To a solution of cyclohexanecarboxaldehyde 1-1 (4.5 g, 40.1 mmol, Aldrich) in tetrahydrofuran (10.5 mL) and tert-butanol (10.5 mL) was added nitromethane (3.3 mL, 60.2 mmol), followed by addition of potassium tert-butoxide at 0° C. The reaction mixture was stirred at 0° C. for 2 hr, then allowed to warm up to room temperature and stirred overnight. The reaction mixture was poured into water (150 mL) and extracted with t-butyl methyl ether (3×150 mL). The combined organic extracts were washed with brine (100 mL), dried over MgSO$_4$ and concentrated to give compound 1-2. ESI-MS calc. for $C_8H_{15}NO_3$: 173. Found: 196 (M+Na).

Step B:

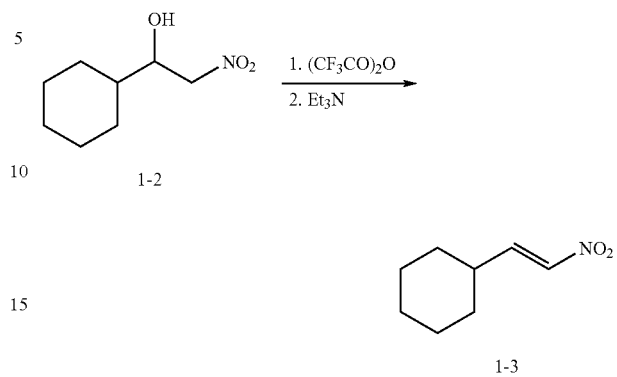

To a solution of compound 1-2 (6.8 g, 39.3 mmol) in dichloromethane (50 mL) was added trifluoroacetic anhydride (5.8 ml, 41.2 mmol) at −10° C. The resulting solution was stirred for 2 minutes, then triethylamine (11.5 ml, 82.5 mmol) was added slowly over 15 minutes. The mixture was stirred for 30 minutes at −10° C., then poured into CH$_2$Cl$_2$ (250 mL) and washed with saturated NH$_4$Cl (2×100 mL). The aqueous layers were back extracted with CH$_2$Cl$_2$ (100 mL). The combined organic layers were washed with brine (100 mL), dried over MgSO$_4$ and concentrated to give a yellow oil, which was purified by chromatography over silica gel (hexane:ethyl acetate=20:1) to give compound 1-3. ESI-MS calc. for $C_8H_{13}NO_2$: 155. Found: 156 (M+H).

Step C:

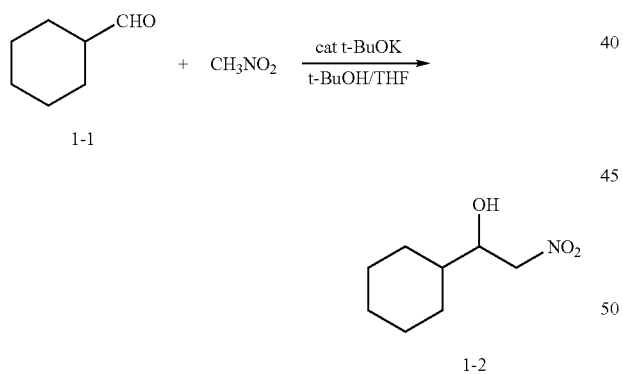

To a solution of compound 1-3 (2.41 g, 15.6 mmol) in CH$_2$Cl$_2$ (20 mL) was added Boc-piperazine 1-4 (2.63 g, 14.1 mmol, Aldrich). The mixture was stirred at room temperature overnight, then concentrated to give a crude product. The crude product was purified by chromatography over silica gel (hexane:ethyl acetate=10:1) to give compound 1-5. ESI-MS calc. for $C_{17}H_{31}N_3O_4$: 341. Found: 342 (M+H).

Step D:

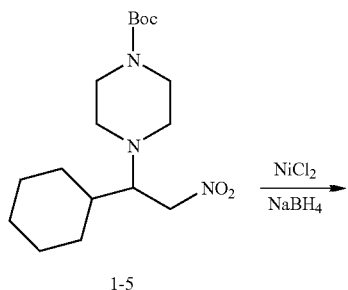

1-5

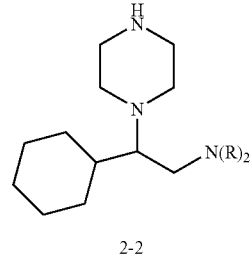

2-2

R is as defined in Scheme B.

Preparation of Piperazine Intermediates of Formula 2-2

Piperazine Intermediate 1

To a solution of compound 1-5 (1.1 g, 3.2 mmol) in methanol (50 mL) was added nickel (II) chloride hexahydrate (1.92 g, 8.1 mmol). The resulting solution was cooled to 0° C., and sodium borohydride (3.1 g, 80.6 mmol) was added slowly. The mixture was stirred at 0° C. for 2 hr, then concentrated to give a residue. To the residue was added $CH_2Cl_2$ (250 mL) and NaOH (1N, 250 mL), and the resulting emulsion was filtered though celite. The organic and aqueous layers were separated; the aqueous was extracted with $CH_2Cl_2$, dried over $Na_2SO_4$ and concentrated to give compound 1-6. ESI-MS calc. for $C_{17}H_{33}N_3O_2$: 311. Found: 312 (M+H).

As shown in Scheme 2, piperazine intermediates of general structure 2-2 were prepared from piperazine amine 1-6 using the procedures below.

Scheme K

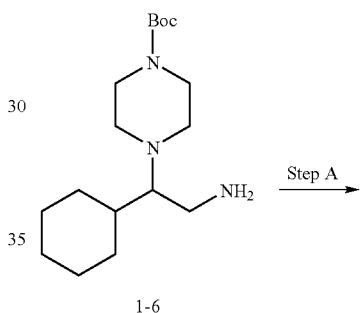

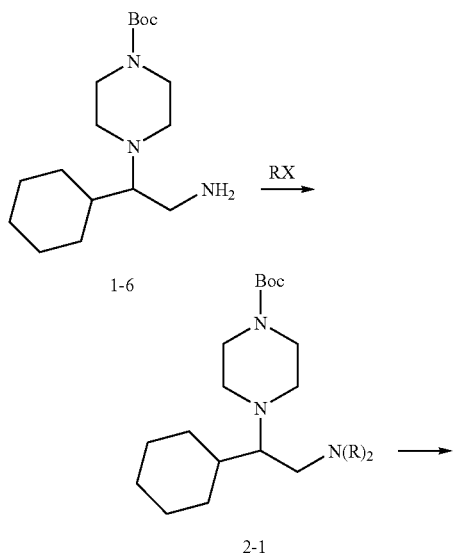

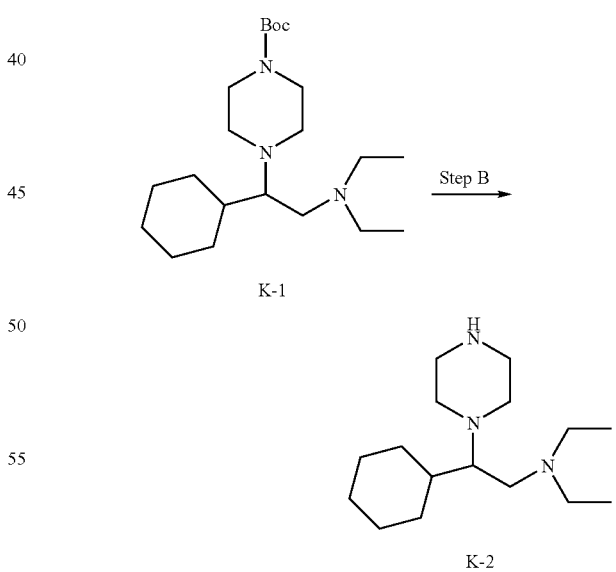

Step A: To a solution of compound 1-6 (0.88 g, 2.83 mmol) in DMF (12 mL) was added potassium carbonate (2.0 g, 14.2 mmol) and ethyl bromide (0.63 ml, 8.5 mmol). The resulting mixture was stirred at room temperature overnight, then diluted with ethyl acetate, washed with brine, dried over Na$_2$SO$_4$, and concentrated to form a crude product. The crude product was purified by chromatography over silica gel (ethyl acetate to 5% CH$_3$OH: 5% Et$_3$N: 90% EtOAc as elution) to give compound K-1. ESI-MS calc. for C$_{21}$H$_{41}$N$_3$O$_2$: 367. Found: 368 (M+H)

Step B: To the intermediate K-1 (0.45 g) was added hydrogen chloride (4.0 mL, 4.0 M in dioxane). The reaction mixture was stirred at room temperature for 30 minutes, then the solvent was removed in vacuo to afford intermediate K-2.

ESI-MS calc. for C$_{16}$H$_{34}$N$_3$: 267. Found: 268 (M+H).

Piperazine Intermediate 2

Piperazine Intermediate 3

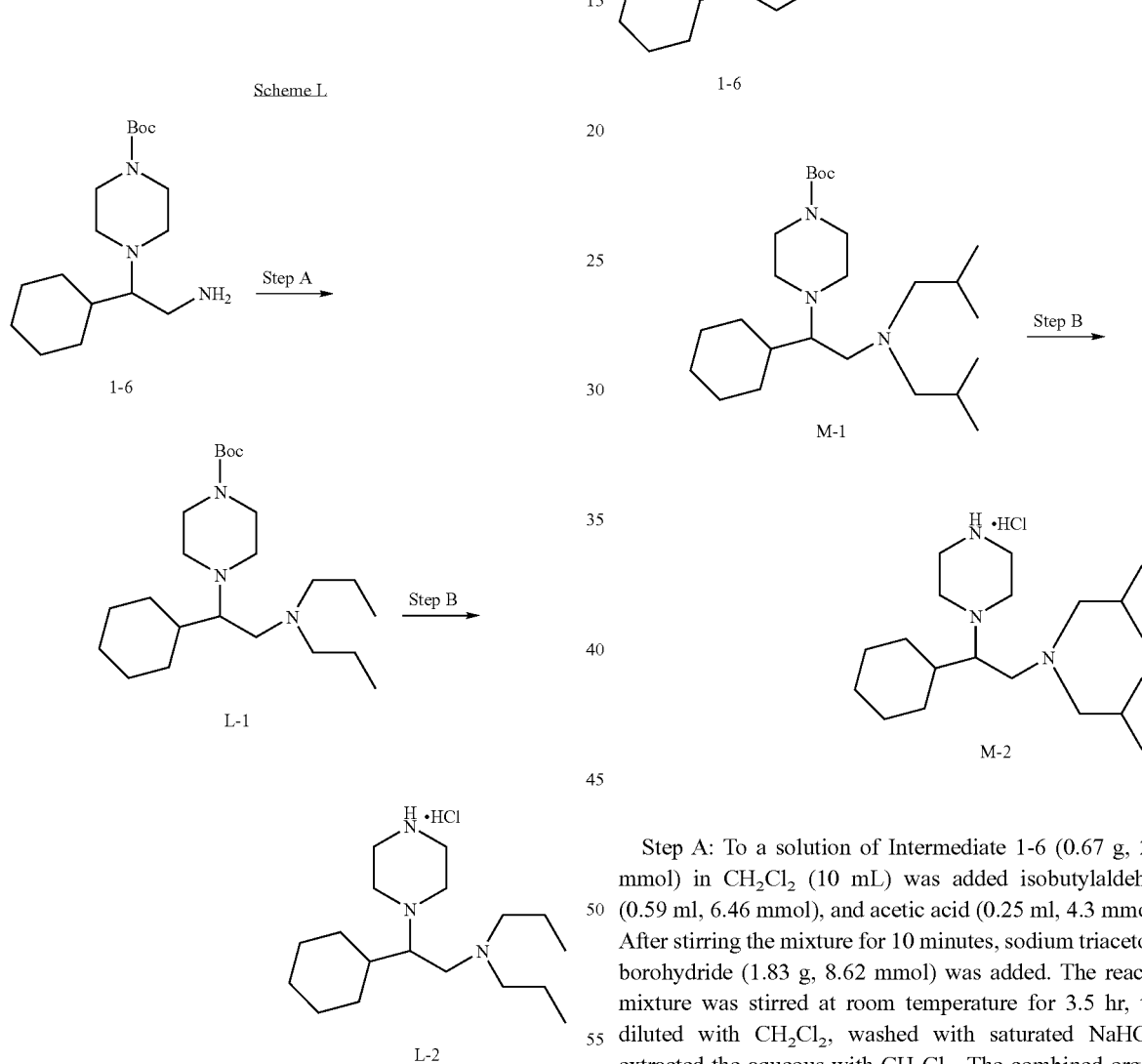

Step A: Intermediate L-1 was prepared from Intermediate 1-6 following a procedure similar to the procedure described for the preparation of Intermediate K-1. ESI-MS calc. for C$_{23}$H$_{45}$N$_3$O$_2$: 395. Found: 396 (M+H).

Step B: Intermediate L-2 was prepared from Intermediate L-1 following a procedure similar to the procedure described for the preparation of Intermediate K-2. ESI-MS calc. for C$_{18}$H$_{37}$N$_3$: 295. Found: 296 (M+H).

Step A: To a solution of Intermediate 1-6 (0.67 g, 2.15 mmol) in CH$_2$Cl$_2$ (10 mL) was added isobutylaldehyde (0.59 ml, 6.46 mmol), and acetic acid (0.25 ml, 4.3 mmole). After stirring the mixture for 10 minutes, sodium triacetoxyborohydride (1.83 g, 8.62 mmol) was added. The reaction mixture was stirred at room temperature for 3.5 hr, then diluted with CH$_2$Cl$_2$, washed with saturated NaHCO$_3$, extracted the aqueous with CH$_2$Cl$_2$. The combined organic layers were washed with brine, dried over Na$_2$SO$_4$ and concentrated to give a crude product. The crude product was purified by chromatography over silica gel (hexane:ethyl acetate=2:1 to ethyl acetate) to give Intermediate M-1. ESI-MS calc. for C$_{25}$H$_{49}$N$_3$O$_2$: 423. Found: 424 (M+H).

Step B: Intermediate M-2 was prepared from Intermediate M-1 following a procedure analogous to the procedure described for the preparation of Intermediate K-2. ESI-MS calc. for C$_{20}$H$_{41}$N$_3$: 323. Found: 324 (M+H).

Piperazine Intermediate 4

Scheme N

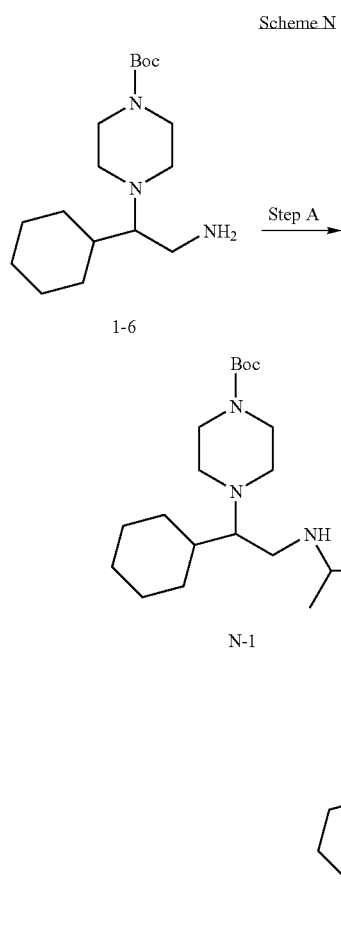

Step A: Intermediate N-1 was prepared from intermediate 1-6 following a procedure analogous to the procedure described for the preparation of Intermediate M-1. ESI-MS calc. for $C_{20}H_{39}N_3O_2$: 353. Found: 354 (M+H).

Step B: Intermediate N-2 was prepared from intermediate N-1 following a procedure analogous to the procedure described for the preparation of Intermediate K-2. ESI-MS calc. for $C_{15}H_{31}N_3$: 253. Found: 254 (M+H).

Piperazine Intermediate 5

Scheme O

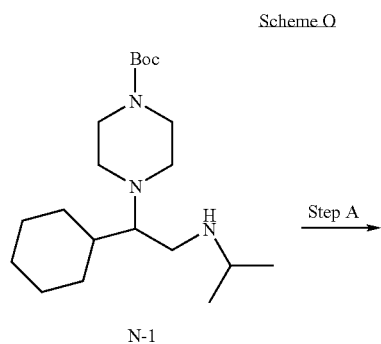

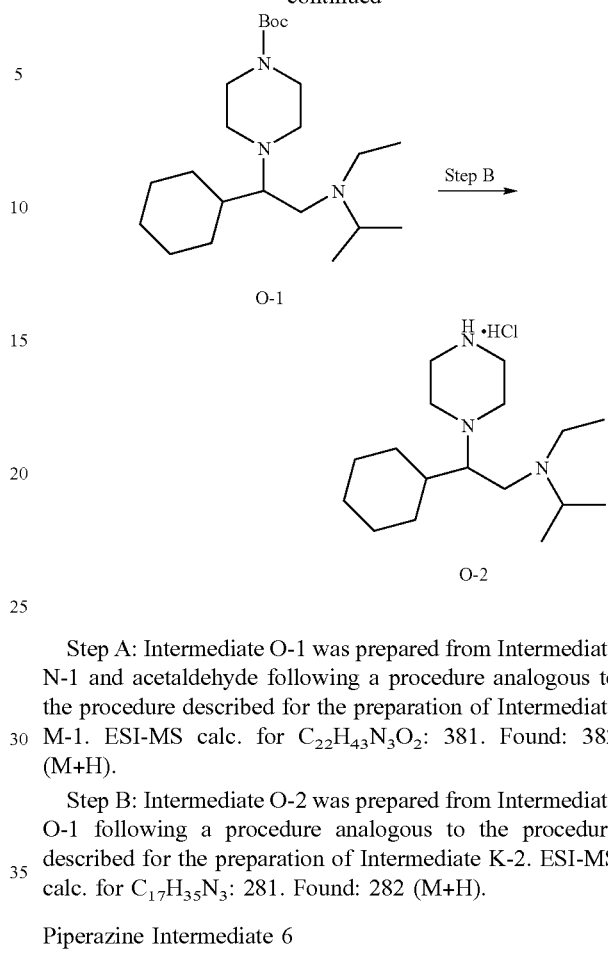

Step A: Intermediate O-1 was prepared from Intermediate N-1 and acetaldehyde following a procedure analogous to the procedure described for the preparation of Intermediate M-1. ESI-MS calc. for $C_{22}H_{43}N_3O_2$: 381. Found: 382 (M+H).

Step B: Intermediate O-2 was prepared from Intermediate O-1 following a procedure analogous to the procedure described for the preparation of Intermediate K-2. ESI-MS calc. for $C_{17}H_{35}N_3$: 281. Found: 282 (M+H).

Piperazine Intermediate 6

Scheme P

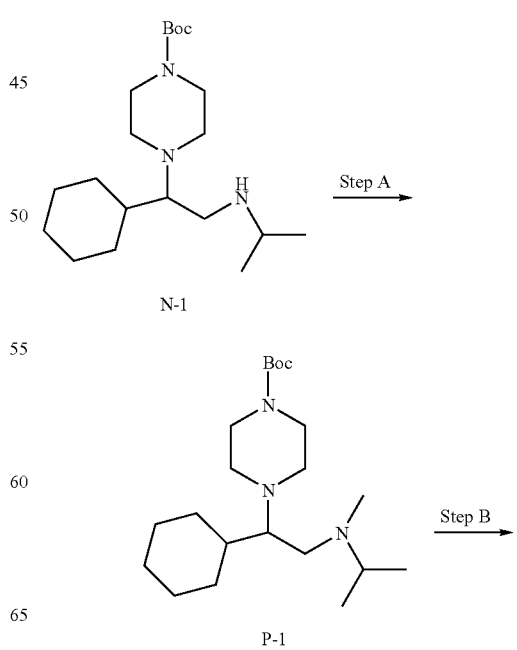

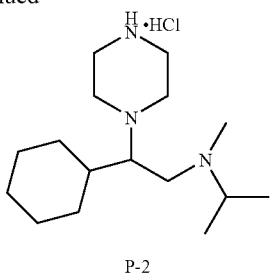

P-2

Step A: Intermediate P-1 was prepared from Intermediate N-1 and formaldehyde following a procedure analogous to the procedure described for the preparation of Intermediate M-1. ESI-MS calc. for $C_{21}H_{41}N_3O_2$: 367. Found: 368 (M+H).

Step B: Intermediate P-2 was prepared from Intermediate P-1 following a procedure analogous to the procedure described for the preparation of Intermediate K-2. ESI-MS calc. for $C_{16}H_{33}N_3$: 267. Found: 268 (M+H).

Piperazine Intermediate 7 water, brine, dried over $Na_2SO_4$ and concentrated to give a crude product, which was purified by chromatography over silica gel (hexane:ethyl acetate=2:1 to hexane:ethyl acetate=1:1) to give Intermediate Q-1. ESI-MS calc. for $C_{22}H_{41}N_3O_3$: 395.6. Found: 396 (M+H), 418 (M+Na).

Step B: Intermediate Q-2 was prepared from Intermediate Q-1 following a procedure analogous to the procedure described for the preparation of Intermediate K-2. ESI-MS 296 (m+1).

Piperazine Intermediate 8

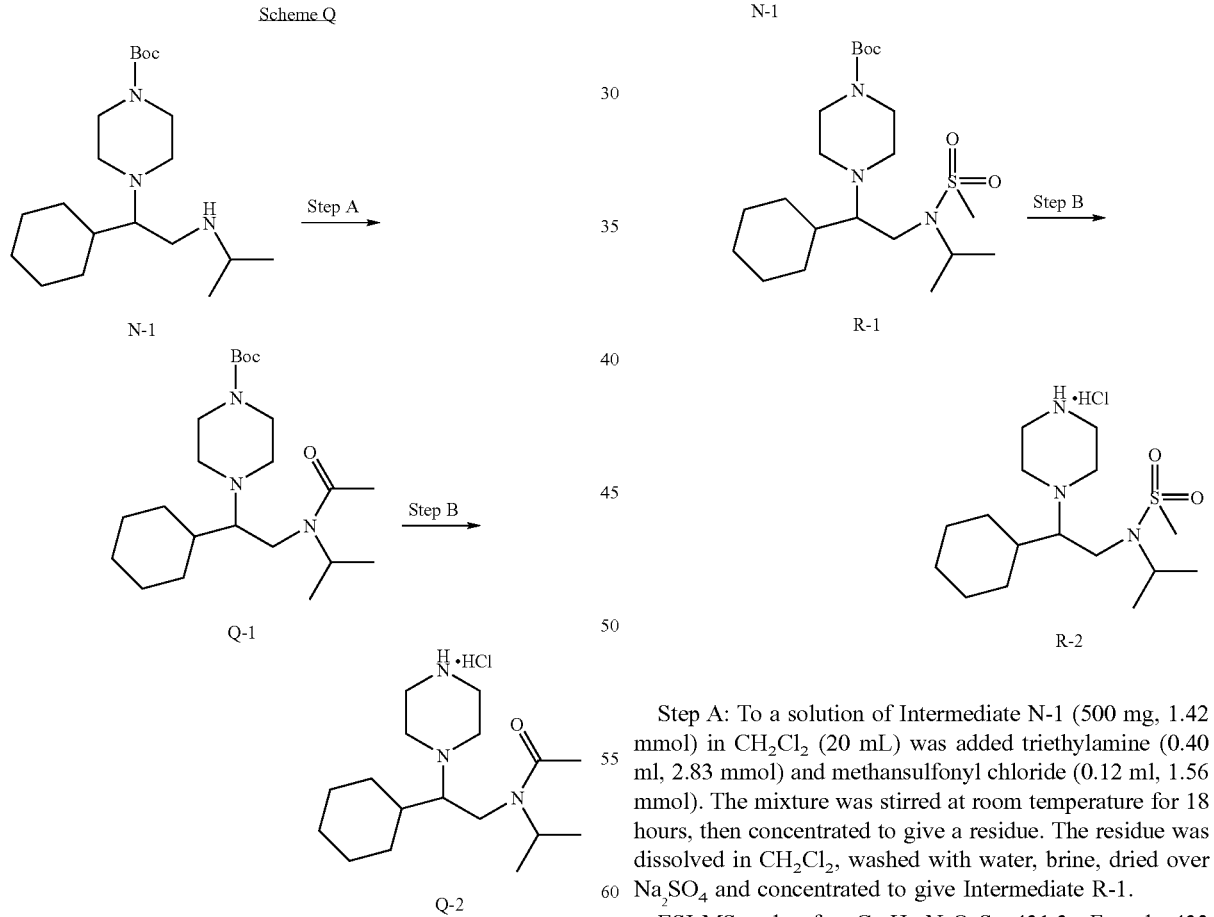

Step A: To a solution of Intermediate N-1 (482 mg, 1.365 mmol) in pyridine (10 mL) was added acetic anhydride (0.13 mL, 1.38 mmol). The reaction mixture was stirred at room temperature for 18 hours, then concentrated to give a residue. The residue was dissolved in $CH_2Cl_2$, washed with Step A: To a solution of Intermediate N-1 (500 mg, 1.42 mmol) in $CH_2Cl_2$ (20 mL) was added triethylamine (0.40 ml, 2.83 mmol) and methansulfonyl chloride (0.12 ml, 1.56 mmol). The mixture was stirred at room temperature for 18 hours, then concentrated to give a residue. The residue was dissolved in $CH_2Cl_2$, washed with water, brine, dried over $Na_2SO_4$ and concentrated to give Intermediate R-1.

ESI-MS calc. for $C_{21}H_{41}N_3O_4S$: 431.3. Found: 432 (M+H).

Step B: Intermediate R-2 was prepared from Intermediate R-1 following a procedure analogous to the procedure described for the preparation of Intermediate K-2. ESI-MS calc. for $C_{16}H_{33}N_3O_2S$: 331. Found: 332 (M+H).

Piperazine Intermediate 9

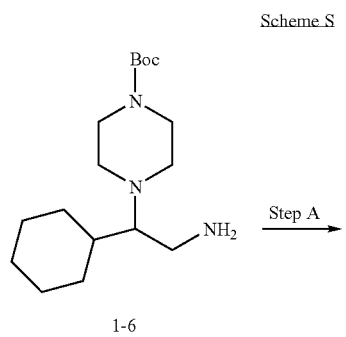

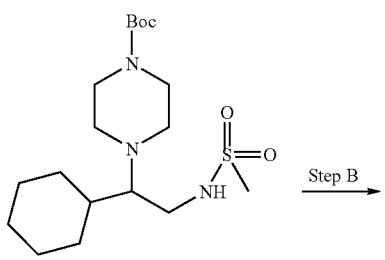

Step A: To a solution of Intermediate 1-6 (400 mg, 1.078 mmol) in $CH_2Cl_2$ (10 mL) was added sodium carbonate (0.57 g in 2 mL $H_2O$, 5.4 mmol) and methansulfonyl chloride (0.09 ml, 1.19 mmol). The reaction mixture was stirred at room temperature for 18 hours, then diluted with $CH_2Cl_2$, separated into an organic and an aqueous layer. The aqueous layer was extracted with $CH_2Cl_2$. The combined organic layers were washed with water, brine, dried over $Na_2SO_4$ and concentrated to give Intermediate S-1. ESI-MS calc. for $C_{18}H_{35}N_3O_4S$: 389.2. Found: 390 (M+H).

Step B: Intermediate S-2 was prepared from Intermediate S-1 following a procedure analogous to the procedure described for the preparation of Intermediate K-2. ESI-MS 290 (M+H).

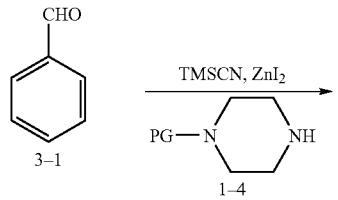

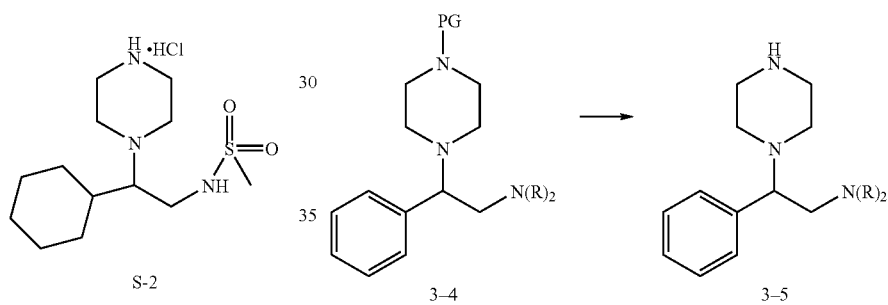

$CH_2N(R)_2=R^7$

PG is a protecting group such as Boc or CBZ

Piperazine Intermediate 10

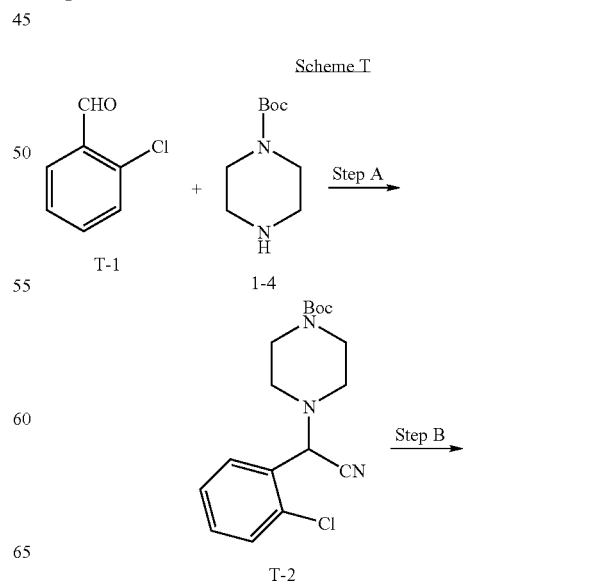

-continued

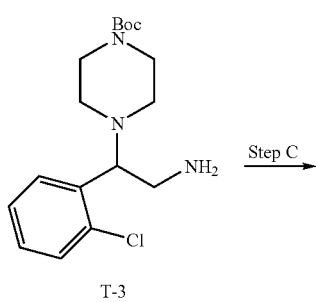

T-3

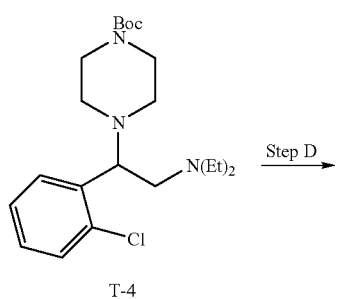

T-4

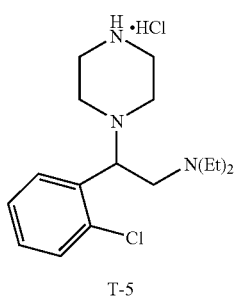

T-5

Step A: To a solution of 2-chlorobenzaldehyde T-1 (3.52 g, 25.0 mmol) in ether (3 mL) was added trimethyl silyl cyanide (4.17 mL, 31.3 mmol) at 0° C., followed by addition of $ZnI_2$ (0.4 g, 1.25 mmol). After stirring the mixture at 0° C. for 40 minutes, a solution of Boc-piperazine 1-4 (4.66 g, 24 mmol, Aldrich) in $CH_3OH$ (20 mL) was added. The reaction mixture was refluxed for 4 hr, then cooled to room temperature and stirred for 18 hr. The reaction mixture was cooled to 0° C., and filtered to give Intermediate T-2. ESI-MS calc. for $C_{17}H_{22}ClN_3O_2$: 335.2. Found: 358 (M+Na).

Step B: To a solution of $NaBH_4$ (1.13 g, 29.85 mmol) in THF (30 mL) at 0° C. was added TFA (2.3 mL, 29.85 mmol) slowly under nitrogen, followed by the slow addition of a solution of Intermediate T-2 (2.0 g, 5.97 mmol) in THF (15 mL) at 0° C. The reaction mixture was allowed to warm up to room temperature and stirred for 48 hr. The reaction mixture was quenched with water, diluted with ethyl acetate. The organic and aqueous layers were separated. The aqueous was extracted with ethyl acetate. The combined organic layers was washed with water, brine, dried over $Na_2SO_4$ and concentrated to give a crude product, which was purified by biotage (10% methanol in ethyl acetate to 10% $CH_3OH$/10% $Et_3N$ in ethyl acetate) to give Intermediate T-3. ESI-MS calc. for $C_{17}H_{26}ClN_3O_2$: 339. Found: 340 (M+H).

Step C: Intermediate T-4 was prepared from Intermediate T-3 and acetaldehyde following a procedure analogous to the procedure described for the preparation of Intermediate M-1. ESI-MS calc. for $C_{21}H_{34}ClN_3O_2$: 395. Found: 396 (M+H).

Step D: Intermediate T-5 was prepared from Intermediate T-4 following a procedure analogous to the procedure described for the preparation of Intermediate K-2. ESI-MS calc. for $C_{16}H_{26}ClN_3$: 295. Found: 296 (M+H).

Piperazine Intermediate 11

Scheme U

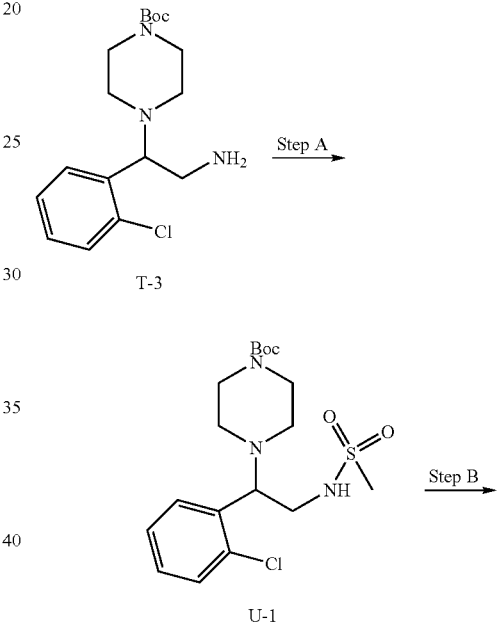

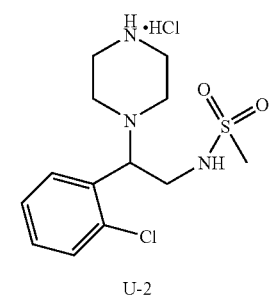

U-2

Step A: Intermediate U-1 was prepared from Intermediate T-3 following a procedure analogous to the procedure described for the preparation of Intermediate R-1. ESI-MS calc. for $C_{18}H_{28}ClN_3O_4S$: 417. Found: 418 (M+H).

Step B: Intermediate U-2 was prepared from Intermediate U-1 following a procedure analogous to the procedure described for the preparation of Intermediate K-2. ESI-MS calc. for $C_{13}H_{20}ClN_3O_2S$: 317. Found: 318 (M+H).

Piperazine Intermediate 12

Scheme V

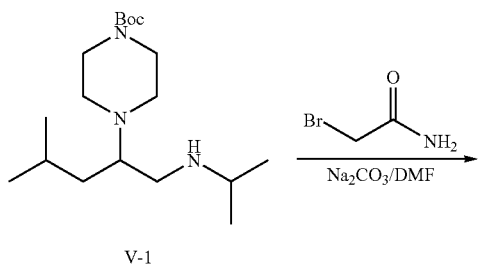

V-1

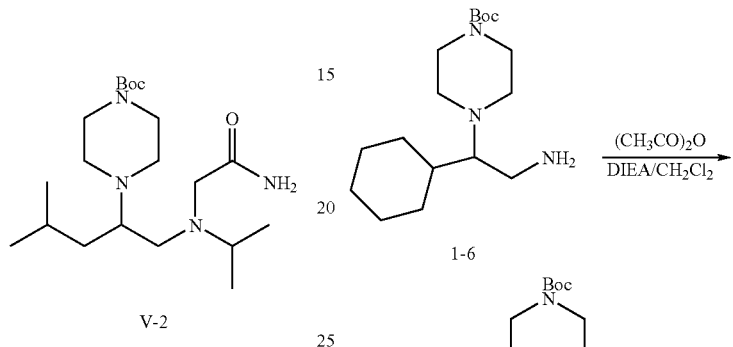

V-2

Step A: Compound V-1 was prepared according to the procedure of Scheme 1 starting with isopropyl aldehyde in place of cyclohexanecarboxaldehyde 1-1.

Step B: To a solution of compound V-1 (280 mg, 0.85 mmole) in DMF (5 ml) was added 2-bromoacetamide (119.1 mg, 0.863 mmole) and sodium carbonate (182.5 mg, 1.722 mmole). After the reaction mixture was stirred at room temperature for 18 hours, water (10 ml) was added. Then the reaction mixture was extracted with $CH_2Cl_2$, washed with $H_2O$, brine, dried over $Na_2SO_4$ and concentrated to give compound V-2 (240 mg) as yellow oil. Mass Spectrum: ESI-MS calc. for $C_{20}H_{40}N_4O_3$: 384. Found: 385 (M+H).

Piperazine Intermediate 13

Scheme W

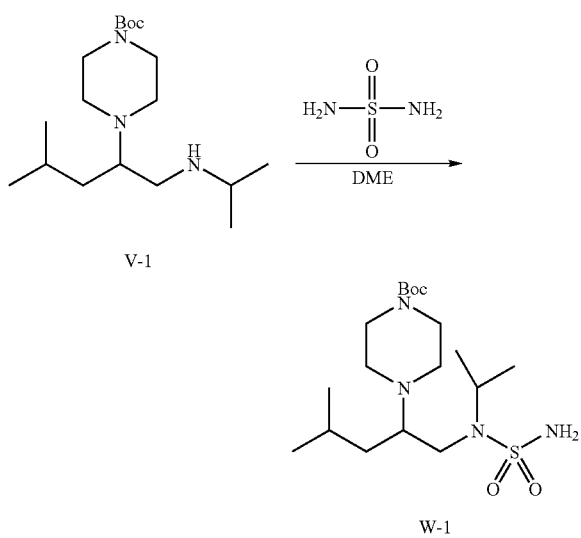

W-1

To a solution of compound V-1 (250 mg, 0.7325 mmole) was added sulfamide (704 mg, 7.324 mmole) in seal bottle and heated at 100° C. for 48 hrs. The reaction mixture was cooled to room temperature and added to $CH_2Cl_2$ and brine, separated two layers. The aqueous was extracted with $CH_2Cl_2$, combined organic was dried over $Na_2SO_4$ and removed solvent to give compound W-1 as yellow oil. Mass Spectrum: ESI-MS calc. for $C_{18}H_{38}N_4O_4S$: 406. Found: 407 (M+H).

Piperazine Intermediate 14

Scheme X

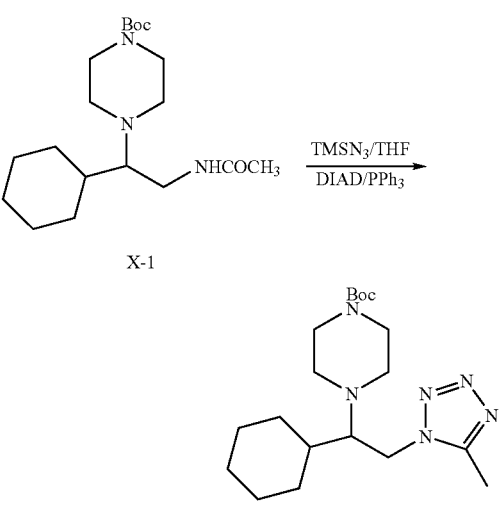

Step A: To a solution of compound 1-6 (512 mg, 1.65 mmole) in $CH_2Cl_2$ (20 ml) was added DIEA (1.06 g, 8.23 mmole), then reaction mixture was cooled to 0° C. and added acetic anhydride. The reaction mixture was warmed up to room temperature and stirred for 18 hrs. and concentrated. The residue was dissolved in $CH_2Cl_2$, washed with $H_2O$, brine and dried over $MgSO_4$, filted and removed solvent to give compound X-1 (0.62 g) as yellow oil. Mass Spectrum: ESI-MS calc. for $C_{19}H_{35}N_3O_3$: 353. Found: 354 (M+H).

Step B: To a solution of compound X-1 (0.326 g, 0.923 mmole) in THF (10 ml) was added triphenylphosphine (0.484 g, 1.85 mmole), DIAD (0.374 g, 1.85 mmole) and $TMSN_3$ (0.213 g, 1.85 mmole). After stirred at room temperature for 24 hrs., the reaction mixture was concentrated, partitioned between $H_2O$ and EtOAc and separated. The aqueous was extracted with EtOAc, washed with $H_2O$, brine and dried over $MgSO_4$, filtered and removed solvent to give yellow oil, which was separated by biotage (Hex: EtOAc=1:1 to 1:2) to give compound X-2 (0.25 g) ESI-MS calc. For $C_{19}H_{34}N_6O_2$: 378. Found: 379 (M+H).

Pyrrolidine Acid Intermediate

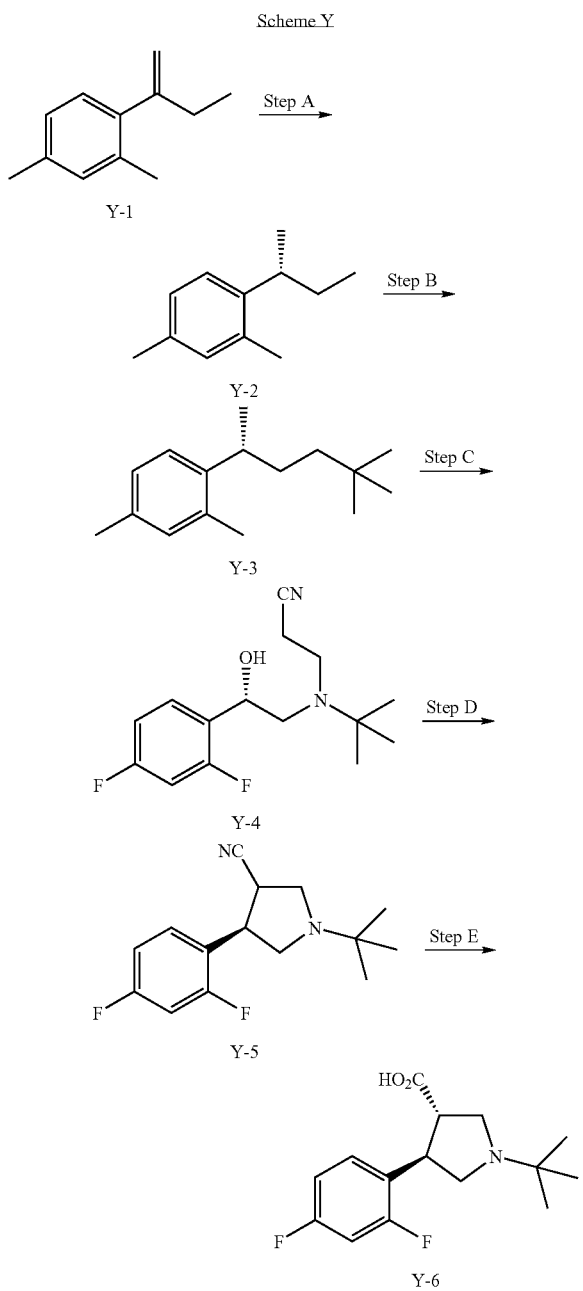

Scheme Y

Step A: A solution of (S)-2-methyl-CBS-oxazaborolidine (131 mL, 1 M in toluene), borane-N,N-diethylaniline (46.36 L) in MTBE (10 L) was heated to 38–42° C., then a solution of 2-chloro-2',4'-di-fluoro-acetophenone Y-1 (4891 g) in MTBE (16 L) was added over 10 hr. The homogeneous solution was stirred at 40° C. for one hour, then allowed to cooled to 18° C. and stirred overnight. Methanol (2.3 L) was added over 60 min, while maintaining the temperature at <20° C. with cooling. The reaction mixture was stirred 30 min, then 5.0 N aq HCl (10 L) was added over 30 min, while maintaining the temperature at 22–25° C. with cooling. After stirring 30 min, the phases were separated, and the organic phase was washed with saturated aqueous NaCl, then concentrated in vacuo to obtain a solution of compound Y-2.

Step B: Compound Y-2 in the MTBE solution from Step A (5040 g, 98 wt %, 25.67 mol) was diluted with methanol (5 L), then tert-butylamine (25 L) was added. The mixture was cooled to 25° C., solid NaOH pellets (1048 g) were added, and the resulting reaction mixture was stirred and warmed to reflux. After 12–20 hr at reflux, the mixture was concentrated in vacuo to ⅓ volume, then water (5 L) and MTBE (20 L) were added. The phases were separated and the aqueous phase was re-extracted with MTBE (2×2 L). The combined extracts were washed with saturated aqueous NaCl (1 L), and then concentrated in vacuo. Heptane (40 L) was added and the concentration was continued to bring the volume to 20 L. The mixture was heated to ~90° C. to dissolve all solids, then allowed to cool to 22° C. to crystallize over 4 hr. The mixture was cooled to 0° C., stirred 12–15 hr, then filtered. The resulting filtrate was washed with cold heptane (2×5 L), then dried in vacuo at 35° C. to obtain compound Y-3.

Step C: A mixture of compound Y-3 (5.205 kg, 99.9%, 22.68 mol) and acrylonitrile (26.9 L, 408 mol) was heated to reflux (~77° C.) under nitrogen atmosphere. After heating for 20 h (~90% conversion), one equivalent each of ethanol (1.32 L, 22.68 mol) and formamide (0.9 L, 22.68 mol) was added and heating was continued for 12 h. After cooling to 22° C., the solution was concentrated to 12 L by distillation (80–90 torr at 20–22° C. pot temperature), and the resulting residue was diluted with isopropyl acetate (22 L) and re-concentrated (55–75 torr and 22–27° C. pot temperature). This was repeated. Then the residue was diluted with isopropyl acetate to a total volume of 34 L, and the supernatant was filtered using a 10–15 μm porosity filter. The filter cake was washed with isopropyl acetate, and the filtrate was diluted with a total of 24 L of isopropyl acetate. The combined filtrate (~54 L) was washed with a solution made up of water (31.2 L), acetic acid (52 mL, 4 mol %), and saturated brine (3.1 L), followed by a 12% aqueous NaCl wash (2×34 L). The organic layer was concentrated (15–45 torr and 5–29° C.) to ~15 L volume and flushed with 5×6 L n-heptane, during which time product crystallized. The slurry was diluted with n-heptane to a volume of 23 L and stirred at 0–5° C. for 1–3 days until a concentration of 10 g/18 L is achieved, then filtered and washed with cold (5° C.) n-heptane (14 L). The wet cake was dried in vacuo at 20° C. with a nitrogen sweep to afford compound Y-4.

Step D: A solution of compound Y-4 (5.73 kg, 99.9%, 20.28 mol) in dry THF (31.3 L) was cooled to −20° C., then chloro diethylphosphate (3.79 kg, 21.29 mol) was added. LiHMDS (1.35 M in THF solution; 31.5 L, 42.58 mol) was slowly added over 1.5 h while maintaining the reaction temperature at −15° C. After stirring at −15° C. for 2 h, the reaction mixture was quenched with water (50.6 L) at <15° C. and extracted with n-heptane (40.5 L) at 20° C. The organic layer was washed with 10% aq NaCl solution (52 L), and extracted with 3 N HCl solution (40.6 L, 121.8 mol) with cooling to keep the temperature <35° C. The aqueous layer (58 L) was adjusted to pH 11–12 with 50% aq NaOH (6.13 L, 116.1 mol) and extracted with n-heptane (54 L). The organic phase was washed once with 10% aq NaCl solution (26 L) and the resulting heptane solution containing compound Y-5 was used in Step E.

Step E: The solution of compound Y-5 (4.88 kg, 18.46 mol) in n-heptane (~65 L total) from the Step D was solvent-switched to ethanol (~20.6 L total). To this solution was added 50% aq NaOH (2.7 L, 51.15 mol) over 2 min with stirring. Upon addition of the NaOH, the temperature of the mixture rose from 16 to 34° C. The mixture was then heated to reflux (78–80° C.) under nitrogen for 5–6 h. After cooling to 20° C., the solution was diluted with ethanol (25.4 L) and methanol (40.6 L). The solution was then cooled to 12° C.; the pH was adjusted to apparent pH 6.8 with 96% H$_2$SO$_4$ (1.42 L, 25.6 mol), while maintaining the temperature at 20° C. The sodium sulfate slurry was filtered through a bed of Solka-Floc® (5 kg) and anhydrous powder Na$_2$SO$_4$ (4 kg), and washed with 1:1 EtOH:MeOH (20 L). The filtrate was filtered, concentrated and solvent-switched to a 2-propanol solution (~15 L volume). The resulting slurry was heated at reflux (~80° C.) for 2 h, then cooled to 16° C. MTBE (30.4 L, 3 vol relative to IPA) was added to the mixture over 5 h. After stirring at 16–17° C. for 3 days, the resulting slurry was filtered and washed with 12 L 1:3 IPA:MTBE. The solids were dried in vacuo (150 torr) at 50° C. with a nitrogen sweep to give compound Y-6.

Piperidine Acid Intermediate

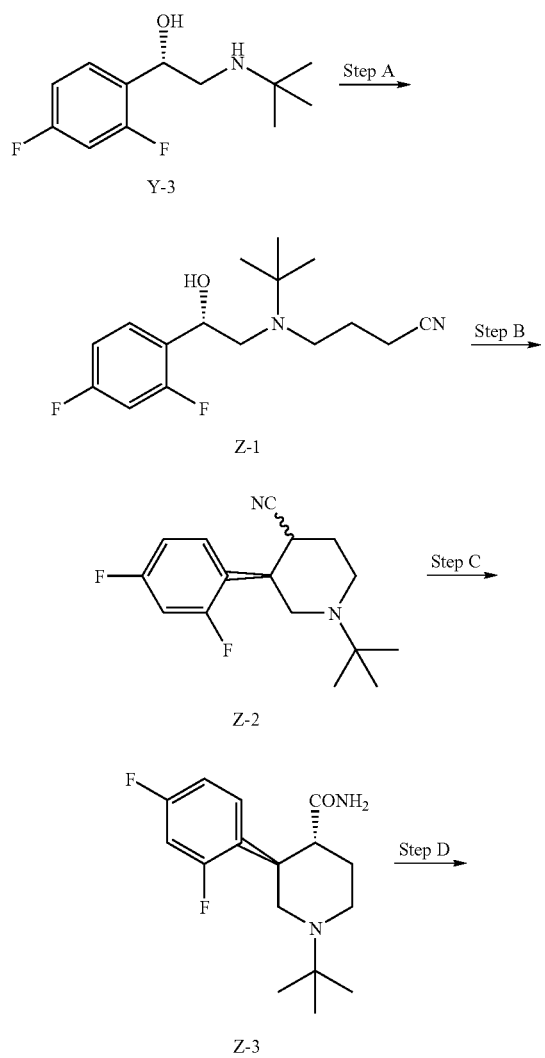

-continued

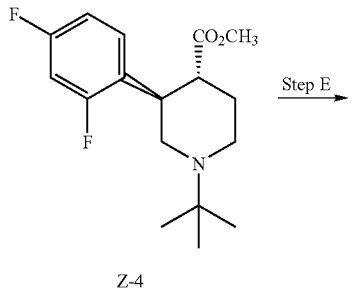

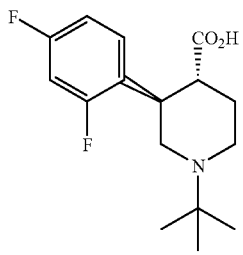

Step A: A mixture of compound Y-3 (24 g, 0.105 mol), 4-bromobutyronitrile (42 g, 0.28 mole, 2.7 eq) K$_2$CO$_3$ (22 g, 0.16 mol, 1.52 eq) and DMF (70 mL) was heated at 50° C. for 64 hr. The reaction was quenched into water (500 mL) and extracted with ether (2×250 mL). The ether layer was extracted with 1N HCl (2×125 mL), and the resulting aqueous layer was extracted with hexanes (2×100 mL). The aqueous layer was then made basic with 5N NaOH, and extracted with ether (2×250 mL). The organic layer was washed with brine, dried with Na$_2$SO$_4$, filtered and concentrated. The residue was chromatographed (silica, 9/1 hexanes/THF then 4:1 hexanes/THF) to give compound Z-1 as a colorless oil.

Step B: Compound Z-1 (50 g, 0.169 mol) was dissolved in THF (500 mL) and the solution was cooled to −15° C. Diethyl chlorophosphonate (25 mL, 1.74 mol, 1.03 eq) was added, followed by the dropwise addition of 1M LiHMDS in THF (350 mL, 2.07 eq). The LiHMDS was added over 100 minutes while maintaining a reaction temperature between −12° C. and −15° C. The reaction was allowed to warm slowly to RT and aged overnight. The reaction was quenched with water and extracted twice with ether. The ether layer was washed with brine, dried with sodium sulfate, filtered and concentrated to give compound Z-2.

Step C: Compound Z-2 was dissolved in ethanol (150 mL), 50% NaOH (24 mL) was added and the mixture was refluxed for 5 hours. The reaction was acidified with 12 N HCl (60 mL) at which point it solidified. The mass was diluted with ethanol (50 nL) and methanol (200 mL), and filtered. The cake was washed with ethanol, and the filtrate was concentrated and flushed with isopropyl alcohol (500 mL). Additional isopropyl alcohol was added and the mixture concentrated to circa 300 mL. The slurry was filtered and the resulting cake was washed with isopropyl alcohol. The solid cakes were combined to give compound Z-3.

Step D: Compound Z-3 was dissolved in methanol (1 L) and saturated with HCl gas. The solution was refluxed for 72 hr, then concentrated and partitioned between ether and saturated NaHCO$_3$ solution. The ether layer was dried with Na$_2$SO$_4$, filtered and concentrated to afford compound Z-4. Additional compound Z-4 was obtained from the filtrate above by similar treatment with HCl/MeOH followed by chromatography (silica 90/10/1 CH$_2$Cl$_2$/MeOH/NH$_4$OH).

Step E: Compound Z-4 was dissolved in 6N HCl (300 mL) and the solution was refluxed for 3 hr. The solution was then concentrated and the resulting residue was dissolved in water and re-concentrated. The residue was then flushed with isopropyl alcohol (2×300 mL) and ethyl acetate (2×500 mL). The resulting slurry was stirred at room temperature for 1 hr and filtered. The resulting solid was washed with ethyl acetate and dried to give compound Z-5.

EXAMPLE 1

Preparation of 2-(4-{[(3S,4R)-1-tert-butyl-4-(2,4-difluorophenyl)pyrrolidin-3-yl]carbonyl}piperazin-1-yl)-2-cyclohexyl-N,N-diethylethanamine 0.138 mmol). The reaction mixture was stirred at room temperature for 18 hrs. The reaction mixture was concentrated, purified by preparative TLC (10:1, CHCl$_3$: 2N NH$_3$ in MeOH) to give a yellow oil, to which was added HCl (1M in ether) and the resulting mixture was concentrated to give the title compound. ESI-MS calc. for C$_{31}$H$_{50}$F$_2$N$_4$O: 532. Found: 533 (M+H). H$^1$ NMR (500 MHz, CD$_3$OD) δ 7.54–7.40 (m, 1H), 7.00–6.82 (m, 2H), 3.92–3.82 (m, 1H), 3.70–3.40 (m, 3H), 3.40–3.25 (m, 2H), 3.24–3.18 (m, 2H), 3.00–2.80 (m, 2H), 2.78–2.42 (m, 8H), 2.40–2.10 (m, 4H), 1.82–1.60 (m, 6H), 1.41–1.00 (m, 19H), Following a procedure similar to that described above for Example 1 but using the corresponding 1-(t-butyl)-3-(2,4-difluorophenyl)-piperidine-4-carboxylic acid intermediate A-4 for the peptide coupling reaction with an appropriately substituted 4-phenyl-piperidine intermediate, the following compound was prepared:

EXAMPLE 2

Preparation of 2-(4-{[(3R,4R)-1-tert-butyl-3-(2,4-difluorophenyl)piperidin-4-yl]carbonyl}piperazin-1-yl)-2-cyclohexyl-N,N-diethylethanamine

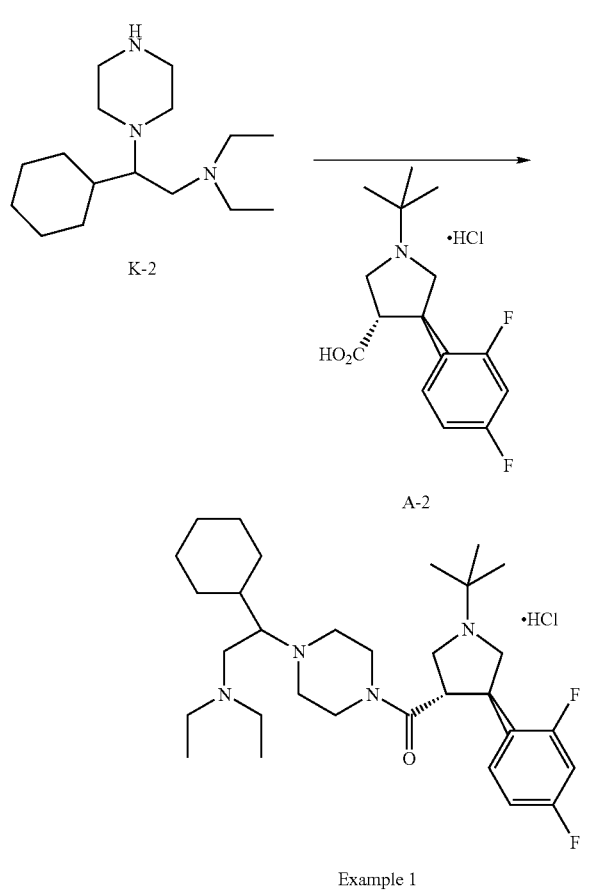

Example 1

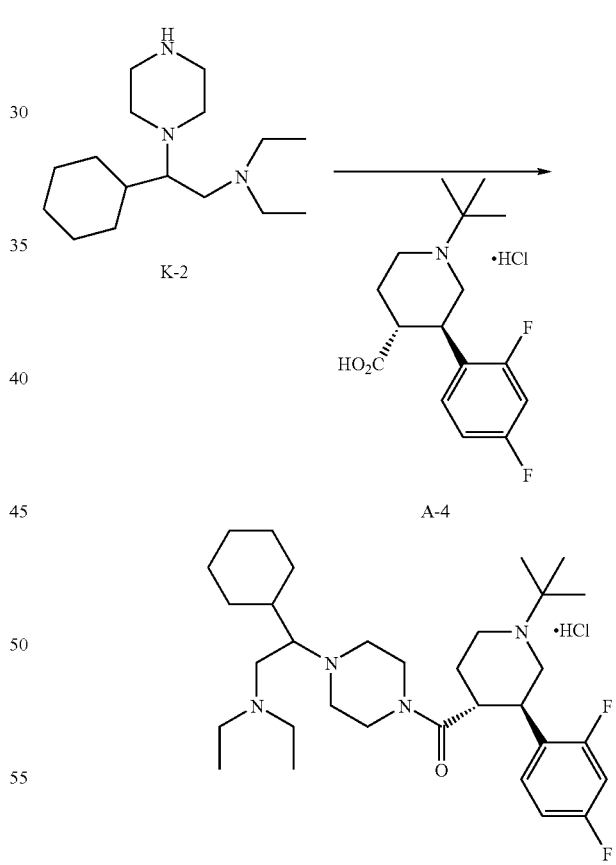

Example 2

To a solution of (3S,4R)-1-tert-butyl-4-(2,4-difluorophenyl)pyrrolidine 3-carboxylic acid A-2 (40 mg, 0.138 mmol) in dichloromethane (10 mL) was added 4-methylmorpholine (0.023 mL, 0.208 mmol), HOBt (20.6 mg, 0.152 mmol), EDC (39.8 mg, 0.208 mmol), and piperazine K-2 (41.9 mg, To a solution of (3S,4R)-1-tert-butyl-3-(2,4-difluorophenyl)-piperidine-4-carboxylic acid A-4 (30 mg, 0.101 mmol) in dichloromethane (5 mL) was added 4-methylmorpholine (0.017 ml, 0.151 mmol), HOBt (15 mg, 0.111 mmol), EDC (29 mg, 0.1514 mmol), and piperazine K-2 (30.6 mg, 0.101 mmol). The reaction mixture was stirred at room temperature for 18 hours. The reaction mixture was then concentrated, purified by preparative TLC (10:1, CHCl$_3$:2N NH$_3$ in MeOH) to give a yellow oil, to which was added HCl (1.0 M in ether) and the resulting mixture was concentrated to give the title compound as a mixture of two diastereomers, D1 and D2. ESI-MS calc. for C$_{32}$H$_{52}$F$_2$N$_4$O: 546. Found: 547 (M+H). D1: NMR (500 MHz, CD$_3$OD) 7.40–7.27 (m, 1H), 6.94–6.82 (m, 2H), 3.68–3.40 (m, 5H), 3.395–3.00 (m, 5H), 2.80–2.20 (m, 11H), 1.94–1.60 (m, 6H), 1.50–0.84 (m, 20H). D2: NMR (500 MHz, CD$_3$OD) 7.40–7.27 (m, 1H), 6.94–6.82 (m, 2H), 3.68–3.00 (m, 10H), 2.80–2.2 (m, 11H), 2.00–1.60 (m, 6H), 1.40–0.80 (m, 20H).

EXAMPLE 3

Preparation of N-[2-(4-{[(3R,4R)-1-tert-butyl-4-(2,4-difluorophenyl)pyrrolidin-3-yl]carbonyl}piperazin-1-yl)-2-cyclohexylethyl]-N-isopropylacetamide

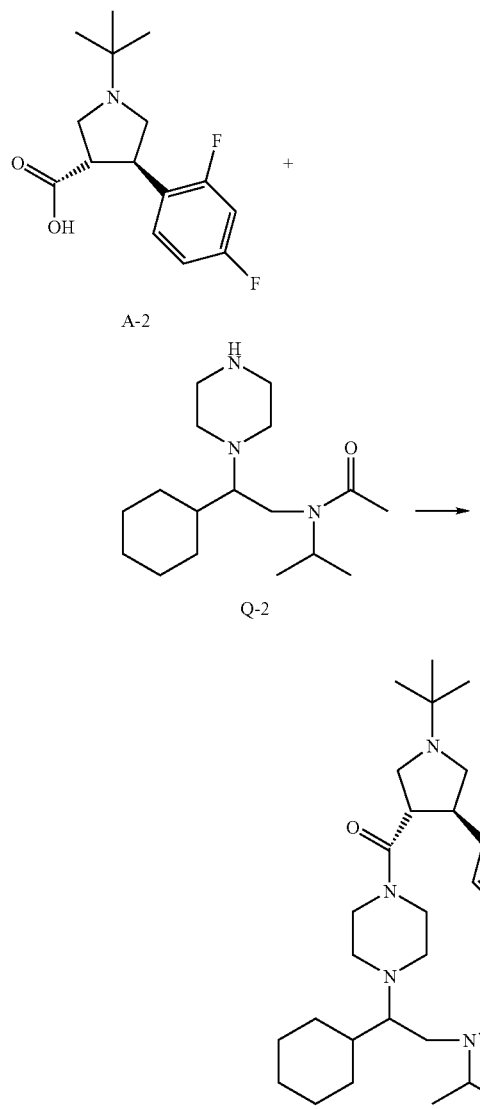

To a solution of (3S,4R)-1-tert-butyl-4-(2,4-difluorophenyl) pyrrolidine 3-carboxylic acid A-2 (38.3 mg, 0.133 mmol) in dichloromethane (5 ml) was added 4-methylmorpholine (0.020 ml, 0.181 mmol), HOBt (17.9 mg, 0.133 mmol), EDC (34.6 mg, 0.181 mmol), and Intermediate Q-2 (40 mg, 0.121 mmol). The reaction mixture was stirred at room temperature for 18 hrs, then it was diluted with dichloromethane, washed with water and brine, dried over Na$_2$SO$_4$ and concentrated, purified by preparative TLC (chloroform: 2N NH$_3$ in methanol=10:1) to give a yellow oil, to which was added HCl (1 M in ether) and the resulting mixture was concentrated to give the title compound as a white solid. ESI-MS calc. For C$_{32}$H$_{50}$F$_2$N$_4$O$_2$: 560. Found: 561 (M+H). $^1$H NMR (500 MHz, CD$_3$OD): δ 7.58–7.42 (m, 1H), 7.00–6.82 (m, 2H), 4.14–4.00 (m, 1H), 3.90–3.80 (m, 1H), 3.80–3.50 (m, 3H), 3.42–3.12 (m, 6H), 3.12–2.20 (m, 7H), 2.20–2.05 (m, 3H), 1.80–1.60 (m, 5H), 1.60–1.40 (m, 1H), 1.40–1.00 (m, 20H).

EXAMPLE 4

Preparation of N-[2-(4-{[(3R,4R)-1-tert-butyl-4-(2,4-difluorophenyl)pyrrolidin-3-yl]carbonyl}piperazin-1-yl)-2-cyclohexylethyl]-N-isopropylmethanesulfonamide

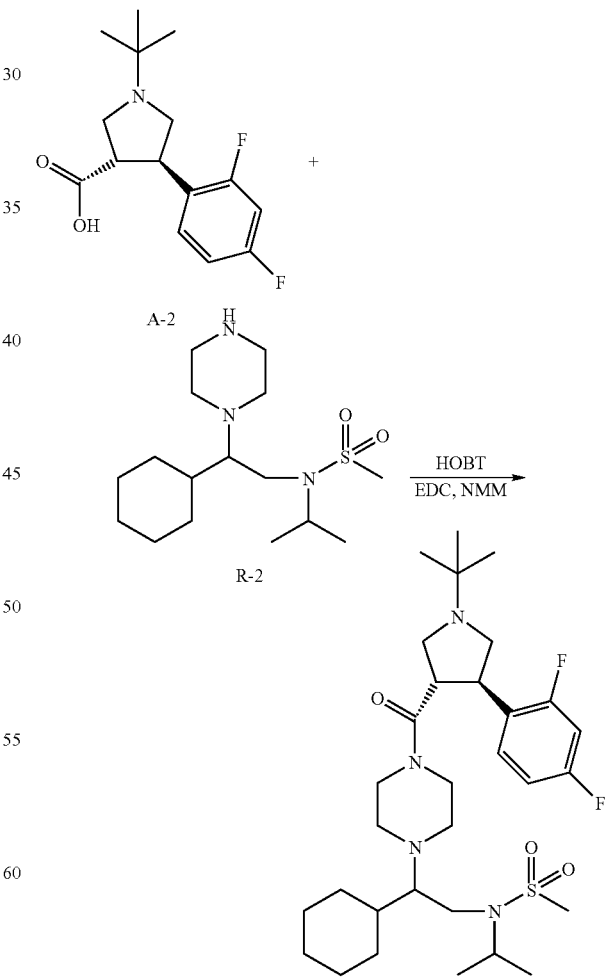

To a solution of (3S,4R)-1-tert-butyl-4-(2,4-difluorophenyl) pyrrolidine-3-carboxylic acid A-2 (47.9 mg, 0.166 mmol) in dichloromethane (5 ml) was added 4-methylmorpholine (0.025 ml, 0.2265 mmol), HOBt (22.4 mg, 0.166 mmol), EDC (43.4 mg, 0.227 mmol), and Intermediate R-2 (50 mg, 0.151 mmol). The reaction mixture was stirred at room temperature for 18 hrs, then it was diluted with dichloromethane, washed with water and brine, dried over $Na_2SO_4$ and concentrated, purified by preparative TLC (chloroform: 2N $NH_3$ in methanol=10:1) to give a yellow oil, to which was added HCl (1 M in ether) and the resulting mixture was concentrated to give the title compound as a yellow solid. ESI-MS calc. for $C_{31}H_{50}F_2N_4O_3S$: 596. Found: 597 (M+H). $^1$H NMR (500 MHz, $CD_3OD$): δ 7.58–7.41 (m, 1H), 7.00–6.83 (m, 2H), 3.90–3.80 (m, 2H), 3.79–3.50 (m, 3H), 3.50–3.10 (m, 6H), 3.10–2.96 (m, 1H), 2.95 (s, 3H), 2.86–2.20 (m, 3H), 2.20–2.00 (m, 3H), 1.80–1.60 (m, 5H), 1.60–1.40 (m, 1H), 1.40–1.01 (m, 20H).

EXAMPLE 5

Preparation of N-{1-[2-(4-{[(3S,4S)-1-tert-butyl-4-(2,4-difluorophenyl)pyrrolidin-3-yl]carbonyl}piperazin-1-yl)-4,5-dimethylphenyl]ethyl}acetamide (5-7)

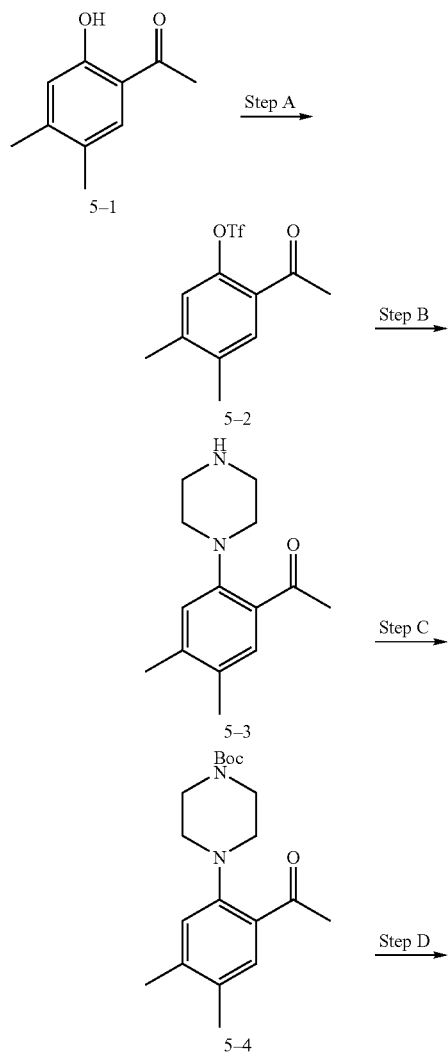

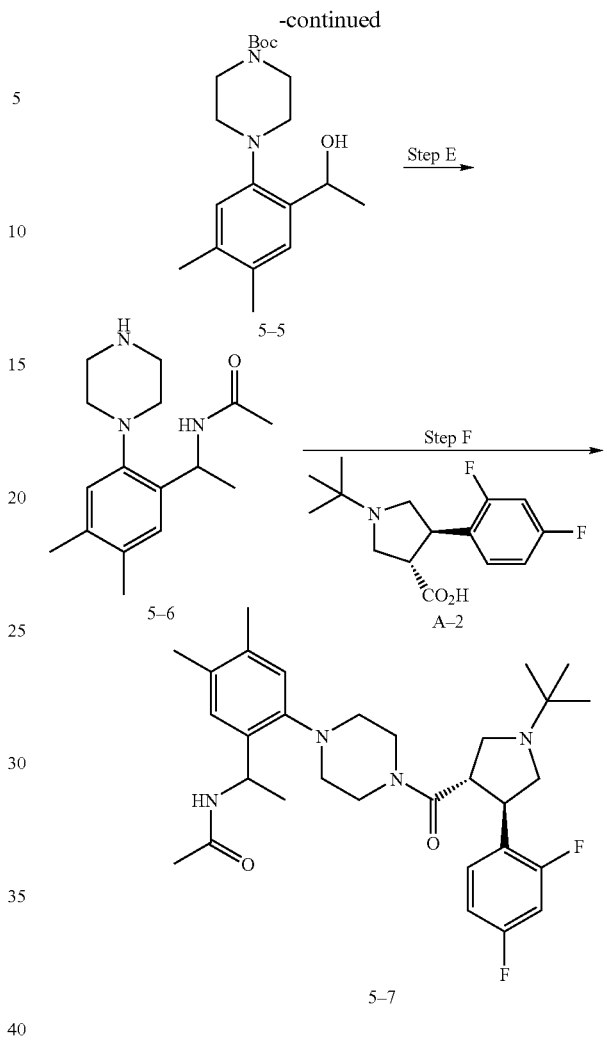

Step A: To a mixture of 2'-hydroxy-4',5'-dimethylacetophenone ketone 5-1 (15.0 g, 91.3 mmol, INDOFINE Chemical Company, Inc.) and 4-dimethylamino-pyridine (1.13 g, 9.30 mmol) in anhydrous methylene chloride (200 mL) at −78° C. was added triethylamine (14.0 mL, 100 mmol) followed by trifluoromethanesulfonic anhydride (28.2 mL, 167 mmol) dropwise via syringe. The reaction was stirred at −78° C. for 3 hours. The reaction mixture was then poured into ice water, diluted with saturated aqueous ammonium chloride, and extracted three times with ethyl acetate. The combined organic extracts were washed with brine. The organic layer was dried over magnesium sulfate, filtered and concentrated in vacuo. The residue was purified on silica using ethyl acetate/hexanes (gradient elution; 4%–100%) to elute the desired product 5-2.

Step B: To a stirred solution of the ketone 5-2 (10.0 g, 33.8 mmol) in anhydrous acetonitrile was added piperazine (14.0 g, 117 mmol). The reaction mixture was stirred at reflux for 18 hours under an atmosphere of nitrogen. The reaction mixture was cooled to room temperature and then was concentrated in vacuo to give the desired product 5-3.

Step C: To a stirred solution of the ketone 5-3 (1.00 g, 4.30 mmol) in anhydrous methylene chloride and triethylamine (4.30 g, 43.0 mmol) was added di-tert-butyl dicarbonate (5.60 g, 25.8 mmol). The reaction mixture was stirred for 18 hours. The reaction mixture was diluted with methylene chloride and washed three times with 1N NaOH, three times with water and once with brine. The combined organic layers were dried over magnesium sulfate, filtered and concentrated in vacuo. The residue was purified on silica using ethyl acetate/heptane (gradient elution; 8%–34%) to elute the desired product 5-4.

Step D: To a stirred solution of the ketone 5-4 (1.0 g, 3.0 mmol) in tetrahydrofuran and methanol (9:1, 30 mL) at −10° C. was added sodium borohydride (238 mg, 6.3 mmol). The reaction was allowed to continue for 72 hours at 5° C. The reaction was quenched with water, poured into saturated aqueous sodium bicarbonate, and extracted three times with methylene chloride. The combined organic extracts were washed with brine. The organic layer was dried over magnesium sulfate, filtered and concentrated in vacuo. The residue was purified on silica using ethyl acetate/heptane (gradient elution; 11%–45%) to elute the desired product 5-5.

Step E: To a stirred solution of the alcohol 5-5 (300 mg, 0.898 mmol) in anhydrous acetonitrile (8.9 ml) was added 18 N sulfuric acid (0.598 ml, 10.8 mmol). The reaction mixture was stirred for 18 hours and then was concentrated in vacuo to give a residue. This residue was diluted with 5N NaOH until litmus paper turns dark blue. This basic aqueous solution was extracted with ethyl acetate three times. The combined organic layers were washed with brine, dried over magnesium sulfate, filtered and concentrated in vacuo to give desired product 5-6.

Step F: To acetamide 5-6 (220 mg, 0.8 mmol) was added (3S,4R)-1-tert-butyl-4-(2,4-difluorophenyl)pyrrolidine-3-carboxylic acid A-2 (254 mg, 0.898 mmol) then DMF (10.0 mL) and DIEA (0.624 mL, 3.6 mmol), followed by HATU (341 mg, 0.898 mmol) to give a yellow reaction mixture. After 18 hours, the reaction mixture was diluted with 1N NaOH and extracted three times with ether. The combined organic extracts were washed with brine three times. The organic layer was dried over magnesium sulfate, filtered and concentrated in vacuo. This residue was purified by preparatory thin layer chromatography on silica (methylene chloride/MeOH/NH$_4$OH: 19/1/0.1). The desired band of silica was cut from the plates. The product was separated from silica by sonication in methanol followed by filtration. The product was concentrated in vacuo, dissolved in methylene chloride and passed through an acrodisk filter. The product was concentrated in vacuo and excess HCl in diethyl ether was added to give the titled compound as a white solid (360 mg, 83% yield). Mass Spectrum: Calcd. for $C_{31}H_{42}N_4O_2F_2$: 540.7. Found: 541.25 (M$^+$+1).

EXAMPLE 6

Preparation of N-{1-[2-(4-{[(3S,4S)-1-tert-butyl-4-(2,4-difluorophenyl)pyrrolidin-3-yl]carbonyl}piperazin-1-yl)-4,5-dimethylphenyl]ethyl}-N-isopropylacetamide (6-4)

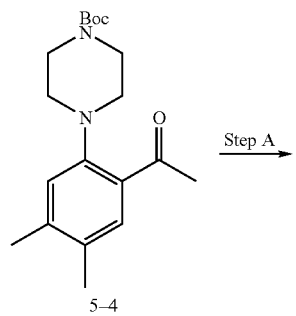
5-4

Step A

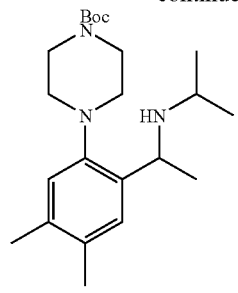
6-1

Step B

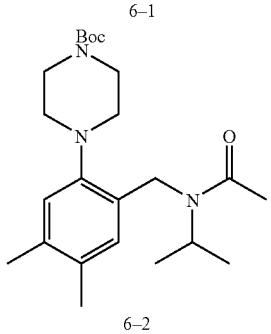
6-2

Step C

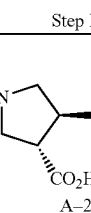
6-3

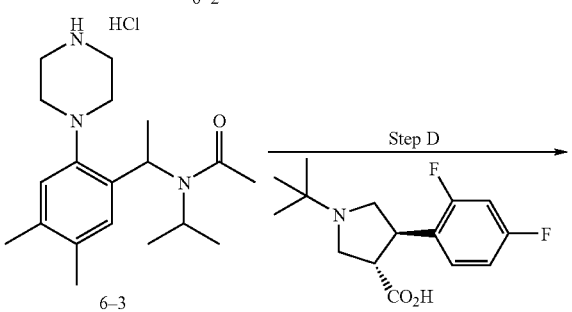
A-2

Step D

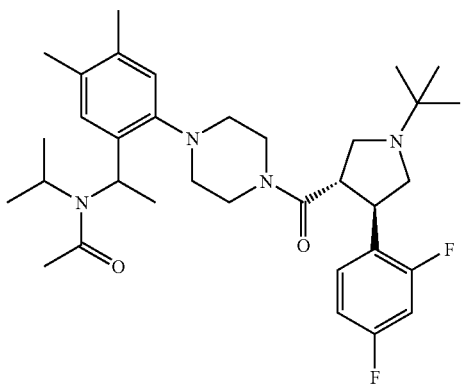
6-4

Step A: To a stirred solution of ketone intermediate 5-4, as prepared in Example 5, Step C (530 mg, 1.59 mmol) in anhydrous methanol (15 ml) was added isopropyl amine (0.27 ml, 3.19 mmol) followed by sodium acetate (651 mg; 7.95 mmol). Molecular sieves were added to remove water (530 mg). The reaction was stirred at reflux for 18 hours. The reaction was cooled to room temperature, filtered through a bed of Celite, and then concentrated. The crude residue was dissolved in anhydrous methylene chloride (15 ml). Sodium cyanoborohydride (1.0 M solution in THF, 4.02 mmol) was added. The reaction mixture was stirred at reflux for 18 hours. The reaction mixture was cooled to room temperature and was washed with a 1N NaOH and then with brine. The organic layer was dried over magnesium sulfate, filtered and concentrated in vacuo to give the desired compound 6-1.

Step B: To a stirred solution of the amine 6-1 (225 mg, 0.60 mmol) in anhydrous methylene chloride (6.0 ml) at 0° C. was added DIEA (0.86 ml, 4.8 mmol) and then acetyl chloride (0.257 ml, 3.60 mmol). The reaction was allowed to stir at room temperature for 18 hours. The reaction mixture was diluted with methylene chloride and washed 1N NaOH and then with brine. The organic layer was dried over magnesium sulfate, filtered and concentrated in vacuo. The residue was purified on silica using ethyl acetate/hexanes (gradient elution; 15%–100%) to elute the desired product 6-2.

Step C: To a stirred solution of acetamide 6-2 (250 mg, 0.60 mmol) in ethyl acetate (6.0 ml) was added 4.0 M hydrogen chloride solution in 1,4-dioxane (6.0 ml). The reaction mixture was stirred at room temperature for 4 hours and evaporated in vacuo to give the desired product 6-3.

Step D: To acetamide intermediate 6-3 (200 mg, 0.56 mmol) was added (3S,4R)-1-tert-butyl-4-(2,4-difluorophenyl)pyrrolidine-3-carboxylic acid A-2 (160 mg, 0.565 mmol) then DMF (10.0 mL) and DIEA (0.402 mL, 2.20 mmol), followed by HATU (215 mg, 0.56 mmol) to give a yellow reaction mixture. After 18 hours, the reaction mixture was diluted with 1N NaOH and extracted three times with ether. The combined organic extracts were washed with brine three times. The organic layer was dried over magnesium sulfate, filtered and concentrated in vacuo to give a residue. This residue was purified by preparative reversed phase high pressure liquid chromatography (YMC Pack Pro C18, gradient elution; 20–100% acetonitrile/water as eluent, 0.1% TFA modifier) gave desired product as the TFA salt after concentration in vacuo. The TFA salt was partitioned between methylene chloride and 1N NaOH. The organic layer was separated and the aqueous phase was extracted twice with methylene chloride. The combined organic extracts were washed with brine. The organic layer was dried over magnesium sulfate, filtered and concentrated in vacuo to give the product as the free base. Excess HCl in diethyl either was added to give the titled compound as a white solid. Mass Spectrum: Calcd. for $C_{34}H_{48}N_4O_2F_2$: 582.7. Found: 583.8 ($M^+$+1).

EXAMPLES 7–14

Using the appropriate starting materials and intermediates, including the (3R,4S)-1-tert-butyl-4-(2,4-difluorophenyl)pyrrolidine-3-carboxylic acid A-2 for the peptide coupling reaction, and following procedures similar to that described above for Example 1, the following compounds 7–14 were prepared:

| Ex. # | $R^5$ | $R^7$ | Calculated MW | Parent Ion m/z (M + H) Found |
|---|---|---|---|---|
| 7 | cyclohexyl-CH< | -CH(-)-N(CH2CH2CH3)(CH2CH2CH3) | $C_{33}H_{54}F_2N_4O$ 560 | 561 (M + H) |
| 8 | cyclohexyl-CH< | -CH(-)-N-piperidinyl-isopropyl | $C_{35}H_{58}F_2N_4O$ 588 | 582 (M + H) |
| 9 | cyclohexyl-CH< | -CH2-NH-C(CH3)- | $C_{30}H_{48}F_2N_4O$ 518 | 518 (M + H) |

-continued
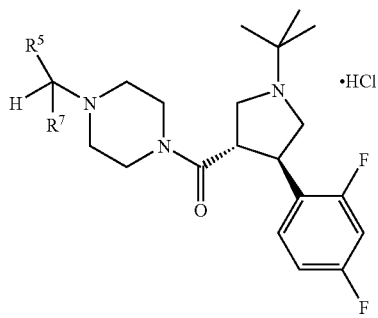
| Ex. # | R⁵ | R⁷ | Calculated MW | Parent Ion m/z (M + H) Found |
|---|---|---|---|---|
| 10 | cyclohexyl | –CH₂–N(CH₃)–CH(CH₃)₂ | C₃₁H₅₀F₂N₄O 532 | 533 (M + H) |
| 11 | cyclohexyl | –CH₂–N(C₂H₅)–CH(CH₃)₂ | C₃₂H₅₂F₂N₄O 546 | 547 (M + H) |
| 12 | cyclohexyl | –CH₂–NH–SO₂–CH₃ | C₂₈H₄₄F₂N₄O₃S 554 | 555 (M + H) |
| 13 | 2-chlorophenyl | –CH₂–NH–SO₂–CH₃ | C₂₈H₃₈ClF₂N₄O₃S 584 | 585 (M + H) |
| 14 | 2-chlorophenyl | –CH₂–N(C₂H₅)₂ | C₃₁H₄₃ClF₂N₄O 561 | 562 (M + H) |

EXAMPLES 15–19

Using the appropriate starting materials and intermediates, including (3S,4R)-1-tert-butyl-3-(2,4-difluorophenyl)-piperidine-4-carboxylic acid A-4 for the peptide coupling reaction, and following procedures similar to that described above for Example 2, the following compounds 15–19 were prepared:

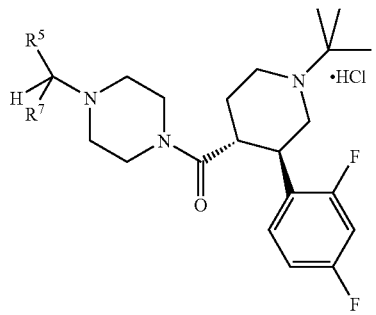

| Ex. # | R⁵ | R⁷ | Calculated MW | Parent Ion m/z (M + H) Found |
|---|---|---|---|---|
| 15 | cyclohexyl-CH₂- | -CH₂-N(propyl)₂ | $C_{34}H_{56}F_2N_4O$ 575 | 576 (M + H) |
| 16 | cyclohexyl-CH₂- | -CH₂-(3,5-dimethylpiperidin-1-yl) | $C_{36}H_{60}F_2N_4O$ 603 | 604 (M + H) |
| 17 | cyclohexyl-CH₂- | -CH₂-NH-iPr | $C_{31}H_{50}F_2N_4O$ 532 | 533 (M + H) |
| 18 | cyclohexyl-CH₂- | -CH₂-N(Et)(iPr) | $C_{33}H_{54}F_2N_4O$ 560 | 561 (M + H) |
| 19 | 2-chlorophenyl-CH(CH₃)- | -CH₂-N(Et)₂ | $C_{32}H_{45}ClF_2N_4O$ 575 | 576 (M + H) |

EXAMPLE 20
Preparation of N-{1S or 1R}-1-[2-(4-{[(3R,4R)-1-tert-butyl-3-(2,4-difluoro-phenyl)piperidine-4-yl]carbonyl}piperazine-1-yl)-4-chloro-5-methylphenyl]ethyl}-N-isopropylacetamide (7-8)
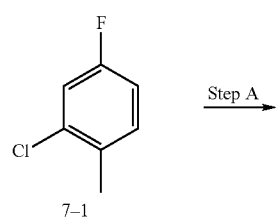
7–1 → Step A
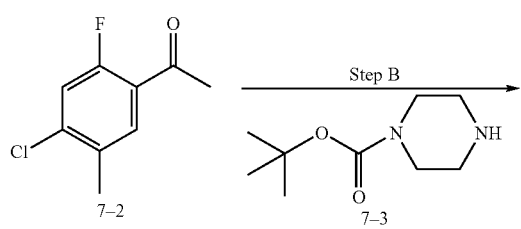
7–2    7–3 → Step B
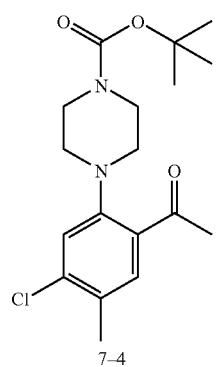
7–4 → Step C
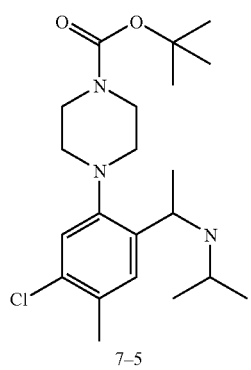
7–5 → Step D
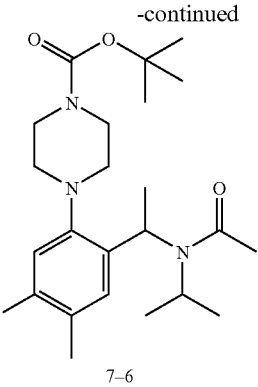
7–6 → Step E
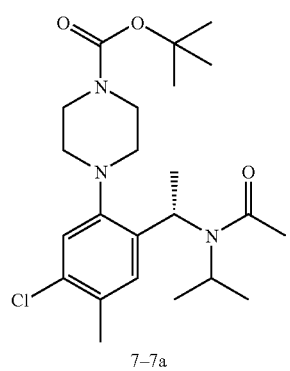
7–7a   +
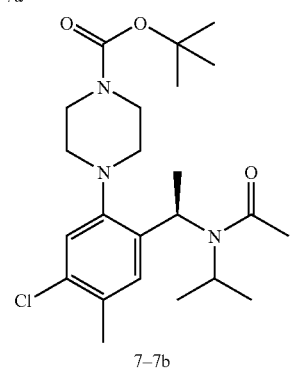
7–7b
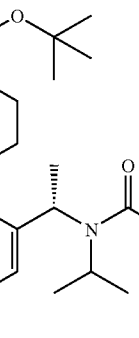
7–7a → Step F
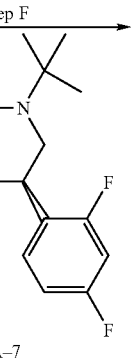
A–7

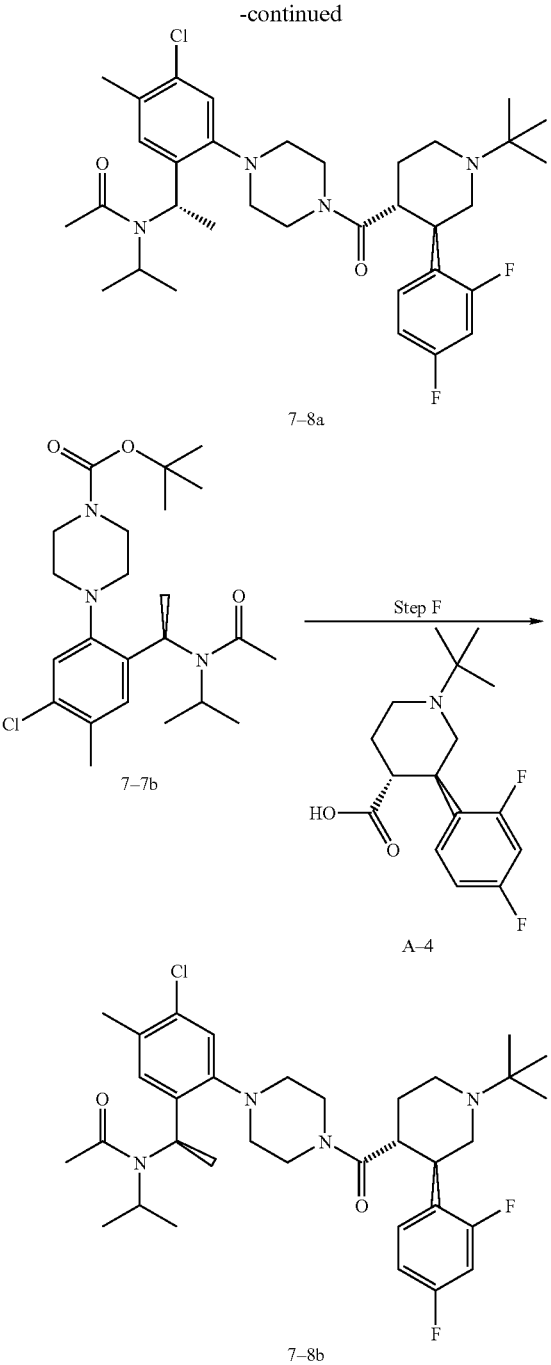

Step A: A slurry of 2-chloro-4-fluorotoluene 7-1 (30.0 g, 207 mmol) and aluminum trichloride (83.0 g, 622 mmol) was prepared in a 1 L three-neck round-bottom flask, then acetyl chloride (57.0 g, 726 mmol) was added at room temp and the reaction mixture was stirred for 72 h at 50° C. The resulting dark purple mass was quenched with ice-cooled water and extracted with methylene chloride. The organic layers were washed with water and brine, dried with anhydrous magnesium sulfate, filtered and concentrated under reduced pressure to give a crude purple product that was purified with flash column chromatography on silica gel (gradient 2–100% EtOAc in heptanes) to give compound 7-2 as a yellow needle solid upon standing. Mass Spectrum: Calcd. for $C_9H_8ClFO$: 186. Found: 187 ($M^++1$).

Step B: A mixture of 1-(4-chloro-2-fluoro-5-methylphenyl)ethanone 7-2 (16.1 g, 86.3 mmol), tert-butyl piperazine-1-carboxylate 7-3 (17.7 g, 94.9 mmol) and potassium carbonate (14.3 g, 104 mmol) was stirred in DMF (200 mL) and heated overnight at 152° C. under an atmosphere of nitrogen. The reaction was then cooled to room temperature and partitioned between EtOAc and a saturated aqueous ammonium chloride solution. The aqueous layer was extracted three times with EtOAc. The EtOAc layers were combined and washed with a saturated aqueous ammonium chloride solution and brine, dried with anhydrous magnesium sulfate, filtered and concentrated. The residue was purified with flash column chromatography on silica gel (gradient 6–100% EtOAc in heptanes) to give compound 7-4 as an orange solid. Mass Spectrum: Calcd. for $C_{18}H_{25}ClN_2O$: 352. Found: 353 ($M^++1$).

Step C: To a solution of tert-butyl 4-(2-acetyl-5-chloro-4-methylphenyl)piperazine-1-carboxylate 7-4 (19.6 g, 55.4 mmol) in anhydrous methanol (200 mL) was added sodium acetate (22.7 g, 277 mmol), 3 Å molecular sieves, and then isopropyl amine (37.8 mL, 443 mmol). The mixture was allowed to stir at 80° C. overnight. Additional 40 mL of isopropyl amine were added and the mixture was stirred for another 2 hours. After cooling to room temperature, sodium borohydride (17.0 g, 449 mmol) was added portionwise. The mixture was stirred for 30 min and quenched with water. Methanol was removed under reduced pressure and mixture was diluted with 1N NaOH aqueous solution and partitioned with EtOAc. The EtOAc layer was dried over anhydrous magnesium sulfate, filtered and concentrated to give compound 7-5 as an oil. Mass Spectrum: Calcd. for $C_{21}H_{34}ClN_3O_2$: 395. Found: 396 ($M^++1$).

Step D: To a solution of tert-butyl 4-{5-chloro-2-[1-(isopropylamino)ethyl]-4-methylphenyl}piperazine-1-carboxylate 7-5 (21.9 g, 55.3 mmol) in pyridine (110 mL) was added acetic anhydride (39.8 mL, 421 mmol) at 0° C. under an atmosphere of nitrogen. After slowly warming up to room temperature, the reaction mixture was stirred overnight. The volatiles were removed under reduced pressure and the residue was purified with flash column chromatography on silica gel (gradient 13–100% EtOAc in heptanes) to give compound 7-6 as oil. Mass Spectrum: Calcd. for $C_{24}H_{36}ClN_3O_3$: 437. Found: 438 ($M^++1$).

Step E: Separation of the racemic mixture of tert-butyl-4-(2-{1-[acetyl(isopropyl)-amino]ethyl}-5-chloro-4-methylphenyl)piperazine-1-carboxylate 7-6 (15.8 g) with Super Critical Fluid Chromatography (SFC) over a ChiralCel OD 20×250 mm column eluting with 25% 1:1 heptanes:EtOH in $CO_2$, flow rate at 50 mL per mine, 0.4 mL per injections with the concentration of the solution as 300 mg per mL, afforded the compounds 7-7a and 7-7b as white solids. The racemic mixture of 7-7a and 7-7b can be converted to a racemic mixture of 7-8a and 7-8b; or alternatively each individual stereoisomer of 7-7 can be converted to the corresponding product (7-7a to 7-8a and 7-7b to 7-8b) as described in Step F.

Alternatively, the racemic mixture of compound 7-6 may be separated into its individual stereoisomers by the following procedure: compound 7-6 (6.83 g, 15.59 mmol) was dissolved in 60 mL IPAC. 5N HCl in isopropyl alcohol (20 mL) was added at room temperature. The resulting solution was stirred over night, then partitioned with 10% aqueous $K_3PO_4$ and extracted. Resulting organic solution was washed with brine, dried and concentrated to provide a 100 mg/mL solution of free base in isopropyl acetate (50 mL solution, 5.09 g, 14.8 mmol). To this solution is added a 100 mg/mL solution of S-(+)-mandelic acid (14.8 mmol, 2.25 g) in MeOH (22.5 mL). The resulting solution is allowed to crystallize and stirred overnight. The mixture was filtered and the solid dried to provide the mandelate salt of 7-7b. The mandelate salt of 7-7a is found in the mother liqour.

Step F: To a solution of (R) or (S)-tert-butyl-4-(2-{1-[acetyl(isopropyl)amino]ethyl}-5-chloro-4-methylphenyl)piperazine-1-carboxylate 7-7a or 7-7b (7.30 g, 16.7 mmol) in dichloromethane (10 mL) was added 4 N HCl in dioxane (50 mL) and the mixture was stirred at room temperature for 30 min. Then the volatiles were removed under reduced pressure and the resulting residue was dissolved in dichloromethane (160 mL) and (3R,4R)-1-tert-butyl-4-carboxy-3-(2,4-difluorophenyl)pyrrolidium chloride A-4 (6.68 g, 20.0 mmol), O-(7-azabenzotriazol-1-yl)-N,N,N',N',-tetramethyluronium hexafluorophosphate (HATU, 7.60 g, 20.0 mmol), 1-hydroxyl-7-azabenzotriazole (HOAT, 2.72 g, 20.0 mmol), and DIEA (10.8 g, 83.3 mmol) were added. The mixture was stirred at room temperature overnight, diluted with dichloromethane, quenched with 1N NaOH aqueous solution. The layers were separated and the organic layer was washed with brine, dried over anhydrous magnesium sulfate, filtered, and concentrated. The resulting residue was purified by a flash column chromatography with silica gel and eluted with 10% MeOH in dichloromethane containing 1% of a 30% NH$_4$OH aqueous solution. The eluates were concentrated and the residue was purified again with semi-prep HPLC on a 20×250 mm C-18 column (gradient 5–95% acetonitrile in water containing 0.1% TFA). The eluates were concentrated and 1N NaOH aqueous solution was added to adjust the solution to basic, and the aqueous mixture was extracted with EtOAc. The combined organic layers were washed with brine, dried over anhydrous magnesium sulfate, filtered, and concentrated to give compound 7-8a or 7-8b as white solid. Mass Spectrum: Calcd. for $C_{34}H_{47}ClF_2N_4O_2$: 616. Found: 617 (M$^+$+1). Compound 7-8a: $^1$H NMR (CD$_3$OD) 7.6 (s, 1H), 7.50 (m, 1H) 7.44 (s, 1H), 7.06 (m, 2H), 5.47 (d, 1H), 3.78–3.87 (m, 4H), 3.64–3.78 (m, 4H), 3.23–3.37 (m, 4H), 2.89 (m, 1H), 2.66 (m, 1H), 2.38 (m, 6H), 2.20 (m, 2H), 1.52–1.58 (d, 4H), 1.44–1.47 (m, 9H), 1.35–1.37 (m, 3H), 0.89–0.95 (m, 1H), 0.75–0.77 (d, 2H). Compound 7-8b: $^1$H NMR (CD$_3$OD) 7.53 (m, 2H), 7.44 (m, 1H), 7.09 (m, 2H), 5.45 (d, 1H), 3.74–3.91 (m, 4H), 3.58–3.73 (m, 4H), 3.22–3.36 (m, 4H), 2.76 (m, 1H), 2.70 (m, 1H), 2.38 (m, 6H), 2.16 (m, 2H), 1.52–1.53 (d, 4H), 1.46–1.47 (m, 9H), 1.35–1.45 (m, 3H), 0.85 (m, 1H), 0.76–0.77 (d, 2H). To the free base of compound 7-8a or 7-8b in isopropyl acetate or isopropyl alcohol at 60–65° C. was added H$_3$PO$_4$ in isopropyl alcohol (2 equivalents). The solution was seeded and then cooled to room temperature and stirred overnight at room temperature. The solid was then filtered, washed with isopropyl acetate, and dried in a vacuum oven under nitrogen swipe at 40–50° C. to form the bis-phosphate salt of the title compound 7-8a or 7-8b.

EXAMPLE 21

Preparation of N-{1-[2-(4-{[(3R,4R)-1-tert-butyl-3-(2,4-difluorophenyl)piperidin-4-yl]carbonyl}piperazin-1-yl)-4-chloro-5-methylphenyl]ethyl}acetamide (21-5)

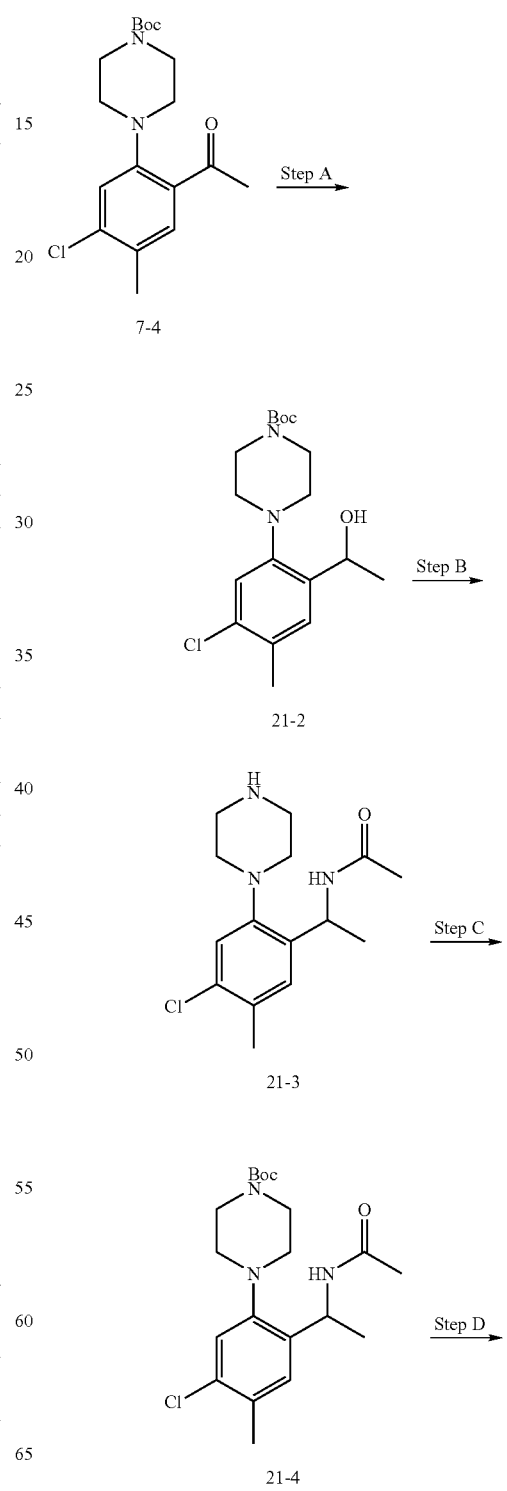

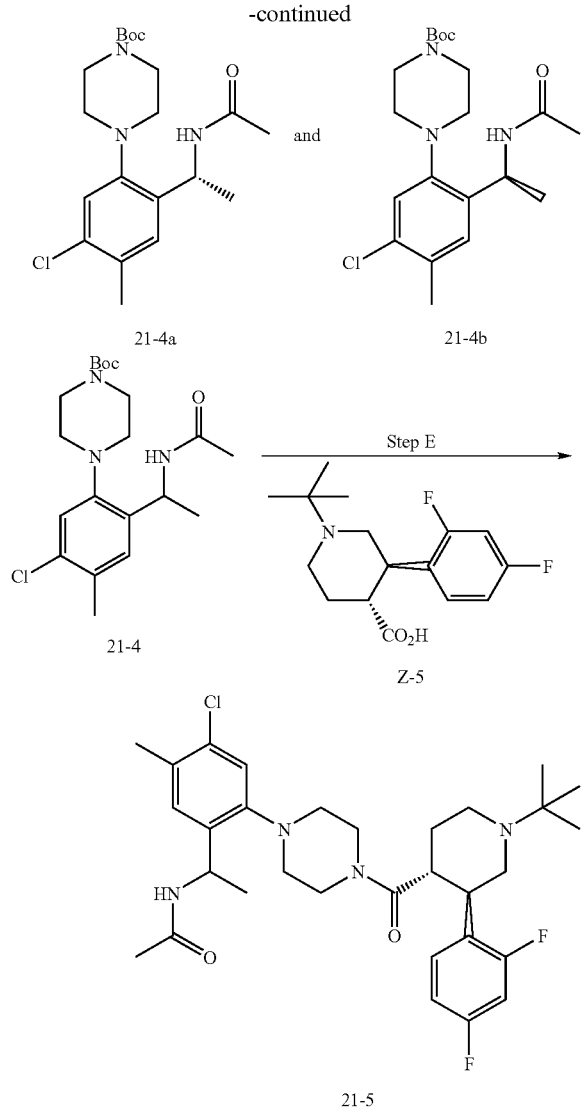

in vacuo to give a residue. The residue was purified on silica using acetone/heptanes (gradient elution; 10%–100%) to give compound 21-4.

Step D: The racemic mixture of tert-butyl 4-{2-[1-(acetylamino)ethyl]-5-chloro-4-methylphenyl}piperazine-1-carboxylate 21-4 (300 mg) was separated on a ChiralCel AD 20×250 mm column eluting with 5% Ethanol/Heptanes at a flow rate at 50 mL per min, 50 mg per injection to afford the compounds 21-4a and 21-4b as white solids.

Step E: To a solution of (R) or (S)-tert-butyl 4-{2-[1-(acetylamino)ethyl]-5-chloro-4-methylphenyl}piperazine-1-carboxylate, 21-4a or 21-4b, (111 mg, 0.280 mmol) in dichloromethane (10 mL) was added 4 N HCl in dioxane (10 mL). The mixture was stirred at room temperature for 30 min, then the volatiles were removed under reduced pressure to dryness. The resulting residue was dissolved in dichloromethane (10 mL) and (3R,4R)-1-tert-butyl-3-(2,4-difluorophenyl)piperidine-4-carboxylic acid Z-5 (112 mg, 0.336 mmol), O-(7-azabenzotriazol-1-yl)-N,N,N',N',-tetramethyluronium hexaflourophosphate (HATU, 128 mg, 0.336 mmol), 1-hydroxyl-7-azabenzotriazole (HOAT, 46 mg, 0.336 mmol), and DIEA (181 mg, 1.4 mmol) were added. The mixture was stirred at room temperature overnight, diluted with dichloromethane, quenched with 1N NaOH aqueous solution. The layers were separated and the organic layer was washed with brine, dried over anhydrous magnesium sulfate, filtered, and concentrated to give a residue. The residue was purified by a flash column chromatography with silica gel and eluted with 10% MeOH in dichloromethane containing 1% of a 30% $NH_4OH$ aqueous solution. The eluates were concentrated and the resulting residue was purified again with semi-prep HPLC on a 20×250 mm C-18 column (gradient 5–95% acetonitrile in water containing 0.1% TFA). The eluates were concentrated and 1N NaOH aqueous solution was added to adjust the solution to basic, and the aqueous mixture was extracted with EtOAc. The combined organic layers were washed with brine, dried over anhydrous magnesium sulfate, filtered, and concentrated to give the (R) or (S) stereoisomer of compound 21-5. Mass Spectrum: ES-MS Calcd. for $C_{31}H_{41}ClF_2N_4O_2$: 575. Found: 576 ($M^+$+1).

Step A: To a stirred solution of compound 7-4 (10.0 g, 30.0 mmol) in tetrahydrofuran/methanol (9:1, 300 mL) at 0° C. was added sodium borohydride (2.39 g, 63 mmol). The reaction was warmed to room temperature, stirred for 3 hours, quenched with 1N NaOH, and extracted three times with EtOAc. The combined organic extracts were washed with brine. The organic layer was dried over magnesium sulfate, filtered and concentrated in vacuo to give desired product 21-2.

Step B: To a stirred solution of the alcohol 21-2 (10.6 g, 30 mmol) in anhydrous acetonitrile (60 ml) was added 18 N sulfuric acid (20 ml, 364 mmol). The reaction mixture was stirred for 18 hours and then was concentrated in vacuo to give the residue 21-3.

Step C: The residue 21-3 (10.6 g, 30 mmol) was diluted with 5 N NaOH at 0° C. until litmus paper turned dark blue. Boc anhydride (10.6 g, 30 mmol) in dioxane (60 ml) was added. The reaction mixture was stirred for 18 hours and then concentrated in vacuo to remove dioxane. The aqueous layer was extracted three times with EtOAc. The combined organic extracts were washed with brine. The organic layer was dried over magnesium sulfate, filtered and concentrated

EXAMPLE 22

Preparation of N-{1-[2-(4-{[(3R,4R)-1-tert-butyl-3-(2,4-difluorophenyl)piperidin-4-yl]carbonyl}piperazin-1-yl)-4-chloro-5-methylphenyl]ethyl}-N-methylacetamide (22-2)

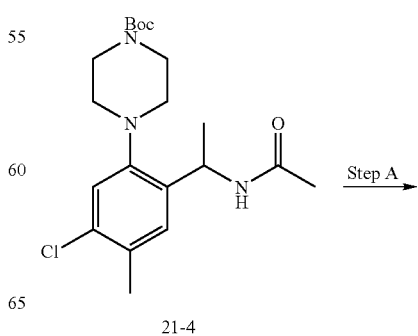

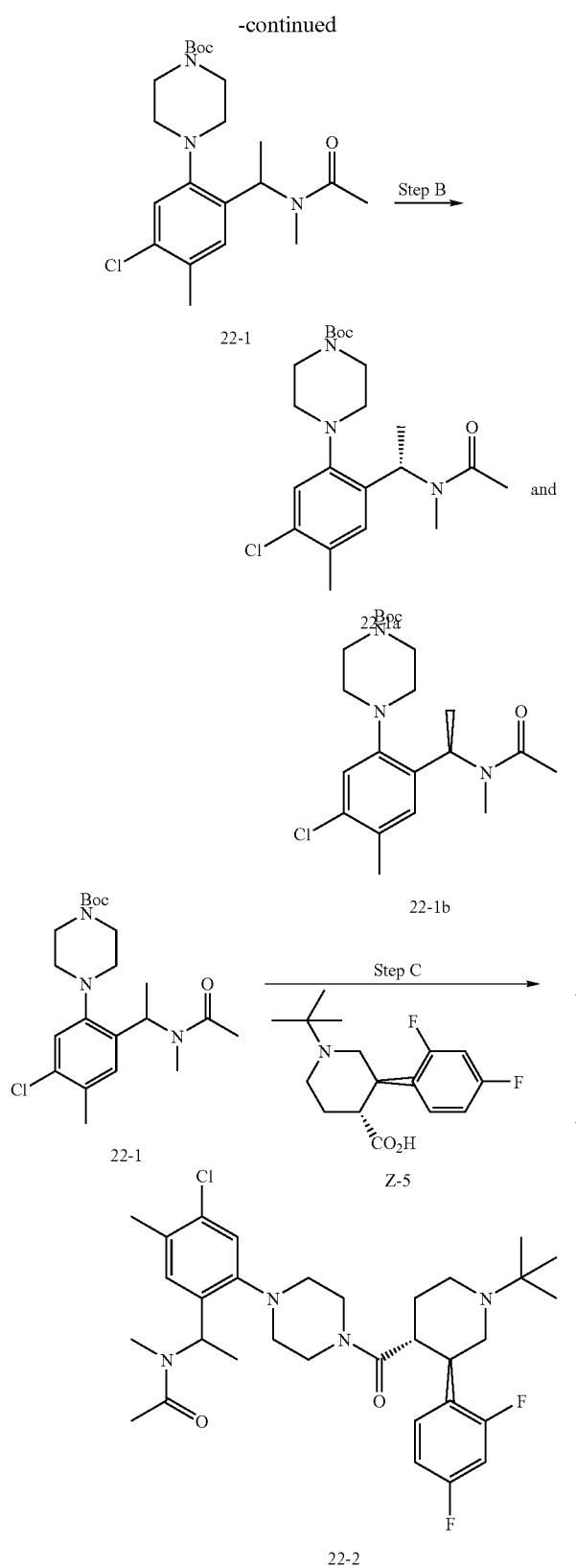

added NaHMDS 1.0 M in THF (1.7 mmol) at −78° C. The reaction was stirred for 1 hour at −78° C., then methyl iodide (497 mg, 3.5 mmol) was added and the reaction was allowed to warm to room temperature. The THF was removed under reduced pressure and the mixture was diluted with 1N NaOH aqueous solution and extracted three times with EtOAc. The combined organic layers were washed with brine, dried over anhydrous magnesium sulfate, filtered, and concentrated to give a residue. The residue was purified on silica using acetone/heptanes (gradient elution; 10%–100%) to elute the desired product 22-1.

Step B: The racemic mixture of tert-butyl 4-(2-{1-[acetyl(methyl)amino]ethyl}-5-chloro-4-methylphenyl)piperazine-1-carboxylate 22-1 was separated on a ChiralCel OJ 20×250 mm column eluting with 10% Ethanol/Heptanes at a flow rate at 50 mL per min, 50 mg per injection to afford 22-1a and 22-1b as white solids.

Step C: To a solution of (R) or (S tert-butyl 4-(2-{1-[acetyl(methyl)amino]-ethyl}-5-chloro-4-methylphenyl)piperazine-1-carboxylate, 22-1a or 22-1b, (130 mg, 0.317 mmol) in dichloromethane (10 mL) was added 4 N HCl in dioxane (10 mL) and the mixture was stirred at room temperature for 30 min and the volatiles were removed under reduced pressure to dryness. The resulting residue was dissolved in DMF (10 mL) and (3R,4R)-1-tert-butyl-3-(2,4-difluorophenyl)piperidine-4-carboxylic acid Z-5 (105 mg, 0.354 mmol), O-(7-azabenzotriazol-1-yl)-N,N,N',N',-tetramethyluronium hexafluorophosphate (HATU, 149 mg, 0.380 mmol), and DIEA (176 mg, 1.3 mmol) were added. The mixture was stirred at room temperature overnight, diluted with EtOAc, quenched with 1N NaOH aqueous solution. The layers were separated and the organic layer was washed with brine, dried over anhydrous magnesium sulfate, filtered, and concentrated. The resulting residue was purified by a flash column chromatography with silica gel and eluted with 10% MeOH in dichloromethane containing 1% of a 30% NH$_4$OH aqueous solution. The eluates were concentrated and 1N NaOH aqueous solution was added and the aqueous mixture was extracted with EtOAc. The combined organic layers were washed with brine, dried over anhydrous magnesium sulfate, filtered, and concentrated to give the (R) or (S) stereoisomer of title compound 22-2. Mass Spectrum: ES-MS: Calcd. for C$_{32}$H$_{43}$ClF$_2$N$_4$O$_2$: 589. Found: 590 (M$^+$+1).

EXAMPLE 23

Preparation of N-{1-[2-(4-{[(3R,4R)-1-tert-butyl-3-(2,4-difluorophenyl)piperidin-yl]carbonyl}piperazin-1-yl)-4-chloro-5-methylphenyl]propyl}acetamide (23-7)

Step A: To a solution of tert-butyl 4-{2-[1-(acetylamino)ethyl]-5-chloro-4-methylphenyl}-piperazine-1-carboxylate 21-4 (462 mg, 1.16 mmol) in anhydrous THF (111 mL) was -continued
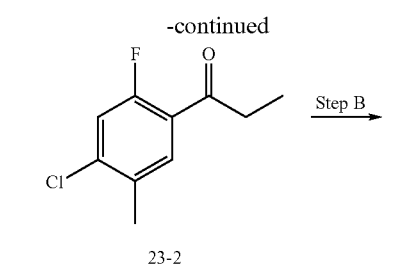
23-2
Step B
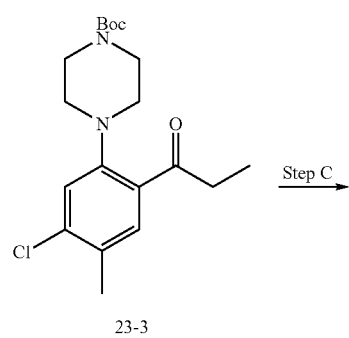
23-3
Step C
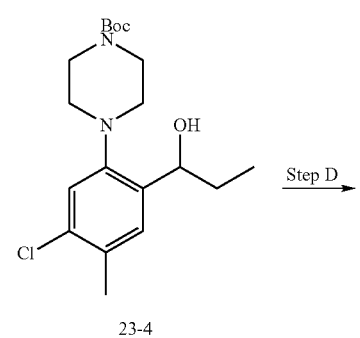
23-4
Step D
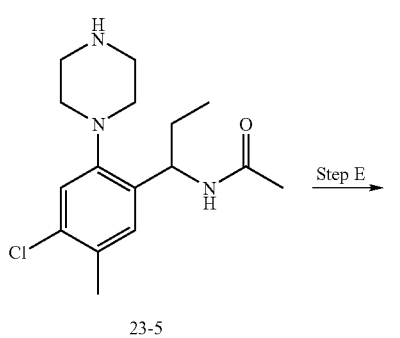
23-5
Step E
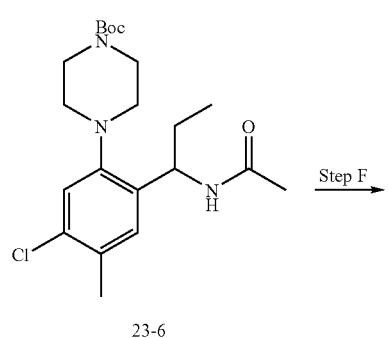
23-6
Step F
-continued
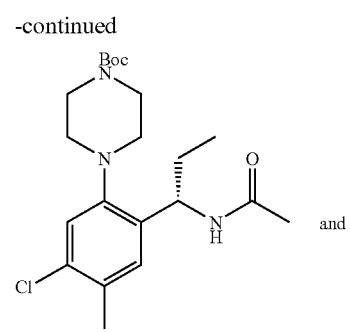
23-6a
and
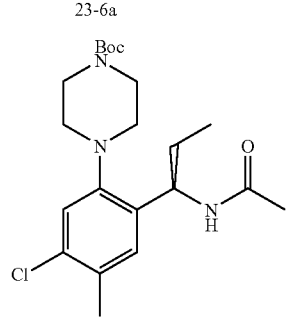
23-6b
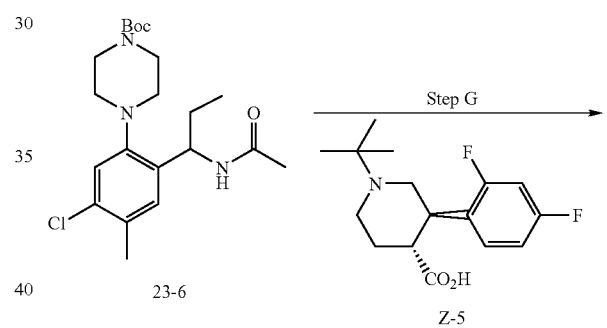
23-6    Z-5
Step G
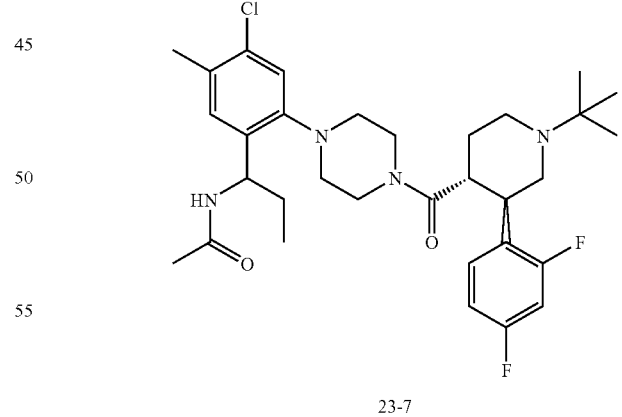
23-7
Step A: To a slurry of 2-chloro-4-fluorotoluene 23-1 (10.0 g, 207 mmol) and aluminum trichloride (21.0 g, 157 mmol) was added propionyl chloride (10.1 g, 110 mmol) at room temperature. The reaction mixture was stirred for 1 hour, then quenched with ice-cooled water and extracted with methylene chloride. The organic layers were washed with water and brine, then dried with anhydrous magnesium sulfate, filtered and concentrated under reduced pressure to give a crude purple product. The resulting product that was purified with a flash column chromatography on silica gel (gradient 6–100% EtOAc in heptanes) to give compound 23-2.

Step B: A mixture of 1-(4-chloro-2-fluoro-5-methylphenyl)propan-1-one 23-2 (4.0 g, 19.9 mmol), tert-butyl piperazine-1-carboxylate (21.9 mmol) and potassium carbonate (24 mmol) was stirred in DMF (40 mL) and heated overnight at 152° C. under an atmosphere of nitrogen. The reaction was cooled to room temperature and partitioned between EtOAc and a saturated aqueous ammonium chloride solution. The aqueous layer was extracted three times with EtOAc. The organic layers were combined and washed with a saturated aqueous ammonium chloride solution and brine, dried with anhydrous magnesium sulfate, filtered and concentrated. The resulting residue was purified with a flash column chromatography on silica gel (gradient 5–100% EtOAc in heptanes) to give compound 23-3.

Step C: To a stirred solution of compound 23-3 (4.4 g, 11.9 mmol) in tetrahydrofuran/methanol (9:1, 300 mL) at 0° C. was added sodium borohydride (953 mg, 25 mmol). The reaction was allowed to warm to room temperature, stirred for 3 hours, then quenched with 1N NaOH and extracted three times with EtOAc. The combined organic extracts were washed with brine. The organic layer was dried over magnesium sulfate, filtered and concentrated in vacuo to give compound 23-4.

Step D: To a stirred solution of the alcohol 23-4 (11.9 mmol) in anhydrous acetonitrile (100 ml) was added 18 N sulfuric acid (8 ml). The reaction mixture was stirred for 18 hours and then was concentrated in vacuo to give a residue 23-5.

Step E: The residue 23-5 (11.9 mmol) was diluted with 40 ml of 5N NaOH at 0° C. until litmus paper turned dark blue. Boc anhydride (3.1 g, 14.3 mmol) in dioxane (60 ml) was added. The reaction mixture was stirred for 18 hours and then was concentrated in vacuo to remove dioxane. The aqueous layer was extracted three times with EtOAc. The combined organic extracts were washed with brine, then dried over magnesium sulfate, filtered and concentrated in vacuo to give a residue. The residue was purified on silica using acetone/heptanes (gradient elution; 10%–100%) to elute the desired product 23-6.

Step F: The racemic mixture of tert-butyl 4-{2-[1-(acetylamino)ethyl]-5-chloro-4-methylphenyl}piperazine-1-carboxylate 23-6 was separated on a ChiralCel AS 20×250 mm column eluting with 10% isopropanol/heptanes at a flow rate at 50 mL per min, 50 mg per injection to afford 23-6a and 23-6b as white solids.

Step G: To a solution of (R) or (S)-tert-butyl 4-{2-[1-(acetylamino)propyl]-5-chloro-4-methylphenyl}piperazine-1-carboxylate, 23-6a or 23-6b, (37 mg, 0.113 mmol) in dichloromethane (10 mL) was added 4 N HCl in dioxane (10 mL) and the mixture was stirred at room temperature for 30 min and the volatiles were removed under reduced pressure to dryness. The residue was dissolved in DMF (10 mL) and (3R,4R)-1-tert-butyl-3-(2,4-difluorophenyl)piperidine-4-carboxylic acid Z-5 (37 mg, 0.125 mmol), O-(7-azabenzotriazol-1-yl)-N,N,N',N',-tetramethyluronium hexafluorophosphate (HATU, 50 mg, 0.132 mmol), and DIEA (62 mg, 0.482 mmol) were added. The mixture was stirred at room temperature overnight, diluted with EtOAc, and quenched with 1N NaOH aqueous solution. The resulting layers were separated and the organic layer was washed with brine, dried over anhydrous magnesium sulfate, filtered, and concentrated. The resulting residue was purified by a flash column chromatography with silica gel and eluted with 10% MeOH in dichloromethane containing 1% of a 30% $NH_4OH$ aqueous solution. The eluates were concentrated and 1N NaOH aqueous solution was added to adjust the solution to basic, and the aqueous mixture was extracted with EtOAc. The combined organic layers were washed with brine, dried over anhydrous magnesium sulfate, filtered, and concentrated to give the (R) or (S) stereoisomer of title compound 23-7. Mass Spectrum: ES-MS: Calcd. for $C_{32}H_{43}ClF_2N_4O_2$: 589. Found: 590 ($M^+$+1).

EXAMPLE 24

Preparation of N-{1-[2-(4-{[(3S,4R)-1-tert-butyl-4-(2,4-difluorophenyl)pyrrolidin-3-yl]carbonyl}piperazin-1-yl)-4-chloro-5-methylphenyl]ethyl}-N-cyclopropylacetamide (24-4)

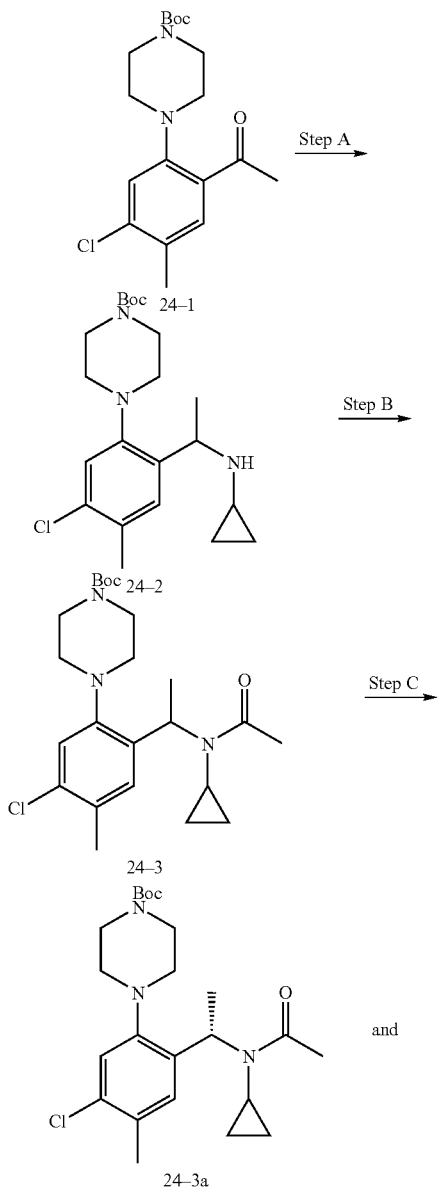

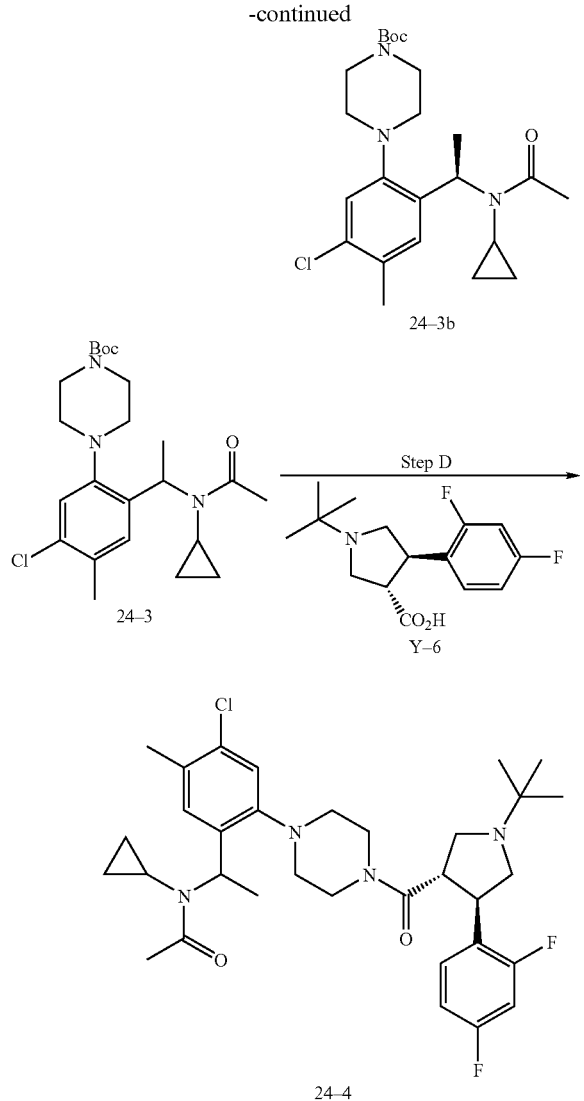

The volatiles were removed under reduced pressure and the residue was purified with a flash column chromatography on silica gel (gradient 12–100% EtOAc in heptanes) to give desired product 24-3.

Step C: The racemic mixture of tert-butyl 4-(2-{1-[acetyl(cyclopropyl)-amino]ethyl}-5-chloro-4-methylphenyl)piperazine-1-carboxylate 24-3 was separated on a ChiralCel AD 20×250 mm column eluting with 3% Ethanol/Heptanes at a flow rate at 50 mL per min, 50 mg per injection to afford 24-3a and 24-3b as white solids.

Step D: To a solution of (R) or (S)-tert-butyl 4-(2-{1-[acetyl(cyclopropyl)-amino]ethyl}-5-chloro-4-methylphenyl)piperazine-1-carboxylate, 24-3a or 24-3b, (52.3 mg, 0.123 mmol) in dichloromethane (10 mL) was added 4 N HCl in dioxane (50 mL) and the mixture was stirred at room temperature for 30 minutes. Then the volatiles were removed under reduced pressure to dryness. The resulting residue was dissolved in DMF (10 mL) and (3S,4R)-1-tert-butyl-4-(2,4-difluorophenyl)-pyrrolidine-3-carboxylic acid Y-6 (42 mg, 0.147 mmol), O-(7-azabenzotriazol-1-yl)-N,N,N',N',-tetramethyluronium hexaflourophosphate (HATU, 46 mg, 0.123 mmol), and DIEA (127 mg, 0.986 mmol) were added. The mixture was stirred at room temperature overnight, diluted with EtOAc, and quenched with 1N NaOH aqueous solution. The layers were separated and the organic layer was washed with brine, dried over anhydrous magnesium sulfate, filtered, and concentrated. The eluates were concentrated and the residue was purified again with semi-prep HPLC on a 20×250 mm C-18 column (gradient 35–100% acetonitrile in water containing 0.1% TFA). The eluates were concentrated and 1N NaOH aqueous solution was added to adjust the solution to basic, and the aqueous mixture was extracted with EtOAc. The combined organic layers were washed with brine, dried over anhydrous magnesium sulfate, filtered, and concentrated to give the (R) or (S) stereoisomer of the title compound 24-4 as white solid. Mass Spectrum: ES-MS: Calcd. for $C_{33}H_{43}ClF_2N_4O_2$: 601. Found: 602 (M$^+$+1).

Step A: To a solution of tert-butyl 4-(2-acetyl-5-chloro-4-methylphenyl)-piperazine-1-carboxylate 24-1 (1.4 g, 3.97 mmol) in anhydrous methanol (40 mL) was added NaOAc (1.62 g, 19.85 mmol), 3 Å molecular sieves, and then cyclopropyl amine (1.81 g, 31.8 mmol). The mixture was stirred at 80° C. over night, then cooled to room temperature, filtered and concentrated under reduced pressure to give a residue. The residue was dissolved in dichloromethane (39 ml) and sodium cyanoborohydride (12 ml of 1 M/THF, 12 mmol) was added dropwise. The mixture was stirred overnight at reflux. The mixture was diluted with 1N NaOH aqueous solution and then extracted with EtOAc. The organic layer was dried over anhydrous magnesium sulfate, filtered and concentrated to give compound 24-2.

Step B: To a solution of tert-butyl 4-{5-chloro-2-[1-(cyclopropylamino)ethyl]-4-methylphenyl}piperazine-1-carboxylate 24-2 (3.97 mmol) in pyridine (39 mL) was added acetic anhydride (39.7 mmol) at 0° C. under an atmosphere of nitrogen. The reaction was allowed to slowly warm up to room temperature and then stirred overnight.

EXAMPLE 25

Preparation of N-{1-[2-(4-{[(3S,4R)-1-tert-butyl-4-(2,4-difluorophenyl)pyrrolidin-3-yl]carbonyl}piperazin-1-yl)-4-chloro-5-methylphenyl]ethyl}-N-methylacetamide (25-1)

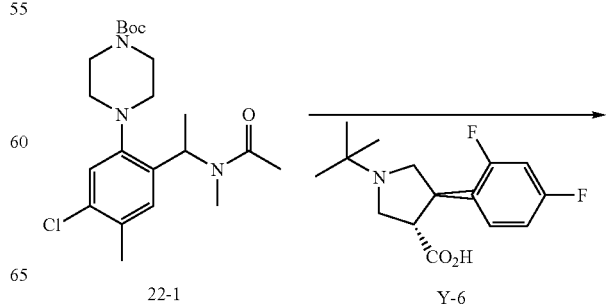

-continued

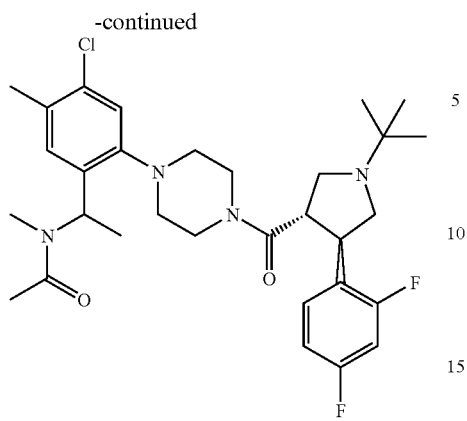

25-1

-continued

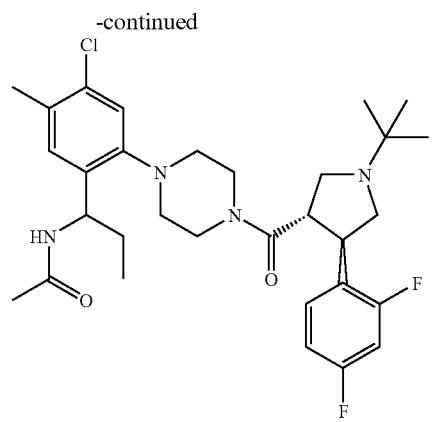

26-1

To a solution of (R) or (S)-tert-butyl 4-(2-{1-[acetyl(methyl)amino]-ethyl}-5-chloro-4-methylphenyl)piperazine-1-carboxylate 22-1 (96.7 mg, 0.253 mmol) in dichloromethane (10 mL) was added 4 N HCl in dioxane (10 mL) and the mixture was stirred at room temperature for 30 minutes. Then the volatiles were removed under reduced pressure to dryness, and the resulting residue was dissolved in DMF (10 mL) and (3S,4R)-1-tert-butyl-4-(2,4-difluorophenyl)-pyrrolidine-3-carboxylic acid Y-6 (86 mg, 0.303 mmol), O-(7-azabenzotriazol-1-yl)-N,N,N',N',-tetramethyluronium hexafluorophosphate (HATU, 124 mg, 0.328 mmol), and DIEA (261 mg, 0.2.02 mmol) were added. The mixture was stirred at room temperature overnight, diluted with ether, quenched with 1N NaOH aqueous solution. The layers were separated and the organic layer was washed with brine, dried over anhydrous magnesium sulfate, filtered, and concentrated. The eluates were concentrated and the residue was purified again with semi-prep HPLC on a 20×250 mm C-18 column (gradient 45–100% acetonitrile in water containing 0.1% TFA). The eluates were concentrated and 1N NaOH aqueous solution was added to adjust the solution to basic, and the aqueous mixture was extracted with EtOAc. The combined organic layers were washed with brine, dried over anhydrous magnesium sulfate, filtered, and concentrated to give the (R) or (S) stereoisomer of title compound 25-1 as a white solid. Mass Spectrum: ES-MS: Calcd. for $C_{31}H_{41}ClF_2N_4O_2$: 575. Found: 576 (M$^+$+1).

EXAMPLE 26

Preparation of N-{1-[2-(4-{[(3S,4R)-1-tert-butyl-4-(2,4-difluorophenyl)pyrrolidin-3-yl]carbonyl}piperazin-1-yl)-4-chloro-5-methylphenyl]propyl}acetamide (26-1)

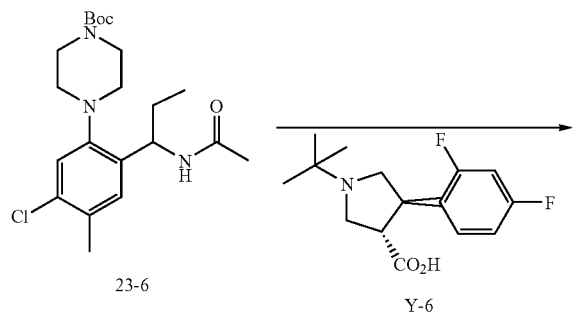

To a solution of (R) or (S)-tert-butyl 4-{2-[1-(acetylamino)propyl]-5-chloro-4-methylphenyl}piperazine-1-carboxylate 23-6 (440 mg, 1.4 mmol) in dichloromethane (10 mL) was added 4 N HCl in dioxane (10 mL) and the mixture was stirred at room temperature for 30 minutes. Then the volatiles were removed under reduced pressure to dryness, and the resulting residue was dissolved in DMF (10 mL) and (3S,4R)-1-tert-butyl-4-(2,4-difluorophenyl)-pyrrolidine-3-carboxylic acid Y-6 (440 mg 1.5 mmol), O-(7-azabenzotriazol-1-yl)-N,N,N',N', -tetramethyluroniumhexafluoro-phosphate (HATU, 550 mg, 1.4 mmol), and DIEA (1.49 g, 11.28 mmol) were added. The mixture was stirred at room temperature overnight, diluted with ether, quenched with 1N NaOH aqueous solution. The layers were separated and the organic layer was washed with brine, dried over anhydrous magnesium sulfate, filtered, and concentrated. The residue was purified by a flash column chromatography with silica gel and eluted with 10% MeOH in dichloromethane containing 1% of a 30% NH$_4$OH aqueous solution. The eluates were concentrated and 1N NaOH aqueous solution was added and the aqueous mixture was extracted with EtOAc. The combined organic layers were washed with brine, dried over anhydrous magnesium sulfate, filtered, and concentrated to give the (R) or (S) stereoisomer of title compound 26-1 as white solid. Mass Spectrum: ES-MS: Calcd. for $C_{31}H_{41}ClF_2N_4O_2$: 575. Found: 576 (M$^+$+1).

EXAMPLE 27

Preparation of Compound (27-9)

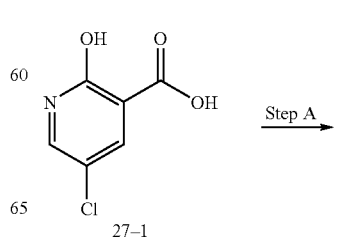

27–1

Step A

-continued
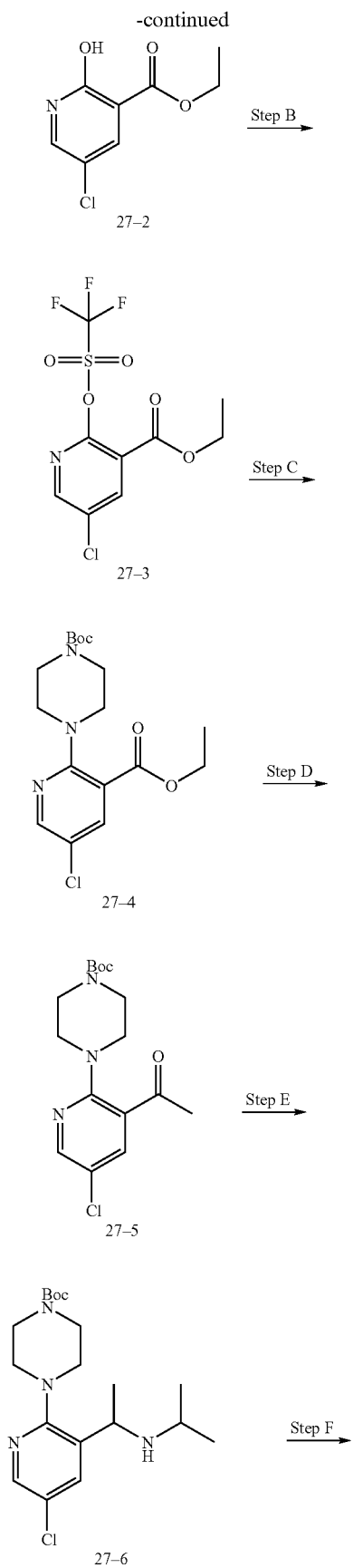
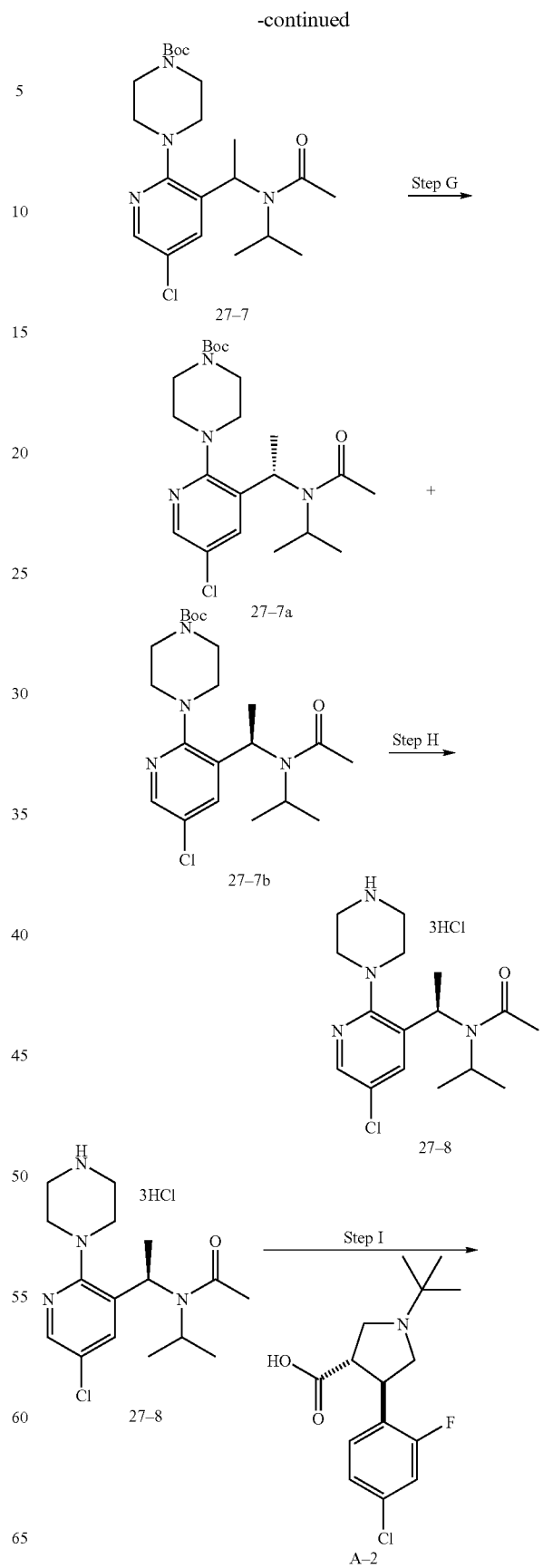

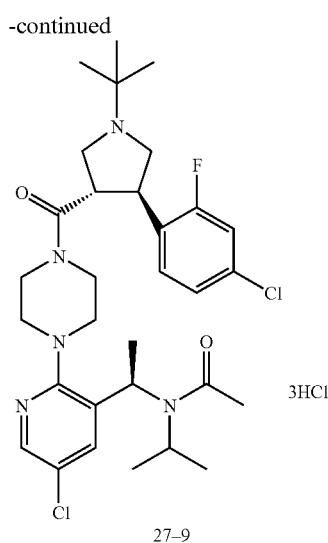

27-9 3HCl

Step A: To a solution of ethanol (150 ml) was added thionyl chloride dropwise (8.4 ml), followed by 5-chloro-2-hydroxy nicotinic acid 27-1 (5.0 g, 28.8 mmol, Avocado). The reaction was refluxed for 2 hours, then evaporated to dryness to afford compound 27-2.

Step B: To the stirred solution of compound 27-2 (5.64 g, 28 mmol) in dry $CH_2Cl_2$ (150 ml) at −10° C. was added pyridine (4.5 ml, 56 mmol) and trifluoromethanesulfonic anhydride (5.2 ml, 30.8 mmol). The mixture was slowly warmed to room temperature. The reaction was stirred at room temperature for 2 hours, then concentrated in vacuo to afford compound 27-3.

Step C: Compound 27-3 (9 g, 27 mmol) was dissolved in 15 ml DMF in a high pressure reaction vessel, then $K_2CO_3$ (5.6 g, 40.5 mmol) and tert-butyl 1-piperazine-carboxylate (7.54 g, 40.5 mmol, Aldrich) were added. The reaction mixture was stirred in the sealed vessel at 150° C. overnight, allowed to cool to room temperature, then di-tert-butyl dicarbonate (5 g, 23 mmol) and diisopropyl ethyl amine (5 ml, 29 mmol) were added. The reaction mixture was stirred at room temperature for 4 hours. The crude product was purified by MPLC (Horizon system, Biotage column) using 0%–80% EtOAc/hexane gradient eluting solvent to give compound 27-4.

Step D: To the stirred solution of compound 27-4 (1.0 g, 2.705 mmol) in dry THF (20 ml) was added methyl magnesium bromide (1.4 M in Toluene-THF, 10 ml, 13.5 mmol) at −78° C. The reaction mixture was allowed to slowly warm up to room temperature, and stirred at room temperature for 1 hour then saturated $NaHCO_3$ (30 ml) was added. The mixture was extracted three times with ethyl acetate (50 mL), then the combined the organic phases were dried it over $Na_2SO_4$. MPLC purification (Horizon system, Biotage column) using 0%–50% EtOAc/hexane gradient eluting solvent afforded compound 27-5.

Step E: Compound 27-5 (235 mg, 0.693 mmol) was dissolved in dry $CH_2Cl_2$ (<1 mL), followed by the addition of isopropyl amine (235 μL, 77 mmol) and titanium (IV) ethoxide (287 μL, 1.386 mmol). The reaction mixture was stirred at room temperature overnight, followed by addition of methanol (10 ml) and $NaBH_4$ (77 mg, 2.08 mmol). The reaction was stirred at room temperature for 30 minutes, then quenched by addition of a saturated aqueous $NaHCO_3$ solution (10 ml), and extracted five times with ethyl acetate (15 mL). The combined the organic phases were dried it over $Na_2SO_4$, and concentrated in vacuo to give compound 27-6.

Step F: Compound 27-6 (264 mg, 0.69 mmol) was dissolved in pyridine (2 mL), then acetic anhydride (652 μL, 6.9 mmol) was added. The reaction mixture was stirred at 80° C. overnight. MPLC purification (Horizon system, Biotage column) using 0%–40% EtOAc/hexane gradient eluting solvent afforded compound 27-7.

Step G: The racemic mixture of compound 27-7 (150 mg) was dissolved in 5% EtOH in heptane (6 ml) and separated on a ChiralPak AD column, 3% EtOH/Heptane as eluting solvent, flow rate=9 ml/min, 0.5 ml per injection to give compound 27-7a (slow eluting isomer, RT=24.39) and 27-7b (faster eluting isomer).

Step H: Compound 27-7a (48 mg) was dissolved in 4N HCl in dioxane (10 ml) and stirred at room temperature for 60 minutes. Concentration to dryness afforded compound 27-8.

Step I: To the stirred solution of compound 27-8 (49 mg, 0.113 mmol) in $CH_2Cl_2$ (2 mL) was added DIEA (98 μL, 0.565 mmol), pyrrolidine acid A-2 (34 mg, 0.113 mmol, synthesized by a procedure similar to the synthetic procedure for difluorophenyl pyrrolidine acid Y-6), HOAt (15.4 mg, 0.113 mmol) and HATU (86 mg, 0.226 mmol) at room temperature. The mixture was stirred at room temperature over night. The desired product was isolated by preparative TLC purification using 10% MeOH in $CH_2Cl_2$ as an eluting solvent, and then converted to the HCl salt by adding 1N HCl in ether (0.5 ml) to give compound 27-9 as white solid. Mass Spectrum: LC-MS Calc. for $C_{31}H_{42}Cl_2FN_5O_2$: 605. Found: 606 (M+1) and 608 (M+3).

EXAMPLE 28

Preparation of Compound (28-10)

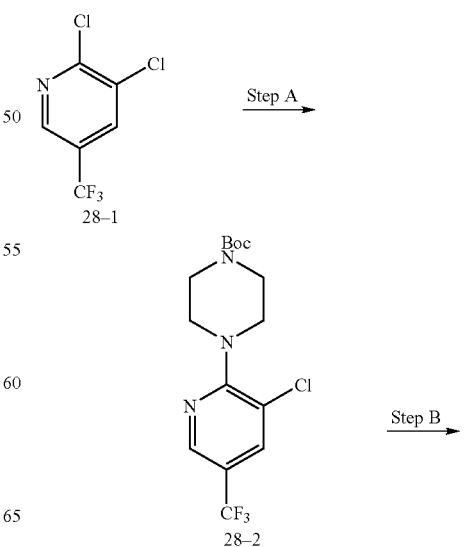

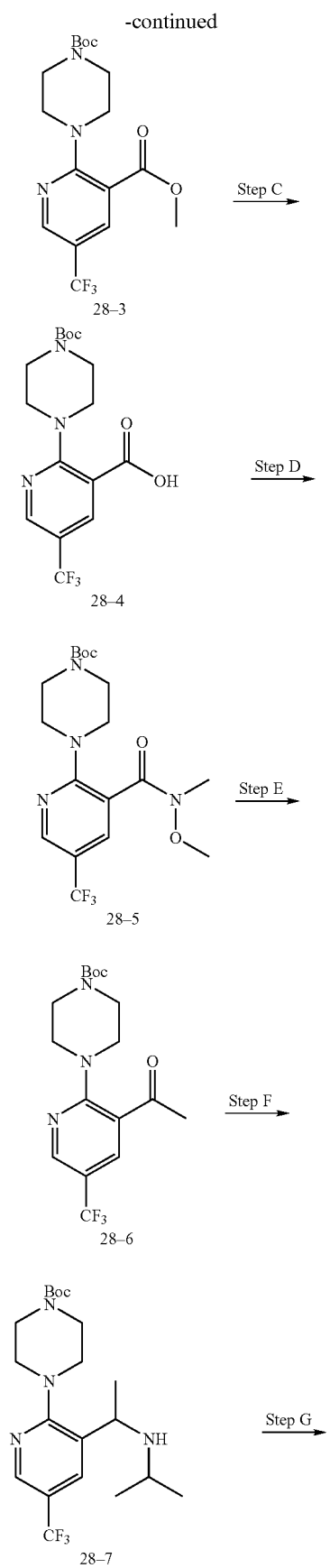
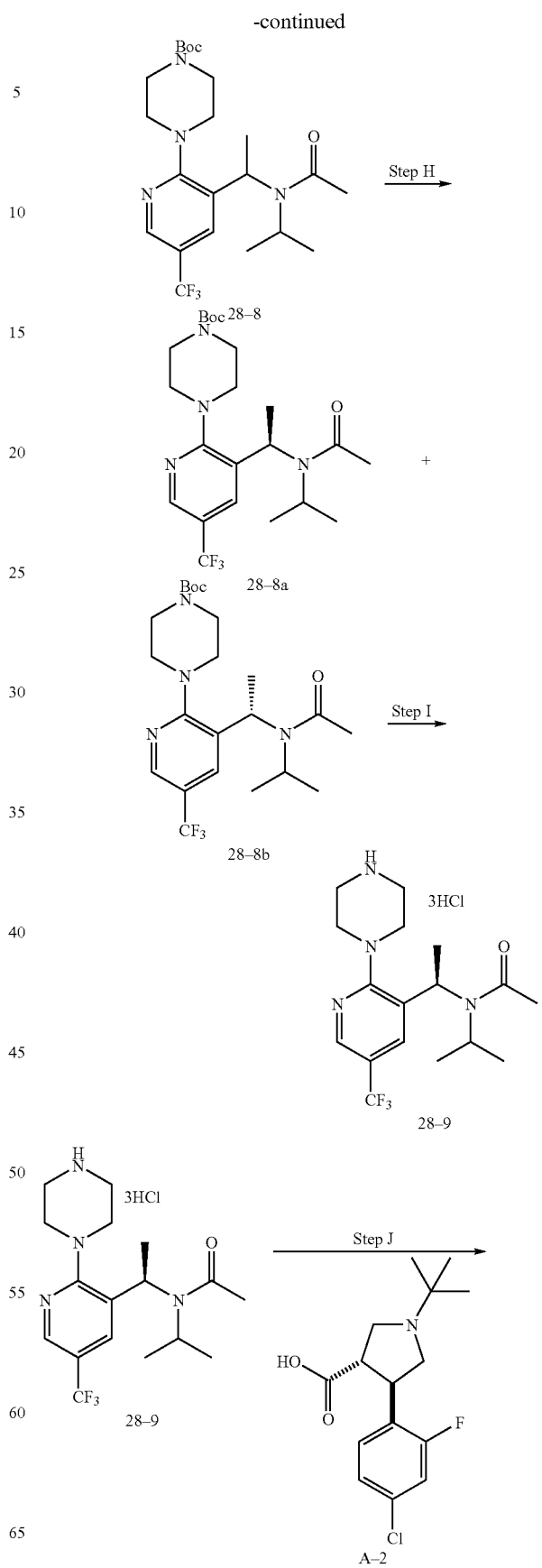

-continued

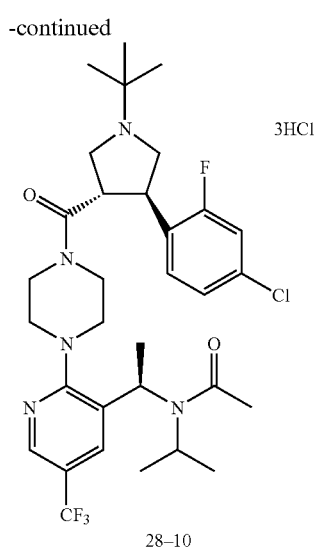

28-10

Step A: Compound 28-1 (10 g, 46.3 mmol, Aldrich) was dissolved in 5 ml DMF in a high pressure reaction vessel, then $K_2CO_3$ (9.6 g, 69.45 mmol) and tert-butyl 1-piperazine-carboxylate (10.3 g, 55.56 mmol, Aldrich) were added. The mixture was stirred in the sealed reaction vessel at 150° C. overnight, and then cooled to room temperature. $CH_2Cl_2$ (100 ml) was added, the resulting solid was filtered, and washed with $CH_2Cl_2$ (100 ml). The filtrate was concentrated and purified by MPLC (Horizon system, Biotage column) using 0%–60% EtOAc/hexane gradient eluting solvent to give compound 28-2.

Step B: A mixture of compound 28-2 (2 g, 5.47 mmol), DIEA (1.43 ml, 8.2 mmol), $PdCl_2(PPh_3)_2$ (383 mg, 0.547 mmol) and $PPh_3$ (287 mg, 1.09 mmol) in MeOH (25 ml) was charged under nitrogen into a stainless steel autoclave equipped with a magnetic stirrer bar. After sealing, the reactor was pressurized to 725 psi with CO, and then heated to 150° C. and stirred at 150° C. for 10 hours. The reactor was cooled to room temperature, the pressure was released, and the solid was filtered off. The filtrate was concentrated in vacuo, and the resulting crude mixture was purified by purified by MPLC (Horizon system, Biotage column) using 0%–30% EtOAc/hexane gradient eluting solvent to give compound 28-3.

Step C: To the stirred solution of compound 28-3 (415 mg, 1.066 mmol) in MeOH-THF (5 ml—5 ml) was added $LiOH \cdot H_2O$ (179 mg, 4.26 mmol) in $H_2O$ (5 ml) at room temperature. The reaction mixture stirred at room temperature overnight, then the volatiles were evaporated, and 1N HCl in ether (5 ml) was added. The mixture was evaporated to dryness to give compound 28-4.

Step D: To a stirred solution of compound 28-4 (1.05 mmol) in $CH_2Cl_2$ (3 ml) was added N,O-dimethylhydroxylamine hydrochloride (204.8 mg, 2.1 mmol, Aldrich), DIEA (Aldrich, 548.7 µl, 3.15 mmol), HOAt (143 mg, 1.05 mmol) and then HATU (798.4 mg, 2.10 mmol). The reaction mixture stirred at room temperature overnight, then diluted with $CH_2Cl_2$, washed with $H_2O$, and saturated $NaHCO_3$. The organic phase was separated, dried over $Na_2SO_4$, concentrated and purified by MPLC (Horizon system, Biotage column) using 0%–40% EtOAc/hexane gradient eluting solvent to give compound 28-5.

Step E: To a stirred solution of compound 28-5 (175 mg, 0.418 mmol) in dry THF (10 ml) was added methyl magnesium bromide (1.4 M in Toluene-THF, 1.2 ml, 13.5 mmol) at 0° C. The reaction was stirred at 0° C. for 4 hours, then quenched by adding saturated $NaHCO_3$ (10 ml). The mixture was extracted three times with ethyl acetate (20 mL); the combined organic phases were dried over $Na_2SO_4$ and concentrated in vacuo to give compound 28-6.

Step F: Compound 28-6 (160 mg, 0.4 mmol) was mixed with isopropyl amine (146 µL, 1.6 mmol) and titanium (IV) ethoxide (178 µM, 0.8 mmol). The mixture was stirred at room temperature overnight, followed by the addition of methanol (10 ml) and $NaBH_4$ (15 mg, 2.08 mmol). The reaction was stirred at room temperature for 30 minutes, then quenched with saturated aqueous $NaHCO_3$ solution (10 ml). The aqueous layer was extracted five times with ethyl acetate (10 mL); the combined the organic phases were dried over $Na_2SO_4$, and concentrated in vacuo to give compound 28-7.

Step G: Compound 28-7 (175 mg, 0.42 mmol) was dissolved in pyridine (5 ml), then acetic anhydride (397 µL, 4.2 mmol) was added. The reaction was stirred at 80° C. overnight. MPLC purification (Horizon system, Biotage column) using 0%–30% EtOAc/hexane gradient eluting solvent afforded compound 28-8.

Step H: The racemic mixture of compound 28-8 (127 mg) was dissolved in 10% EtOH in heptane (3 ml) and separated on a ChiralPak AD column, 4% EtOH/Heptane as eluting solvent, flow rate=9 ml/min, 0.6 ml per injection to give compound 28-8a and 28-8b.

Step I: Compound 28-8a (50 mg, 0.11 mmol) was dissolved in 4N HCl in dioxane (10 ml), and stirred at room temperature for 60 minutes. Concentration to dryness afforded compound 28-9.

Step J: To the stirred solution of compound 28-9 (46.8 mg, 0.10 mmol) in $CH_2Cl_2$ (2 ml) was added DIEA (104 µl, 0.6 mmol), pyrrolidine acid A-2 (36 mg, 0.12 mmol, synthesized by a procedure similar to the synthetic procedure for difluorophenyl pyrrolidine acid Y-6), HOAt (15 mg, 0.10 mmol) and HATU (83 mg, 0.2 mmol) at room temperature. The reaction was stirred at room temperature over night. The desired product was isolated by preparative TLC purification using 7% MeOH in $CH_2Cl_2$ as an eluting solvent, and then converted to the HCl salt by adding 1N HCl in ether (0.5 ml) to give compound 28-10. Mass Spectrum: LC-MS Calc. for $C_{32}H_{42}ClF_4N_5O_2$: 639. Found: 640 (M+1).

EXAMPLE 29

Preparation of Compounds (29-3a) and (29-3b)

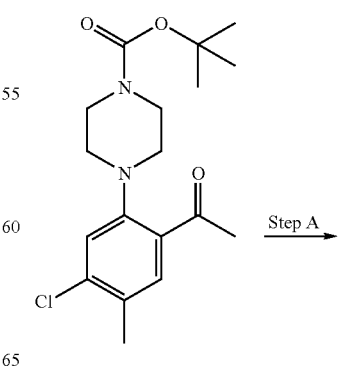

21-1

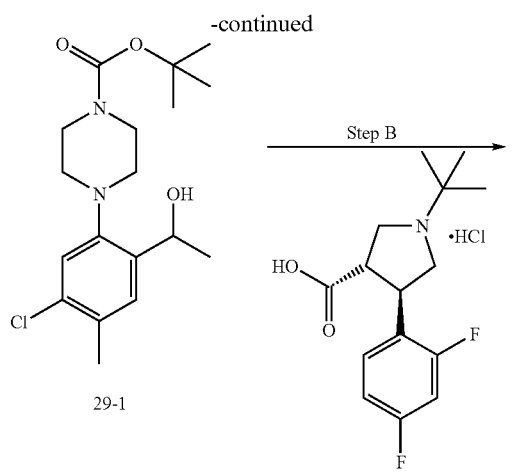

29-1

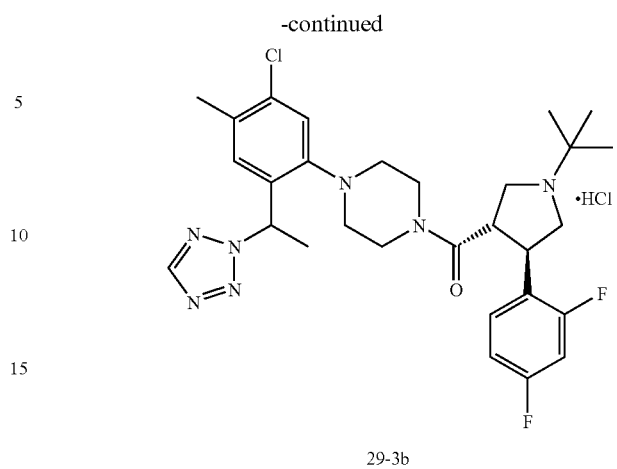

29-3b

Y-6

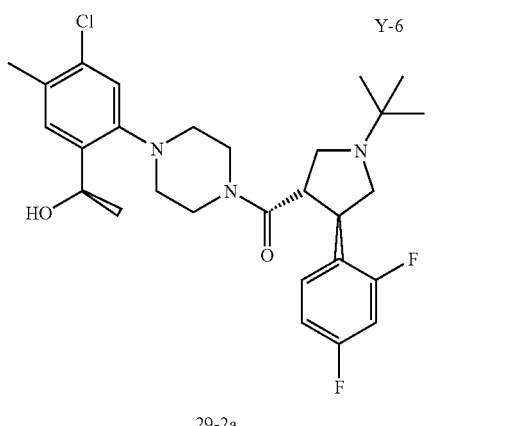

29-2a

+

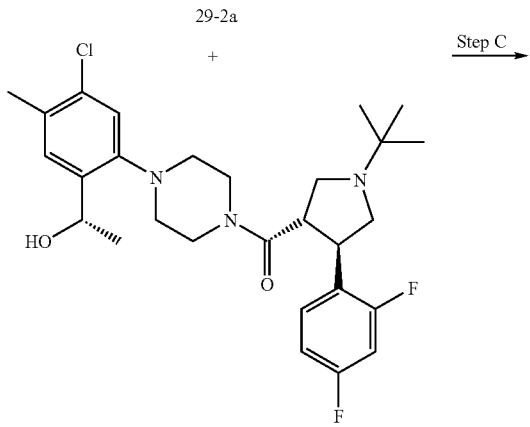

29-2b

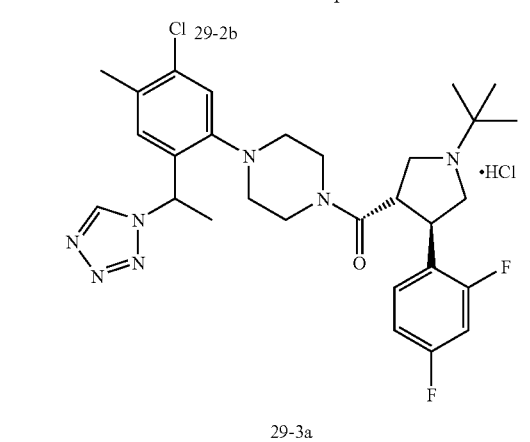

29-3a

Step A: Sodium borohydride (0.235 g, 6.2 mmol) was added to a solution of 21-1 (4.38 g, 12.4 mmol) in methylene chloride (9 mL) and methanol (54 mL) at approximately 0° C. After stirring at that temperature for 10 min then at ambient temperature for 2 hr, the reaction mixture was concentrated and partitioned between ethyl acetate and aqueous 1N sodium hydroxide. The organic phase was separated and washed with brine, dried (sodium sulfate) and concentrated to give compound 29-1.

Step B: Compound 29-2 was prepared as a mixture of two diastereomers from 29-1 following a coupling procedure with pyrrolidine acid Y-6 similar to that described for Example 1. The diastereomers of compound 29-2 were separated by HPLC (ChiralCel OD 20×250 mm column eluting with 10% isopropanol/n-heptane at a flow rate at 9 mL per minute to 0.5 mL per minute, 1 mL per injection of a 100 mg per mL solution) to afford compound 29-2a and compound 29-2b. Mass Spectrum: (m/z (ES) 520 (MH+)).

Step C: Diisopropyl azodicarboxylate (0.16 mL, 0.808 mmol) was added dropwise over 30 min to a suspension of diphenylphosphino-polystyrene (2.2 mmol/g) (393 mg, 0.865 mmol) in a solution of tetrazole (2.56 mL of a 0.45 M solution in acetonitrile, 1.15 mmol) and the (R) or (S) stereoisomer of compound 29-2a or 29-2b (60 mg, 0.115 mmol) in methylene chloride (1.5 mL) at ambient temperature. After stirring at ambient temperature overnight, the reaction mixture was filtered and concentrated in vacuo to give a crude residue. Purification of the crude residue by flash chromatography over silica gel (gradient elution; 0%–12% methanol/methylene chloride as eluent) afforded two compounds 29-3a and 29-3b, which were dissolved in the minimum amount of methylene chloride and acidified with hydrogen chloride (1M solution in diethyl ether). The volatiles were removed in vacuo to afford the HCl salt of the (R) or (S) stereoisomer of compound 29-3a and 29-3b. Mass Spectrum: (m/z (ES) 572 (MH+)).

Following procedures similar to that described above for Example 29, the following compounds were prepared:

EXAMPLE 37
Preparation of Compound (37-3)
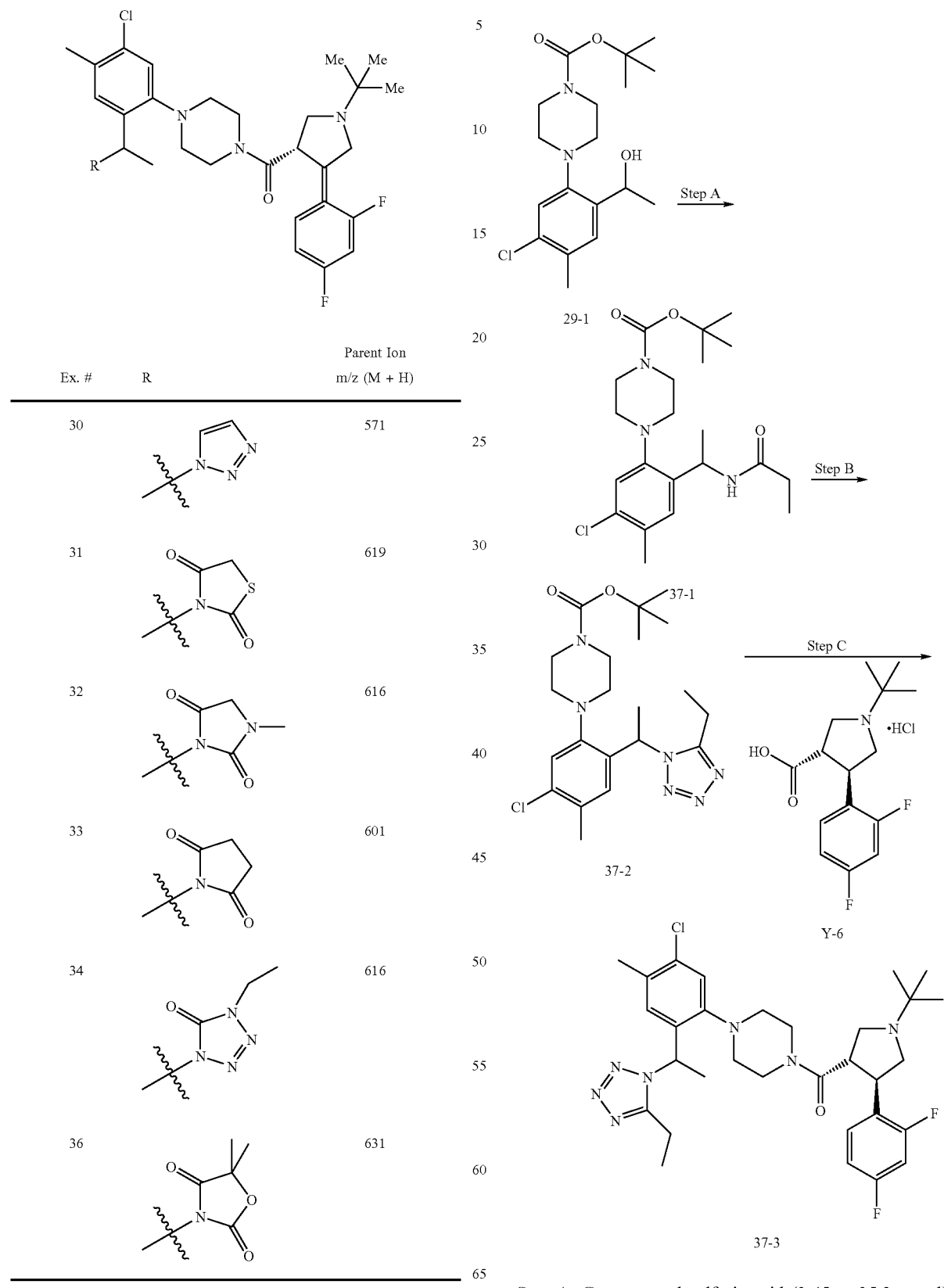
| Ex. # | R | Parent Ion m/z (M + H) |
|---|---|---|
| 30 | triazolyl | 571 |
| 31 | thiazolidine-2,4-dione | 619 |
| 32 | 3-methyl-imidazolidine-2,4-dione | 616 |
| 33 | succinimidyl (pyrrolidine-2,5-dione) | 601 |
| 34 | 4-ethyl-5-oxo-tetrazolyl | 616 |
| 36 | 5,5-dimethyl-oxazolidine-2,4-dione | 631 |
Step A: Concentrated sulfuric acid (3.45 g, 35.2 mmol) was added dropwise to a solution of compound 29-1 (0.5 g, 1.41 mmol) in propionitrile (10.5 mL) at ambient temperature. After stirring the reaction mixture at ambient temperature overnight, sodium hydroxide was added (until pH>10) followed by dioxane (10 mL) and di-tert-butyl dicarbonate (615 mg, 2.82 mmol). After stirring the resultant solution at ambient temperature for 1 hr, the organic phase was separated, washed with brine, dried (magnesium sulfate), and concentrated in vacuo to give a crude residue 37-1. Mass Spectrum: (m/z (ES) 410 (MH+)).

Step B: Phosphoros pentachloride (0.046 g, 0.22 mmol) was added to a solution of compound 37-1 (0.053 g, 0.129 mmol) in methylene chloride at approximately 0° C. After stirring at ambient temperature for 20 min, the solution was recooled to approximately 0° C. and azidotrimethylsilane (0.034 mL, 0.259 mmol) was added. After stirring the reaction mixture at ambient temperature overnight, aqueous saturated sodium bicarbonate was added. The organic phase was separated, washed with brine, dried (magnesium sulfate), and concentrated in vacuo to give a crude residue. Purification of the crude residue by flash chromatography over silica gel (gradient elution; 0%–50% ethyl acetate/hexane as eluent) afforded compound 37-2. Mass Spectrum: (m/z (ES) 435 (MH+)).

Step C: To a solution of compound 37-2 (11 mg, 0.025 mmol) in dioxane was added HCl (9 mg, 0.253 mmol, 10 eq). The reaction was stirred at room temperature for 1 hr, then concentrated in vacuo to give a residue. To a solution of the residue, (3S,4R)-1-tert-butyl-4-(2,4-difluorophenyl)-pyrrolidine-3-carboxylic acid Y-6 (9 mg, 0.033 mmol), O-(7-azabenzotriazol-1-yl)-N,N,N',N',-tetramethyluronium hexafluoro-phosphate (HATU, 14 mg, 0.036 mmol), 1-hydroxy-7-azabenzotriazole (HOAT, 4 mg, 0.033 mmol) in dichloromethane (3 mL) was added DIEA (15 mg, 0.021 mL, 0.119 mmol). The mixture was stirred at room temperature overnight. The solution was washed with saturated aq. NaHCO₃ (10 mL), brine (10 mL), dried over anhydrous magnesium sulfate, filtered, and concentrated to give compound 37-3. Mass Spectrum: (m/z (ES) 600 (MH+)). $^1$H NMR (500 MHz, CDCl₃) δ 7.2–7.1 (m, 4H), 6.1 (q, 0.6H), 5.3 (s), 4.3–4.0 (m, 2.7 H), 3.8–3.2 (m, 7.2 H), 2.9–2.5 (m), 2.7 (s, 1 H), 2.4–2.3 (m, 3 H), 2.3 (d, 2.8 H), 2.2 (s, 2.8 H), 1.97 (q, 3.3 H), 1.8–1.0 (m, 27 H), 1.0–0.8 (m, 4 H).

EXAMPLE 38

Preparation of Compound (38-3)

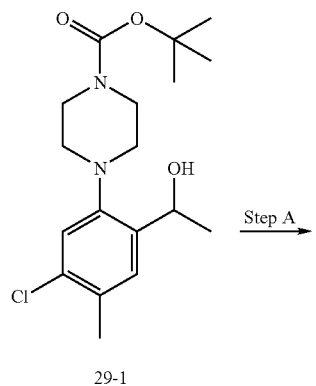

29-1

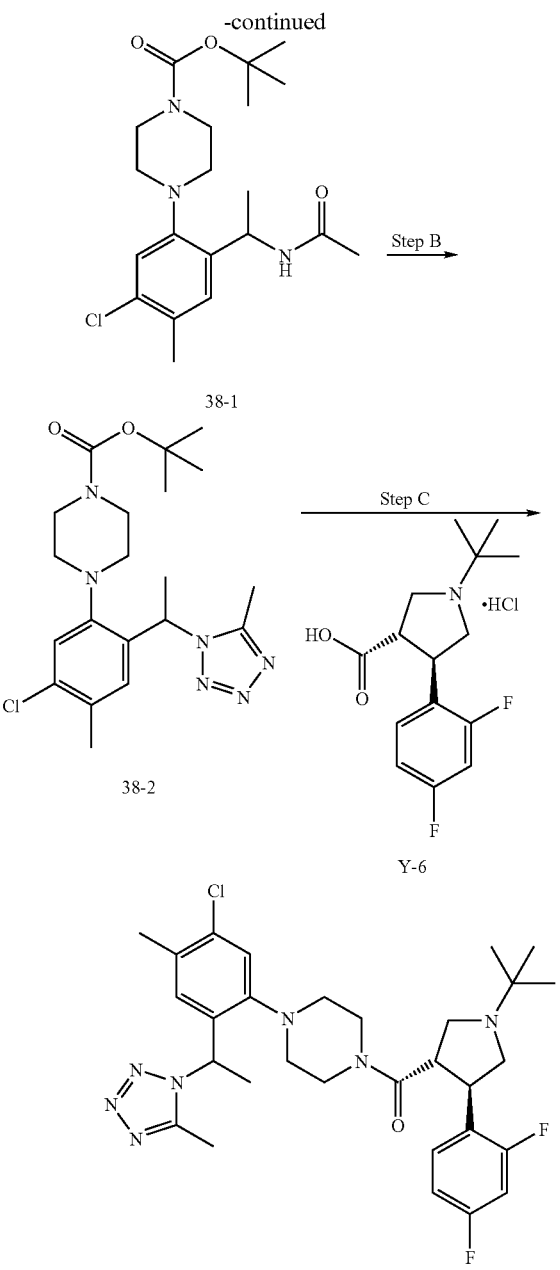

Step A: Compound 38-1 was prepared from compound 29-1 by treatment with acetonitrile in the place of proprionitrile and following a similar procedure as that described in Example 37, Step A.

Step B: Phosphoros pentachloride (0.101 g, 0.485 mmol) was added to a solution of compound 38-1 (0.113 g, 0.285 mmol) in methylene chloride (14 mL) at approximately 0° C. After stirring at ambient temperature for 20 min, the solution was recooled to approximately 0° C. and azidotrimethylsilane (0.076 mL, 0.571 mmol) was added. After stirring the reaction mixture at ambient temperature overnight, aqueous saturated sodium bicarbonate was added. The organic phase was separated, washed with brine, dried (magnesium sulfate) and concentrated in vacuo to give a crude residue. Purification of the crude residue by flash chromatography over silica gel (Biotage 2M, gradient elution; 0%–50% ethyl acetate/hexane as eluent) afforded compound 38-2.

Step C: The BOC protecting group of compound 38-2 was removed by treatment with HCl in dioxane following the procedure of Example 37, Step C to give the free piperazine analog of compound 38-2. To a solution of the free piperazine analog of compound 38-2 (71 mg, 0.221 mmol), (3S,4R)-1-tert-butyl-4-(2,4-difluorophenyl)-pyrrolidine-3-carboxylic acid Y-6 (69 mg, 0.243 mmol), O-(7-azabenzotriazol-1-yl)-N,N,N',N',-tetramethyluronium hexafluorophosphate (HATU, 101 mg, 0.266 mmol), 1-hydroxy-7-azabenzotriazole (HOAT, 33 mg, 0.243 mmol) in dichloromethane (3 mL) was added DIEA (114 mg, 0.154 mL, 0.885 mmol). The mixture was stirred at room temperature overnight. The solution was washed with saturated aq. NaHCO$_3$ (10 mL), brine (10 mL), dried over anhydrous magnesium sulfate, filtered, and concentrated to give compound 38-3. Mass Spectrum: (m/z (ES) 587 (MH$^+$).

EXAMPLES 39–66

Using the appropriate starting materials and intermediates, including the (3R,4S)-1-tert-butyl-4-(2,4-difluorophenyl)pyrrolidine-3-carboxylic acid Y-6 for the peptide coupling reaction, and following procedures similar to that described above for Example 1, the following compounds 39–66 were prepared:

| Ex. # | R$^5$ | R$^7$ | Calculated MW | Parent Ion m/z (M + H) Found |
|---|---|---|---|---|
| 39 | 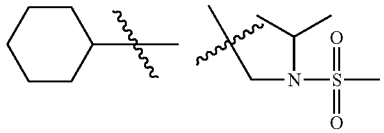 | 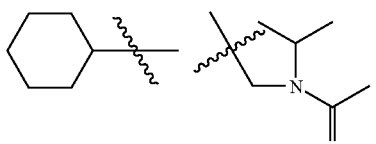 | C$_{31}$H$_{50}$F$_2$N$_4$O$_3$S 597 | 598 (M + H) |
| 40 | 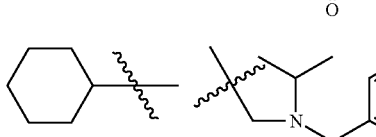 | | C$_{32}$H$_{50}$F$_2$N$_4$O$_2$ 561 | 562 (M + H) |
| 41 | |  | C$_{36}$H$_{51}$F$_2$N$_5$O$_2$ 624 | 625 (M + H) |
| 42 | | | C$_{35}$H$_{50}$F$_2$N$_6$O$_2$ 625 | 626 (M + H) |
| 43 | | 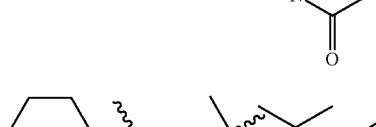 | C$_{35}$H$_{50}$F$_2$N$_6$O$_2$ 625 | 626 (M + H) |

-continued

| Ex. # | R⁵ | R⁷ | Calculated MW | Parent Ion m/z (M + H) Found |
|---|---|---|---|---|
| 44 | cyclohexyl | 2-methyl-pyrrolidinyl-N-C(O)-(1-isopropyl-pyrazol-4-yl) | $C_{37}H_{56}F_2N_6O_2$ 655 | 656 (M + H) |
| 45 | cyclohexyl | 2-methyl-pyrrolidinyl-N-C(O)-(1-methyl-pyrazol-4-yl) | $C_{35}H_{52}F_2N_6O_2$ 627 | 628 (M + H) |
| 46 | cyclohexyl | methyl-pyrazolo-pyrazinone | $C_{35}H_{52}F_2N_6O_2$ 627 | 628 (M + H) |
| 47 | cyclohexyl | 2-methyl-pyrrolidinyl-N-C(O)-(5-CF₃-1H-pyrazol-3-yl) | $C_{35}H_{49}F_5N_6O_2$ 681 | 682 (M + H) |
| 48 | cyclohexyl | 2-methyl-pyrrolidinyl-N-C(O)-(5-cyclopropyl-1H-pyrazol-3-yl) | $C_{35}H_{49}F_5N_6O_2$ 681 | 682 (M + H) |
| 49 | cyclohexyl | 2-methyl-pyrrolidinyl-N-C(O)CH₂-(pyrazol-1-yl) | $C_{35}H_{52}F_2N_6O_2$ 627 | 628 (M + H) |

-continued

| Ex. # | R⁵ | R⁷ | Calculated MW | Parent Ion m/z (M + H) Found |
|---|---|---|---|---|
| 50 | cyclohexyl | 2-methyl-pyrrolidine-N-CH₂-C(O)-N(3,5-dimethylpyrazole) | C₃₇H₅₆F₂N₆O₂ 655 | 656 (M + H) |
| 51 | cyclohexyl | 2-methyl-pyrrolidine-N-C(O)-isoxazole | C₃₄H₄₉F₂N₅O₃ 614 | 615 (M + H) |
| 52 | cyclohexyl | 2-methyl-pyrrolidine-N-C(O)-(5-methyl-1,3,4-oxadiazole) | C₃₄H₅₀F₂N₆O₃ 629 | 630 (M + H) |
| 53 | isobutyl | 2-methyl-pyrrolidine-N-SO₂-CH₃ | C₂₉H₄₈F₂N₄O₃S 571 | 572 (M + H) |
| 54 | isobutyl | 2-methyl-pyrrolidine-N-C(O)CH₃ | C₃₀H₄₈F₂N₄O₂ 535 | 536 (M + H) |
| 55 | isobutyl | 2-methyl-pyrrolidine-N-C(O)-pyrimidine | C₃₃H₄₈F₂N₆O₂ 599 | 600 (M + H) |
| 56 | tert-butyl | 2-methyl-pyrrolidine-N-SO₂-CH₃ | C₂₉H₄₈F₂N₆O₃S 571 | 572 (M + H) |

-continued

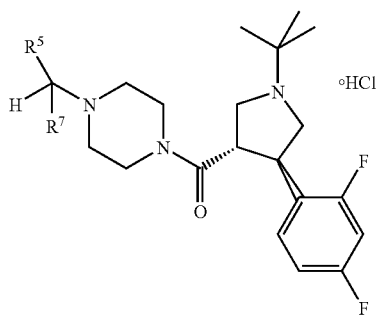

| Ex. # | R⁵ | R⁷ | Calculated MW | Parent Ion m/z (M + H) Found |
|---|---|---|---|---|
| 57 | *t*-Bu (neopentyl) | 2-methyl-1-acetylpyrrolidinyl | $C_{30}H_{48}F_2N_4O_2$ 535 | 536 (M + H) |
| 58 | cyclobutylmethyl | 2-methyl-1-acetylpyrrolidinyl | $C_{30}H_{46}F_2N_4O_2$ 533 | 534 (M + H) |
| 59 | cyclobutylmethyl | 2-methyl-1-methanesulfonylpyrrolidinyl | $C_{29}H_{46}F_2N_4O_3S$ 569 | 570 (M + H) |
| 60 | 2-ethylbutyl | 2-methyl-1-acetylpyrrolidinyl | $C_{31}H_{50}F_2N_4O_2$ 549 | 550 (M + H) |
| 61 | 2-ethylbutyl | 2-methyl-1-methanesulfonylpyrrolidinyl | $C_{30}H_{50}F_2N_4O_3S$ 585 | 586 (M + H) |
| 62 | isobutyl | 2-methyl-1-sulfamoylpyrrolidinyl | $C_{28}H_{47}F_2N_5O_3S$ 572 | 573 (M + H) |

-continued
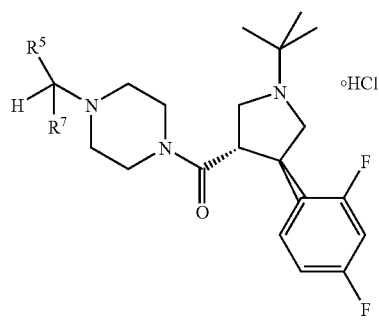
| Ex. # | R⁵ | R⁷ | Calculated MW | Parent Ion m/z (M + H) Found |
|---|---|---|---|---|
| 63 | 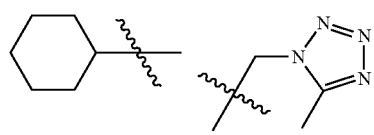 | | $C_{29}H_{43}F_2N_7O$ 544 | 545 (M + H) |
| 64 | 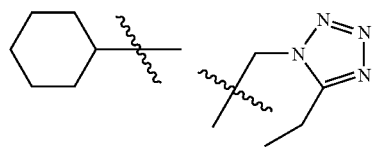 | | $C_{30}H_{45}F_2N_7O$ 558 | 559 (M + H) |
| 65 | 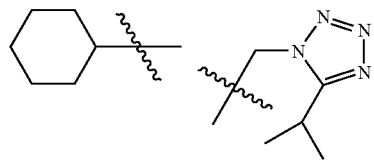 | | $C_{31}H_{47}F_2N_7O$ 572 | 573 (M + H) |
| 66 | 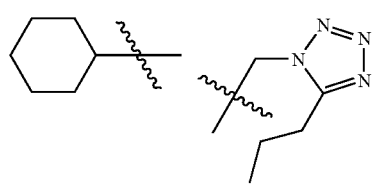 | | $C_{31}H_{47}F_2N_7O$ 572 | 573 (M + H) |

EXAMPLES 67–70

Using the appropriate starting materials and intermediates, including the (3R,4S)-1-tert-butyl-4-(2-fluoro-4-chlorophenyl)pyrrolidine-3-carboxylic acid A-2 for the peptide coupling reaction, and following procedures similar to that described above for Example 1, the following compounds 67–70 were prepared:

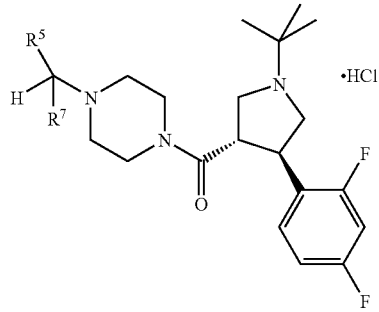

| Ex. # | $R^5$ | $R^7$ | Calculated MW | Parent Ion m/z (M + H) Found |
|---|---|---|---|---|
| 67 | isobutyl | N-methylsulfonyl pyrrolidinyl | $C_{29}H_{48}ClFN_4O_3S$ 587 | 588 (M + H) |
| 68 | isobutyl | N-(pyrimidin-2-ylcarbonyl) pyrrolidinyl | $C_{33}H_{48}ClFN_6O_2$ 615 | 616 (M + H) |
| 69 | tert-butyl | N-acetyl pyrrolidinyl | $C_{30}H_{48}ClFN_4O_2$ 551 | 552 (M + H) |
| 70 | cyclohexyl | tetrazolylmethyl pyrrolidinyl | $C_{29}H_{43}ClFN_7O$ 560 | 561 (M + H) |

EXAMPLE 71
Preparation of Compound (71-8)
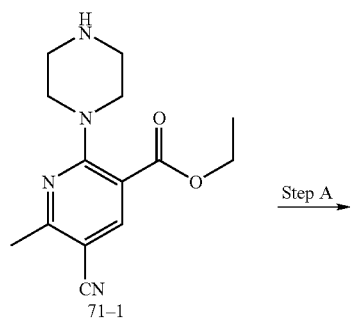
71-1
Step A →
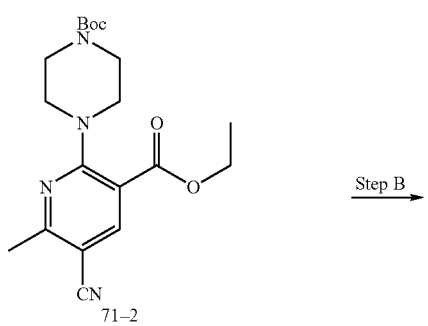
71-2
Step B →
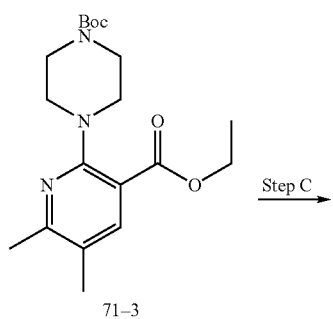
71-3
Step C →
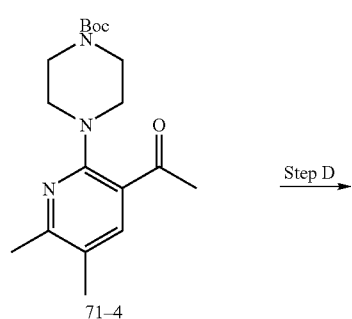
71-4
Step D →
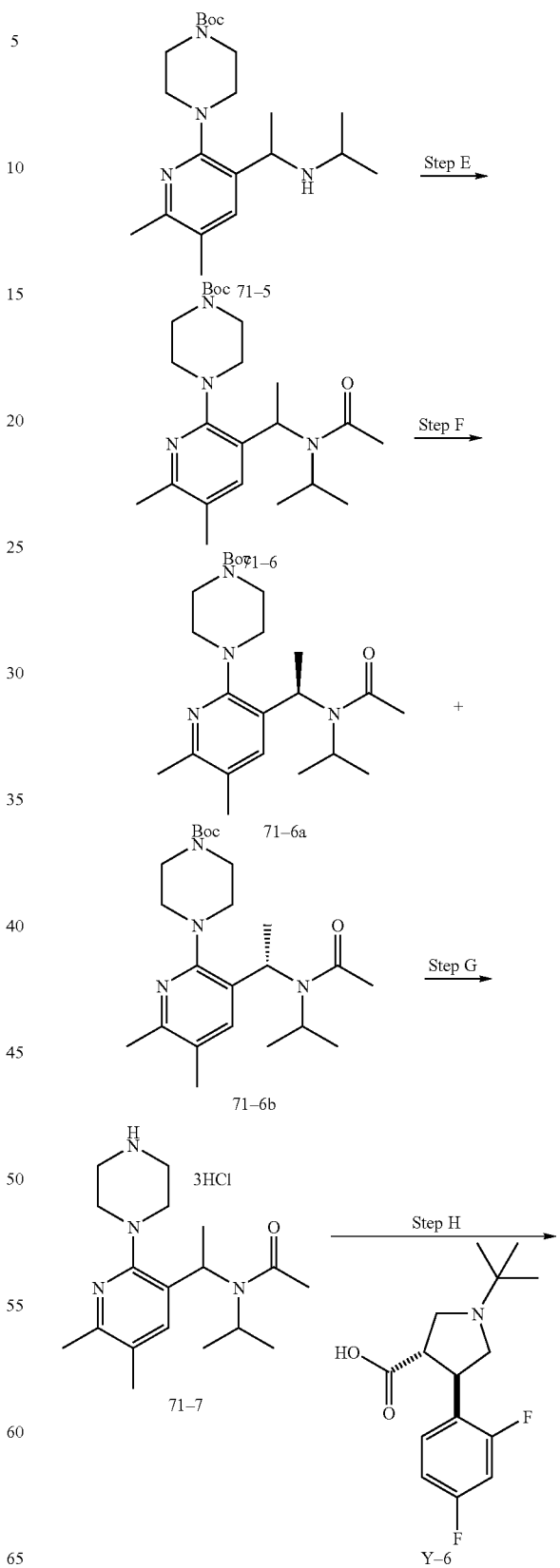

-continued

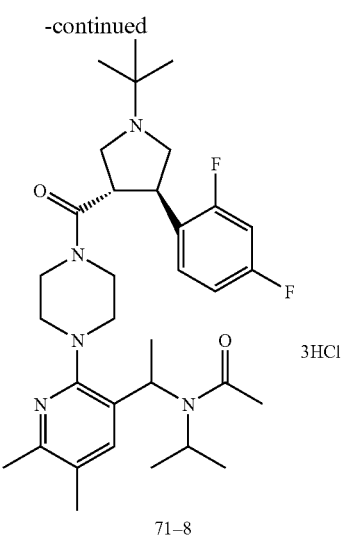

71-8

Step A: To the stirred solution of ethyl 5-cyano-6-methyl-2-piperazinonicotinate 71-1 (1.0 g, 3.65 mmol, Oakwood) in CH$_2$Cl$_2$, was added DIEA (636 µl, 3.65 mmol) and Boc anhydride (875 mg, 4.01 mmol). The mixture was stirred at room temperature over night, then evaporated to dryness to give compound 71-2 as white solid.

Step B: Compound 71-2 (950 mg, 2.54 mmol) was dissolved in dry MeOH (150 ml), then Pd(OH)$_2$/C (Aldrich) (475 mg, Aldrich) was added, then the reaction was stirred at room temperature in the presence of a hydrogen (balloon) for 48 hours. The catalyst was filtered off, and the filtrate was concentrated in vacuo to give compound 71-3. Mass Spectrum: LC-MS Calc. for C$_{19}$H$_{29}$N$_3$O$_4$: 363. found: 364 (M+1) and 386 (M+Na).

Step C: To a stirred solution of compound 71-3 (726 mg, 2.0 mmol) in dry THF (20 ml) was added methyl magnesium bromide (Aldrich, 1.4 M in Toluene-THF, 5.7 ml, 8.0 mmol) at −10° C. The reaction mixture was allowed to slowly warm up to room temperature, and then stirred at room temperature for 5 hour before adding saturated NaHCO$_3$ (30 ml). The mixture was extracted five times with ethyl acetate (60 ml), and the combined organic phases were dried over Na$_2$SO$_4$. MPLC purification (Horizon system, Biotage column) using 0%–40% EtOAc/hexane gradient eluting solvent afforded compound 71-4 as clear oil. Mass Spectrum: LC-MS Calc. for C$_{18}$H$_{27}$N$_3$O$_3$: 333. found: 334 (M+1).

Step D: Compound 71-4 (525 mg, 1.576 mmol) was dissolved in dry CH$_2$Cl$_2$ (<1 ML), then isopropyl amine (537 µL, 6.3 mmol) and titanium (IV) ethoxide (654 µL 3.2 mmol) were added. The mixture was stirred at room temperature overnight, followed by the addition of methanol (10 ml) and NaBH$_4$ (292 mg, 7.88 mmol). The reaction stirred at room temperature for 30 min, then quenched by addition of saturated aqueous NaHCO$_3$ solution (10 ml) and extracted five times with ethyl acetate (50 mL). The combined organic phases were dried it over Na$_2$SO$_4$, and concentrated in vacuo to give compound 71-5.

Step E: Compound 71-5 (507 mg, 1.35 mmol) was dissolved in pyridine (15 ml), then acetic anhydride (1.4 ml, 14.85 mmol) was added, and the reaction mixture was allowed to stir at 80° C. overnight. MPLC purification (Horizon system, Biotage column) using 0%–40% EtOAc/hexane gradient eluting solvent afforded compound 71-6 as a white foam solid. Mass Spectrum: LC-MS Calc. for C$_{23}$H$_{38}$N$_4$O$_3$: 418. found: 419 (M+1).

Step F: The racemic mixture of compound 71-6 (150 mg) was dissolved in 5% EtOH in heptane (6 ml) and separated on a ChiralPak AD column, 2.8% EtOH/Heptane as eluting solvent, flow rate=9 ml/min, 0.5 ml per injection to give compound 71-6a and 71-6b.

Step G: The (R) or (S) stereoisomer of compound 71-6 (15 mg) was dissolved in 0.5 mL CH$_2$Cl$_2$, then 4N HCl in dioxane (10 ml) was added, and the reaction mixture was allowed to stir at room temperature for 60 min. The reaction mixture was then concentrated to dryness to give the (R) or (S) stereoisomer of compound 71-7 as white solid. Mass Spectrum: LC-MS Calc. for C$_{18}$H$_{30}$N$_4$O: 318. found: 319 (M+1).

Step H: To the stirred solution of the (R) or (S) stereoisomer of compound 71-7 (14.8 mg, 0.0347 mmol) in CH$_2$Cl$_2$ (1 ml) was added DIEA (98 µl, 0.565 mmol), difluorophenyl pyrrolidine acid Y-6 (9.8 mg, 0.0347 mmol), HOAt (4.7 mg, 0.0347 mmol) and HATU (26.4 mg, 0.069 mmol) at room temperature. The mixture was stirred at room temperature over night. The (R) or (S) stereoisomer of compound 71-8 was isolated by preparative TLC purification using 10% MeOH in CH$_2$Cl$_2$ as an eluting solvent, and then converted to the HCl salt by adding 1N HCl in ether (0.2 ml). Mass Spectrum: LC-MS Calc. for C$_{33}$H$_{47}$F$_2$N$_5$O$_2$: 583. found: 584 (M+1).

EXAMPLE 72

Preparation of Compound (72-6)

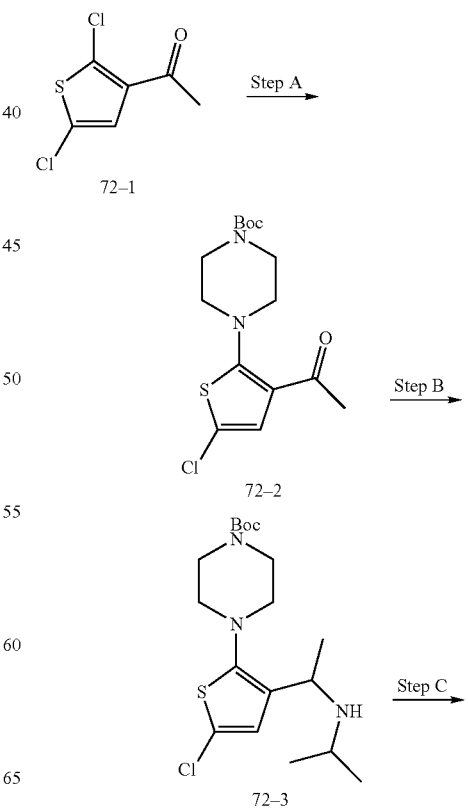

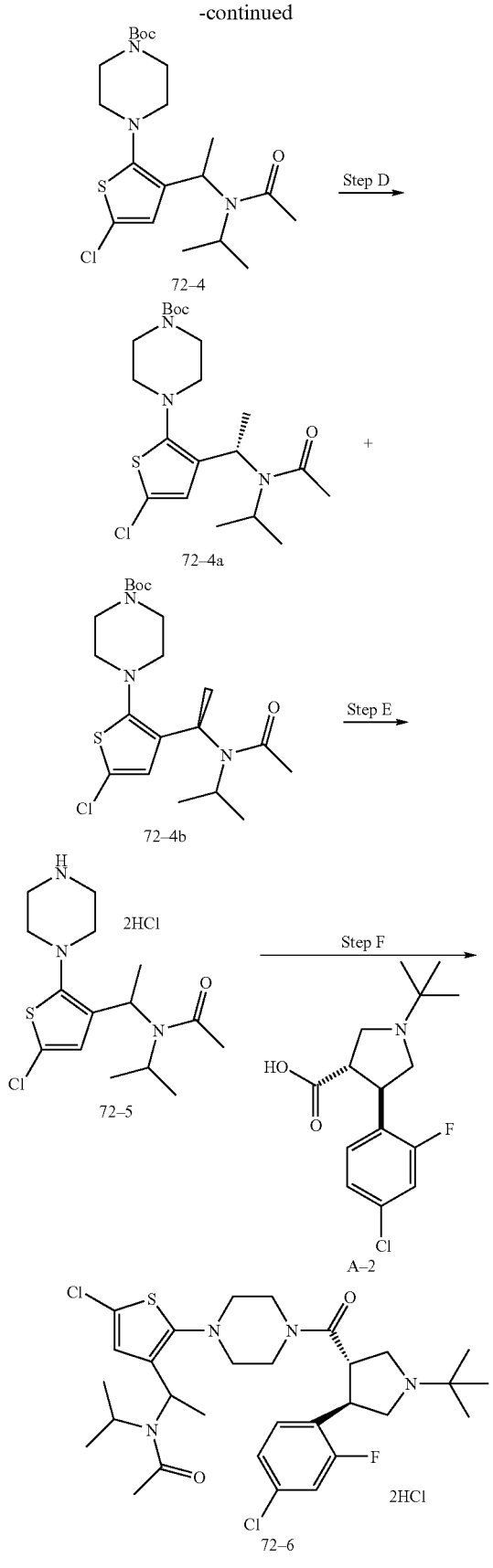

Step A: 3-acetyl-2,5-dichlorothiophene 72-1 (1.0 g, 5.12 mmol, Acros) was dissolved in 2 ml DMF in a high pressure reaction vessel, then K$_2$CO$_3$ (1.42 g, 10.24 mmol) and tert-butyl 1-piperazine-carboxylate (1.43 g, 7.68 mmol, Aldrich) were added. The reaction was stirred in the sealed reaction vessel at 150° C. overnight, and then cooled to room temperature before addition of CH$_2$Cl$_2$ (100 ml). The resulting solid was filtered off and washed with CH$_2$Cl$_2$ (100 ml) and the filtrate was concentrated and purified by MPLC (Horizon system, Biotage column) using 0%–30% EtOAc/hexane gradient eluting solvent to give compound 72-2. Mass Spectrum: LC-MS Calc. for C$_{15}$H$_{21}$ClN$_2$O$_3$S: 344. found: 367 (M+Na).

Step B: Compound 72-2 (1.1 g, 3.19 mmol) was dissolved in isopropyl amine (1.1 mL, 12.76 mmol) and titanium (IV) ethoxide (1.3 mL 6.38 mmol). The mixture was stirred at room temperature overnight, followed by the addition of methanol (25 ml) and NaBH$_4$ (354 mg, 9.57 mmol). The reaction stirred at room temperature for 30 minutes, then quenched by the addition of saturated NaHCO$_3$ aqueous solution (50 ml), and extracted five times with ethyl acetate (80 mL). The combined organic phases were dried it over Na$_2$SO$_4$, and concentrated in vacuo to give compound 72-3. Mass Spectrum: LC-MS Calc. for C$_{18}$H$_{30}$ClN$_3$O$_2$S: 387. found: 388 (M+1).

Step C: Compound 72-3 (1100 mg, 2.87 mmol) was dissolved in pyridine (20 ml), then acetic anhydride (2.7 ml, 28.7 mmol) was added. The reaction mixture was stirred at 80° C. overnight. MPLC purification (Horizon system, Biotage column) using 0%–40% EtOAc/hexane gradient eluting solvent afforded compound 72-4. Mass Spectrum: LC-MS Calc. for C$_{20}$H$_{32}$ClN$_3$O$_3$S: 429. found: 430 (M+1).

Step D: The racemic mixture of compound 72-4 (330 mg) was dissolved in 10% EtOH in heptane (8 mL) and separated on a ChiralPak AD column, 2.1% EtOH/Heptane as eluting solvent, flow rate=9 ml/min, 0.5 ml per injection to give compound 72-4a and 72-4b. Mass Spectrum: LC-MS Calc. for C$_{20}$H$_{32}$ClN$_3$O$_3$S: 429. found: 430 (M+1).

Step E: Compound 72-4 (89 mg) was dissolved in 0.5 mL CH$_2$Cl$_2$, then 4N HCl in dioxane (10 ml) was added and the reaction was stirred at room temperature for 60 min. Concentration to dryness afforded 72-5 as the HCl salt. Mass Spectrum: LC-MS Calc. for C$_{15}$H$_{25}$ClN$_3$OS: 329. found: 330 (M+1).

Step F: To the stirred solution of compound 72-5 (40.3 mg, O. 1 mmol) in CH$_2$Cl$_2$ (2 ml) was added DIEA (87 µl, 0.5 mmol), compound A-2 (30 mg, 0.1 mmol; synthesized by a procedure similar to the synthetic procedure for difluorophenyl pyrrolidine acid Y-6), HOAt (14.0 mg, 0.1 mmol) and HATU (76 mg, 0.2 mmol) at room temperature. The mixture was stirred at room temperature over night. Compound 72-6 was isolated by preparative TLC purification using 5% MeOH in CH$_2$Cl$_2$ as an eluting solvent, and converted to the HCl salt by mixing with 1N HCl in ether (0.4 ml). Mass Spectrum: LC-MS Calc. for C$_{30}$H$_{41}$Cl$_2$FN$_4$O$_2$S: 610. found: 611 (M+1).

EXAMPLE 73

Preparation of Compound (73-1)

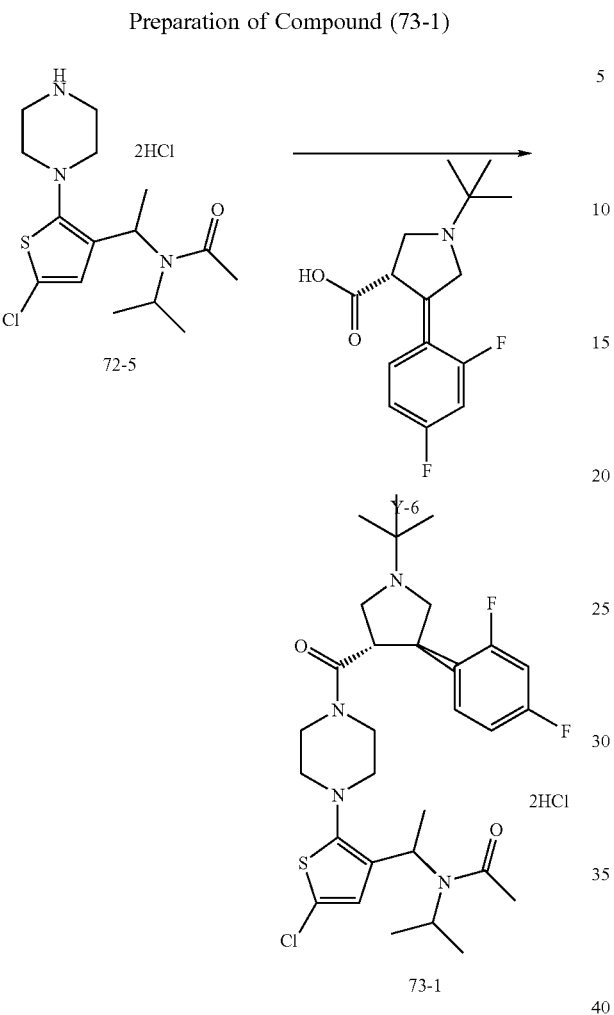

To the stirred solution of compound 72-5 (40.3 mg, 0.1 mmol) in $CH_2Cl_2$ (2 ml) was added DIEA (87 μl, 0.5 mmol), difluorophenyl pyrrolidine acid Y-6 (30 mg, 0.1 mmol), HOAt (14.0 mg, 0.1 mmol) and HATU (76 mg, 0.2 mmol) at room temperature. The mixture was stirred at room temperature over night. Compound 73-1 was isolated by preparative TLC purification using 5% MeOH in $CH_2Cl_2$ as an eluting solvent, and then converted to the HCl salt by mixing it with 1N HCl in ether (0.4 ml). Mass Spectrum: LC-MS Calc. for $C_{30}H_{41}ClF_2N_4O_2S$: 594. found: 595 (M+1).

EXAMPLE 74

Preparation of Compound (74-7)

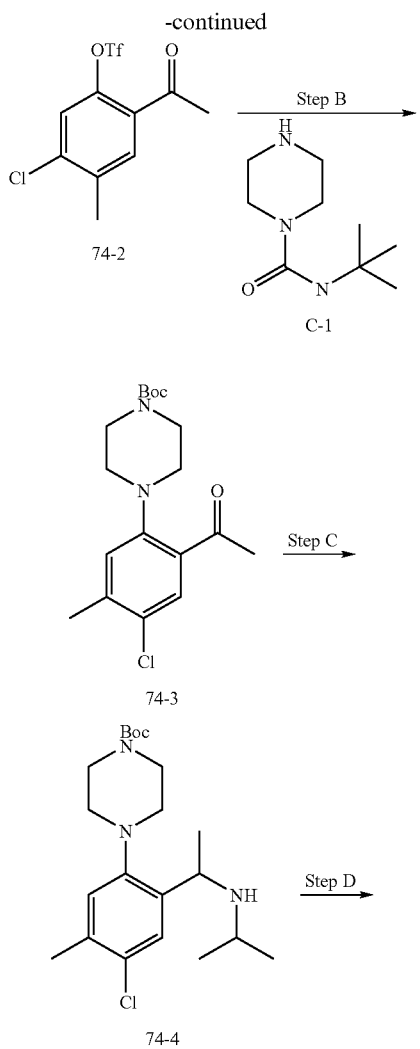

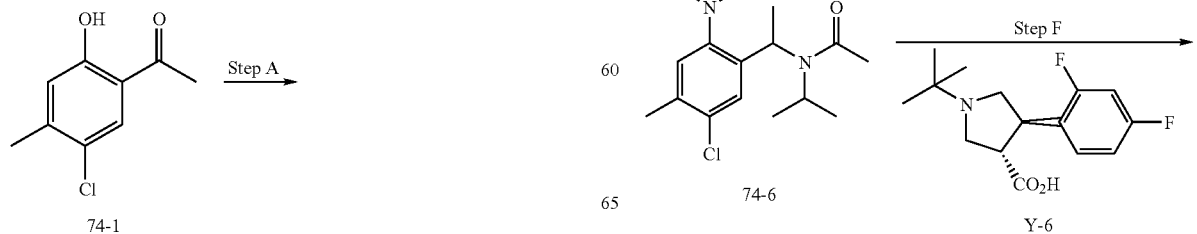

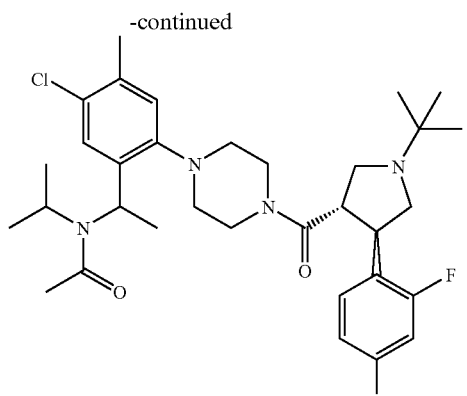

74-7

Step A: To a stirred solution of 5'-chloro-2'-hydroxy-4'-methyl acetophenone 74-1 (1.0 g, 5.4 mmol, Aldrich) and a catalytic amount of DMAP (0.06 g, 0.54 mmol) in anhydrous dichloromethane (40 mL) was added TEA (0.6 g, 5.9 mmol) at −78° C. To this mixture was added trifluoromethane sulfonic anhydride (3 g, 10.8 mmol) and the reaction was stirred for 2 h, then cooled to room temperature, poured into ice-water and extracted with dichloromethane, washed with saturated $NH_4Cl$, brine, filtered and concentrated under reduced pressure to give compound 74-2.

Step B: A stirred solution of compound 74-2 (4.0 g, 12.84 mmol), BOC piperazine C-1 (2.0, 10.7 mmol, Aldrich), cesium carbonate (2.9 g, 14.98 mmol), $Pd(OAc)_2$ (0.7 g, 0.32 mmol), 18-crown-6 (1.4 g, 5.3 mmol) and BINAP (0.3 g, 0.53 mmol) in toluene (100 mL) was heated to 85° C. and stirred overnight. Then the reaction was cooled to room temperature, filtered through celite and concentrated. The resulting residue was dissolved in EtOAc, washed with bicarbonate, brine, dried $Na_2SO_4$, filtered, concentrated and purified on silica gel, using 10% EtOAc/hexane as the eluting solvent, to give compound 74-3.

Step C: To a solution of tert-butyl 4-(2-acetyl-4-chloro-5-methylphenyl)piperazine-1-carboxylate 74-3 (1.4 g, 3.97 mmol) in anhydrous methanol (40 mL), was added NaOAc (1.62 g, 19.85 mmol), 3 Å molecular sieves, and isopropyl amine (1.87 g, 31.8 mmol). The mixture was stirred at 80° C. overnight. The reaction was then cooled to room temperature, filtered and concentrated under reduced pressure to give a residue. The residue was dissolved in dichloromethane (39 ml), then sodium cyano-borohydride (12 ml of 1 M solution in THF, 12 mmol) was added dropwise. The mixture was stirred overnight at reflux, then diluted with 1N NaOH aqueous solution and extracted with EtOAc. The organic layer was dried over anhydrous sodium sulfate, filtered and concentrated to give compound 74-4.

Step D: To a solution of tert-butyl 4-{5-chloro-2-[1-(cyclopropylamino)ethyl]-4-methylphenyl}piperazine-1-carboxylate 74-4 (3.97 mmol) in pyridine (39 mL) was added acetic anhydride (39.7 mmol) at 0° C. The reaction was allowed to slowly warm up to room temperature, then stirred overnight. The volatiles were removed under reduced pressure and the residue was purified via flash column chromatography on silica gel (gradient 12–100% EtOAc/heptanes) to give compound 74-5.

Step E: To a stirred solution of the compound 74-5 (0.1 g, 0.23 mmol) in EtOAc (10 mL), was added HCl (5 mL, 4M in dioxane) and the reaction mixture stirred at room temperature for 1 h. The reaction was then concentrated under reduced pressure to give compound 74-6 as the amine HCl salt.

Step F: Compound 74-6 (0.059 g, 174 mmol) was dissolved in DMF (10 mL) and (3S,4R)-1-tert-butyl-4-(2,4-difluorophenyl)pyrrolidine-3-carboxylic acid Y-6 (42 mg, 0.147 mmol), O-(7-azabenzotriazol-1-yl)-N,N,N',N',-tetramethyluronium hexafluorophosphate (HATU, 46 mg, 0.123 mmol), and DIEA (127 mg, 0.986 mmol) were added. The mixture was stirred at room temperature overnight, then diluted with EtOAc, and quenched with 1N NaOH aqueous solution. The layers were separated and the organic layer was washed with brine, dried over anhydrous magnesium sulfate, filtered, and concentrated. The resulting residue was purified with semi-prep HPLC on a 20×250 mm C-18 column (gradient 20–100% acetonitrile in water containing 0.1% TFA) and the resulting eluates was lyophilized under vacuum to give compound 74-7. Mass Spectrum: ES-MS Calcd. for $C_{33}H_{45}ClF_2N_4O_2$: 602. Found: 603 (M+1).

EXAMPLE 75

Preparation of Compound (75-1)

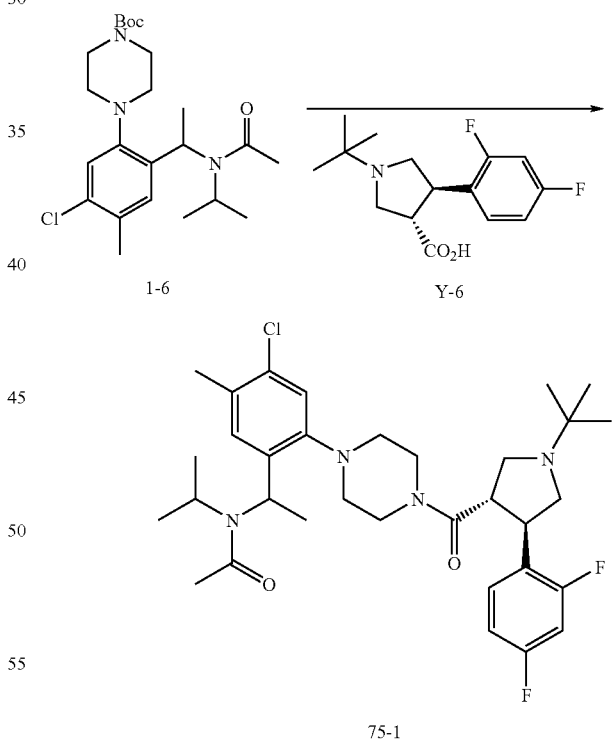

75-1

To a solution of (R or S)-tert-butyl 4-(2-{1-[acetyl(isopropyl)-amino]ethyl}-5-chloro-4-methylphenyl)piperazine-1-carboxylate 16 (427 mg, 0.97 mmol) in dichloromethane (10 mL) was added 4 N HCl in dioxane (10 mL) and the mixture was stirred at room temperature for 30 min. The volatiles were removed under reduced pressure to dryness, then 215 mg (0.523 mmol) of the residue was dissolved in DMF (10 mL) and (3S,4R)-1-tert-butyl-4-(2,4-difluorophenyl)-pyrrolidine-3-carboxylic acid Y-6 (177 mg, 0.627 mmol), O-(7-azabenzotriazol-1-yl)-N,N,N',N',-tetramethyluronium hexafluorophosphate (HATU, 219 mg, 0.575 mmol), and DIEA (540 mg, 4.18 mmol) were added. The mixture was stirred at room temperature overnight, diluted with ether, quenched with 1N NaOH aqueous solution. The layers were separated and the organic layer was washed with brine, dried over anhydrous magnesium sulfate, filtered, and concentrated. The resulting residue was purified by a semi-prep HPLC on a 20×250 mm C-18 column (gradient 40–100% acetonitrile in water containing 0.1% TFA). The eluates were concentrated and 1N NaOH aqueous solution was added to adjust the solution to basic, then aqueous mixture was extracted with EtOAc. The combined organic layers were washed with brine, dried over anhydrous magnesium sulfate, filtered, and concentrated to give compound 75-1 as a white solid. Mass Spectrum: ES-MS: Calcd. for $C_{33}H_{45}ClF_2N_4O_2$: 603. Found: 604 (M+1). First stereoisomer: $^1$H NMR (CD$_3$OD) 7.67 (m, 2H), 7.40 (m, 1H), 7.11–7.09 (m, 2H), 5.46–5.44 (d, 1H), 4.04–3.85 (m, 4H), 3.82 (m, 2H), 3.69–3.57 (m, 1H)3.53 (m, 1H) 3.31 (m, 1H), 2.82 (m, 1H), 2.59 (m, 1H), 2.41–2.38 (m, 6H), 2.23 (m, 3H), 1.63–1.62 (m, 2H)1.53–1.52 (d, 2H), 1.50 (m, 9H), 1.42–1.41 (m, 2H), 1.42–1.41 (m, 2H), 1.36–1.35 (m, 2H), 0.93 (m, 2H), 0.75–0.74 (d, 2H). Second stereoisomer: $^1$H NMR (CD$_3$OD) 7.63 (m, 2H), 7.49–7.36 (m, 1H), 7.10–7.08 (m, 2H), 5.46–5.20 (d, 2H), 4.22–3.79 (m, 6H), 3.60–3.37 (m, 3H), 3.13 (m, 1H), 2.66 (m, 1H), 2.38–2.19 (m, 9H), 1.96 (m, 2H)1.59 (m, 1H), 1.50 (m, 9H), 1.46 (m, 2H), 1.39–1.35 (m, 2H), 1.13 (d, 2H).

EXAMPLE 76

Preparation of Compound (76-1)

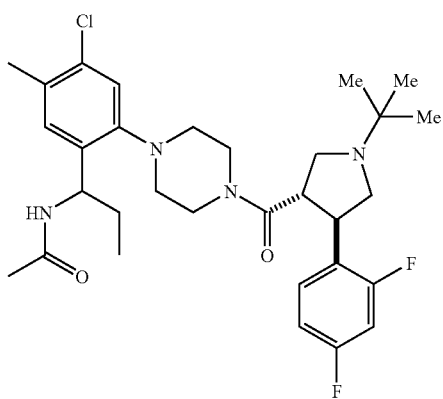

Compound 76-1 was prepared from 2-chloro-4-fluoro toluene following a procedure analogous to the procedure described for the preparation of compound 7-8 by replacing the acetyl chloride in Step A of the synthesis of compound 7-8 with propionyl chloride, and by replacing the piperidine acid Z-5 in Step F of the synthesis of compound 7-8 with difluorophenyl pyrrolidine acid Y-6. Mass Spectrum: Calcd. for $C_{31}H_{41}ClF_2N_4O_2$: 575. Found: 576 (M+1).

EXAMPLE 77

Preparation of Compound (77-5)

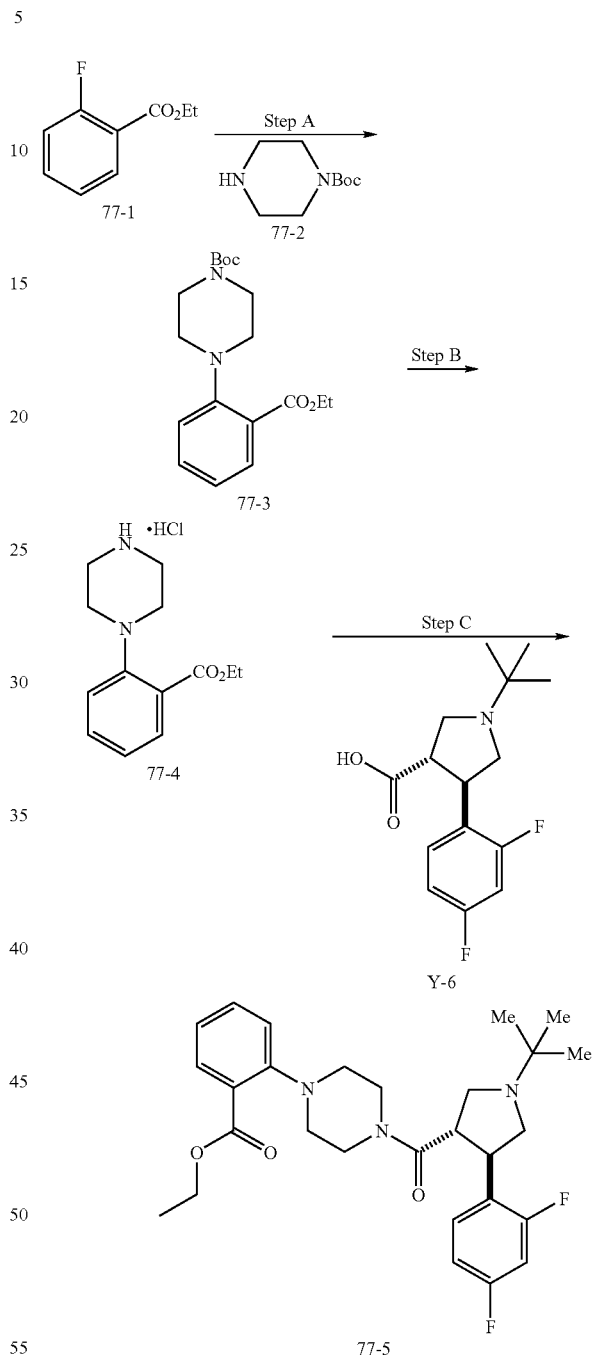

Step A: A mixture of compound 77-1 (2 g, 0.0535 mol), Boc piperazine 77-2 (3.32 g, 0.0178 mol, Aldrich), K$_2$CO$_3$ (7.39 g, 0.0535 mol) and copper (0.0756 g, 0.00119 mmol) in DMF (25 mL) was refluxed at 185 C overnight. The solution was cooled to room temperature, poured into 50 mL of ice water (50 mL) and extracted with EtOAc (3×50 mL). The combined organic layers were dried and concentrated in vacuo to give compound 77-3.

Step B: A solution of compound 77-3 (19 mg, 56.8 µmol) in HCl/EtOAc:CH$_2$Cl$_2$ (1:1, 3 mL) was aged at room temperature for 2 hours. The volatiles were evaporated to give 77-4, which was used in the next step without further purification.

Step C: To compound 77-4 (15 mg, 0.055 mmol) was added (3S,4R)-1-tert-butyl-4-(2,4-difluorophenyl)pyrrolidine-3-carboxylic acid Y-6 (17.7 mg, 0.055 mmol) then DMF (0.5 mL) and DIEA (29 μL, 0.166 mmol), followed by HATU (31.6 mg, 0.083 mmol) and HOAT (11.3 mg, 0.083 mmol). The reaction was stirred overnight, then diluted with 1N NaOH and extracted three times with ether. The combined organic extracts were washed with brine three times, dried over magnesium sulfate, filtered and concentrated in vacuo to give a residue. This residue was purified by reverse phase HPLC ($H_2O$/Acetonitrile/0.1% TFA modifier; gradient elution), then lyophilized to give compound 77-5. Mass Spectrum: Calcd. for $C_{28}H_{35}F_2N_3O_3$: 499.6. Found: 500.3 (M+H) and 523.3 (M+Na).

EXAMPLE 78

Preparation of Compound (78-2)

Step A: A solution of compound 5-4 (100 mg, 0.45 mmol) in HCl dioxane was stirred for 2 hours, then concentrated to give a residue. The residue was dissolved in 1N NaOH/$CH_2Cl_2$ and extracted twice with $CH_2Cl_2$. The organic layer was washed with brine, dried over magnesium sulfate, filtered and concentrated to give compound 78-1.

Step B: To compound 78-1 (100 mg, 0.45 mmol) and (3S,4R)-1-tert-butyl-4-(2,4-difluorophenyl)pyrrolidine-3-carboxylic acid Y-6 (127 mg, 0.45 mmol) was added DMF (10 mL) and DIEA (232 mg, 0.8 mmol), followed by HATU (171 mg, 0.45 mmol). The reaction was stirred overnight, then diluted with 1N NaOH and extracted three times with ether. The combined organic extracts were washed with brine three times, dried over magnesium sulfate, filtered and concentrated in vacuo to give a residue. The residue was purified by preparative TLC (20:1 $CH_2Cl_2$/MeOH) and concentrated in vacuo. The resulting residue was dissolved in $CH_2Cl_2$, filtered through an Acrodisk® filter, concentrated and excess HCl in diethyl either was added to give compound 78-2. Mass Spectrum: Calcd. for $C_{29}H_{37}F_2N_3O_2$: 497. Found: 498 (M+1).

EXAMPLE 79

Preparation of Compound (79-2)

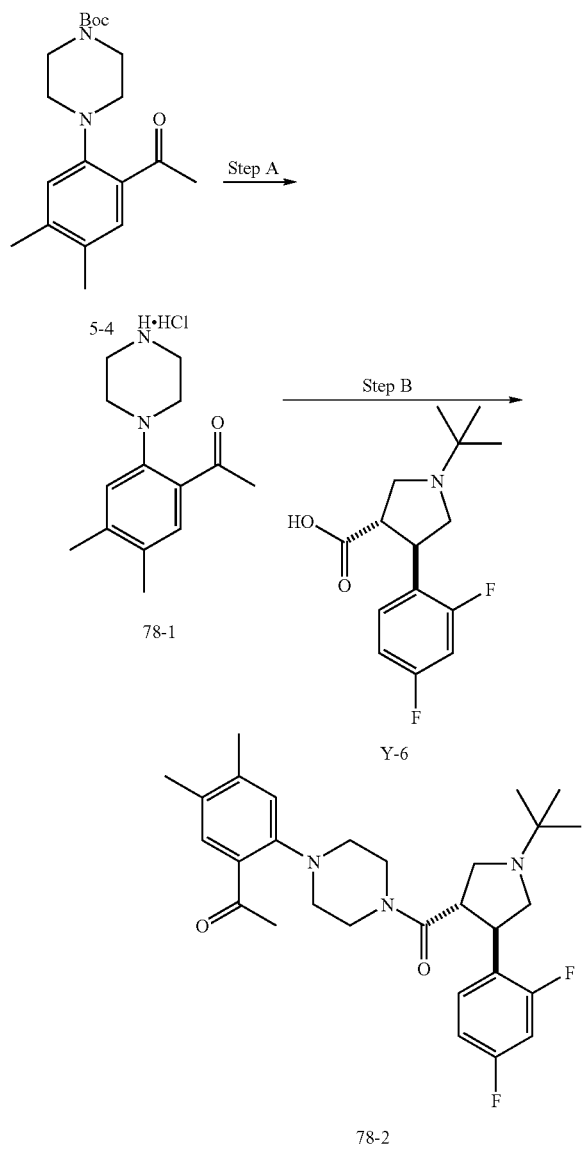

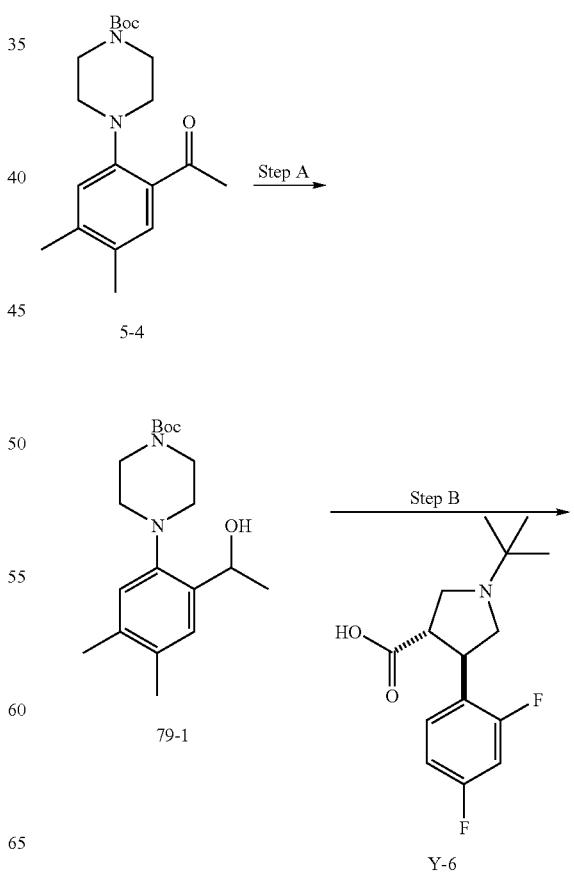

-continued

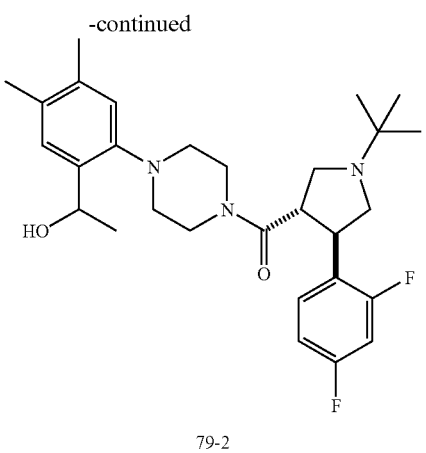

79-2

Step A: To a solution of compound 5-4 (1 g, 3 mmol) in THF/MeOH (9:1, 30 mL) at −10 C was added NaBH$_4$ (238 mg, 6.3 mmol). The reaction was refrigerated until complete, then quenched with water, poured into saturated aqueous sodium bicarbonate and extracted three times with EtOAc. The combined organic extracts were dried over magnesium sulfate, filtered and concentrated in vacuo. The residue was purified via silica chromatography (Biotage, 11%–45% EtOAc/Heptane gradient elution) to give compound 79-1.

Step B: HCl/dioxane (4 M, 0.299 µmol, 0.299 µl) was added to a solution of compound 79-1 (100 mg, 0.45 mmol) in ether (1.2 mL), the resulting mixture was stirred for 4 hours, then concentrated to give a residue. To the residue in DMF (5 mL) was added (3S,4R)-1-tert-butyl-4-(2,4-difluorophenyl)pyrrolidine-3-carboxylic acid Y-6 (21 mg, 0.0748 mmol) and DIEA (38.5 mg, 0.299 mmol), followed by HATU (28 mg, 0.0748 mmol). The reaction was stirred overnight, then diluted with 1N NaOH and extracted three times with ether. The combined organic extracts were washed with brine three times, dried over magnesium sulfate, filtered and concentrated in vacuo to give a residue. This residue was purified by preparative TLC (20:1 CH$_2$Cl$_2$/MeOH) and concentrated in vacuo, then excess HCl in diethyl ether was added and the mixture was filtered to give compound 79-2 as a solid. Mass Spectrum: Calcd. for C$_{29}$H$_{39}$F$_2$N$_3$O$_2$: 499.6. Found: 500 (M+1).

BIOLOGICAL ASSAYS

A. Binding Assay. The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 ml 10% heat-inactivated fetal bovine serum (Sigma); 10 mL 10,000 unit/mL penicillin & 10,000 µg/mL streptomycin (Gibco/BR1); 10 ml 200 mM L-glutamine (Gibco/BR1); 1 mg/mL geneticin (G418) (Gibco/BR1). The cells were grown at 37° C. with CO$_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2–7.4; 4 µg/mL Leupeptin (Sigma); 10 µM Phosphoramidon (Boehringer Mannheim); 40 µg/mL Bacitracin (Sigma); 5 µg/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500–1000 µL/tube) and quick frozen in liquid nitrogen and then stored at −80° C.

Test compounds or unlabelled NDP-α-MSH was added to 100 µL of membrane binding buffer to a final concentration of 1 µM. The membrane binding buffer had the composition: 50 mM Tris pH 7.2; 2 mM CaCl$_2$; 1 mM MgCl$_2$; 5 mM KCl; 0.2% BSA; 4 µg/mL Leupeptin (SIGMA); 10 µM Phosphoramidon (Boehringer Mannheim); 40 µg/mL Bacitracin (SIGMA); 5 µg/mL Aprotinin (SIGMA); and 10 mM Pefabloc (Boehringer Mannheim). One hundred µL of membrane binding buffer containing 10–40 µg membrane protein was added, followed by 100 µM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 µL of Packard Microscint-20 was added to each well. The top was sealed and the radioactivity quantitated in a Packard Topcount Microplate Scintillation counter.

B. Functional assay. Functional cell based assays were developed to discriminate melanocortin receptor agonists from antagonists.

Cells (for example, CHO— or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997 March; 11(3): 274–80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM MgCl$_2$, 1 mM glutamine and 1 mg/ml bovine serum albumin. Cells were counted and diluted to 1 to 5×10$^6$/mL. The phosphodiesterase inhibitor 3-isobutyl-1-methylxanthine was added to cells to 0.6 mM.

Test compounds were diluted in dimethylsulfoxide (DMSO) (10$^{-5}$ to 10$^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min, and an $EC_{50}$ dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In Vivo Food Intake Models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276–R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

Representative compounds of the present invention were tested and found to bind to the melanocortin-4 receptor. These compounds were generally found to have $IC_{50}$ values less than 10 μM. Representative compounds of the present invention were also tested in the functional assay and found generally to activate the melanocortin-4 receptor with $EC_{50}$ values less than 10 μM.

EXAMPLES OF PHARMACEUTICAL COMPOSITIONS

As a specific embodiment of an oral composition of a composition of the present invention, 5 mg of Example 3 is formulated with sufficient finely divided lactose to provide a total amount of 580 to 1000 mg to fill a size O hard gelatin capsule.

As another specific embodiment of an oral composition of a compound of the present invention, 2.5 mg of Example 4 is formulated with sufficient finely divided lactose to provide a total amount of 580 to 1000 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

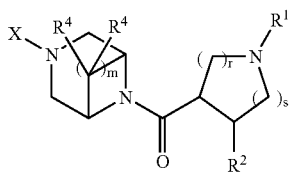

or a pharmaceutically acceptable salt thereof; wherein
X is selected from the group consisting of
(1) $C_{1-8}$ alkyl,
(2) $-(CH_2)_n C_{3-8}$ cycloalkyl,
(3) $-(CH_2)_n$-phenyl,
(4) $-(CH_2)_n$-naphthyl,
(5) $-(CH_2)_n$-heteroaryl,
(6) $-(CH_2)_n$heterocycloalkyl,
(7) $-(CH_2)_n C(R^5)(R^6)(R^7)$,
(8) $-(CH_2)_n C\equiv N$,
(9) $-(CH_2)_n CON(R^8)_2$,
(10) $-(CH_2)_n CO_2 R^8$,
(11) $-(CH_2)_n COR^8$,
(12) $-(CH_2)_n NR^8 C(O)R^8$,
(13) $-(CH_2)_n NR^8 CO_2 R^8$,
(14) $-(CH_2)_n NR^8 C(O)N(R^8)_2$,
(15) $-(CH_2)_n NR^8 SO_2 R^8$,
(16) $-(CH_2)_n S(O)_p R^8$,
(17) $-(CH_2)_n SO_2 N(R^8)_2$,
(18) $-(CH_2)_n OR^8$,
(19) $-(CH_2)_n OC(O)R^8$,
(20) $-(CH_2)_n OC(O)OR^8$,
(21) $-(CH_2)_n OC(O)N(R^8)_2$,
(22) $-(CH_2)_n N(R^8)_2$, and
(23) $-(CH_2)_n NR^8 SO_2 N(R^8)_2$,
wherein heteroaryl is selected from pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, and isoquinolyl, and wherein phenyl, naphthyl, and heteroaryl are unsubstituted or substituted with one to three groups independently selected from $R^3$, and alkyl, cycloalkyl, and heterocycloalkyl are unsubstituted or substituted with one to three groups independently selected from $R^3$ and oxo, and wherein any methylene ($CH_2$) in X is unsubstituted or substituted with one to two groups independently selected from halogen, hydroxy, and $C_{1-4}$ alkyl;

$R^1$ is selected from the group consisting of
(1) hydrogen,
(2) amidino,
(3) $C_{1-4}$ alkyliminoyl,
(4) $C_{1-10}$ alkyl,
(5) $-(CH_2)_n - C_{3-7}$ cycloalkyl,
(6) $-(CH_2)_n$-phenyl,
(7) $-(CH_2)_n$-naphthyl, and
(8) $-(CH_2)_n$-heteroaryl,
wherein phenyl, naphthyl, and heteroaryl are unsubstituted or substituted with one to three groups independently selected from $R^3$, and alkyl and cycloalkyl are unsubstituted or substituted with one to three groups independently selected from $R^3$ and oxo;

$R^2$ is selected from the group consisting of
(1) phenyl, and
(2) naphthyl,
wherein phenyl and naphthyl are unsubstituted or substituted with one to three groups independently selected from $R^3$;

each $R^3$ is independently selected from the group consisting of
(1) $C_{1-8}$ alkyl,
(2) $C_{2-8}$ alkenyl,
(3) $-(CH_2)_n$-phenyl,
(4) $-(CH_2)_n$-naphthyl,
(5) $-(CH_2)_n$-heteroaryl,
(6) $-(CH_2)_n C_{2-7}$ heterocycloalkyl,
(7) $-(CH_2)_n C_{3-7}$ cycloalkyl,
(8) halogen,
(9) $OR^9$,
(10) $-(CH_2)_n C(O)R^9$,
(11) $-(CH_2)_n OC(O)R^9$,
(12) $-(CH_2)_n C(O)OR^9$,
(13) $-(CH_2)_n C\equiv N$,
(14) $NO_2$,
(15) $-(CH_2)_n N(R^9)_2$,
(16) $-(CH_2)_n C(O)N(R^9)_2$,
(17) $-(CH_2)_n NR^9 C(O)R^9$,
(18) $-(CH_2)_n NR^9 C(O)OR^9$,
(19) $-(CH_2)_n NR^9 C(O)$-heteroaryl,
(20) $-(CH_2)_n NR^9 C(O)N(R^9)_2$,
(21) $-(CH_2)_n C(O)NR^9 N(R^9)_2$,
(22) $-(CH_2)_n C(O)NR^9 NR^9 C(O)R^9$,
(23) $-(CH_2)_n NR^9 S(O)_p R^9$,
(24) $-(CH_2)_n S(O)_p N(R^9)_2$,
(25) $-(CH_2)_n S(O)_p R^9$,
(26) $O(CH_2)_n C(O)N(R^9)_2$,
(27) $CF_3$,
(28) $CH_2 CF_3$,
(29) $OCF_3$, and
(30) $OCH_2 CF_3$,
wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
(1) hydrogen,
(2) $C_{1-8}$ alkyl,
(3) —$(CH_2)_n C_{3-6}$ cycloalkyl,
(4) —$(CH_2)_n$-aryl,
(5) hydroxy,
(6) halogen, and
(7) amino;

$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_n C_{3-7}$ cycloalkyl,
(7) —$(CH_2)_n C_{2-7}$ heterocycloalkyl,
(8) —$(CH_2)_n$-phenyl,
(9) —$(CH_2)_n$-naphthyl,
(10) —$(CH_2)_n$-heteroaryl, and
(11) —$(CH_2)_n C_{3-7}$ bicycloalkyl,
wherein phenyl, naphthyl, and heteroaryl are unsubstituted or substituted with one to three groups independently selected from $R^3$, and alkyl, alkenyl, alkynyl, alkoxy, cycloalkyl, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
(1) hydrogen, and
(2) $C_{1-8}$ alkyl;

$R^7$ is selected from the group consisting of
(1) —$(CH_2)_n N(R^8)_2$,
(2) —$(CH_2)_n NR^8 C(O)R^8$,
(3) —$(CH_2)_n NR^8 C(O)OR^8$,
(4) —$(CH_2)_n NR^8 C(O)N(R^8)_2$,
(5) —$(CH_2)_n NR^8 S(O)R^8$,
(6) —$(CH_2)_n NR^8 S(O)_2 R^8$, and
(7) —$(CH_2)_n NR^8 S(O)_2 N(R^8)_2$,
wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
(1) hydrogen,
(2) $C_{1-8}$ alkyl,
(3) $C_{2-8}$ alkenyl,
(4) —$(CH_2)_n C_{3-7}$ cycloalkyl,
(5) —$(CH_2)_n C_{2-7}$ heterocycloalkyl,
(6) —$(CH_2)_n C_{3-7}$ bicycloalkyl,
(7) —$(CH_2)_n$-phenyl,
(8) —$(CH_2)_n$-naphthyl, and
(9) —$(CH_2)_n$-heteroaryl,
wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_n$ heterocycloalkyl, and
(6) $C_{3-6}$ cycloalkyl,
wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;

r is 1 or 2;
s is 1;
m is 0;
n is 0, 1, 2, 3, or 4; and
p is 0, 1, or 2.

2. The compound of claim 1 wherein $R^1$ is selected from the group consisting of hydrogen, $C_{1-6}$ alkyl, —$(CH_2)_{0-1} C_{3-6}$ cycloalkyl, and —$(CH_2)_{0-1}$-phenyl, wherein phenyl is unsubstituted or substituted with one to three groups independently selected from $R^3$, and alkyl and cycloalkyl are optionally substituted with one to three groups independently selected from $R^3$ and oxo; and pharmaceutically acceptable salts thereof.

3. The compound of claim 1 wherein $R^2$ is phenyl, optionally substituted with one to three groups independently selected from $R^3$; and pharmaceutically acceptable salts thereof.

4. The compound of claim 3 wherein $R^2$ is phenyl optionally substituted with one to three groups independently selected from $R^3$; and pharmaceutically acceptable salts thereof.

5. The compound of claim 1 wherein X is selected from the group consisting of
(1) $C_{1-8}$ alkyl,
(2) —$(CH_2)_n C_{3-8}$ cycloalkyl,
(3) —$(CH_2)_n$-phenyl,
(4) —$(CH_2)_n$-heteroaryl,
(5) —$(CH_2)_n$ heterocycloalkyl, and
(6) —$(CH_2)_n C(R^5)(R^6)(R^7)$,
wherein heteroaryl is selected from pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, and isoquinolyl, and wherein phenyl and heteroaryl are unsubstituted or substituted with one to three groups independently selected from $R^3$, and alkyl, cycloalkyl, and heterocycloalkyl are unsubstituted or substituted with one to three groups independently selected from $R^3$ and oxo, and wherein any methylene ($CH_2$) in X is unsubstituted or substituted with one to two groups independently selected from halogen, hydroxy, and $C_{1-4}$ alkyl; and pharmaceutically acceptable salts thereof.

6. The compound of claim 5 wherein X is phenyl or heteroaryl optionally substituted with one to three groups independently selected from $R^3$, wherein heteroaryl is selected from pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, and isoquinolyl; and pharmaceutically acceptable salts thereof.

7. The compound of claim 6 wherein X is phenyl optionally substituted with one to three groups independently selected from $R^3$; and pharmaceutically acceptable salts thereof.

8. The compound of claim 5 wherein X is $-(CH_2)_nC(R^5)(R^6)(R^7)$; and pharmaceutically acceptable salts thereof.

9. The compound of claim 8 wherein
n is 0;
$R^5$ is selected from the group consisting of
(1) $C_{1-8}$ alkyl,
(2) $-(CH_2)_nC_{3-7}$ cycloalkyl,
(3) $-(CH_2)_nC_{2-7}$ heterocycloalkyl,
(4) $-(CH_2)_n$-phenyl, and
(5) $-(CH_2)_n$-heteroaryl,
wherein phenyl, and heteroaryl are unsubstituted or substituted with one to three groups independently selected from $R^3$, and alkyl, cycloalkyl and heterocycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl; and
$R^6$ is hydrogen; and
pharmaceutically acceptable salts thereof.

10. The compound of claim 1 wherein r is 1.
11. The compound of claim 1 wherein r is 2.
12. The compound of claim 1 wherein $R^2$ is phenyl substituted with one to three groups independently selected from $R^3$.
13. The compound of claim 1 of structural formula IIa or IIb of the indicated trans relative stereochemical configuration:

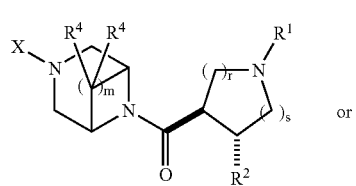
(IIa)

or

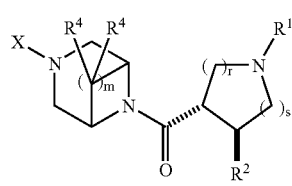
(IIb)

or a pharmaceutically acceptable salt thereof;

wherein
X is selected from the group consisting of
(1) $C_{1-8}$ alkyl,
(2) $-(CH_2)_nC_{3-8}$ cycloalkyl,
(3) $-(CH_2)_n$-phenyl,
(4) $-(CH_2)_n$-heteroaryl,
(5) $-(CH_2)_n$heterocycloalkyl, and
(6) $-(CH_2)_nC(R^5)(R^6)(R^7)$,
wherein heteroaryl is selected from pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, and isoquinolyl, and wherein phenyl and heteroaryl are unsubstituted or substituted with one to three groups independently selected from $R^3$, and alkyl, cycloalkyl, and heterocycloalkyl are unsubstituted or substituted with one to three groups independently selected from $R^3$ and oxo, and wherein any methylene ($CH_2$) in X is unsubstituted or substituted with one to two groups independently selected from halogen, hydroxy, and $C_{1-4}$ alkyl;
$R^1$ is selected from the group consisting of hydrogen, amidino, $C_{1-4}$ alkyliminoyl, $C_{1-6}$ alkyl, $C_{5-6}$ cycloalkyl, $-(CH_2)_{0-1}$ phenyl, and $-(CH_2)_{0-1}$ heteroaryl, wherein phenyl and heteroaryl are unsubstituted or substituted with one to three groups independently selected from $R^3$, and alkyl and cycloalkyl are unsubstituted or substituted with one to three groups independently selected from $R^3$ and oxo;
$R^2$ is phenyl, optionally substituted with one to three groups independently selected from $R^3$;
each $R^3$ is independently selected from the group consisting of
(1) $C_{1-8}$ alkyl,
(2) $C_{2-8}$ alkenyl,
(3) $-(CH_2)_n$-phenyl,
(4) $-(CH_2)_n$-naphthyl,
(5) $-(CH_2)_n$-heteroaryl,
(6) $-(CH_2)_nC_{2-7}$ heterocycloalkyl,
(7) $-(CH_2)_nC_{3-7}$ cycloalkyl,
(8) halogen,
(9) $OR^9$,
(10) $-(CH_2)_nC(O)R^9$,
(11) $-(CH_2)_nOC(O)R^9$,
(12) $-(CH_2)_nC(O)OR^9$,
(13) $-(CH_2)_nC\equiv N$,
(14) $NO_2$,
(15) $-(CH_2)_nN(R^9)_2$,
(16) $-(CH_2)_nC(O)N(R^9)_2$,
(17) $-(CH_2)_nNR^9C(O)R^9$,
(18) $-(CH_2)_nNR^9C(O)OR^9$,
(19) $-(CH_2)_nNR^9C(O)$-heteroaryl,
(20) $-(CH_2)_nNR^9C(O)N(R^9)_2$,
(21) $-(CH_2)_nC(O)NR^9N(R^9)_2$,
(22) $-(CH_2)_nC(O)NR^9NR^9C(O)R^9$,
(23) $-(CH_2)_nNR^9S(O)_pR^9$,
(24) $-(CH_2)_nS(O)_pN(R^9)_2$,
(25) $-(CH_2)_nS(O)_pR^9$,
(26) $O(CH_2)_nC(O)N(R^9)_2$,
(27) $CF_3$,
(28) $CH_2CF_3$,
(29) $OCF_3$, and
(30) $OCH_2CF_3$,
wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
(1) hydrogen,
(2) $C_{1-8}$ alkyl,
(3) —$(CH_2)_{0-1}C_{3-6}$ cycloalkyl,
(4) —$(CH_2)_{0-1}$-aryl,
(5) hydroxy,
(6) halogen, and
(7) amino;

$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_nC_{3-7}$ cycloalkyl,
(7) —$(CH_2)_nC_{2-7}$ heterocycloalkyl,
(8) —$(CH_2)_n$-phenyl,
(9) —$(CH_2)_n$-naphthyl,
(10) —$(CH_2)_n$-heteroaryl, and
(11) —$(CH_2)_nC_{3-7}$ bicycloalkyl,
wherein phenyl, naphthyl, and heteroaryl are unsubstituted or substituted with one to three groups independently selected from $R^3$, and alkyl, alkenyl, alkynyl, alkoxy, cycloalkyl, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
(1) hydrogen, and
(2) $C_{1-8}$ alkyl;

$R^7$ is selected from the group consisting of
(1) —$(CH_2)_nN(R^8)_2$,
(2) —$(CH_2)_nNR^8C(O)R^8$,
(3) —$(CH_2)_nNR^8C(O)OR^8$,
(4) —$(CH_2)_nNR^8C(O)N(R^8)_2$,
(5) —$(CH_2)_nNR^8S(O)R^8$,
(6) —$(CH_2)_nNR^8S(O)_2R^8$, and
(7) —$(CH_2)_nNR^8S(O)_2N(R^8)_2$,
wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
(1) hydrogen,
(2) $C_{1-8}$ alkyl,
(3) $C_{2-8}$ alkenyl,
(4) —$(CH_2)_nC_{3-7}$ cycloalkyl,
(5) —$(CH_2)_nC_{2-7}$ heterocycloalkyl,
(6) —$(CH_2)_nC_{3-7}$ bicycloalkyl,
(7) —$(CH_2)_n$-phenyl,
(8) —$(CH_2)_n$-naphthyl, and
(9) —$(CH_2)_n$-heteroaryl, wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_n$ heterocycloalkyl, and
(6) $C_{3-6}$ cycloalkyl,
wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;

r is 1 or 2;
s is 1;
m is 0;
n is 0, 1, 2, 3 or 4; and
p is 0, 1, or 2.

14. The compound of claim 1 of the following structural formula with the indicated trans relative stereochemical configuration:

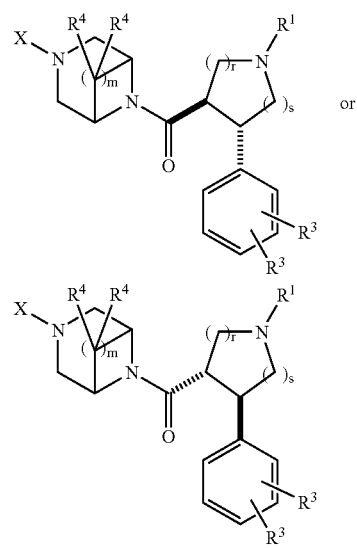

or a pharmaceutically acceptable salt thereof; wherein
X is selected from the group consisting of
(1) —$(CH_2)_{0-1}$-phenyl,
(2) —$(CH_2)_{0-1}$-heteroaryl, and
(3) —$(CH_2)_{0-1}C(R^5)(R^6)(R^7)$, wherein heteroaryl is selected from pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, and isoquinolyl, and wherein phenyl and heteroaryl are unsubstituted or substituted with one to three groups independently selected from $R^3$, and wherein any methylene ($CH_2$) in X is unsubstituted or substituted with one to two groups independently selected from halogen, hydroxy, and $C_{1-4}$ alkyl;

$R^1$ is selected from the group consisting of hydrogen, $C_{1-4}$ alkyl, and —$(CH_2)_{0-1}$ phenyl;

each $R^3$ is independently selected from the group consisting of
- (1) $C_{1-8}$ alkyl,
- (2) $C_{2-8}$ alkenyl,
- (3) —$(CH_2)_{0-1}$-phenyl,
- (4) —$(CH_2)_{0-1}$-naphthyl,
- (5) —$(CH_2)_{0-1}$-heteroaryl,
- (6) —$(CH_2)_{0-1}$—$C_{2-7}$ heterocycloalkyl,
- (7) —$(CH_2)_{0-1}$—$C_{3-7}$ cycloalkyl,
- (8) halogen,
- (9) $OR^9$,
- (10) —$(CH_2)_{0-1}$—$C(O)R^9$,
- (11) —$(CH_2)_{0-1}$—$OC(O)R^9$,
- (12) —$(CH_2)_{0-1}$—$C(O)OR^9$,
- (13) —$(CH_2)_{0-1}$—$C{\equiv}N$,
- (14) $NO_2$,
- (15) —$(CH_2)_{0-1}$—$N(R^9)_2$,
- (16) —$(CH_2)_{0-1}$—$C(O)N(R^9)_2$,
- (17) —$(CH_2)_{0-1}$—$NR^9C(O)R^9$,
- (18) —$(CH_2)_{0-1}$—$NR^9C(O)OR^9$,
- (19) —$(CH_2)_{0-1}NR^9C(O)$-heteroaryl,
- (20) —$(CH_2)_{0-1}NR^9C(O)N(R^9)_2$,
- (21) —$(CH_2)_{0-1}C(O)NR^9N(R^9)_2$,
- (22) —$(CH_2)_{0-1}$—$C(O)NR^9NR^9C(O)R^9$,
- (23) —$(CH_2)_{0-1}$—$NR^9S(O)_{1-2}R^9$,
- (24) —$(CH_2)_{0-1}$—$S(O)_{1-2}N(R^9)_2$,
- (25) —$(CH_2)_{0-1}$—$S(O)_{0-2}R^9$,
- (26) $O(CH_2)_{0-1}$—$C(O)N(R^9)_2$,
- (27) $CF_3$,
- (28) $CH_2CF_3$,
- (29) $OCF_3$, and
- (30) $OCH_2CF_3$, wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
- (1) hydrogen,
- (2) $C_{1-8}$ alkyl,
- (3) —$(CH_2)_{0-1}$—$C_{3-6}$ cycloalkyl,
- (4) —$(CH_2)_{0-1}$-aryl,
- (5) hydroxy,
- (6) halogen, and
- (7) amino;

$R^5$ is independently selected from the group consisting of
- (1) hydrogen,
- (2) $C_{1-8}$ alkyl,
- (3) $C_{2-8}$ alkenyl,
- (4) $C_{2-8}$ alkynyl,
- (5) $C_{1-8}$ alkoxy,
- (6) —$(CH_2)_{0-1}$—$C_{3-7}$ cycloalkyl,
- (7) —$(CH_2)_{0-1}$—$C_{2-7}$ heterocycloalkyl,
- (8) —$(CH_2)_{0-1}$-phenyl,
- (9) —$(CH_2)_{0-1}$-naphthyl,
- (10) —$(CH_2)_{0-1}$-heteroaryl, and
- (11) —$(CH_2)_{0-1}$—$C_{3-7}$ bicycloalkyl, wherein phenyl, naphthyl, and heteroaryl are unsubstituted or substituted with one to three groups independently selected from $R^3$, and alkyl, alkenyl, alkynyl, alkoxy, cycloalky, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
- (1) hydrogen, and
- (2) $C_{1-8}$ alkyl;

$R^7$ is selected from the group consisting of
- (1) —$(CH_2)_{0-3}$—$N(R^8)_2$,
- (2) —$(CH_2)_{0-3}$—$NR^8C(O)R^8$,
- (3) —$(CH_2)_{0-3}$—$NR^8C(O)OR^8$,
- (4) —$(CH_2)_{0-3}$—$NR^8C(O)N(R^8)_2$,
- (5) —$(CH_2)_{0-3}$—$NR^8S(O)R^8$,
- (6) —$(CH_2)_{0-3}$—$NR^8S(O)_2R^8$, and
- (7) —$(CH_2)_{0-3}$—$NR^8S(O)_2N(R^8)_2$, wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
- (1) hydrogen,
- (2) $C_{1-8}$ alkyl,
- (3) $C_{2-8}$ alkenyl,
- (4) —$(CH_2)_{0-1}$—$C_{3-7}$ cycloalkyl,
- (5) —$(CH_2)_{0-1}$—$C_{2-7}$ heterocycloalkyl,
- (6) —$(CH_2)_{0-1}$—$C_{3-7}$ bicycloalkyl,
- (7) —$(CH_2)_{0-1}$-phenyl,
- (8) —$(CH_2)_{0-1}$-naphthyl, and
- (9) —$(CH_2)_{0-1}$-heteroaryl, wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_{0-1}$ heterocycloalkyl, and
(6) $C_{3-6}$ cycloalkyl,
wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;
r is 1 or 2;
s is 1; and
m is 0;

15. The compound of claim 1 of structural formula IV:

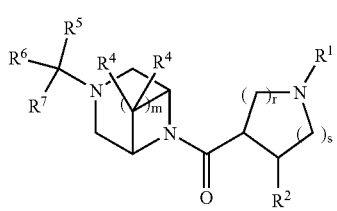

IV or a pharmaceutically acceptable salt thereof; wherein
$R^1$ is selected from the group consisting of
(1) hydrogen,
(2) amidino,
(3) $C_{1-4}$ alkyliminoyl,
(4) $C_{1-10}$ alkyl,
(5) —$(CH_2)_n$—$C_{3-7}$ cycloalkyl,
(6) —$(CH_2)_n$-phenyl,
(7) —$(CH_2)_n$-naphthyl, and
wherein phenyl, naphthyl, and heteroaryl are unsubstituted or substituted with one to three groups independently selected from $R^3$, and alkyl and cycloalkyl are unsubstituted or substituted with one to three groups independently selected from $R^3$ and oxo;
$R^2$ is selected from the group consisting of
(1) phenyl, and
(2) naphthyl,
wherein phenyl and naphthyl are unsubstituted or substituted with one to three groups independently selected from $R^3$;
each $R^3$ is independently selected from the group consisting of
(1) $C_{1-8}$ alkyl,
(2) $C_{2-8}$ alkenyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^9$,
(10) —$(CH_2)_nC(O)R^9$,
(11) —$(CH_2)_nOC(O)R^9$,
(12) —$(CH_2)_nC(O)OR^9$,
(13) —$(CH_2)_nC\equiv N$,
(14) $NO_2$,
(15) —$(CH_2)_nN(R^9)_2$,
(16) —$(CH_2)_nC(O)N(R^9)_2$,
(17) —$(CH_2)_nNR^9C(O)R^9$,
(18) —$(CH_2)_nNR^9C(O)OR^9$,
(19) —$(CH_2)_nNR^9C(O)$-heteroaryl,
(20) —$(CH_2)_nNR^9C(O)N(R^9)_2$,
(21) —$(CH_2)_nC(O)NR^9N(R^9)_2$,
(22) —$(CH_2)_nC(O)NR^9NR^9C(O)R^9$,
(23) —$(CH_2)_nNR^9S(O)_pR^9$,
(24) —$(CH_2)_nS(O)_pN(R^9)_2$,
(25) —$(CH_2)_nS(O)_pR^9$,
(26) $O(CH_2)_nC(O)N(R^9)_2$,
(27) $CF_3$,
(28) $CH_2CF_3$,
(29) $OCF_3$, and
(30) $OCH_2CF_3$,
wherein alkenyl, phenyl, naphthyl, heteroaryl are unsubstituted or substituted with one to three substituents independently selected from halogen, hydroxy, $C_{1-4}$ alkyl, trifluoromethyl, and $C_{1-4}$ alkoxy, and wherein any alkyl, cycloalkyl, heterocycloalkyl, and methylene ($CH_2$) carbon atom in $R^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;
each $R^4$ is independently selected from the group consisting of
(1) hydrogen,
(2) $C_{1-8}$ alkyl,
(3) —$(CH_2)_nC_{3-6}$ cycloalkyl,
(4) —$(CH_2)_n$-aryl,
(5) hydroxy,
(6) halogen, and
(7) amino;
$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_nC_{3-7}$ cycloalkyl,
(7) —$(CH_2)_nC_{2-7}$ heterocycloalkyl,
(8) —$(CH_2)_n$-phenyl,
(9) —$(CH_2)_n$-naphthyl,
(10) —$(CH_2)_n$-heteroaryl, and
(11) —$(CH_2)_nC_{3-7}$ bicycloalkyl,
wherein phenyl, naphthyl, and heteroaryl are unsubstituted or substituted with one to three groups independently selected from $R^3$, and alkyl, alkenyl, alkynyl, alkoxy, cycloalkyl, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;
$R^6$ is selected from the group consisting of
(1) hydrogen, and
(2) $C_{1-8}$ alkyl;
$R^7$ is selected from the group consisting of
(1) —$(CH_2)_nN(R^8)_2$,
(2) —$(CH_2)_nNR^8C(O)R^8$,
(3) —$(CH_2)_nNR^8C(O)OR^8$,
(4) —$(CH_2)_nNR^8C(O)N(R^8)_2$,
(5) —$(CH_2)_nNR^8S(O)R^8$, (6) —(CH$_2$)$_n$NR$^8$S(O)$_2$R$^8$, and (7) —(CH$_2$)$_n$NR$^8$S(O)$_2$N(R$^8$)$_2$, wherein any methylene (CH$_2$) in R$^7$ is unsubstituted or substituted with one to two groups independently selected from halogen, hydroxy, and C$_{1-4}$ alkyl, or two R$^8$ substituents together with the carbon, nitrogen or sulfur atom to which they are attached form a 5, 6, or 7-membered saturated or unsaturated nitrogen containing ring optionally substituted with one to three groups independently selected from C$_{1-8}$ alkyl and oxo;

each R$^8$ is independently selected from the group consisting of (1) hydrogen, (2) C$_{1-8}$ alkyl, (3) C$_{2-8}$ alkenyl, (4) —(CH$_2$)$_n$C$_{3-7}$ cycloalkyl, (5) —(CH$_2$)$_n$C$_{2-7}$ heterocycloalkyl, (6) —(CH$_2$)$_n$C$_{3-7}$ bicycloalkyl, (7) —(CH$_2$)$_n$-phenyl, (8) —(CH$_2$)$_n$-naphthyl, and (9) —(CH$_2$)$_n$-heteroaryl, wherein alkyl, alkenyl, cycloalkyl, heterocycloalkyl, and bicycloalkyl are unsubstituted or substituted with one to three groups independently selected from R$^3$ and oxo, and wherein phenyl, naphthyl, and heteroaryl are unsubstituted or substituted with one to three groups independently selected from R$^3$, and wherein any methylene (CH$_2$) in R$^8$ is unsubstituted or substituted with one to two groups independently selected from halogen, hydroxy, and C$_{1-4}$ alkyl, or two R$^8$ groups together with the atom to which they are attached form a 5- to 8-membered mono- or bicyclic ring system optionally containing an additional heteroatom selected from O, S, and —NC$_{1-4}$ alkyl;

each R$^9$ is independently selected from the group consisting of (1) hydrogen, (2) C$_{1-8}$ alkyl, (3) phenyl, (4) heteroaryl, (5) —(CH$_2$)$_n$ heterocycloalkyl, and (6) C$_{3-6}$ cycloalkyl, wherein alkyl, phenyl, heteroaryl, heterocycloalkyl, and cycloalkyl are unsubstituted or substituted with one to three groups independently selected from halogen, C$_{1-4}$ alkyl, hydroxy, and C$_{1-4}$ alkoxy, or two R$^9$ groups together with the atom to which they are attached form a 4- to 8-membered mono- or bicyclic ring system optionally containing an additional heteroatom selected from O, S, and —NC$_{1-4}$ alkyl;

r is 1 or 2;

s is 1;

m is 0;

n is 0, 1, 2, 3, or 4; and p is 0, 1, or 2.

16. The compound of claim 1 of the following structural formula with the indicated trans relative stereochemical configuration:

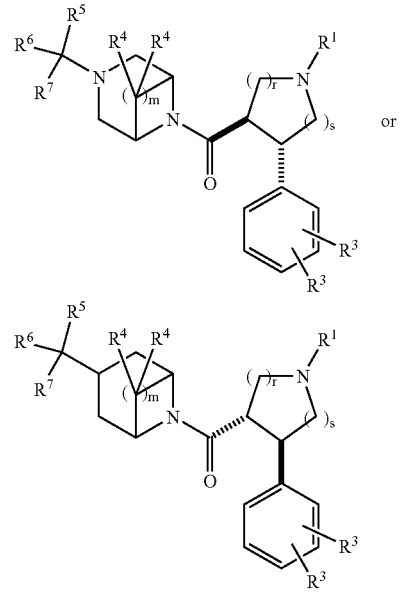

or a pharmaceutically acceptable salt thereof; wherein
R$^1$ is selected from the group consisting of hydrogen, C$_{1-4}$ alkyl, and —(CH$_2$)$_{0-1}$ phenyl;

each R$^3$ is independently selected from the group consisting of (1) C$_{1-8}$ alkyl, (2) C$_{2-8}$ alkenyl, (3) —(CH$_2$)$_{0-1}$-phenyl, (4) —(CH$_2$)$_{0-1}$-naphthyl, (5) —(CH$_2$)$_{0-1}$-heteroaryl, (6) —(CH$_2$)$_{0-1}$—C$_{2-7}$ heterocycloalkyl, (7) —(CH$_2$)$_{0-1}$—C$_{3-7}$ cycloalkyl, (8) halogen, (9) OR$^9$,

(10) —(CH$_2$)$_{0-1}$—C(O)R$^9$,

(11) —(CH$_2$)$_{0-1}$—OC(O)R$^9$,

(12) —(CH$_2$)$_{0-1}$—C(O)OR$^9$,

(13) —(CH$_2$)$_{0-1}$—C≡N,

(14) NO$_2$,

(15) —(CH$_2$)$_{0-1}$—N(R$^9$)$_2$,

(16) —(CH$_2$)$_{0-1}$—C(O)N(R$^9$)$_2$,

(17) —(CH$_2$)$_{0-1}$—NR$^9$C(O)R$^9$,

(18) —(CH$_2$)$_{0-1}$—NR$^9$C(O)OR$^9$,

(19) —(CH$_2$)$_{0-1}$NR$^9$C(O)-heteroaryl,

(20) —(CH$_2$)$_{0-1}$NR$^9$C(O)N(R$^9$)$_2$,

(21) —(CH$_2$)$_{0-1}$C(O)NR$^9$N(R$^9$)$_2$,

(22) —(CH$_2$)$_{0-1}$—C(O)NR$^9$NR$^9$C(O)R$^9$,

(23) —(CH$_2$)$_{0-1}$—NR$^9$S(O)$_{1-2}$R$^9$,

(24) —(CH$_2$)$_{0-1}$—S(O)$_{-1-2}$N(R$^9$)$_2$,

(25) —(CH$_2$)$_{0-1}$—S(O)$_{0-2}$R$^9$,

(26) O(CH$_2$)$_{0-1}$—C(O)N(R$^9$)$_2$,

(27) CF$_3$,

(28) CH$_2$CF$_3$,

(29) OCF$_3$, and

(30) OCH$_2$CF$_3$, wherein alkenyl, phenyl, naphthyl, heteroaryl are unsubstituted or substituted with one to three substituents independently selected from halogen, hydroxy, C$_{1-4}$ alkyl, trifluoromethyl, and C$_{1-4}$ alkoxy, and wherein any alkyl, cycloalkyl, heterocycloalkyl, and methylene (CH$_2$) carbon atom in R$^3$ is unsubstituted or substituted with one to two groups independently selected from halogen, hydroxy, oxo, $C_{1-4}$ alkyl, trifluoromethyl, and $C_{1-4}$ alkoxy, or two $R^3$ substituents on the same carbon atom are taken together with the carbon atom to form a cyclopropyl group;

each $R^4$ is independently selected from the group consisting of
(1) hydrogen,
(2) $C_{1-8}$ alkyl,
(3) —$(CH_2)_{0-1}$—$C_{3-6}$ cycloalkyl,
(4) —$(CH_2)_{0-1}$-aryl,
(5) hydroxy,
(6) halogen, and
(7) amino;

$R^5$ is independently selected from the group consisting of
(1) hydrogen,
(2) $C_{1-8}$ alkyl,
(3) $C_{2-8}$ alkenyl,
(4) $C_{2-8}$ alkynyl,
(5) $C_{1-8}$ alkoxy,
(6) —$(CH_2)_{0-1}$—$C_{3-7}$ cycloalkyl,
(7) —$(CH_2)_{0-1}$—$C_{2-7}$ heterocycloalkyl,
(8) —$(CH_2)_{0-1}$-phenyl,
(9) —$(CH_2)_{0-1}$-naphthyl,
(10) —$(CH_2)_{0-1}$-heteroaryl, and
(11) —$(CH_2)_{0-1}$—$C_{3-7}$ bicycloalkyl,
wherein phenyl, naphthyl, and heteroaryl are unsubstituted or substituted with one to three groups independently selected from $R^3$, and alkyl, alkenyl, alkynyl, alkoxy, cycloalky, heterocycloalkyl, and bicycloalkyl are unsubstituted or substituted with one to three groups independently selected from $R^3$ and oxo, and wherein any methylene ($CH_2$) in $R^5$ is unsubstituted or substituted with one to two groups independently selected from halogen, hydroxy, and $C_{1-4}$ alkyl;

$R^6$ is selected from the group consisting of
(1) hydrogen, and
(2) $C_{1-8}$ alkyl;

$R^7$ is selected from the group consisting of
(1) —$(CH_2)_{0-3}$—$N(R^8)_2$,
(2) —$(CH_2)_{0-3}$—$NR^8C(O)R^8$,
(3) —$(CH_2)_{0-3}$—$NR^8C(O)OR^8$,
(4) —$(CH_2)_{0-3}$—$NR^8C(O)N(R^8)_2$,
(5) —$(CH_2)_{0-3}$—$NR^8S(O)R^8$,
(6) —$(CH_2)_{0-3}$—$NR^8S(O)_2R^8$, and
(7) —$(CH_2)_{0-3}$—$NR^8S(O)_2N(R^8)_2$,
wherein any methylene ($CH_2$) in $R^7$ is unsubstituted or substituted with one to two groups independently selected from halogen, hydroxy, and $C_{1-4}$ alkyl, or two $R^8$ substituents together with the carbon, nitrogen or sulfur atom to which they are attached form a 5, 6, or 7-membered saturated or unsaturated nitrogen containing ring optionally substituted with one to three groups independently selected from $C_{1-8}$ alkyl and oxo;

each $R^8$ is independently selected from the group consisting of
(1) hydrogen,
(2) $C_{1-8}$ alkyl,
(3) $C_{2-8}$ alkenyl,
(4) —$(CH_2)_{0-1}$—$C_{3-7}$ cycloalkyl,
(5) —$(CH_2)_{0-1}$—$C_{2-7}$ heterocycloalkyl,
(6) —$(CH_2)_{0-1}$—$C_{3-7}$ bicycloalkyl,
(7) —$(CH_2)_{0-1}$-phenyl,
(8) —$(CH_2)_{0-1}$-naphthyl, and
(9) —$(CH_2)_{0-1}$-heteroaryl,
wherein alkyl, alkenyl, cycloalkyl, heterocycloalkyl, and bicycloalkyl are unsubstituted or substituted with one to three groups independently selected from $R^3$ and oxo, and wherein phenyl, naphthyl, and heteroaryl are unsubstituted or substituted with one to three groups independently selected from $R^3$, and wherein any methylene ($CH_2$) in $R^8$ is unsubstituted or substituted with one to two groups independently selected from halogen, hydroxy, and $C_{1-4}$ alkyl, or two $R^8$ groups together with the atom to which they are attached form a 5- to 8-membered mono- or bicyclic ring system optionally containing an additional heteroatom selected from O, S, and —$NC_{1-4}$ alkyl;

each $R^9$ is independently selected from the group consisting of
(1) hydrogen,
(2) $C_{1-8}$ alkyl,
(3) phenyl,
(4) heteroaryl,
(5) —$(CH_2)_{0-1}$ heterocycloalkyl, and
(6) $C_{3-6}$ cycloalkyl,
wherein alkyl, phenyl, heteroaryl, heterocycloalkyl, and cycloalkyl are unsubstituted or substituted with one to three groups independently selected from halogen, $C_{1-4}$ alkyl, hydroxy, and $C_{1-4}$ alkoxy, or two $R^9$ groups together with the atom to which they are attached form a 4- to 8-membered mono- or bicyclic ring system optionally containing an additional heteroatom selected from O, S, and —$NC_{1-4}$ alkyl;

r is 1 or 2;
s is 1; and
m is 0;

17. The compound of claim 1 selected from the group consisting of:

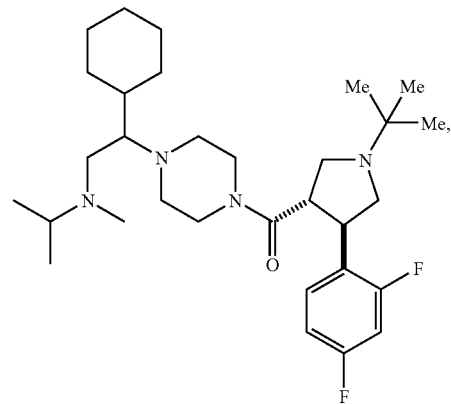

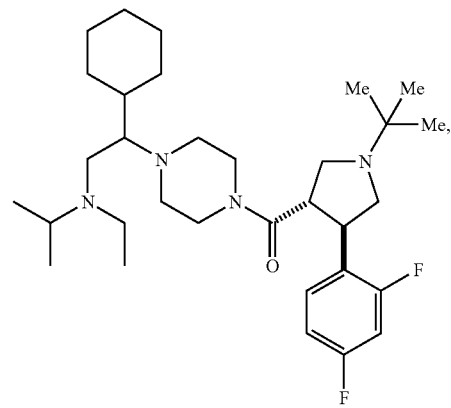

-continued
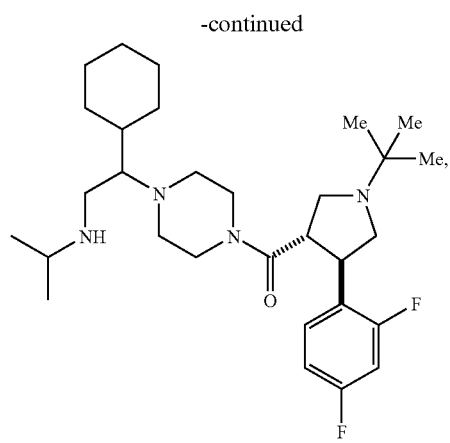 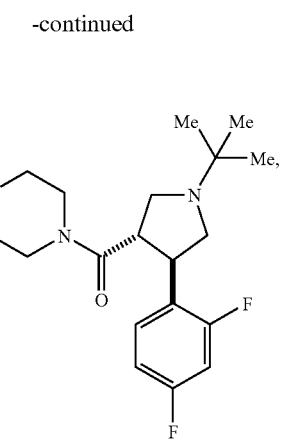
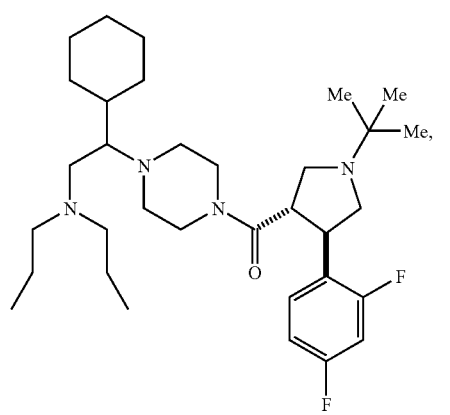 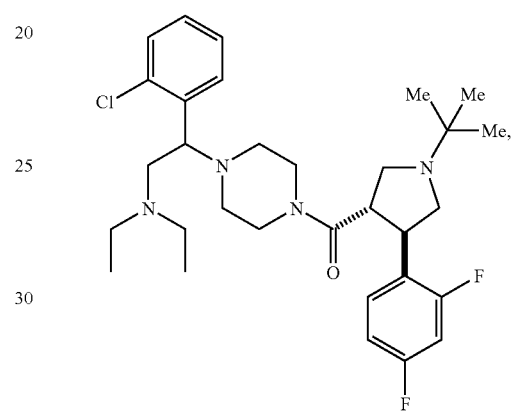
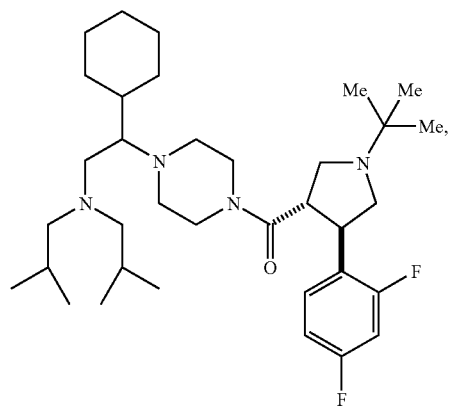 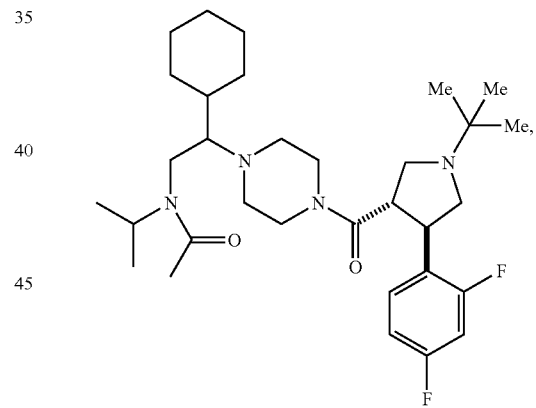
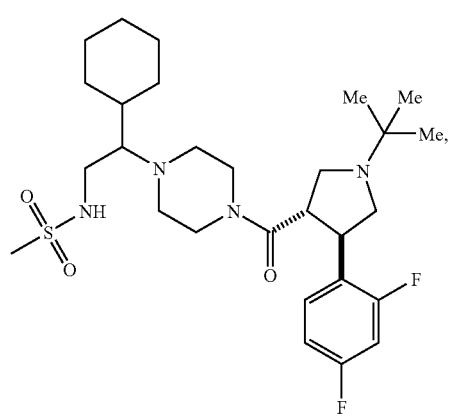 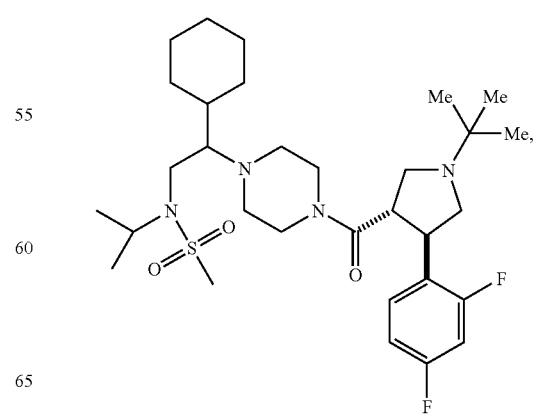

-continued
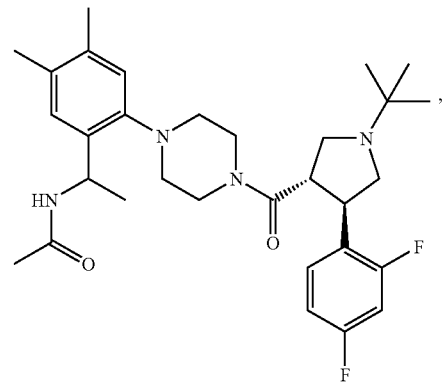
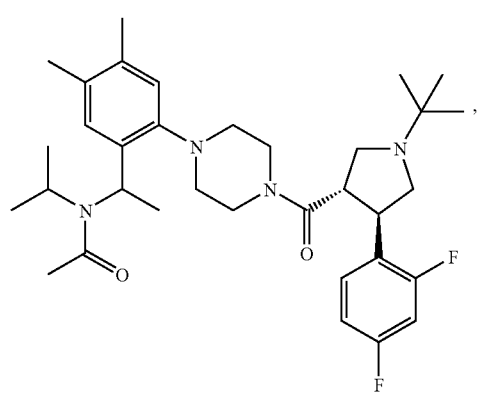
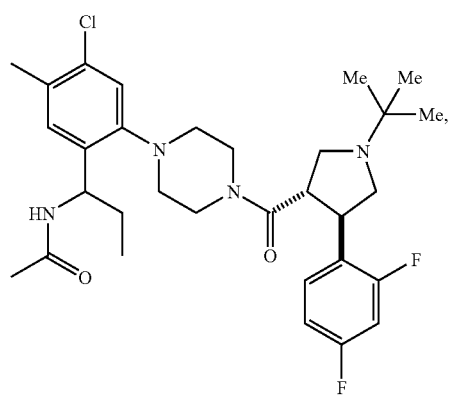
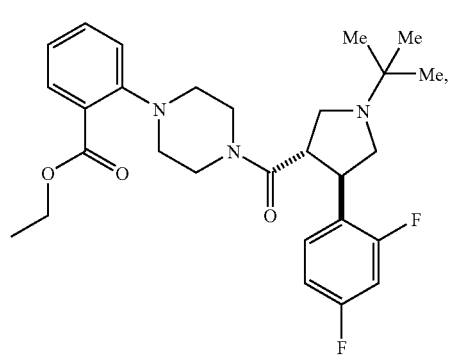
-continued
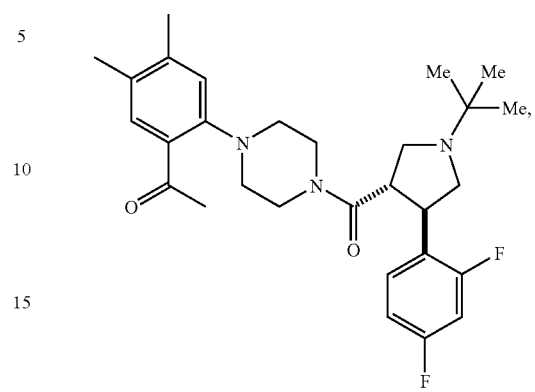
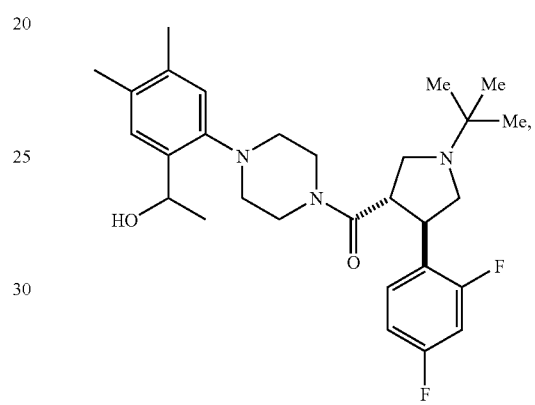
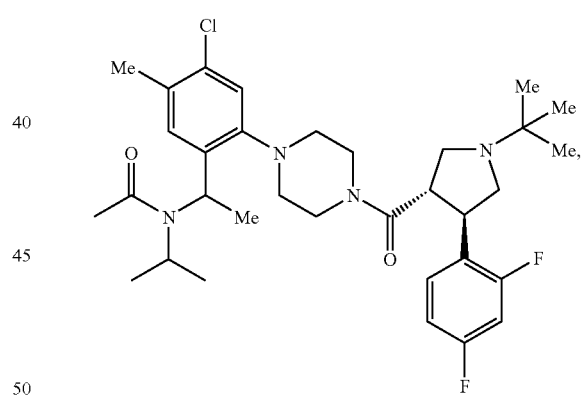
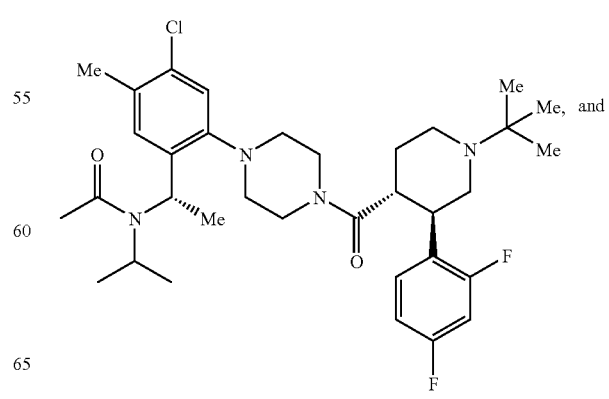

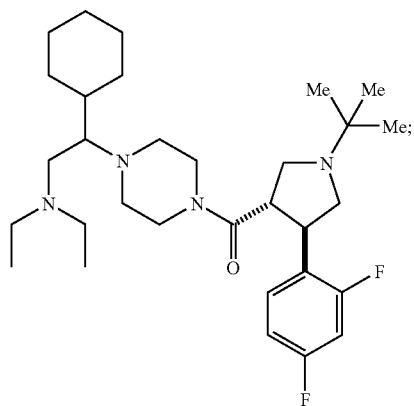
or a pharmaceutically acceptable salt thereof.
18. The compound of claim 1 selected from the group consisting of:
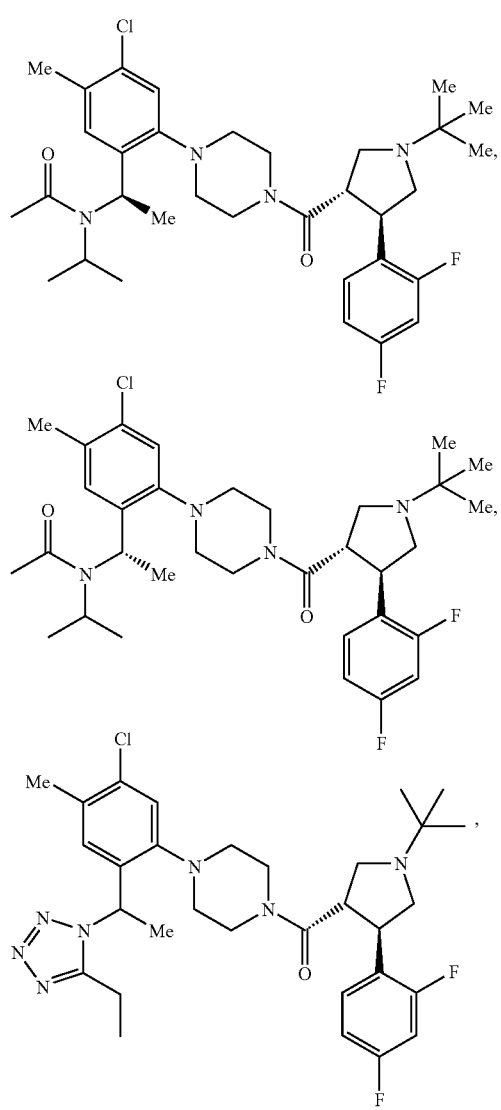
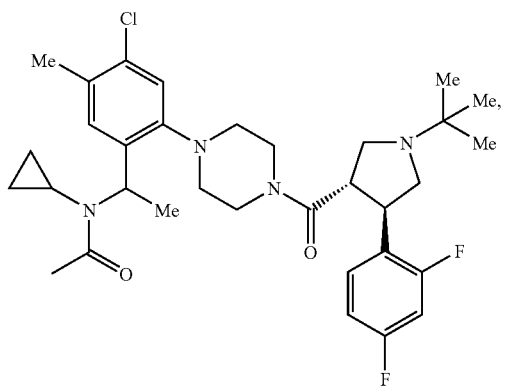
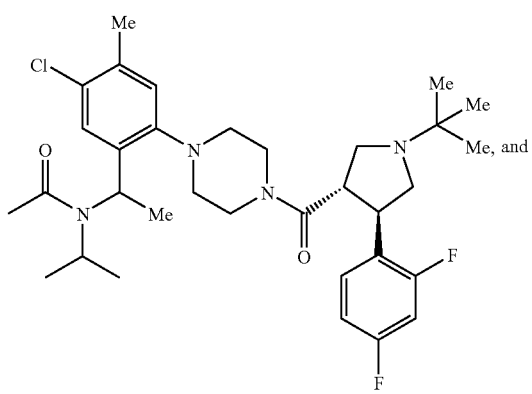
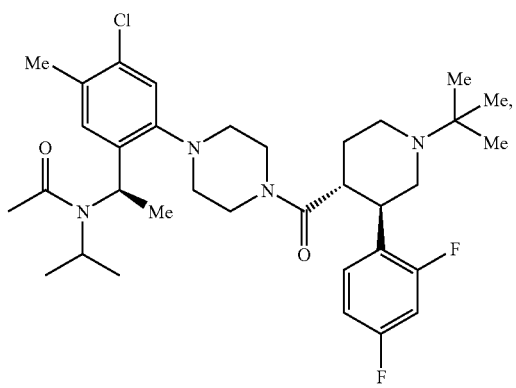
or a pharmaceutically acceptable salt thereof.

19. The compound of claim 17 which is:

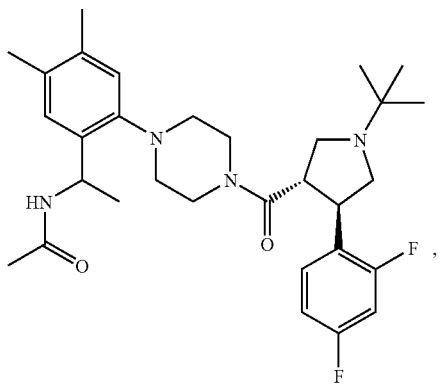

or a pharmaceutically acceptable salt thereof.

20. The compound of claim 17 which is:

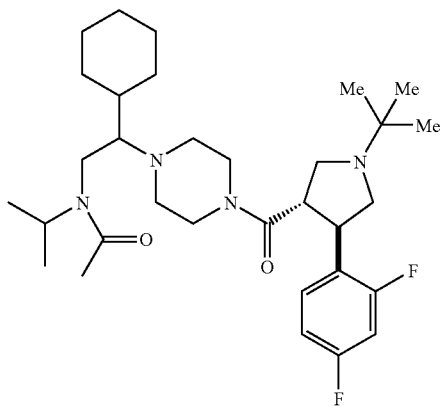

or a pharmaceutically acceptable salt thereof.

21. The compound of claim 17 which is:

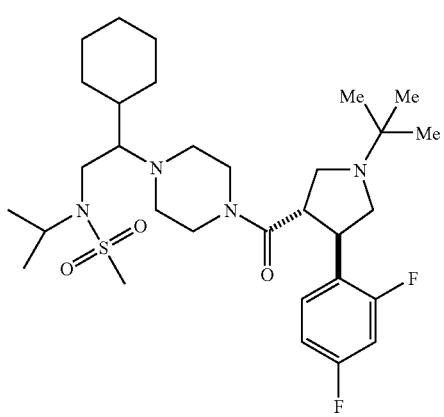

or a pharmaceutically acceptable salt thereof.

22. The compound of claim 17 which is:

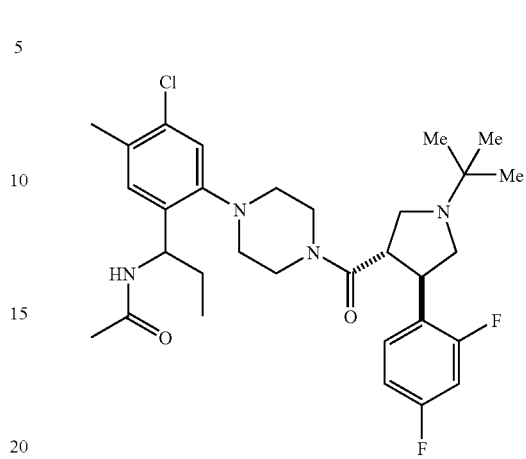

or a pharmaceutically acceptable salt thereof.

23. The compound of claim 17 which is:

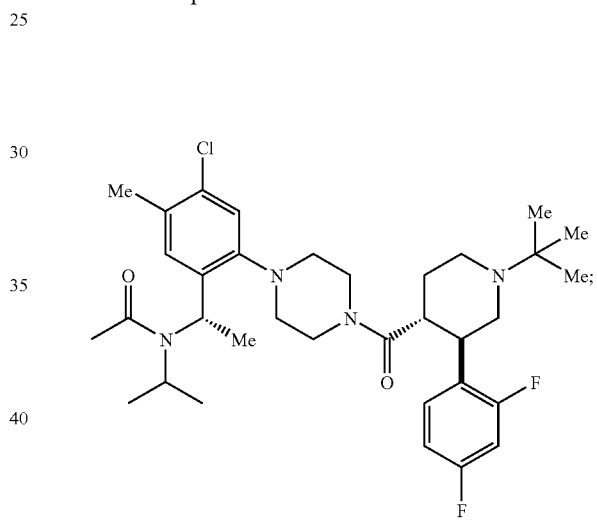

or a pharmaceutically acceptable salt thereof.

24. A method for the treatment of obesity in a mammal in need thereof which comprises administering to the mammal a therapeutically effective amount of a compound according to claim 1.

25. A method for the treatment of diabetes mellitus in a mammal in need thereof comprising administering to the mammal a therapeutically effective amount of a compound according to claim 1.

26. A pharmaceutical composition which comprises a compound of claim 1 and a pharmaceutically acceptable carrier.

27. The compound of claim 1 wherein the pharmaceutically acceptable salt thereof is the hydrochloride salt.

28. The compound of claim 1 wherein the pharmaceutically acceptable salt thereof is the trifluoroacetic acid salt.

29. The compound of claim 1 wherein the pharmaceutically acceptable salt thereof is the bis phosphate salt.

30. The compound of claim 18 which is:
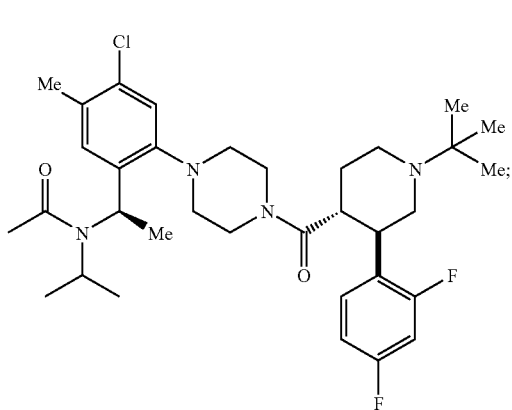
or a pharmaceutically acceptable salt thereof.
31. The compound of claim 18 which is:
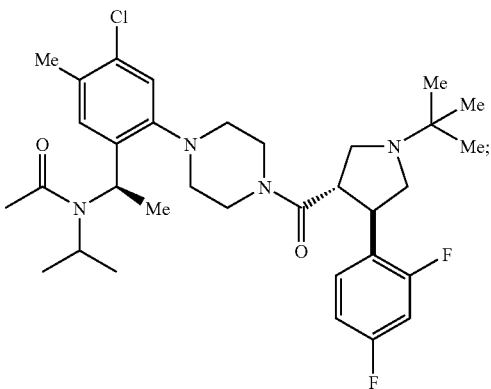
or a pharmaceutically acceptable salt thereof.
* * * * *